United States Patent
Baker et al.

(10) Patent No.: US 7,081,340 B2
(45) Date of Patent: Jul. 25, 2006

(54) GENE EXPRESSION PROFILING IN BIOPSIED TUMOR TISSUES

(75) Inventors: Joffre B. Baker, Montara, CA (US); Maureen T. Cronin, Los Altos, CA (US); Michael C. Kiefer, Clayton, CA (US); Steve Shak, Hillsborough, CA (US); Michael Graham Walker, Sunnyvale, CA (US)

(73) Assignee: Genomic Health, Inc., Redwood City, CA (US)

( * ) Notice: Subject to any disclaimer, the term of this patent is extended or adjusted under 35 U.S.C. 154(b) by 410 days.

(21) Appl. No.: 10/388,360

(22) Filed: Mar. 12, 2003

(65) Prior Publication Data

US 2003/0225528 A1 Dec. 4, 2003

Related U.S. Application Data

(60) Provisional application No. 60/412,049, filed on Sep. 18, 2002, provisional application No. 60/364,890, filed on Mar. 13, 2002.

(51) Int. Cl.
*C07H 21/04* (2006.01)
*C12Q 1/68* (2006.01)

(52) U.S. Cl. .................. 435/6; 435/287.2; 536/23.1; 536/24.3

(58) Field of Classification Search .................... None
See application file for complete search history.

(56) References Cited

U.S. PATENT DOCUMENTS

| | | | |
|---|---|---|---|
| 5,563,035 A | 10/1996 | Weigel | 435/6 |
| 6,180,333 B1 | 1/2001 | Giordano | 435/4 |
| 6,316,208 B1 | 11/2001 | Roberts et al. | 435/7.21 |
| 6,331,396 B1 | 12/2001 | Silverman et al. | |

FOREIGN PATENT DOCUMENTS

| | | |
|---|---|---|
| WO | WO 99/02714 | 1/1999 |
| WO | WO 00/50595 | 8/2000 |
| WO | WO 00/55173 | 9/2000 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/10436 | 2/2002 |
| WO | WO 02/46467 | 6/2002 |
| WO | WO 02/055988 | 7/2002 |
| WO | WO 02/059377 | 8/2002 |
| WO | WO 02/068579 | 9/2002 |
| WO | WO 02/103320 | 12/2002 |
| WO | WO 03/083096 | 10/2003 |

OTHER PUBLICATIONS

Bhattacharjee et al., "Classification of human lung carcinomas by mRNA expression profiling reveals distinct adenocarcinoma subclasses", Proceedings of the National Academy of Sciences of USA, vol. 98, No. 24, pp. 13790-13795 (2001).
Chen-Hsiang Yeang et al., "Molecular Classification of Multiple Tumor Types", Bioinformatics, vol. 17, Suppl. 1, pp. S316-S322 (2001).
Golub et al., "Molecular Classification of Cancer: Class Discovery and Class Prediction by Gene Expression Monitoring", Science, vol. 286, pp. 531-537 (1999).
Martin et al., "Linking Gene Expression Patterns to Therapeutic Groups in Breast Cancer", Cancer Research, vol. 60, pp. 2232-2238 (2000).
Perou et al., "Molecular portraits of human breast tumors", Nature, vol. 406, pp. 747-752 (2000).
Ramaswamy et al., "Multiclass cancer diagnosis using tumor gene expression signatures", Proceedings of the National Academy of Sciences of USA, vol. 98, No. 26, pp. 15149-15154 (2001).
Sorlie et al., "Gene Expression patterns of breast carcinomas distinguish tumor subclass with clinical implications", Proceedings of the National Academy of Sciences of USA, vol. 98, No. 19, pp. 10869-10874 (2001).
West et al., "Predicting the clinical status of human breast cancer by using gene expression profiles", Proceedings of the National Academy of Sciences of USA, vol. 98, No. 20, pp. 11462-11467 (2001).

(Continued)

*Primary Examiner*—Jeanine A. Goldberg
(74) *Attorney, Agent, or Firm*—Ginger R. Dreger; Heller Ehrman LLP

(57) ABSTRACT

The invention concerns sensitive methods to measure mRNA levels in biopsied tumor tissues, including archived paraffin-embedded biopsy material. Th invention also concerns breast cancer gene sets important in the diagnosis and treatment of breast cancer, and methods for assigning the most optimal treatment options to breast cancer patient based upon knowledge derived from gene expression studies.

7 Claims, 9 Drawing Sheets

OTHER PUBLICATIONS

Yan et al., "Dissecting Complex Epigenetic Alterations in Breast Cancer Using CpG Island Microarrays", Cancer Research, vol. 61, pp. 8375-7380 (2001).

Affymetrix Inc.: "Affymetrix GeneChip Human Genome U95 Version 2 Set HG-U95A," *GEO, XX, XX*, 1-243 (2002).

Chang, J. et al., "Biologic Markers as Predictors of Clinical Outcome from Systemic Therapy for Primary Operable Breast Cancer," *Journal of Clinical Oncology: Official Journal of the American Society of Clinical Oncology*, vol. 17:(10) 3058-3063 (1999).

Cox, G. et al., "Bcl-2 is an Independent Prognostic Factor and Adds to a Biological Model for Predicting Outcome in Operable Non-Small Cell Lung Cancer," *Lung Cancer*, vol. 34:(3) 417-426 (2001).

Dijkema, I.M. et al., "Influence of p53 and bcl-2 on Proliferative Activity and Treatment Outcome in head and Neck Cancer Patients," *Oral Oncology, Elsevier Science*, vol. 36:(1) 54-60 (2000).

Guerin, M. et al., "Structure and Expression of C-ERBB-2 and EGF Receptor Genes in Inflammatory and Non-Inflammatory Breast Cancer: Prognostic Significance," *International Journal of Cancer*, vol. 43 201-208 (1989).

Joensuu, H. et al., "Bcl-2 Protein Expression and Long-Term Survival in Breast Cancer," *American Journal of Pathology*, vol. 145:(5) 1191-1198 (1994).

Kymionis, G.D., et al., "Can Expression of Apoptosis Genes, bcl-2 and Bax, Predict Survival and Responsiveness to Chemotherapy in Node-Negative Breast Cancer Patients?" *The Journal of Surgical Research*, vol. 99:(2) 161-168 (2001).

Locker, A.P. et al., "Ki67 Immunoreactivity in Breast Carcinoma: Relationships to prognostic Variable and Short time Survival," *Euroean Journal of Surgical Oncology*, vol. 18:(3) 224-229 (1992).

Murray, P.A. et al., "The Prognostic Significance of Transforming Growth Factors in Human Breast Cancer," *British Journal of Cancer*, vol. 67:(6) 1408-1412 (1993).

Sens, Mary Ann et al., "Metallothionein Isoform 3 Overexpression is Associated with Breast Cancers Having a Poor Prognosis," *American Journal of Pathology*, vol. 159:(1) 21-26 (2001).

Specht K. et al., "Quantitative Gene Expression Analysis in Microdissected Archival Formalin-Fixed and Paraffin-Embedded Tumor Tissue," 158:(2) 419-429 (2001).

Steinbach, Daniel et al., "Clinical Implications of PRAME Gene Expression in Childhood Acute Myeloid Leukemia," *Cancer Genetics and Cytogenetics*, vol. 133:(2) 118-123 (2002).

Veer Van 'T.L.J. et al., "Gene Expression Profiling Predicts Clinical Outcome of Breast Cancer," *Nature, Macmillan Journals Ltd.*, vol. 415:(6871) 530-536 (2002).

Overall FPET/RT-PCR Flow Chart

GENE EXPRESSION PROFILING IN BIOPSIED TUMOR TISSUES

CROSS-REFERENCE

This application claims the benefit under 35 U.S.C. 119(e) of provisional applications Ser. Nos. 60/412,049, filed Sep. 18, 2002 and 60/364,890, filed Mar. 13, 2002, the entire disclosures which are herby incorporated by reference.

BACKGROUND OF THE INVENTION

Field of the Invention

The present invention relates to gene expression profiling in biopsied tumor tissues. In particular, the present invention concerns sensitive methods to measure mRNA levels in biopsied tumor tissues, including archived paraffin-embedded biopsy material. In addition, the invention provides a set of genes the expression of which is important in the diagnosis and treatment of breast cancer.

Oncologists have a number of treatment options available to them, including different combinations of chemotherapeutic drugs that are characterized as "standard of care," and a number of drugs that do not carry a label claim for a particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286:531–537 (1999); Bhattacharjee et al., *Proc. Natl. Acad. Sci. USA* 98:13790–13795 (2001); Chen-Hsiang et al., *Bioinformatics* 17 (Suppl. 1):S316–S322 (2001); Ramaswamy et al., *Proc. Natl. Acad. Sci. USA* 98:15149–15154 (2001)). Certain classifications of human breast cancers based on gene expression patterns have also been reported (Martin et al., *Cancer Res.* 60:2232–2238 (2000); West et al., *Proc. Natl. Acad. Sci. USA* 98:11462–11467 (2001); Sorlie et al., *Proc. Natl. Acad. Sci. USA* 98:10869–10874 (2001); Yan et al., *Cancer Res.* 61:8375–8380 (2001)). However, these studies mostly focus on improving and refining the already established classification of various types of cancer, including breast cancer, and generally do not provide new insights into the relationships of the differentially expressed genes, and do not link the findings to treatment strategies in order to improve the clinical outcome of cancer therapy.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to maximize outcome. Hence, a need exists for tests that simultaneously provide predictive information about patient responses to the variety of treatment options. This is particularly true for breast cancer, the biology of which is poorly understood. It is clear that the classification of breast cancer into a few subgroups, such as $ErbB2^+$ subgroup, and subgroups characterized by low to absent gene expression of the estrogen receptor (ER) and a few additional transcriptional factors (Perou et al., *Nature* 406:747–752 (2000)) does not reflect the cellular and molecular heterogeneity of breast cancer, and does not allow the design of treatment strategies maximizing patient response.

SUMMARY OF THE INVENTION

The present invention provides (1) sensitive methods to measure mRNA levels in biopsied tumor tissue, (2) a set of approximately 190 genes, the expression of which is important in the diagnosis of breast cancer, and (3) the significance of abnormally low or high expression for the genes identified and included in the gene set, through activation or disruption of biochemical regulatory pathways that influence patient response to particular drugs used or potentially useful in the treatment of breast cancer. These results permit assessment of genomic evidence of the efficacy of more than a dozen relevant drugs.

The present invention accommodates the use of archived paraffin-embedded biopsy material for assay of all markers in the set, and therefore is compatible with the most widely available type of biopsy material. The invention presents an efficient method for extraction of RNA from wax-embedded, fixed tissues, which reduces cost of mass production process for acquisition of this information without sacrificing quality of the analysis. In addition, the invention describes a novel highly effective method for amplifying mRNA copy number, which permits increased assay sensitivity and the ability to monitor expression of large numbers of different genes given the limited amounts of biopsy material. The invention also captures the predictive significance of relationships between expressions of certain markers in the breast cancer marker set. Finally, for each member of the gene set, the invention specifies the oligonucleotide sequences to be used in the test.

In one aspect, the invention concerns a method for predicting clinical outcome for a patient diagnosed with cancer, comprising determining the expression level of one or more genes, or their expression products, selected from the group consisting of p53BP2, cathepsin B, cathepsin L, Ki67/MiB1, and thymidine kinase in a cancer tissue obtained from the patient, normalized against a control gene or genes, and compared to the amount found in a reference cancer tissue set, wherein a poor outcome is predicted if:

(a) the expression level of p53BP2 is in the lower $10^{th}$ percentile; or (b) the expression level of either cathepsin B or cathepsin L is in the upper $10^{th}$ percentile; or (c) the expression level of any either Ki67/MiB1 or thymidine kinase is in the upper $10^{th}$ percentile.

Poor clinical outcome can be measured, for example, in terms of shortened survival or increased risk of cancer recurrence, e.g. following surgical removal of the cancer.

In another embodiment, the inventor concerns a method of predicting the likelihood of the recurrence of cancer, following treatment, in a cancer patient, comprising determining the expression level of p27, or its expression product, in a cancer tissue obtained from the patient, normalized against a control gene or genes, and compared to the amount found in a reference cancer tissue set, wherein an expression level in the upper 10th percentile indicates decreased risk of recurrence following treatment.

In another aspect, the invention concerns a method for classifying cancer comprising, determining the expression level of two or more genes selected from the group consisting of Bcl2, hepatocyte nuclear factor 3, ER, ErbB2, and Grb7, or their expression products, in a cancer tissue, normalized against a control gene or genes, and compared to the amount found in a reference cancer tissue set, wherein (i) tumors expressing at least one of Bcl2, hepatocyte nuclear factor 3, and ER, or their expression products, above the mean expression level in the reference tissue set are classified as having a good prognosis for disease free and overall patient survival following treatment; and (ii) tumors expressing elevated levels of ErbB2 and Grb7, or their expression products, at levels ten-fold or more above the mean expression level in the reference tissue set are classified as having poor prognosis of disease free and overall patient survival following treatment.

All types of cancer are included, such as, for example, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer. The foregoing methods are particularly suitable for prognosis/classification of breast cancer.

In all previous aspects, in a specific embodiment, the expression level is determined using RNA obtained from a formalin-fixed, paraffin-embedded tissue sample. While all techniques of gene expression profiling, as well as proteomics techniques, are suitable for use in performing the foregoing aspects of the invention, the gene expression levels are often determined by reverse transcription polymerase chain reaction (RT-PCR).

If the source of the tissue is a formalin-fixed, paraffin embedded tissue sample, the RNA is often fragmented.

The expression data can be further subjected to multivariate analysis, for example using the Cox Proportional Hazards model.

In a further aspect, the invention concerns a method for the preparation of nucleic acid from a fixed, wax-embedded tissue specimen, comprising:

(a) incubating a section of the fixed, wax-embedded tissue specimen at a temperature of about 56° C. to 70° C. in a lysis buffer, in the presence of a protease, without prior dewaxing, to form a lysis solution;

(b) cooling the lysis solution to a temperature where the wax solidifies; and (c) isolating the nucleic acid from the lysis solution.

The lysis buffer may comprise urea, such as 4M urea. In a particular embodiment, incubation in step (a) of the foregoing method is performed at about 65° C.

In another particular embodiment, the protease used in the foregoing method is proteinase K.

In another embodiment, the cooling in step (b) is performed at room temperature.

In a further embodiment, the nucleic acid is isolated after protein removal with. 2.5 M NH$_4$OAc.

The nucleic acid can, for example, be total nucleic acid present in the fixed, wax-embedded tissue specimen.

In yet another embodiment, the total nucleic acid is isolated by precipitation from the lysis solution, following protein removal, with 2.5 M NH$_4$OAc. The precipitation may, for example, be performed with isopropanol.

The method described above may further comprise the step of removing DNA from the total nucleic acid, for example by DNAse treatment.

The tissue specimen may, for example, be obtained from a tumor, and the RNA may be obtained from a microdissected portion of the tissue specimen enriched for tumor cells.

All types of tumor are included, such as, without limitation, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer, in particular breast cancer.

The method described above may further comprise the step of subjecting the RNA to gene expression profiling. Thus, the gene expression profile may be completed for a set of genes comprising at least two of the genes listed in Table 1.

Although all methods of gene expression profiling are contemplated, in a particular embodiment, gene expression profiling is performed by RT-PCR which may be preceded by an amplification step.

In another aspect, the invention concerns a method for preparing fragmented RNA for gene expression analysis, comprising the steps of:

(a) mixing the RNA with at least one gene-specific, single-stranded DNA scaffold under conditions such that fragments of the RNA complementary to the DNA scaffold hybridize with the DNA scaffold;

(b) extending the hybridized RNA fragments with a DNA polymerase to form a DNA-DNA duplex; and (c) removing the DNA scaffold from the duplex.

In a specific embodiment, in step (b) of this method, the RNA may be mixed with a mixture of single-stranded DNA templates specific for each gene of interest.

The method can further comprise the step of heat-denaturing and reannealing the duplexed DNA to the DNA scaffold, with or without additional overlapping scaffolds, and further extending the duplexed sense strand with DNA polymerase prior to removal of the scaffold in step (c).

The DNA templates may be, but do not need to be, fully complementary to the gene of interest.

In a particular embodiment, at least one of the DNA templates is complementary to a specific segment of the gene of interest.

In another embodiment, the DNA templates include sequences complementary to polymorphic variants of the same gene.

The DNA template may include one or more dUTP or rNTP sites. In this case. iin step (c) the DNA template may be removed by fragmenting the DNA template present in the DNA-DNA duplex formed in step (b) at the dUTP or rNTP sites.

In an important embodiment, the RNA is extracted from fixed, wax-embedded tissue specimens, and purified sufficiently to act as a substrate in an enzyme assay. The RNA purification may, but does not need to, include an oligo-dT based step.

In a further aspect, the invention concerns a method for amplifying RNA fragments in a sample comprising fragmented RNA representing at least one gene of interest, comprising the steps of:

(a) contacting the sample with a pool of single-stranded DNA scaffolds comprising an RNA polymerase promoter at the 5' end under conditions such that the RNA fragments complementary to the DNA scaffolds hybridize with the DNA scaffolds;

(b) extending the hybridized RNA fragments with a DNA polymerase along the DNA scaffolds to form DNA-DNA duplexes;

(c) amplifying the gene or genes of interest by in vitro transcription; and (d) removing the DNA scaffolds from the duplexes.

An exemplary promoter is the T7 RNA polymerase promoter, while an exemplary DNA polymerase is DNA polymerase I.

In step (d) the DNA scaffolds may be removed, for example, by treatment with DNase I.

In a further embodiment, the pool of single-stranded DNA scaffolds comprises partial or complete gene sequences of interest, such as a library of cDNA clones.

In a specific embodiment, the sample represents a whole genome or a fraction thereof. In a preferred embodiment, the genome is the human genome.

In another aspect, the invention concerns a method of preparing a personalized genomics profile for a patient, comprising the steps of:

(a) subjecting RNA extracted from a tissue obtained from the patient to gene expression analysis;

(b) determining the expression level in such tissue of at least two genes selected from the gene set listed in Table 1, wherein the expression level is normalized against a control gene or genes, and is compared to the amount found in a cancer tissue reference set;

(c) and creating a report summarizing the data obtained by the gene expression analysis.

The tissue obtained from the patient may, but does not have to, comprise cancer cells. Just as before, the cancer can, for example, be breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, or brain cancer, breast cancer being particularly preferred.

In a particular embodiment, the RNA is obtained from a microdissected portion of breast cancer tissue enriched for cancer cells. The control gene set may, for example, comprise S-actin, and ribosomal protein LPO.

The report prepared for the use of the patient or the patient's physician, may include the identification of at least one drug potentially beneficial in the treatment of the patient.

Step (b) of the foregoing method may comprise the step of determining the expression level of a gene specifically influencing cellular sensitivity to a drug, where the gene can, for example, be selected from the group consisting of aldehyde dehydrogenase 1A1, aldehyde dehydrogenase 1A3, amphiregulin, ARG, BRK, BCRP, CD9, CD31, CD82/KAI-1, COX2, c-abl, c-kit, c-kit L, CYP1B1, CYP2C9, DHFR, dihydropyrimidine dehydrogenase, EGF, epiregulin, ER-alpha, ErbB-1, ErbB-2, ErbB-3, ErbB-4, ER-beta, farnesyl pyrophosphate synthetase, gamma-GCS (glutamyl cysteine synthetase), GATA3, geranyl geranyl pyrophosphate synthetase, Grb7, GST-alpha, GST-pi, HB-EGF, hsp 27, human chorionic gonadotropin/CGA, IGF-1, IGF-2, IGF1R, KDR, LIV1, Lung Resistance Protein/MVP, Lot1, MDR-1, microsomal epoxide hydrolase, MMP9, MRP1, MRP2, MRP3, MRP4, PAI1, PDGF-A, PDGF-B, PDGF-C, PDGF-D, PGDFR-alpha, PDGFR-beta, PLAGa (pleiomorphic adenoma 1), PREP prolyl endopeptidase, progesterone receptor, pS2/trefoil factor 1, PTEN, PTB1b, RAR-alpha, RAR-beta2, Reduced Folate Carrier, SXR, TGF-alpha, thymidine phosphorylase, thymidine synthase, topoisomerase II-alpha, topoisomerase II-beta, VEGF, XIST, and YB-1.

In another embodiment, step (b) of the foregoing process includes determining the expression level of multidrug resistance factors, such as, for example, gamma-glutamyl-cysteine synthetase (GCS), GST-α, GST-π, MDR-1, MRP1-4, breast cancer resistance protein (BCRP), lung cancer resistance protein (MVP), SXR, or YB-1.

In another embodiment, step (b) of the foregoing process comprises determination of the expression level of eukaryotic translation initiation factor 4E (EIF4E).

In yet another embodiment, step (b) of the foregoing process comprises determination of the expression level of a DNA repair enzyme.

In a further embodiment, step (b) of the foregoing process comprises determination of the expression level of a cell cycle regulator, such as, for example, c-MYC, c-Src, Cyclin D1, Ha-Ras, mdm2. p14ARF, p21WAF1/CI, p16INK4a/p14, p23, p27, p53, PI3K, PKC-epsilon, or PKC-delta.

In a still further embodiment, step (b) of the foregoing process comprises determination of the expression level of a tumor suppressor or a related protein, such as, for example, APC or E-cadherin.

In another embodiment, step (b) of the foregoing method comprises determination of the expression level of a gene regulating apoptosis, such as, for example, p53, BCl2, Bcl-x1, Bak, Bax, and related factors, NFκ-B, CIAP1, CIAP2, survivin, and related factors, p53BP1/ASPP1, or p53BP2/ASPP2.

In yet another embodiment, step (b) of the foregoing process comprises determination of the expression level of a factor that controls cell invasion or angiogenesis, such as, for example, uPA, PAI1, cathepsin B, C, and L, scatter factor (HGF), c-met, KDR, VEGF, or CD31.

In a different embodiment, step (b) of the foregoing method comprises determination of the expression level of a marker for immune or inflammatory cells or processes, such as, for example, Ig light chain λ, CD18, CD3, CD68. Fas(CD95), or Fas Ligand.

In a further embodiment, step (b) of the foregoing process comprises determination of the expression level of a cell proliferation marker, such as, for example, Ki67/MiB1, PCNA, Pin1, or thymidine kinase.

In a still further embodiment, step (b) of the foregoing process comprises determination of the expression level of a growth factor or growth factor receptor., such as, for example, IGF1, IGF2, IGFBP3, IGF1R, FGF2, CSF-1, CSF-1R/fms, SCF-1, IL6 or IL8.

In another embodiment, step (b) of the foregoing process comprises determination of the expression level of a gene marker that defines a subclass of breast cancer, where the gene marker can, for example, be GRO1 oncogene alpha, Grb7, cytokeratins 5 and 17, retinol binding protein 4, hepatocyte nuclear factor 3, integrin subunit alpha 7, or lipoprotein lipase.

In a still further aspect, the invention concerns a method for predicting the response of a patient diagnosed with breast cancer to 5-fluorouracil (5-FU) or an analog thereof, comprising the steps of:

(a) subjecting RNA extracted from a breast cancer tissue obtained from the patient to gene expression analysis;

(b) determining the expression level in the tissue of thymidylate synthase mRNA, wherein the expression level is normalized against a control gene or genes, and is compared to the amount found in a reference breast cancer tissue set; and (c) predicting patient response based on the normalized thymidylate synthase mRNA level.

Step (d) of the foregoing method can further comprise determining the expression level of dihydropyrimidine phosphorylase.

In another embodiment, step (b) of the method can further comprise determining the expression level of thymidine phosphorylase.

In yet another embodiment, a positive response to 5-FU or an analog thereof is predicted if: (i) normalized thymidylate synthase mRNA level determined in step (b) is at or below the $15^{th}$ percentile; or (ii) the sum of normalized expression levels of thymidylate synthase and dihydropyrimidine phosphorylase determined in step (b) is at or below the $25^{th}$ percentile; or (iii) the sum of normalized expression levels of thymidylate synthase, dihydropyrimidine phosphorylase, plus thymidine phosphorylase determined in step (b) is at or below the $20^{th}$ percentile.

In a further embodiment, in step (b) of the foregoing method the expression level of c-myc and wild-type p53 is determined. In this case, a positive response to 5-FU or an analog thereof is predicted, if the normalized expression level of c-myc relative to the normalized expression level of wild-type p53 is in the upper $15^{th}$ percentile.

In a still further embodiment, in step (b) of the foregoing method, expression level of NFκB and cIAP2 is determined. In this particular embodiment, resistance to 5-FU or an analog thereof is typically predicted if the normalized expression level of NFκB and cIAP2 is at or above the $10^{th}$ percentile.

In another aspect, the invention concerns a method for predicting the response of a patient diagnosed with breast cancer to methotrexate or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting decreased patient sensitivity to methotrexate or analog if (i) DHFR levels are more than tenfold higher than the average expression level of DHFR in the control gene set, or (ii) the normalized expression levels of members of the reduced folate carrier (RFC) family are below the $10^{th}$ percentile.

In yet another aspect, the invention concerns a method for predicting the response of a patient diagnosed with breast cancer to an anthracycline or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient resistance or decreased sensitivity to the anthracycline or analog if (i) the normalized expression level of topoisomerase IIα is below the $10^{th}$ percentile, or (ii) the normalized expression level of topoisomerase IIβ is below the $10^{th}$ percentile, or (iii) the combined normalized topoisomerase IIα or IIβ expression levels are below the $10^{th}$ percentile.

In a different aspect, the invention concerns a method for predicting the response of a patient diagnosed with breast cancer to a docetaxol, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to docetaxol if the normalized expression level of CYP1B1 is in the upper $10^{th}$ percentile.

The invention further concerns a method for predicting the response of a patient diagnosed with breast cancer to cyclophosphamide or an analog thereof, comprising (a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to the cyclophosphamide or analog if the sum of the expression levels of aldehyde dehydrogenase 1A1 and 1A3 is more than tenfold higher than the average of their combined expression levels in the reference tissue set.

In a further aspect, the invention concerns a method for predicting the response of a patient diagnosed with breast cancer to anti-estrogen therapy, comprising (a) subjecting RNA extracted from a breast cancer tissue obtained from the patient to gene expression analysis, wherein gene expression levels are normalized against a control gene or genes, and compared to the amount found in a reference breast cancer tissue set that contains both specimens negative for and positive for estrogen receptor-α (ERα) and progesterone receptor-α (PRα); and (b) predicting patient response based upon the normalized expression levels of ERα or PRα, and at least one of microsomal epoxide hydrolase, pS2/trefoil factor 1, GATA3 and human chorionic gonadotropin.

In a specific embodiment, lack of response or decreased responsiveness is predicted if (i) the normalized expression level of microsomal epoxide hydrolase is in the upper $10^{th}$ percentile; or (ii) the normalized expression level of pS2/trefoil factor 1, or GATA3 or human chorionic gonaostropin is at or below the corresponding average expression level in said breast cancer tissue set, regardless of the expression level of ERα or PRα in the breast cancer tissue obtained from the patient.

In another aspect, the invention concerns a method for predicting the response of a patient diagnosed with breast cancer to a taxane, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting reduced sensitivity to taxane if (i) no or minimal XIST expression is detected; or (ii) the normalized expression level of GST-π or propyl endopeptidase (PREP) is in the upper $10^{th}$ percentile; or (iii) the normalized expression level of PLAG1 is in the upper $10^{th}$ percentile.

The invention also concerns a method for predicting the response of a patient diagnosed with breast cancer to cisplatin or an analog thereof, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting resistance or reduced sensitivity if the normalized expression level of ERCC1 is in the upper $10^{th}$ percentile.

The invention further concerns a method for predicting the response of a patient diagnosed with breast cancer to an ErbB2 or EGFR antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting patient response based on the normalized expression levels of at least one of Grb7, IGF1R, IGF1 and IGF2.

In particular embodiment, a positive response is predicted if the normalized expression level of Grb7 is in the upper $10^{th}$ percentile, and the expression of IGF1R, IGF1 and IGF2 is not elevated above the $90^{th}$ percentile.

In a further particular embodiment, a decreased responsiveness is predicted if the expression level of at least one of IGF1R, IGF1 and IGF2 is elevated.

In another aspect, the invention concerns a method for predicting the response of a patient diagnosed with breast cancer to a bis-phosphonate drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the breast cancer tissue obtained from the patient expresses mutant Ha-Ras and additionally expresses farnesyl pyrophosphate synthetase or geranyl pyrophosphone synthetase at a normalized expression level at or above the $90^{th}$ percentile.

In yet another aspect, the invention concerns a method for predicting the response of a patient diagnosed with breast cancer to treatment with a cyclooxygenase 2 inhibitor, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if the normalized expression level of COX2 in the breast cancer tissue obtained from the patient is at or above the $90^{th}$ percentile.

The invention further concerns a method for predicting the response of a patient diagnosed with breast cancer to an EGF receptor (EGFR) antagonist, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response to an EGFR antagonist, if (i) the normalized expression level of EGFR is at or above the $10^{th}$ percentile, and (ii) the normalized expression level of at least one of epiregulin, TGF-α, amphiregulin, ErbB3, BRK, CD9, MMP9, CD82, and Lot1 is above the $90^{th}$ percentile.

In another aspect, the invention concerns a method for monitoring the response of a patient diagnosed with breast cancer to treatment with an EGFR antagonist, comprising monitoring the expression level of a gene selected from the group consisting of epiregulin, TGF-α, amphiregulin, ErbB3, BRK, CD9, MMP9, CD82, and Lot1 in the patient during treatment, wherein reduction in the expression level is indicative of positive response to such treatment.

In yet another aspect, the invention concerns a method for predicting the response of a patient diagnosed with breast cancer to a drug targeting a tyrosine kinase selected from the group consisting of abl, c-kit, PDGFR-α, PDGFR-β and ARG, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set;

(b) determining the normalized expression level of a tyrosine kinase selected from the group consisting of abl, c-kit, PDGFR-α, PDGFR-β and ARG, and the cognate ligand of the tyrosine kinase, and if the normalized expression level of the tyrosine kinase is in the upper $10^{th}$ percentile, (c) determining whether the sequence of the tyrosine kinase contains any mutation, wherein a positive response is predicted if (i) the normalized expression level of the tyrosine kinase is in the upper $10^{th}$ percentile, (ii) the sequence of the tyrosine kinase contains an activating mutation, or (iii) the normalized expression level of the tyrosine kinase is normal and the expression level of the ligand is in the upper $10^{th}$ percentile.

Another aspect of the invention is a method for predicting the response of a patient diagnosed with breast cancer to treatment with an anti-angiogenic drug, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) predicting a positive response if (i) the normalized expression level of VEGF is in the upper $10^{th}$ percentile and (ii) the normalized expression level of KDR or CD31 is in the upper $20^{th}$ percentile.

A further aspect of the invention is a method for predicting the likelihood that a patient diagnosed with breast cancer develops resistance to a drug interacting with the MRP-1 gene coding for the multidrug resistance protein P-glycoprotein, comprising the steps of:

(a) subjecting RNA extracted from a breast cancer tissue obtained from the patient to gene expression analysis to determine the expression level of PTP1b, wherein the expression level is normalized against a control gene or genes, and compared to the amount found in a reference breast cancer tissue set; and (b) concluding that the patient is likely to develop resistance to said drug if the normalized expression level of the MRP-1 gene is above the 90$^{th}$ percentile.

The invention further relates to a method for predicting the likelihood that a patient diagnosed with breast cancer develops resistance to a chemotherapeutic drug or toxin used in cancer treatment, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of at least one of the following genes: MDR1, SGTα, GSTπ, SXR, BCRP YB-1, and LRP/MVP, wherein the finding of a normalized expression level in the upper 4$^{th}$ percentile is an indication that the patient is likely to develop resistance to the drug.

Also included herein is a method for measuring the translational efficiency of VEGF mRNA in a breast cancer tissue sample, comprising determining the expression levels of the VEGF and EIF4E mRNA in the sample, normalized against a control gene or genes, and compared to the amount found in a reference breast cancer tissue set, wherein a higher normalized EIF4E expression level for the same VEGF expression level is indicative of relatively higher translational efficiency for VEGF.

In another aspect, the invention provides a method for predicting the response of a patient diagnosed with breast cancer to a VEGF antagonist, comprising determining the expression level of VEGF and EIF4E mRNA normalized against a control gene or genes, and compared to the amount found in a reference breast cancer tissue set, wherein a VEGF expression level above the 90$^{th}$ percentile and an EIF4E expression level above the 50$^{th}$ percentile is a predictor of good patient response.

The invention further provides a method for predicting the likelihood of the recurrence of breast cancer in a patient diagnosed with breast cancer, comprising determining the ratio of p53:p21 mRNA expression or p53:mdm2 mRNA expression in a breast cancer tissue obtained from the patient, normalized against a control gene or genes, and compared to the amount found in a reference breast cancer tissue set, wherein an above normal ratio is indicative of a higher risk of recurrence. Typically, a higher risk of recurrence is indicated if the ratio is in the upper 10$^{th}$ percentile.

In yet another aspect, the invention concerns a method for predicting the likelihood of the recurrence of breast cancer in a breast cancer patient following surgery, comprising determining the expression level of cyclin D1 in a breast cancer tissue obtained from the patient, normalized against a control gene or genes, and compared to the amount found in a reference breast cancer tissue set, wherein an expression level in the upper 10$^{th}$ percentile indicates increased risk of recurrence following surgery. In a particular embodiment of this method, the patient is subjected to adjuvant chemotherapy, if the expression level is in the upper 10$^{th}$ percentile.

Another aspect of the invention is a method for predicting the likelihood of the recurrence of breast cancer in a breast cancer patient following surgery, comprising determining the expression level of APC or E-cadherin in a breast cancer tissue obtained from the patient, normalized against a control gene or genes, and compared to the amount found in a reference breast cancer tissue set, wherein an expression level in the upper 5$^{th}$ percentile indicates high risk of recurrence following surgery, and heightened risk of shortened survival.

A further aspect of the invention is a method for predicting the response of a patient diagnosed with breast cancer to treatment with a proapoptotic drug comprising determining the expression levels of BCl2 and c-MYC in a breast cancer tissue obtained from the patient, normalized against a control gene or genes, and compared to the amount found in a reference breast cancer tissue set, wherein (i) a BCl2 expression level in the upper 10$^{th}$ percentile in the absence of elevated expression of c-MYC indicates good response, and (ii) a good response is not indicated if the expression level c-MYC is elevated, regardless of the expression level of BCl2.

A still further aspect of the invention is a method for predicting treatment outcome for a patient diagnosed with breast cancer, comprising the steps of:

(a) subjecting RNA extracted from a breast cancer tissue obtained from the patient to gene expression analysis, wherein gene expression levels are normalized against a control gene or genes, and compared to the amount found in a reference breast cancer tissue set; and (b) determining the normalized expression levels of NFκB and at least one gene selected from the group consisting of cIAP1, cIAP2, XIAP, and Survivin, wherein a poor prognosis is indicated if the expression levels for NFκB and at least one of the genes selected from the group consisting of cIAP1, cIAP2, XIAP, and Survivin is in the upper 5$^{th}$ percentile.

The invention further concerns a method for predicting treatment outcome for a patient diagnosed with breast cancer, comprising determining the expression levels of p53BP1 and p53BP2 in a breast cancer tissue obtained from the patient, normalized against a control gene or genes, and compared to the amount found in a reference breast cancer tissue set, wherein a poor outcome is predicted if the expression level of either p53BP1 or p53BP2 is in the lower 10$^{th}$ percentile.

The invention additionally concerns a method for predicting treatment outcome for a patient diagnosed with breast cancer, comprising determining the expression levels of uPA and PAI1 in a breast cancer tissue obtained from the patient, normalized against a control gene or genes, and compared to the amount found in a reference breast cancer tissue set, wherein (i) a poor outcome is predicted if the expression levels of uPA and PAI1 are in the upper 20$^{th}$ percentile, and (ii) a decreased risk of recurrence is predicted if the expression levels of uPA and PAI1 are not elevated above the mean observed in the breast cancer reference set. In a particular embodiment, poor outcome is measured in terms of shortened survival or increased risk of cancer recurrence following surgery. In another particular embodiment, uPA and PAI1 are expressed at normal levels, and the patient is subjected to adjuvant chemotherapy following surgery.

Another aspect of the invention is a method for predicting treatment outcome in a patient diagnosed with breast cancer, comprising determining the expression levels of cathepsin B and cathepsin L in a breast cancer tissue obtained from the patient, normalized against a control gene or genes, and compared to the amount found in a reference breast cancer tissue set, wherein a poor outcome is predicted if the expression level of either cathepsin B or cathepsin L is in the upper 10$^{th}$ percentile. Just as before, poor treatment outcome may be measured, for example, in terms of shortened survival or increased risk of cancer recurrence.

A further aspect of the invention is a method for devising the treatment of a patient diagnosed with breast cancer, comprising the steps of
(a) determining the expression levels of scatter factor and c-met in a breast cancer tissue obtained from the patient, normalized against a control gene or genes, and compared to the amount found in a reference breast cancer tissue set, and
(b) suggesting prompt aggressive chemotherapeutic treatment if the expression levels of scatter factor and c-met or the combination of both, are above the $90^{th}$ percentile.

A still further aspect of the invention is a method for predicting treatment outcome for a patient diagnosed with breast cancer, comprising determining the expression levels of VEGF, CD31, and KDR in a breast cancer tissue obtained from the patient, normalized against a control gene or genes, and compared to the amount found in a reference breast cancer tissue set, wherein a poor treatment outcome is predicted if the expression level of any of VEGF, CD31, and KDR is in the upper $10^{th}$ percentile.

Yet another aspect of the invention is a method for predicting treatment outcome for a patient diagnosed with breast cancer, comprising determining the expression levels of Ki67/MiB1, PCNA, Pin1, and thymidine kinase in a breast cancer tissue obtained from the patient, normalized against a control gene or genes, and compared to the amount found in a reference breast cancer tissue set, wherein a poor treatment outcome is predicted if the expression level of any of Ki67/MiB1, PCNA, Pin1, and thymidine kinase is in the upper $10^{th}$ percentile.

The invention further concerns a method for predicting treatment outcome for a patient diagnosed with breast cancer, comprising determining the expression level of soluble and full length CD95 in a breast cancer tissue obtained from the patient, normalized against a control gene or genes, and compared to the amount found in a reference breast cancer tissue set, wherein the presence of soluble CD95 correlates with poor patient survival.

The invention also concerns a method for predicting treatment outcome for a patient diagnosed with breast cancer, comprising determining the expression levels of IGF1, IGF1R and IGFBP3 in a breast cancer tissue obtained from the patient, normalized against a control gene or genes, and compared to the amount found in a reference breast cancer tissue set, wherein a poor treatment outcome is predicted if the sum of the expression levels of IGF1, IGF1R and IGFBP3 is in the upper $10^{th}$ percentile.

The invention additionally concerns a method for classifying breast cancer comprising, determining the expression level of two or more genes selected from the group consisting of Bcl12, hepatocyte nuclear factor 3, LIV1, ER, lipoprotein lipase, retinol binding protein 4, integrin α7, cytokeratin 5, cytokeratin 17, GRO oncogen, ErbB2 and Grb7, in a breast cancer tissue, normalized against a control gene or genes, and compared to the amount found in a reference breast cancer tissue set, wherein (i) tumors expressing at least one of Bcl1, hepatocyte nuclear factor 3, LIV1, and ER above the mean expression level in the reference tissue set are classified as having a good prognosis for disease free and overall patient survival following surgical removal; (ii) tumors characterized by elevated expression of at least one of lipoprotein lipase, retinol binding protein 4, integrin α7 compared to the reference tissue set are classified as having intermediate prognosis of disease free and overall patient survival following surgical removal; and (iii) tumors expressing either elevated levels of cytokeratins 5 and 17, and GRO oncogen at levels four-fold or greater above the mean expression level in the reference tissue set, or ErbB2 and Grb7 at levels ten-fold or more above the mean expression level in the reference tissue set are classified as having poor prognosis of disease free and overall patient survival following surgical removal.

Another aspect of the invention is a panel of two or more gene specific primers selected from the group consisting of the forward and reverse primers listed in Table 2.

Yet another aspect of the invention is a method for reverse transcription of a fragmented RNA population in RT-PCR amplification, comprising using a multiplicity of gene specific primers as the reverse primers in the amplification reaction. In a particular embodiment, the method uses between two and about 40,000 gene specific primers in the same amplification reaction. In another embodiment, the gene specific primers are about 18 to 24 bases, such as about 20 bases in length. In another embodiment, the Tm of the primers is about 58–60° C. The primers can, for example, be selected from the group consisting of the forward and reverse primers listed in Table 2.

The invention also concerns a method of reverse transcriptase driven first strand cDNA synthesis, comprising using a gene specific primer of about 18 to 24 bases in length and having a Tm optimum between about 58° C. and about 60° C. In a particular embodiment, the first strand cDNA synthesis is followed by PCR DNA amplification, and the primer serves as the reverse primer that drives the PCR amplification. In another embodiment, the method uses a plurality of gene specific primers in the same first strand cDNA synthesis reaction mixture. The number of the gene specific primers can, for example, be between 2 and about 40,000.

In a different aspect, the invention concerns a method of predicting the likelihood of long-term survival of a breast cancer patient without the recurrence of breast cancer, following surgical removal of the primary tumor, comprising determining the expression level of one or more prognostic RNA transcripts or their product in a breast cancer tissue sample obtained from said patient, normalized against the expression level of all RNA transcripts or their products in said breast cancer tissue sample, or of a reference set of RNA transcripts or their products, wherein the prognostic transcript is the transcript of one or more genes selected from the group consisting of: FOXM1, PRAME, Bcl2, STK15, CEGP1, Ki-67, GSTM1, CA9, PR, BBC3, NME1, SURV, GATA3, TFRC, YB-1, DPYD, GSTM3, RPS6KB1, Src, Chk1, ID1, EstR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, DIABLO, CDH1, HIF1α, IGFBP3, CTSB, and Her2, wherein overexpression of one or more of FOXM1, PRAME, STK15, Ki-67, CA9, NME1, SURV, TFRC, YB-1, RPS6KB1, Src, Chk1, CCNB1, Chk2, CDC25B, CYP3A4, EpCAM, VEGFC, hENT1, BRCA2, EGFR, TK1, VDR, EPHX1, IF1A, Contig51037, CDH1, HIF1α, IGFBP3, CTSB, Her2, and pENT1 indicates a decreased likelihood of long-term survival without breast cancer recurrence, and the overexpression of one or more of Bcl2, CEGP1, GSTM1, PR, BBC3, GATA3, DPYD, GSTM3, ID1, EstR1, p27, XIAP, IGF1R, AK055699, P13KC2A, TGFB3, BAGI1, pS2, WISP1, HNF3A, NFKBp65, and DIABLO indicates an increased likelihood of long-term survival without breast cancer recurrence.

In a particular embodiment of this method, the expression level of at least 2, preferably at least 5, more preferably at least 10, most preferably at least 15 prognostic transcripts or their expression products is determined.

When the breast cancer is invasive breast carcinoma, including both estrogen receptor (ER) overexpressing (ER positive) and ER negative tumors, the analysis includes determination of the expression levels of the transcripts of at least two of the following genes, or their expression products: FOXM1, PRAME, Bcl2, STK15, CEGP1, Ki-67, GSTM1, PR, BBC3, NME1, SURV, GATA3, TFRC, YB-1, DPYD, Src, CA9, Contig51037, RPS6K1 and Her2.

When the breast cancer is ER positive invasive breast carcinoma, the analysis includes dtermination of the expression levels of the transcripts of at least two of the following genes, or their expression products: PRAME, Bcl2, FOXM1, DIABLO, EPHX1, HIF1A, VEGFC, Ki-67, IGF1R, VDR, NME1, GSTM3, Contig51037, CDC25B, CTSB, p27, CDH1, and IGFBP3.

Just as before, it is preferred to determine the expression levels of at least 5, more preferably at least 10, most preferably at least 15 genes, or their respective expression products.

In a particular embodiment, the expression level of one or more prognostic RNA transcripts is determined, where RNA may, for example, be obtained from a fixed, wax-embedded breast cancer tissue specimen of the patient. The isolation of RNA can, for example, be carried out following any of the procedures described above or throughout the application, or by any other method known in the art.

In yet another aspect, the invention concerns an array comprising polynucleotides hybridizing to the following genes: FOXM1, PRAME, Bcl2, STK15, CEGP1, Ki-67, GSTM1, PR, BBC3, NME1, SURV, GATA3, TFRC, YB-1, DPYD, CA9, Contig51037, RPS6K1 and Her2, immobilized on a solid surface.

In a particular embodiment, the array comprosies polynucleotides hybridizing to the following genes: FOXM1, PRAME, Bcl2, STK15, CEGP1, Ki-67, GSTM1, CA9, PR, BBC3, NME1, SURV, GATA3, TFRC, YB-1, DPYD, GSTM3, RPS6KB1, Src, Chk1, ID1, EstR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, CDH1, HIF1α, IGFBP3, CTSB, Her2 and DIABLO.

In a further aspect, the invention concerns a method of predicting the likelihood of long-term survival of a patient diagnosed with invasive breast cancer, without the recurrence of breast cancer, following surgical removal of the primary tumor, comprising the steps of:

(1) determining the expression levels of the RNA transcripts or the expression products of genes of a gene set selected from the group consisting of
(a) Bcl2, cyclinG1, NFKBp65, NME1, EPHX1, TOP2B, DR5, TERC, Src, DIABLO;
(b) Ki67, XIAP, hENT1, TS, CD9, p27, cyclinG1, pS2, NFKBp65, CYP3A4;
(c) GSTM1, XIAP, Ki67, TS, cyclinG1, p27, CYP3A4, pS2, NFKBp65, ErbB3;
(d) PR, NME1, XIAP, upa, cyclinG1, Contig51037, TERC, EPHX1, ALDH1A3, CTSL;
(e) CA9, NME1, TERC, cyclinG1, EPHX1, DPYD, Src, TOP2B, NFKBp65, VEGFC;
(f) TFRC, XIAP, Ki67, TS, cyclinG1, p27, CYP3A4, pS2, ErbB3, NFKBp65;
(g) Bcl2, PRAME, cyclinG1, FOXM1, NFKBp65, TS, XIAP, Ki67, CYP3A4, p27;
(h) FOXM1, cyclinG1, XIAP, Contig51037, PRAME, TS, Ki67, PDGFRa, p27, NFKBp65;
(i) PRAME, FOXM1, cyclinG1, XIAP, Contig51037, TS, Ki6, PDGFRa, p27, NFKBp65;
(j) Ki67, XIAP, PRAME, hENT1, contig51037, TS, CD9, p27, ErbB3, cyclinG1;
(k) STK15, XIAP, PRAME, PLAUR, p27, CTSL, CD18, PREP, p53, RPS6KB1;
(l) GSTM1, XIAP, PRAME, p27, Contig51037, ErbB3, GSTp, EREG, ID1, PLAUR;
(m) PR, PRAME, NME1, XIAP, PLAUR, cyclinG1, Contig51037, TERC, EPHX1, DR5;
(n) CA9, FOXM1, cyclinG1, XIAP, TS, Ki67, NFKBp65, CYP3A4, GSTM3, p27;
(o) TFRC, XIAP, PRAME, p27, Contig51037, ErbB3, DPYD, TERC, NME1, VEGFC; and
(p) CEGP1, PRAME, hENT1, XIAP, Contig51037, ErbB3, DPYD, NFKBp65, ID1, TS in a breast cancer tissue sample obtained from said patient, normalized against the expression levels of all RNA transcripts or their products in said breast cancer tissue sample, or of a reference set of RNA transcripts or their products;

(2) subjecting the data obtained in step (a) to statistical analysis; and (3) determining whether the likelihood of said long-term survival has increased or decreased.

In a still further aspect, the invention concerns a method of predicting the likelihood of long-term survival of a patient diagnosed with estrogen receptor (ER)-positive invasive breast cancer, without the recurrence of breast cancer, following surgical removal of the primary tumor, comprising the steps of:

(1) determining the expression levels of the RNA transcripts or the expression products of genes of a gene set selected from the group consisting of
(a) PRAME, p27, IGFBP2, HIF1A, TIMP2, ILT2, CYP3A4, ID1, EstR1, DIABLO;
(b) Contig51037, EPHX1, Ki67, TIMP2, cyclinG1, DPYD, CYP3A4, TP, AIB1, CYP2C8;
(c) Bcl2, hENT1, FOXM1, Contig51037, cyclinG1, Contig46653, PTEN, CYP3A4, TIMP2, AREG;
(d) HIF1A, PRAME, p27, IGFBP2, TIMP2, ILT2, CYP3A4, ID1, EstR1, DIABLO;
(e) IGF1R, PRAME, EPHX1, Contig51037, cyclinG1, Bcl2, NME1, PTEN, TBP, TIMP2;
(f) FOXM1, Contig51037, VEGFC, TBP, HIF1A, DPYD, RAD51C, DCR3, cyclinG1, BAG1;
(g) EPHX1, Contig51037, Ki67, TIMP2, cyclinG1, DPYD, CYP3A4, TP, AIB1, CYP2C8;
(h) Ki67, VEGFC, VDR, GSTM3, p27, upa, ITGA7, rhoC, TERC, Pin1;
(i) CDC25B, Contig51037, hENT1, Bcl2, HLAG, TERC, NME1, upa, ID1, CYP;
(j) VEGFC, Ki67, VDR, GSTM3, p27, upa, ITGA7, rhoC, TERC, Pin1;
(k) CTSB, PRAME, p27, IGFBP2, EPHX1, CTSL, BAD, DR5, DCR3, XIAP;
(l) DIABLO, Ki67, hENT1, TIMP2, ID1, p27, KRT19, IGFBP2, TS, PDGFB;
(m) p27, PRAME, IGFBP2, HIF1A, TIMP2, ILT2, CYP3A4, ID1, EstR1, DIABLO;
(n) CDH1; PRAME, VEGFC; HIF1A; DPYD, TIMP2, CYP3A4, EstR1, RBP4, p27;
(o) IGFBP3, PRAME, p27, Bcl2, XIAP, EstR1, Ki67, TS, Src, VEGF;
(p) GSTM3, PRAME, p27, IGFBP3, XIAP, FGF2, hENT1, PTEN, EstR1, APC;

(q) hENT1, Bcl2, FOXM1, Contig51037, CyclinG1, Contig46653, PTEN, CYP3A4, TIMP2, AREG;
(r) STK15, VEGFC, PRAME, p27, GCLC, hENT1, ID1, TIMP2, EstR1, MCP1;
(s) NME1, PRAM, p27, IGFBP3, XIAP, PTEN, hENT1, Bcl2, CYP3A4, HLAG;
(t) VDR, Bcl2, p27, hENT1, p53, PI3KC2A, EIF4E, TFRC, MCM3, ID1;
(u) EIF4E, Contig51037, EPHX1, cyclinG1, Bcl2, DR5, TBP, PTEN, NME1, HER2;
(v) CCNB1, PRAME, VEGFC, HIF1A, hENT1, GCLC, TIMP2, ID1, p27, upa;
(w) ID1, PRAME, DIABLO, hENT1, p27, PDGFRa, NME1, BIN1, BRCA1, TP;
(x) FBXO5, PRAME, IGFBP3, p27, GSTM3, hENT1, XIAP, FGF2, TS, PTEN;
(y) GUS, HIA1A, VEGFC, GSTM3, DPYD, hENT1, EBXO5, CA9, CYP, KRT18; and
(z) Bclx, Bcl2, hENT1, Contig51037, HLAG, CD9, ID1, BRCA1, BIN1, HBEGF;

(2) subjecting the data obtained in step (1) to statistical analysis; and (3) determining whether the likelihood of said long-term survival has increased or decreased.

In a different aspect, the invention concerns an array comprising polynucleotides hybridizing to a gene set selected from the group consisting of:
(a) Bcl2, cyclinG1, NFKBp65, NME1, EPHX1, TOP2B, DR5, TERC, Src, DIABLO;
(b) Ki67, XIAP, hENT1, TS, CD9, p27, cyclinG1, pS2, NFKBp65, CYP3A4;
(c) GSTM1, XIAP, Ki67, TS, cyclinG1, p27, CYP3A4, pS2, NFKBp65, ErbB3;
(d) PR, NME1, XIAP, upa, cyclinG1, Contig51037, TERC, EPHX1, ALDH1A3, CTSL;
(e) CA9, NME1, TERC, cyclinG1, EPHX1, DPYD, Src, TOP2B, NFKBp65, VEGFC;
(f) TFRC, XIAP, Ki67, TS, cyclinG1, p27, CYP3A4, pS2, ErbB3, NFKBp65;
(g) Bcl2, PRAME, cyclinG1, FOXM1, NFKBp65, TS, XIAP, Ki67, CYP3A4, p27;
(h) FOXM1, cyclinG1, XIAP, Contig51037, PRAME, TS, Ki67, PDGFRa, p27, NFKBp65;
(i) PRAME, FOXM1, cyclinG1, XIAP, Contig51037, TS, Ki6, PDGFRa, p27, NFKBp65;
(j) Ki67, XIAP, PRAME, hENT1, contig51037, TS, CD9, p27, ErbB3, cyclinG1;
(k) STK15, XIAP, PRAME, PLAUR, p27, CTSL, CD18, PREP, p53, RPS6KB1;
(l) GSTM1, XIAP, PRAME, p27, Contig51037, ErbB3, GSTp, EREG, ID1, PLAUR;
(m) PR, PRAME, NME1, XIAP, PLAUR, cyclinG1, Contig51037, TERC, EPHX1, DR5;
(n) CA9, FOXM1, cyclinG1, XIAP, TS, Ki67, NFKBp65, CYP3A4, GSTM3, p27;
(o) TFRC, XIAP, PRAME, p27, Contig51037, ErbB3, DPYD, TERC, NME1, VEGFC; and
(p) CEGP1, PRAME, hENT1, XIAP, Contig51037, ErbB3, DPYD, NFKBp65, ID1, TS, immobilized on a solid surface.

In an additional aspect, the invention concerns an array comprising polynucleotides hybridizing to a gene set selected from the group consisting of:
(a) PRAME, p27, IGFBP2, HIF1A, TIMP2, ILT2, CYP3A4, ID1, EstR1, DIABLO;
(b) Contig51037, EPHX1, Ki67, TIMP2, cyclinG1, DPYD, CYP3A4, TP, AIB1, CYP2C8;
(c) Bcl2, hENT1, FOXM1, Contig51037, cyclinG1, Contig46653, PTEN, CYP3A4, TIMP2, AREG;
(d) HIF1A, PRAME, p27, IGFBP2, TIMP2, ILT2, CYP3A4, ID1, EstR1, DIABLO;
(e) IGF1R, PRAME, EPHX1, Contig51037, cyclinG1, Bcl2, NME1, PTEN, TBP, TIMP2;
(f) FOXM1, Contig51037, VEGFC, TBP, HIF1A, DPYD, RAD51C, DCR3, cyclinG1, BAG1;
(g) EPHX1, Contig51037, Ki67, TIMP2, cyclinG1, DPYD, CYP3A4, TP, AIB1, CYP2C8;
(h) Ki67, VEGFC, VDR, GSTM3, p27, upa, ITGA7, rhoC, TERC, Pin1;
(i) CDC25B, Contig51037, hENT1, Bcl2, HLAG, TERC, NME1, upa, ID1, CYP;
(j) VEGFC, Ki67, VDR, GSTM3, p27, upa, ITGA7, rhoC, TERC, Pin1;
(k) CTSB, PRAME, p27, IGFBP2, EPHX1, CTSL, BAD, DR5, DCR3, XIAP;
(l) DIABLO, Ki67, hENT1, TIMP2, ID1, p27, KRT19, IGFBP2, TS, PDGFB;
(m) p27, PRAME, IGFBP2, HIF1A, TIMP2, ILT2, CYP3A4, ID1, EstR1, DIABLO;
(n) CDH1; PRAME, VEGFC; HIF1A; DPYD, TIMP2, CYP3A4, EstR1, RBP4, p27;
(o) IGFBP3, PRAME, p27, Bcl2, XIAP, EstR1, Ki67, TS, Src, VEGF;
(p) GSTM3, PRAME, p27, IGFBP3, XIAP, FGF2, hENT1, PTEN, EstR1, APC;
(q) hENT1, Bcl2, FOXM1, Contig51037, CyclinG1, Contig46653, PTEN, CYP3A4, TIMP2, AREG;
(r) STK15, VEGFC, PRAME, p27, GCLC, hENT1, ID1, TIMP2, EstR1, MCP1;
(s) NME1, PRAM, p27, IGFBP3, XIAP, PTEN, hENT1, Bcl2, CYP3A4, HLAG;
(t) VDR, Bcl2, p27, hENT1, p53, PI3KC2A, EIF4E, TFRC, MCM3, ID1;
(u) EIF4E, Contig51037, EPHX1, cyclinG1, Bcl2, DR5, TBP, PTEN, NME1, HER2;
(v) CCNB1, PRAME, VEGFC, HIF1A, hENT1, GCLC, TIMP2, ID1, p27, upa;
(w) ID1, PRAME, DIABLO, hENT1, p27, PDGFRa, NME1, BIN1, BRCA1, TP;
(x) FBXO5, PRAME, IGFBP3, p27, GSTM3, hENT1, XIAP, FGF2, TS, PTEN;
(y) GUS, H1A1A, VEGFC, GSTM3, DPYD, hENT1, FBXO5, CA9, CYP, KRT18; and
(z) Bclx, Bcl2, hENT1, Contig51037, HLAG, CD9, ID1, BRCA1, BIN1, HBEGF, immobilized on a solid surface.

In all aspects, the polynucleotides can be cDNAs ("cDNA arrays") that are typically about 500 to 5000 bases long, although shorter or longer cDNAs can also be used and are within the scope of this invention. Alternatively, the polynucleotids can be oligonucleotides (DNA microarrays), which are typically about 20 to 80 bases long, although shorter and longer oligonucleotides are also suitable and are within the scope of the invention. The solid surface can, for example, be glass or nylon, or any other solid surface typically used in preparing arrays, such as microarrays, and is typically glass.

Figure 1:
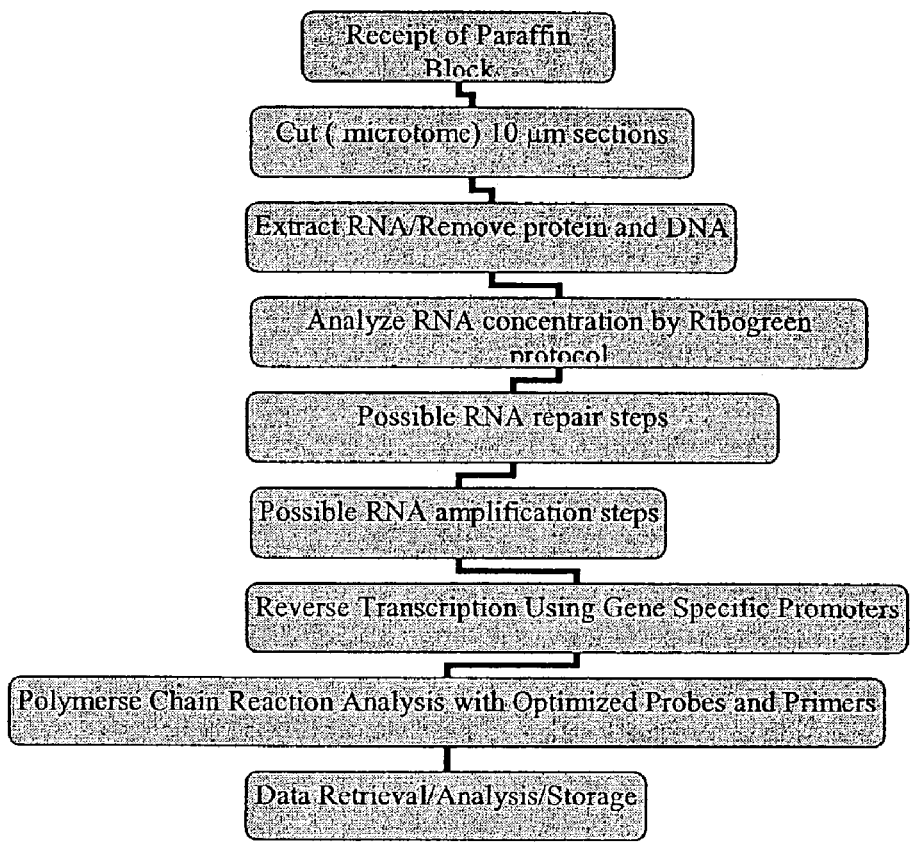
FIG. 1 is a chart illustrating the overall workflow of the process of the invention for measurement of gene expression. In the Figure, FPET stands for "fixed paraffin-embedded tissue," and "RT-PCR" stands for "reverse transcriptase PCR." RNA concentration is determined by using the commercial RiboGreen™ RNA Quantitation Reagent and Protocol.

Table 1 shows a breast cancer gene list.

Table 2 sets forth amplicon and primer sequences used for amplification of fragmented mRNA.

Table 3 shows the Accession Nos. and SEQ ID NOS of the breast cance genes examined.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer. The term "prediction" is used herein to refer to the likelihood that a patient will respond either favorably or unfavorably to a drug or set of drugs, and also the extent of those responses. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy.

The term "increased resistance" to a particular drug or treatment option, when used in accordance with the present invention, means decreased response to a standard dose of the drug or to a standard treatment protocol.

The term "decreased sensitivity" to a particular drug or treatment option, when used in accordance with the present invention, means decreased response to a standard dose of the drug or to a standard treatment protocol, where decreased response can be compensated for (at least partially) by increasing the dose of drug, or the intensity of treatment.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like. In the context of the present invention, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of an eukaryotic cell.

In theory, the term "exon" refers to any segment of an interrupted gene that is represented in the mature RNA product (B. Lewin. *Genes IV* Cell Press, Cambridge Mass. 1990). In theory the term "intron" refers to any segment of DNA that is transcribed but removed from within the transcript by splicing together the exons on either side of it. Operationally, exon sequences occur in the mRNA sequence of a gene as defined by Ref. Seq ID numbers. Operationally, intron sequences are the intervening sequences within the genomic DNA of a gene, bracketed by exon sequences and having GT and AG splice consensus sequences at their 5' and 3' boundaries.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247–283 (1999)); RNAse protection assays (Hod, *Biotechniques* 13:852–854 (1992)); and reverse transcription polymerase chain reaction (RT-PCR) (Weis et al., *Trends in Genetics* 8:263–264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible, quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest*. 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy minicolumns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, Taq-Man® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986–994 (1996).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106–149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10–14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484–487 (1995); and Velculescu et al., *Cell* 88:243–51 (1997).

5. Gene Expression Analysis by Massively Parallel Signature Sequencing (MPSS)

This method, described by Brenner et al., *Nature Biotechnology* 18:630–634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

6. General Description of the mRNA Isolation, Purification and Amplification Methods of the Invention The steps of a representative protocol of the invention, including mRNA isolation, purification, primer extension and amplification are illustrated in FIG. 1. As shown in FIG.

1, this representative process starts with cutting about 10 μm thick sections of paraffin-embedded tumor tissue samples. The RNA is then extracted, and protein and DNA are removed, following the method of the invention described below. After analysis of the RNA concentration, RNA repair and/or amplification steps may be included, if necessary, and RNA is reverse transcribed using gene specific promoters followed by RT-PCR. Finally, the data are analyzed to identify the best treatment option(s) available to the patient on the basis of the characteristic gene expression pattern identified in the tumor sample examined. The individual steps of this protocol will be discussed in greater detail below.

7. Improved Method for Isolation of Nucleic Acid from Archived Tissue Specimens

As discussed above, in the first step of the method of the invention, total RNA is extracted from the source material of interest, including fixed, paraffin-embedded tissue specimens, and purified sufficiently to act as a substrate in an enzyme assay. Despite the availability of commercial products, and the extensive knowledge available concerning the isolation of nucleic acid, such as RNA, from tissues, isolation of nucleic acid (RNA) from fixed, paraffin-embedded tissue specimens (FPET) is not without difficulty.

In one aspect, the present invention concerns an improved method for the isolation of nucleic acid from archived, e.g. FPET tissue specimens. Measured levels of mRNA species are useful for defining the physiological or pathological status of cells and tissues. RT-PCR (which is discussed above) is one of the most sensitive, reproducible and quantitative methods for this "gene expression profiling". Paraffin-embedded, formalin-fixed tissue is the most widely available material for such studies. Several laboratories have demonstrated that it is possible to successfully use fixed-paraffin-embedded tissue (FPET) as a source of RNA for RT-PCR (Stanta et al., *Biotechniques* 11:304–308 (1991); Stanta et al., *Methods Mol. Biol.* 86:23–26 (1998); Jackson et al., *Lancet* 1:1391 (1989); Jackson et al., *J. Clin. Pathol.* 43:499–504 (1999); Finke et al., *Biotechniques* 14:448–453 (1993); Goldsworthy et al., *Mol. Carcinog.* 25:86–91 (1999); Stanta and Bonin, *Biotechniques* 24:271–276 (1998); Godfrey et al., *J. Mol. Diagnostics* 2:84 (2000); Specht et al., *J. Mol. Med.* 78:B27 (2000); Specht et al., *Am. J. Pathol.* 158:419–429 (2001)). This allows gene expression profiling to be carried out on the most commonly available source of human biopsy specimens, and therefore potentially to create new valuable diagnostic and therapeutic information.

The most widely used protocols utilize hazardous organic solvents, such as xylene, or octane (Finke et al., supra) to dewax the tissue in the paraffin blocks before nucleic acid (RNA and/or DNA) extraction. Obligatory organic solvent removal (e.g. with ethanol) and rehydration steps follow, which necessitate multiple manipulations, and addition of substantial total time to the protocol, which can take up to several days. Commercial kits and protocols for RNA extraction from FPET [MasterPure™ Complete DNA and RNA Purification Kit (EPICENTRE®, Madison, Wis.); Paraffin Block RNA Isolation Kit (Ambion, Inc.) and RNeasy™ Mini kit (Qiagen, Chatsworth, Calif.)] use xylene for deparaffinization, in procedures which typically require multiple centrifugations and ethanol buffer changes, and incubations following incubation with xylene.

The present invention provides an improved nucleic acid extraction protocol that produces nucleic acid, in particular RNA, sufficiently intact for gene expression measurements. The key step in the nucleic acid extraction protocol herein is the performance of dewaxing without the use of any organic solvent, thereby eliminating the need for multiple manipulations associated with the removal of the organic solvent, and substantially reducing the total time to the protocol. According to the invention, wax, e.g. paraffin is removed from wax-embedded tissue samples by incubation at 65–75° C. in a lysis buffer that solubilizes the tissue and hydrolyzes the protein, following by cooling to solidify the wax.

Figure 2:
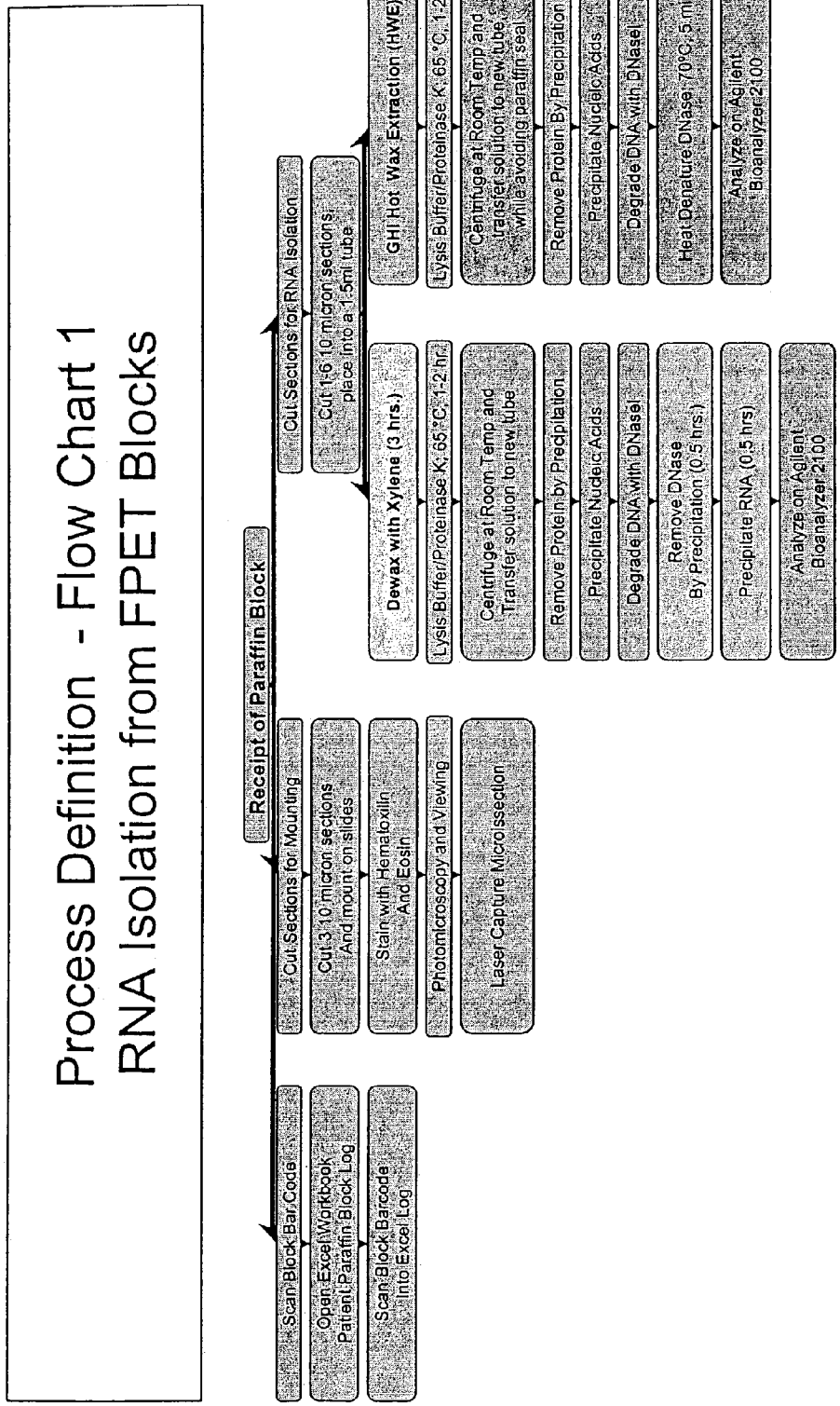
FIG. 2 is a flow chart showing the steps of an RNA extraction method according to the invention alongside a flow chart of a representative commercial method.

FIG. 2 shows a flow chart of an RNA extraction protocol of the present invention in comparison with a representative commercial method, using xylene to remove wax. The times required for individual steps in the processes and for the overall processes are shown in the chart. As shown, the commercial process requires approximately 50% more time than the process of the invention.

The lysis buffer can be any buffer known for cell lysis. It is, however, preferred that oligo-dT-based methods of selectively purifying polyadenylated mRNA not be used to isolate RNA for the present invention, since the bulk of the mRNA molecules are expected to be fragmented and therefore will not have an intact polyadenylated tail, and will not be recovered or available for subsequent analytical assays. Otherwise, any number of standard nucleic; acid purification schemes can be used. These include chaotrope and organic solvent extractions, extraction using glass beads or filters, salting out and precipitation based methods, or any of the purification methods known in the art to recover total RNA or total nucleic acids from a biological source.

Lysis buffers are commercially available, such as, for example, from Qiagen, Epicentre, or Ambion. A preferred group of lysis buffers typically contains urea, and Proteinase K or other protease. Proteinase K is very useful in the isolation of high quality, undamaged DNA or RNA, since most mammalian DNases and RNases are rapidly inactivated by this enzyme, especially in the presence of 0.5–1% sodium dodecyl sulfate (SDS). This is particularly important in the case of RNA, which is more susceptible to degradation than DNA. While DNases require metal ions for activity, and can therefore be easily inactivated by chelating agents, such as EDTA, there is no similar co-factor requirement for RNases.

Cooling and resultant solidification of the wax permits easy separation of the wax from the total nucleic acid, which can be conveniently precipitated, e.g. by isopropanol. Further processing depends on the intended purpose. If the proposed method of RNA analysis is subject to bias by contaminating DNA in an extract, the RNA extract can be further treated, e.g. by DNase, post purification to specifically remove DNA while preserving RNA. For example, if the goal is to isolate high quality RNA for subsequent RT-PCR amplification, nucleic acid precipitation is followed by the removal of DNA, usually by DNase treatment. However, DNA can be removed at various stages of nucleic acid isolation, by DNase or other techniques well known in the art.

While the advantages of the nucleic acid extraction protocol of the invention are most apparent for the isolation of RNA from archived, paraffin embedded tissue samples, the wax removal step of the present invention, which does not involve the use of an organic solvent, can also be included in any conventional protocol for the extraction of total nucleic acid (RNA and DNA) or DNA only. All of these aspects are specifically within the scope of the invention.

By using heat followed by cooling to remove paraffin, the process of the present invention saves valuable processing time, and eliminates a series of manipulations, thereby potentially increasing the yield of nucleic acid. Indeed, experimental evidence presented in the examples below, demonstrates that the method of the present invention does not compromise RNA yield.

8. 5'-Multiplexed Gene Specific Priming of Reverse Transcription

RT-PCR requires reverse transcription of the test RNA population as a first step. The most commonly used primer for reverse transcription is oligo-dT, which works well when RNA is intact. However, this primer will not be effective when RNA is highly fragmented as is the case in FPE tissues.

The present invention includes the use of gene specific primers, which are roughly 20 bases in length with a Tm optimum between about 58° C. and 60° C. These primers will also serve as the reverse primers that drive PCR DNA amplification.

Figure 9:
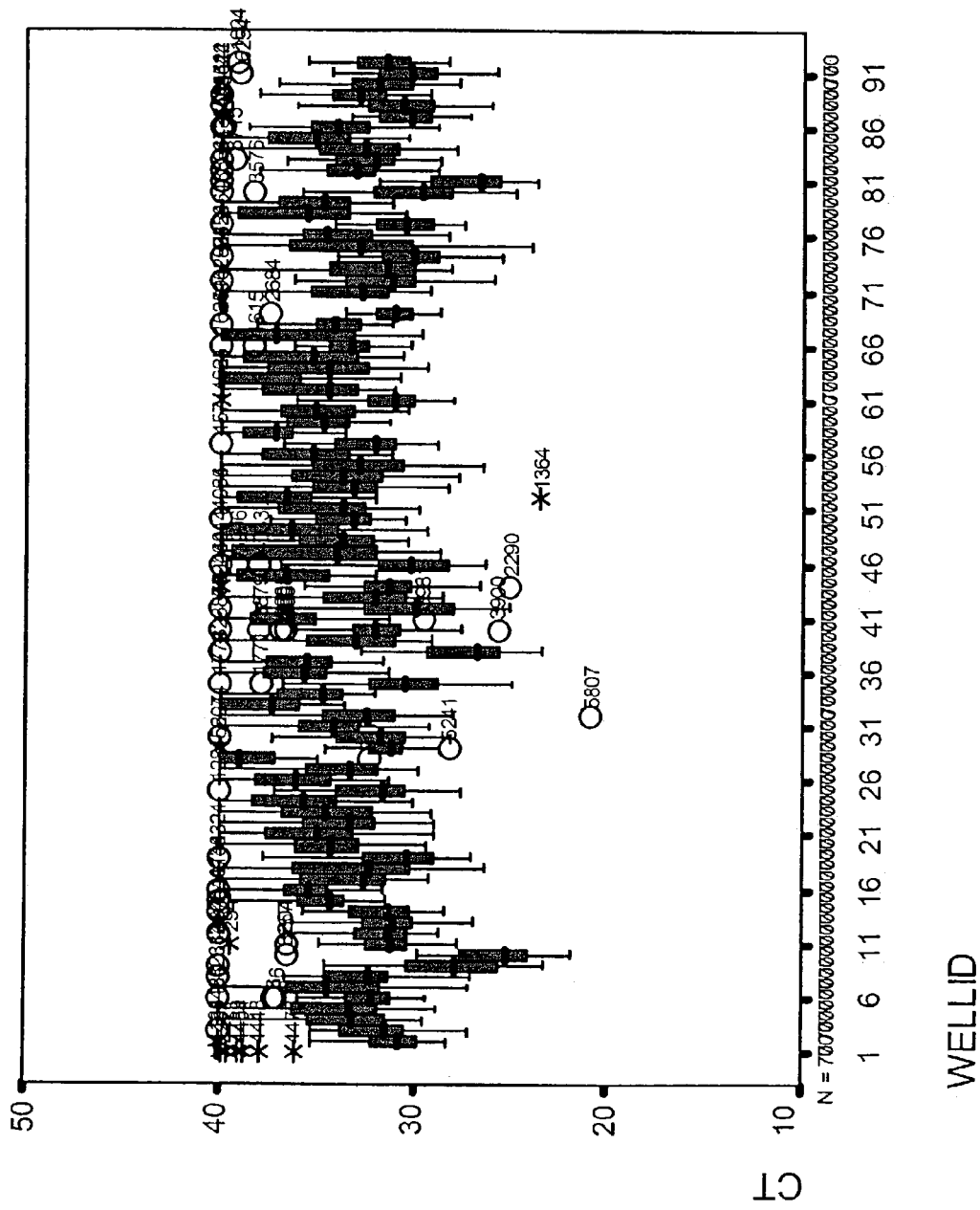
FIG. 9 is a representation of the expression of 92 genes across 70 FPE breast cancer specimens. The y-axis shows expression as cycle threshold times. These genes are a subset of the genes listed in Table 1.

Another aspect of the invention is the inclusion of multiple gene-specific primers in the same reaction mixture. The number of such different primers can vary greatly and can be as low as two and as high as 40,000 or more. Table 2 displays examples of reverse primers that can be successfully used in carrying out the methods of the invention. FIG. 9 shows expression data obtained using this multiplexed gene-specific priming strategy. Specifically, FIG. 9 is a representation of the expression of 92 genes (a subset of genes listed in Table 1) across 70 FPE breast cancer specimens. The y-axis shows expression as cycle threshold times.

An alternative approach is based on the use of random hexamers as primers for cDNA synthesis. However, we have experimentally demonstrated that the method of using a multiplicity of gene-specific primers is superior over the known approach using random hexamers.

9. Preparation of Fragmented mRNA for Expression Profiling Assays

It is of interest to analyze the abundance of specific mRNA species in biological samples, since this expression profile provides an index of the physiological state of that sample. mRNA is notoriously difficult to extract and maintain in its native state, consequently, mRNA recovered from biological sources is often fragmented or somewhat degraded. This is especially true of human tissue specimen which have been chemically fixed and stored for extended periods of time.

In one aspect, the present invention provides a means of preparing the mRNA extracted from various sources, including archived tissue specimens, for expression profiling in a way that its relative abundance is preserved and the mRNA's of interest can be successfully measured. This method is useful as a means of preparing mRNA for analysis by any of the known expression profiling methods, including RT-PCR coupled with 5' exonuclease of reporter probes (TaqMan® type assays), as discussed above, flap endonuclease assays (Cleavase® and Invader® type assays), oligonucleotide hybridization arrays, cDNA hybridization arrays, oligonucleotide ligation assays, 3' single nucleotide extension assays and other assays designed to assess the abundance of specific mRNA sequences in a biological sample.

According to the method of the invention, total RNA is extracted from the source material and sufficiently purified to act as a substrate in an enzyme assay. The extraction procedure, including a new and improved way of removing the wax (e.g. paraffin) used for embedding the tissue samples, has been discussed above. It has also been noted that it is preferred that oligo-dT based methods of selectively purifying polyadenylated mRNA not be used to isolate RNA for this invention since the bulk of the mRNA is expected to be fragmented, will not be polyadenylated and, therefore, will not be recovered and available for subsequent analytical assays if an oligo-dT based method is used.

Figure 3:
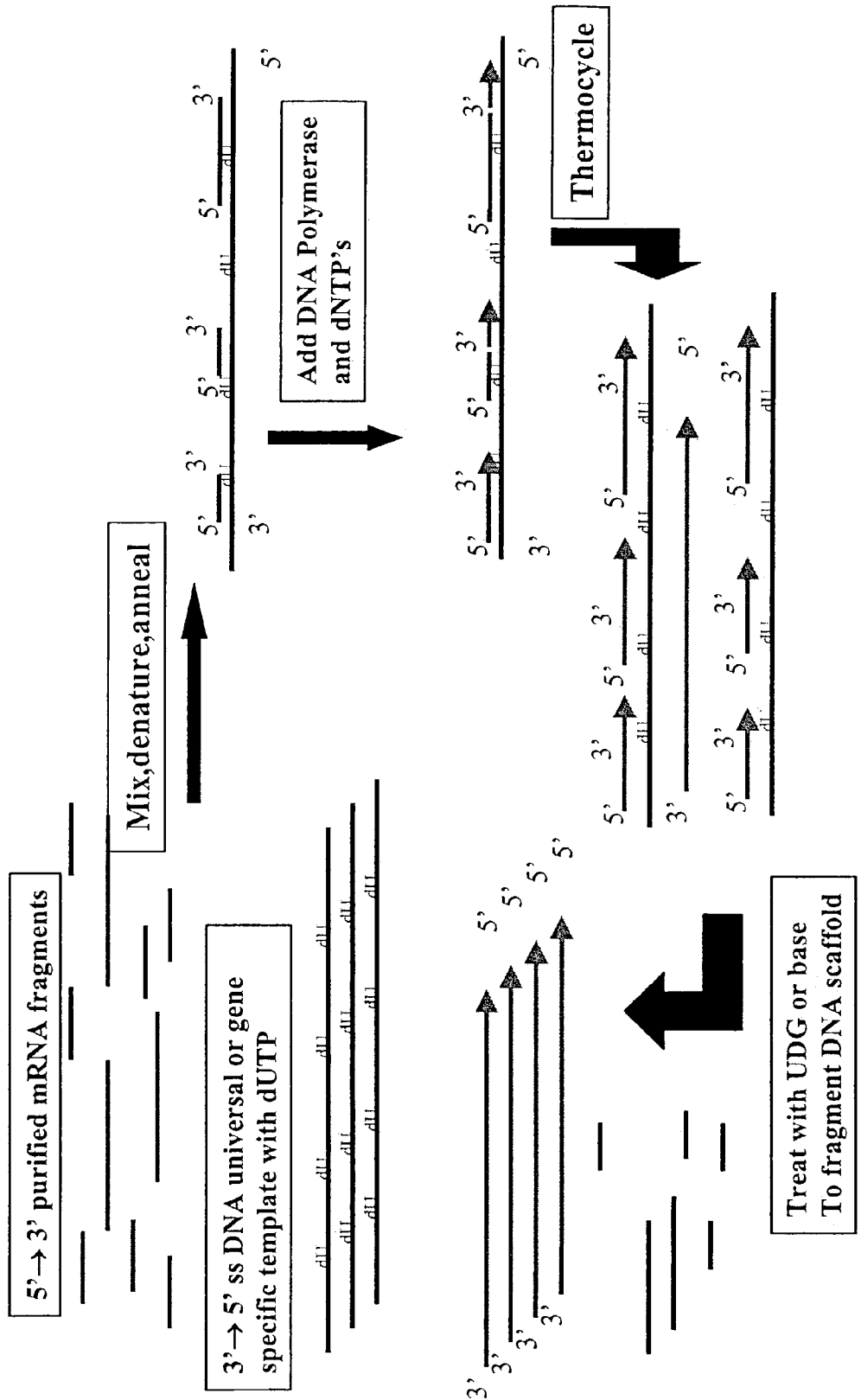
FIG. 3 is a scheme illustrating the steps of an improved method for preparing fragmented mRNA for expression profiling analysis.

A diagram of an improved method for repairing fragmented RNA is shown in FIG. 3. The fragmented RNA purified from the tissue sample is mixed with universal or gene-specific, single-stranded, DNA templates for each mRNA species of interest. These templates may be full length DNA copies of the mRNA derived from cloned gene sources, they may be fragments of the gene representing only the segment of the gene to be assayed, they may be a series of long oligonucleotides representing either the full length gene or the specific segment(s) of interest. The template can represent either a single consensus sequence or be a mixture of polymorphic variants of the gene. This DNA template, or scaffold, will preferably include one or more dUTP or rNTP sites in its length. This will provide a means of removing the template prior to carrying out subsequent analytical steps to avoid its acting as a substrate or target in later analysis assays. This removal is accomplished by treating the sample with uracil-DNA glycosylase (UDG) and heating it to cause strand breaks where UDG has generated abasic sites. In the case of rNTP's, the sample can be heated in the presence of a basic buffer (pH~10) to induce strand breaks where rNTP's are located in the template.

The single stranded DNA template is mixed with the purified RNA, the mixture is denatured and annealed so that the RNA fragments complementary to the DNA template effectively become primers that can be extended along the single stranded DNA templates. DNA polymerase I requires a primer for extension but will efficiently use either a DNA or an RNA primer. Therefore in the presence of DNA polymerase I and dNTP's, the fragmented RNA can be extended along the complementary DNA templates. In order to increase the efficiency of the extension, this reaction can be thermally cycled, allowing overlapping templates and extension products to hybridize and extend until the overall population of fragmented RNA becomes represented as double stranded DNA extended from RNA fragment primers.

Following the generation of this "repaired" RNA, the sample should be treated with UDG or heat-treated in a mildly based solution to fragment the DNA template (scaffold) and prevent it from participating in subsequent analytical reactions.

The product resulting from this enzyme extension can then be used as a template in a standard enzyme profiling assay that includes amplification and detectable signal generation such as fluorescent, chemiluminescent, colorimetric or other common read outs from enzyme based assays. For example, for TaqMan® type assays, this double stranded DNA product is added as the template in a standard assay; and, for array hybridization, this product acts as the cDNA template for the cRNA labeling reaction typically used to generate single-stranded, labeled RNA for array hybridization.

This method of preparing template has the advantage of recovering information from mRNA fragments too short to effectively act as templates in standard cDNA generation schemes. In addition, this method acts to preserve the specific locations in mRNA sequences targeted by specific analysis assays. For example, TaqMan® assays rely on a single contiguous sequence in a cDNA copy of mRNA to act as a PCR amplification template targeted by a labeled reporter probe. If mRNA strand breaks occur in this sequence, the assay will not detect that template and will underestimate the quantity of that mRNA in the original sample. This target preparation method minimizes that effect from RNA fragmentation.

The extension product formed in the RNA primer extension assay can be controlled by controlling the input quantity of the single stranded DNA template and by doing limited cycling of the extension reaction. This is important in preserving the relative abundance of the mRNA sequences targeted for analysis.

This method has the added advantage of not requiring parallel preparation for each target sequence since it is easily multiplexed. It is also possible to use large pools of random sequence long oligonucleotides or full libraries of cloned sequences to extend the entire population of mRNA sequences in the sample extract for whole expressed genome analysis rather than targeted gene specific analysis.

10. Amplification of mRNA Species Prior to RT-PCR

Due to the limited amount and poor quality of mRNA that can be isolated from FPET, a new procedure that could accurately amplify mRNAs of interest would be very useful, particularly for real time quantitation of gene expression (TaqMan®) and especially for quantitatively large number (>50) of genes >50 to 10,000.

Figure 4:
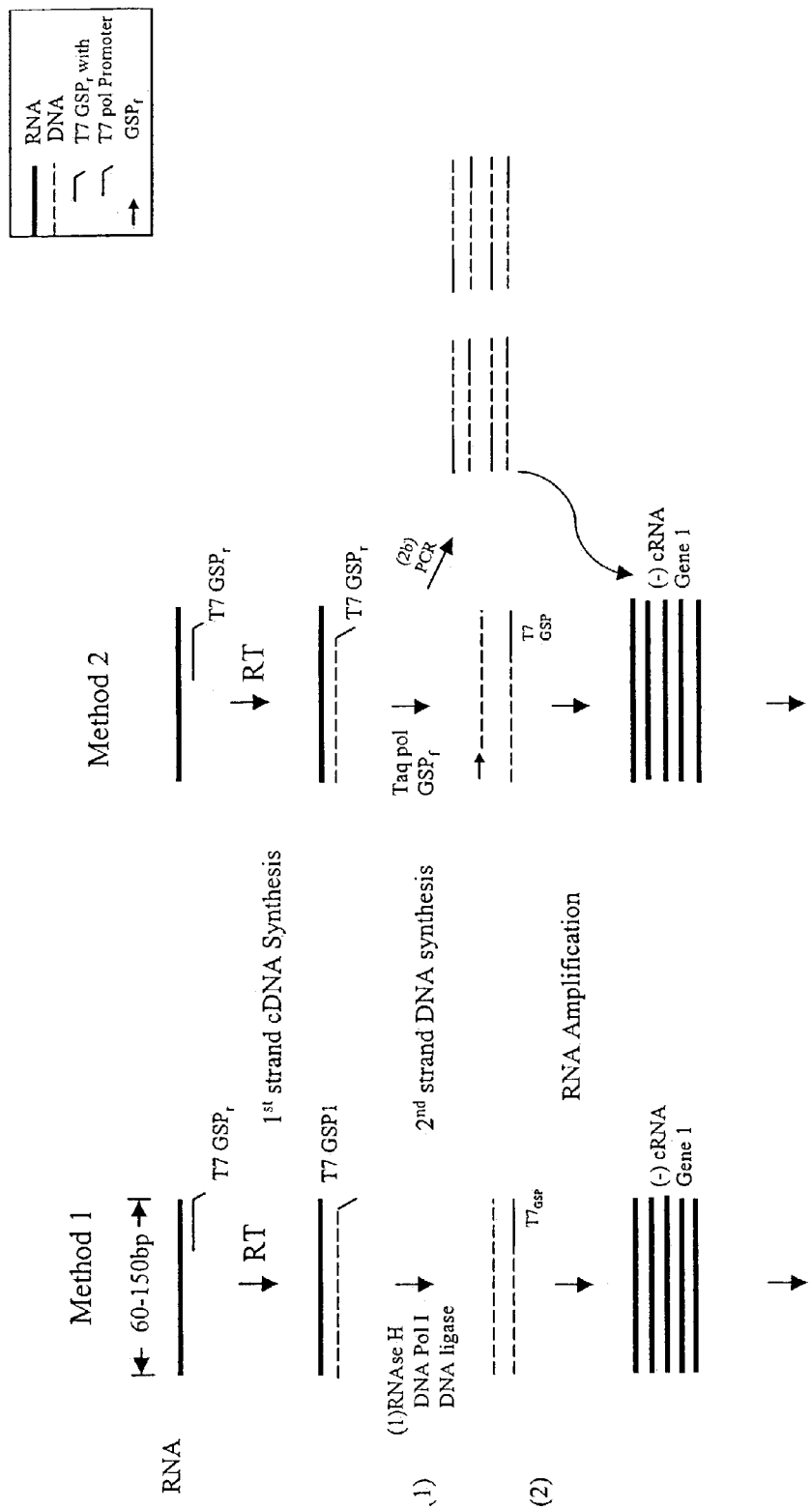
FIG. 4 illustrates methods for amplification of RNA prior to RT-PCR.

Current protocols (e.g. Eberwine, *Biotechniques* 20:584–91 (1996)) are optimized for mRNA amplification from small amount of total or poly $A^+$ RNA mainly for microarray analysis. The present invention provides a protocol optimized for amplification of small amounts of fragmented total RNA (average size about 60–150 bps), utilizing gene-specific sequences as primers, as illustrated in FIG. 4.

The amplification procedure of the invention uses a very large number, typically as many as 100–190,000 gene specific primers (GSP's) in one reverse transcription run. Each GSP contains an RNA polymerase promoter, e.g. a T7 DNA-dependent RNA polymerase promoter, at the 5' end for subsequent RNA amplification. GSP's are preferred as primers because of the small size of the RNA. Current protocols utilize dT primers, which would not adequately represent all reverse transcripts of mRNAs due to the small size of the FPET RNA. GSP's can be designed by optimizing usual parameters, such as length, Tm, etc. For example, GSP's can be designed using the Primer Express® (Applied Biosystems), or Primer 3 (MIT) software program. Typically at least 3 sets per gene are designed, and the ones giving the lowest Ct on FPET RNA (best performers) are selected.

Second strand cDNA synthesis is performed by standard procedures (see FIG. 4, Method 1), or by $GSP_f$ primers and Taq pol under PCR conditions (e.g., 95° C., 10 mm (Taq activation) then 60° C., 45 sec). The advantages of the latter method are that the second gene specific primer, $SGF_f$ adds additional specificity (and potentially more efficient second strand synthesis) and the option of performing several cycles of PCR, if more starting DNA is necessary for RNA amplification by T7 RNA polymerase. RNA amplification is then performed under standard conditions to generate multiple copies of cRNA, which is then used in a standard TaqMan® reaction.

Although this process is illustrated by using T7-based RNA amplification, a person skilled in the art will understand that other RNA polymerase promoters that do not require a primer, such as T3 or Sp6 can also, be used, and are within the scope of the invention.

11. A method of Elongation of Fragmented RNA and Subsequent Amplification

Figure 5:
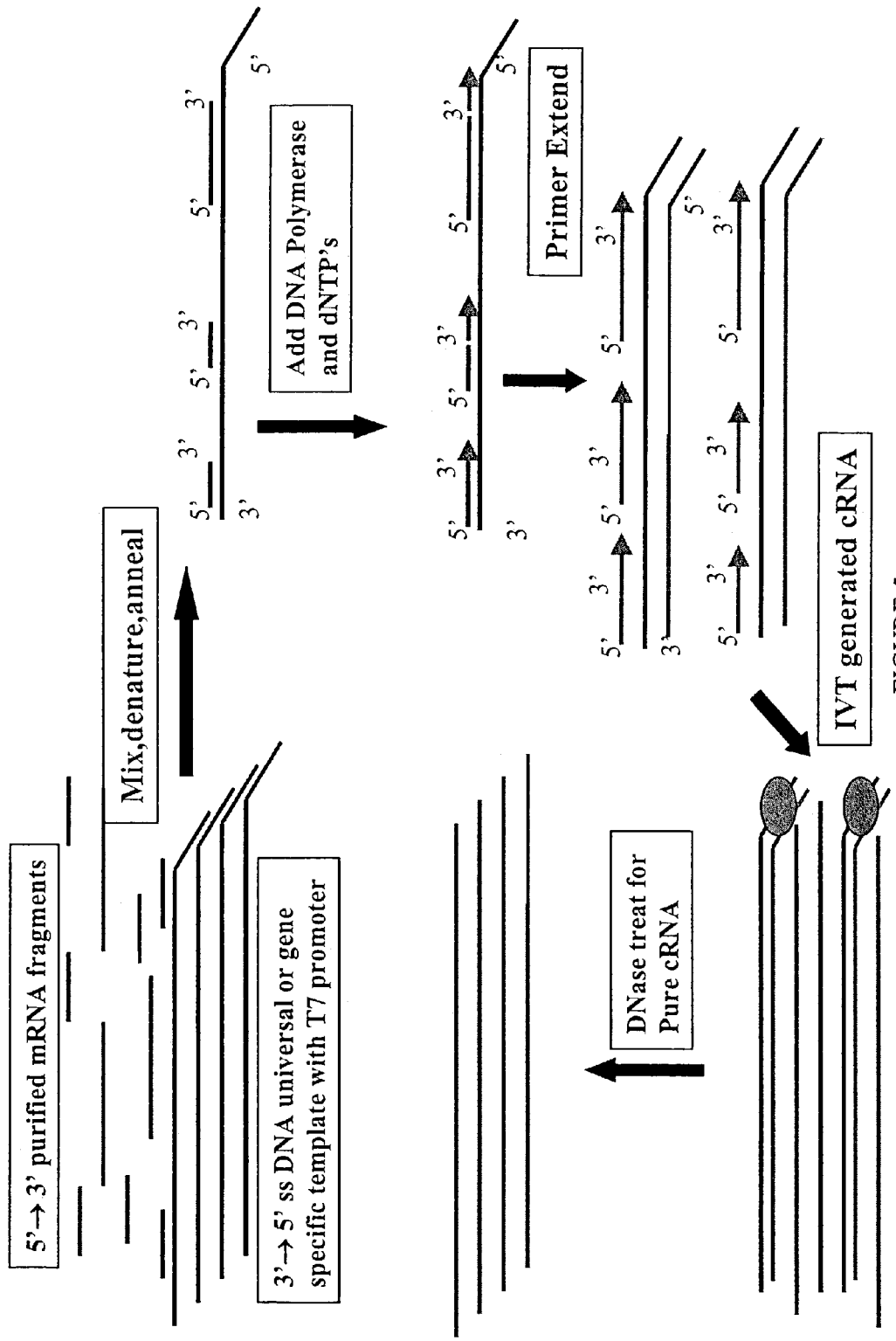
FIG. 5 illustrates an alternative scheme for repair and amplification of fragmented mRNA.

This method, which combines and modifies the inventions described in sections 9 and 10 above, is illustrated in FIG. 5. The procedure begins with elongation of fragmented mRNA. This occurs as described above except that the scaffold DNAs are tagged with the T7 RNA polymerase promoter sequence at their 5' ends, leading to double-stranded DNA extended from RNA fragments. The template sequences need to be removed after in vitro transcription. These templates can include dUTP or rNTP nucleotides, enabling enzymatic removal of the templates as described in section 9, or the templates can be removed by DNaseI treatment.

The template DNA can be a population representing different mRNAs of any number. A high sequence complexity source of DNA templates (scaffolds) can be generated by pooling RNA from a variety of cells or tissues. In one embodiment, these RNAs are converted into double stranded DNA and cloned into phagemids. Single stranded DNA can then be rescued by phagemid growth and single stranded DNA isolation from purified phagemids.

This invention is useful because it increases gene expression profile signals two different ways: both by increasing test mRNA polynucleotide sequence length and by in vitro transcription amplification. An additional advantage is that it eliminates the need to carry out reverse transcription optimization with gene specific primers tagged with the T7 RNA polymerase promoter sequence, and thus, is comparatively fast and economical.

This invention can be used with a variety of different methods to profile gene expression, e.g., RT-PCR or a variety of DNA array methods. Just as in the previous protocol, this approach is illustrated by using a T7 promoter but the invention is not so limited. A person skilled in the art will appreciate, however, that other RNA polymerase promoters, such as T3 or Sp6 can also be used.

12. Breast Cancer Gene Set, Assayed Gene Subsequences, and Clinical Application of Gene Expression Data An important aspect of the present invention is to use the measured expression of certain genes by breast cancer tissue to match patients to best drugs or drug combinations, and to provide prognostic information. For this purpose it is necessary to correct for (normalize away) both differences in the amount of RNA assayed and variability in the quality of the RNA used. Therefore, the assay measures and incorporates the expression of certain normalizing genes, including well known housekeeping genes, such as GAPDH and Cyp1. Alternatively, normalization can be based on the mean or median signal (Ct) of all of the assayed genes or a large subset thereof (global normalization approach). On a gene-by-gene basis, measured normalized amount of a patient tumor mRNA is compared to the amount found in a breast cancer tissue reference set. The number (N) of breast cancer tissues in this reference set should be sufficiently high to ensure that different reference sets (as a whole) behave essentially the same way. If this condition is met, the identity of the individual breast cancer tissues present in a particular set will have no significant impact on the relative amounts of the genes assayed. Usually, the breast cancer tissue reference set consists of at least about 30, preferably at least about 40 different FPE breast cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

The breast cancer gene set is shown in Table 1. The gene Accession Numbers, and the SEQ ID NOs for the forward primer, reverse primer and amplicon sequences that can be used for gene amplification, are listed in Table 2. The basis for inclusion of markers, as well as the clinical significance of mRNA level variations with respect to the reference set, is indicated below. Genes are grouped into subsets based on the type of clinical significance indicated by their expression levels: A. Prediction of patient response to drugs used in breast cancer treatment, or to drugs that are approved for other indications and could be used off-label in the treatment of breast cancer. B. Prognostic for survival or recurrence of cancer.

C. Prediction of Patient Response to Therapeutic Drugs

1. Molecules that Specifically Influence Cellular Sensitivity to Drugs

Table 1 lists 74 genes (shown in italics) that specifically influence cellular sensitivity to potent drugs, which are also listed. Most of the drugs shown are approved and already used to treat breast cancer (e.g., anthracyclines; cyclophosphamide; methotrexate; 5-FU and analogues). Several of the drugs are used to treat breast cancer off-label or are in clinical development phase (e.g., bisphosphonates and anti-VEGF mAb). Several of the drugs have not been widely used to treat breast cancer but are used in other cancers in which the indicated target is expressed (e.g., Celebrex is used to treat familial colon cancer; cisplatin is used to treat ovarian and other cancers.)

Patient response to 5FU is indicated if normalized thymidylate synthase mRNA amount is at or below the $15^{th}$ percentile, or the sum of expression of thymidylate synthase plus dihydropyrimidine phosphorylase is at or below the $25^{th}$ percentile, or the sum of expression of these mRNAs plus thymidine phosphorylase is at or below the $20^{th}$ percentile. Patients with dihydropyrimidine dehydrogenase below $5^{th}$ percentile are at risk of adverse response to 5FU, or analogs such as Xeloda.

When levels of, thymidylate synthase, and dihydropyrimidine dehydrogenase, are within the acceptable range as defined in the preceding paragraph, amplification of c-myc mRNA in the upper 15%, against a background of wild-type p53 [as defined below] predicts a beneficial response to 5FU (see D. Arango et al., Cancer Res. 61:4910–4915 (2001)). In the presence of normal levels of thymidylate synthase and dihydropyrimidine dehydrogenase, levels of NFκB and cIAP2 in the upper 10% indicate resistance of breast tumors to the chemotherapeutic drug 5FU.

Patient resistance to anthracyclines is indicated if the normalized mRNA level of topoisomerase IIα is below the $10^{th}$ percentile, or if the topoisomerase IIβ normalized mRNA level is below the $10^{th}$ percentile or if the combined normalized topoisomerase IIα and β signals are below the $10^{th}$ percentile.

Patient sensitivity to methotrexate is compromised if DHFR levels are more than tenfold higher than the average reference set level for this mRNA species, or if reduced folate carrier levels are below $10^{th}$ percentile.

Patients whose tumors express CYP1B1 in the upper 10%, have reduced likelihood of responding to docetaxol.

The sum of signals for aldehyde dehydrogenase 1A1 and 1A3, when more than tenfold higher than the reference set average, indicates reduced likelihood of response to cyclophosphamide.

Figure 6:
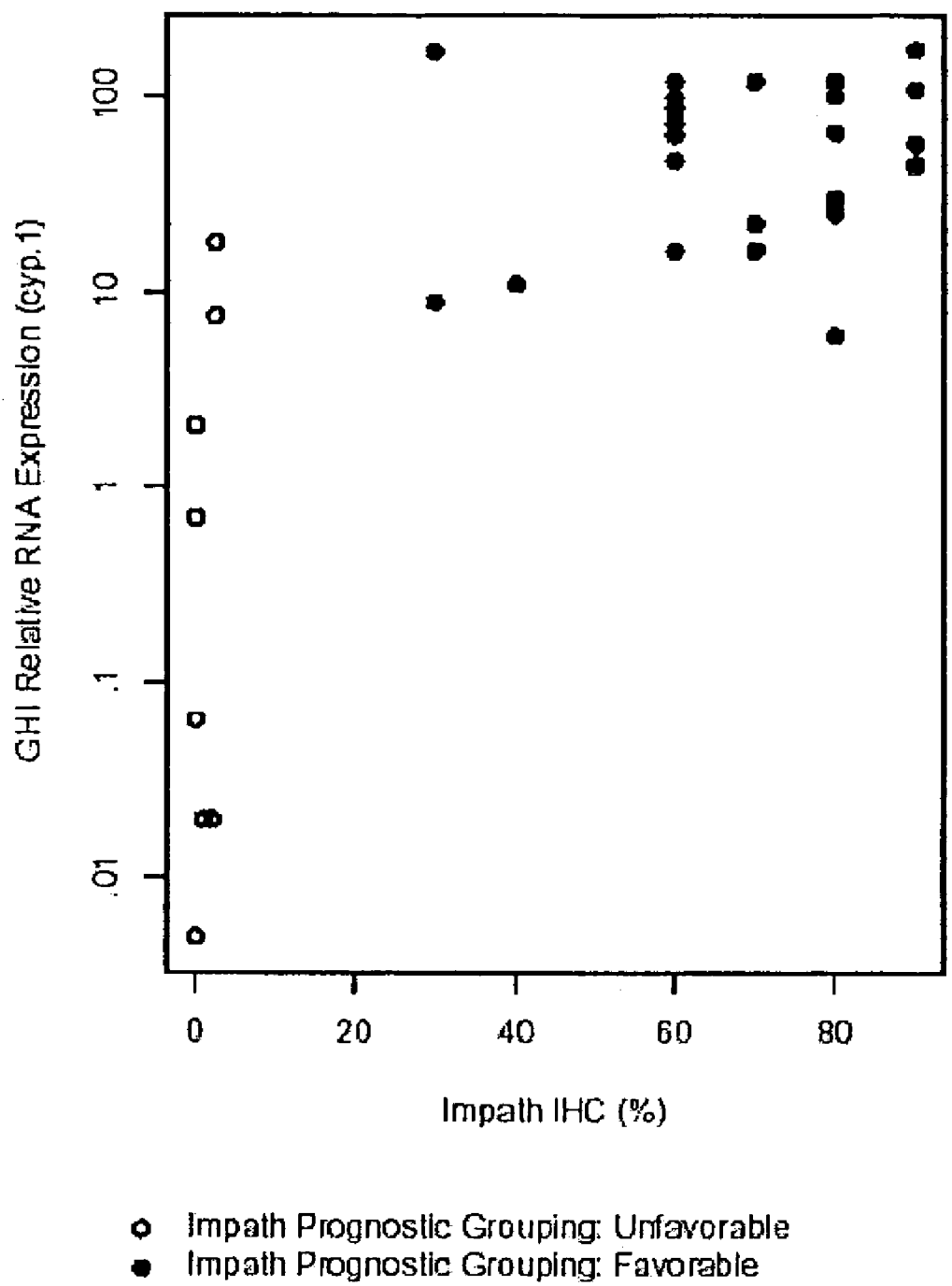
FIG. 6 shows the measurement of estrogen receptor mRNA levels in 40 FPE breast cancer specimens via RT-PCR. Three 10 micron sections were used for each measurement. Each data point represents the average of triplicate measurements.
Figure 7:
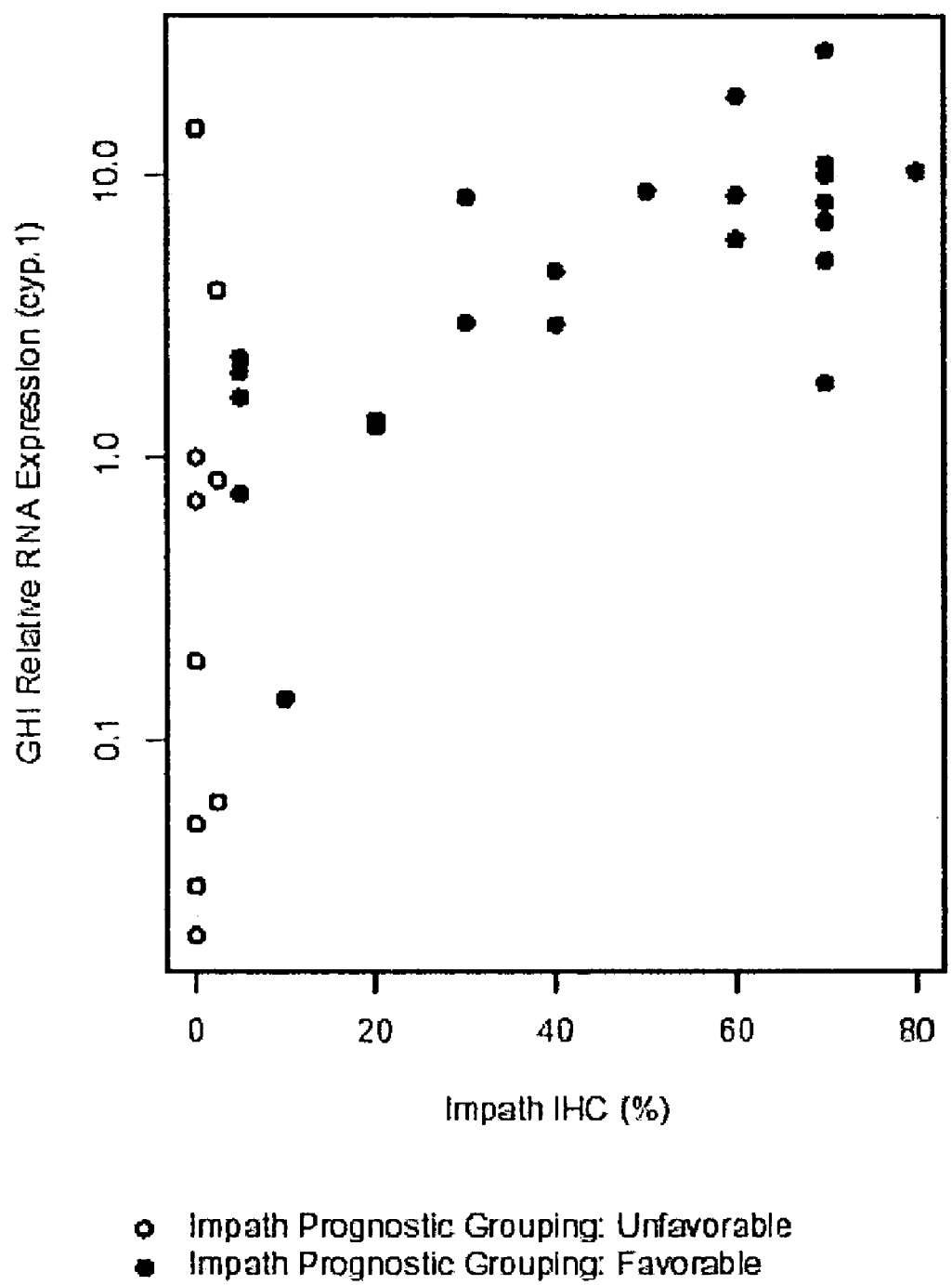
FIG. 7 shows the results of the measurement of progesterone receptor mRNA levels in 40 FPE breast cancer specimens via RT-PCR performed as described in the legend of FIG. 6 above.

Currently, estrogen and progesterone receptor expression as measured by immunohistochemistry is used to select patients for anti-estrogen therapy. We have demonstrated RT-PCR assays for estrogen and progesterone receptor mRNA levels that predict levels of these proteins as determined by a standard clinical diagnostic tests, with high degree of concordance (FIGS. 6 and 7).

Patients whose tumors express ERα or PR mRNA in the upper 70%, are likely to respond to tamoxifen or other anti-estrogens (thus, operationally, lower levels of ERα than this are to defined ERα-negative). However, when the signal for microsomal epoxide hydrolase is in the upper 10% or when mRNAs for pS2/trefoil factor, GATA3 or human chorionic gonadotropin are at or below average levels found in ERα-negative tumors, anti-estrogen therapy will not be beneficial.

Absence of XIST signal compromises the likelihood of response to taxanes, as does elevation of the GST-π or prolyl endopeptidase [PREP] signal in the upper 10%. Elevation of PLAG1 in the upper 10% decreases sensitivity to taxanes.

Expression of ERCC1 mRNA in the upper 10% indicate significant risk of resistance to cisplatin or analogs.

An RT-PCR assay of Her2 mRNA expression predicts Her2 overexpression as measured by a standard diagnostic test, with high degree of concordance (data not shown). Patients whose tumors express Her2 (normalized to cyp.1) in the upper 10% have increased likelihood of beneficial response to treatment with Herceptin or other ErbB2 antagonists. Measurement of expression of Grb7 mRNA serves as a test for HER2 gene amplification, because the Grb7 gene is closely linked to Her2. When Her2 is expression is high as defined above in this paragraph, similarly elevated Grb7 indicates Her2 gene amplification. Overexpression of IGF1R and or IGF1 or IGF2 decreases likelihood of beneficial response to Herceptin and also to EGFR antagonists.

Patients whose tumors express mutant Ha-Ras, and also express farnesyl pyrophosphate synthetase or geranyl pyrophosphonate synthetase mRNAs at levels above the tenth percentile comprise a group that is especially likely to exhibit a beneficial response to bis-phosphonate drugs.

Cox2 is a key control enzyme in the synthesis of prostaglandins. It is frequently expressed at elevated levels in subsets of various types of carcinomas including carcinoma of the breast. Expression of this gene is controlled at the transcriptional level, so RT-PCR serves a valid indicator of the cellular enzyme activity. Nonclinical research has shown that cox2 promotes tumor angiogenesis, suggesting that this enzyme is a promising drug target in solid tumors. Several Cox2 antagonists are marketed products for use in anti-inflammatory conditions. Treatment of familial adenomatous polyposis patients with the cox2 inhibitor Celebrex significantly decreased the number and size of neoplastic polyps. No cox2 inhibitor has yet been approved for treatment of breast cancer, but generally this class of drugs is safe and could be prescribed off-label in breast cancers in which cox2 is over-expressed. Tumors expressing COX2 at levels in the upper ten percentile have increased chance of beneficial response to Celebrex or other cyclooxygenase 2 inhibitors.

The tyrosine kinases ErbB1 [EGFR], ErbB3 [Her3] and ErbB4 [Her4]; also the ligands TGFalpha, amphiregulin, heparin-binding EGF-like growth factor, and epiregulin; also BRK, a non-receptor kinase. Several drugs in clinical development block the EGF receptor. ErbB2–4, the indicated ligands, and BRK also increase the activity of the EGFR pathway. Breast cancer patients whose tumors express high levels of EGFR or EGFR and abnormally high levels of the other indicated activators of the EGFR pathway are potential candidates for treatment with an EGFR antagonist.

Patients whose tumors express less than 10% of the average level of EGFR mRNA observed in the reference panel are relatively less likely to respond to EGFR antagonists [such as Iressa, or ImClone 225]. In cases in which the EGFR is above this low range, the additional presence of epiregulin, TGFα, amphiregulin, or ErbB3, or BRK, CD9, MMP9, or Lot1 at levels above the 90$^{th}$ percentile predisposes to response to EGFR antagonists. Epiregulin gene expression, in particular, is a good surrogate marker for EGFR activation, and can be used to not only to predict response to EGFR antagonists, but also to monitor response to EGFR antagonists [taking fine needle biopsies to provide tumor tissue during treatment]. Levels of CD82 above the 90$^{th}$ percentile suggest poorer efficacy from EGFR antagonists.

The tyrosine kinases abl, c-kit, PDGFRalpha, PDGFbeta, and ARG; also, the signal transmitting ligands c-kit ligand, PDGFA, B, C and D. The listed tyrosine kinases are all targets of the drug Gleevec™ (imatinib mesylate, Novartis), and the listed ligands stimulate one or more of the listed tyrosine kinases. In the two indications for which Gleevec™ is approved, tyrosine kinase targets (bcr-abl and ckit) are overexpressed and also contain activating mutations. A finding that one of the Gleevec™ target tyrosine kinase targets is expressed in breast cancer tissue will prompt a second stage of analysis wherein the gene will be sequenced to determine whether it is mutated. That a mutation found is an activating mutation can be proved by methods known in the art, such as, for example, by measuring kinase enzyme activity or by measuring phosphorylation status of the particular kinase, relative to the corresponding wild-type kinase. Breast cancer patients whose tumors express high levels of mRNAs encoding Gleevec™ target tyrosine kinases, specifically, in the upper ten percentile, or mRNAs for Gleevec™ target tyrosine kinases in the average range and mRNAs for their cognate growth stimulating ligands in the upper ten percentile, are particularly good candidates for treatment with Gleevec™.

VEGF is a potent and pathologically important angiogenic factor. (See below under Prognostic Indicators.) When VEGF mRNA levels are in the upper ten percentile, aggressive treatment is warranted. Such levels particularly suggest the value of treatment with anti-angiogenic drugs, including VEGF antagonists, such as anti-VEGF antibodies. Additionally, KDR or CD31 mRNA level in the upper 20 percentile further increases likelihood of benefit from VEGF antagonists.

Farnesyl pyrophosphatase synthetase and geranyl geranyl pyrophosphatase synthetase. These enzymes are targets of commercialized bisphosphonate drugs, which were developed originally for treatment of osteoporosis but recently have begun to prescribe them off-label in breast cancer. Elevated levels of mRNAs encoding these enzymes in breast cancer tissue, above the 90$^{th}$ percentile, suggest use of bisphosphonates as a treatment option.

2. Multidrug Resistance Factors

These factors include 10 Genes: gamma glutamyl cysteine synthetase [GCS]; GST-α; GST-π; MDR-1; MRP1-4; breast cancer resistance protein [BCRP]; lung resistance protein [MVP]; SXR; YB-1.

GCS and both GST-α and GST-π regulate glutathione levels, which decrease cellular sensitivity to chemotherapeutic drugs and other toxins by reductive derivatization. Glutathione is a necessary cofactor for multi-drug resistant pumps, MDR-1 and the MRPs. MDR1 and MRPs function to actively transport out of cells several important chemotherapeutic drugs used in breast cancer.

GSTs, MDR-1, and MRP-1 have all been studied extensively to determine possible have prognostic or predictive significance in human cancer. However, a great deal of disagreement exists in the literature with respect to these questions. Recently, new members of the MRP family have been identified: MRP-2, MRP-3, MRP-4, BCRP, and lung resistance protein [major vault protein]. These have substrate specificities that overlap with those of MDR-1 and MRP-1. The incorporation of all of these relevant ABC family members as well as glutathione synthetic enzymes into the present invention captures the contribution of this family to drug resistance, in a way that single or double analyte assays cannot.

MRP-1, the gene coding for the multidrug resistance protein.

P-glycoprotein, is not regulated primarily at the transcriptional level. However, p-glycoprotein stimulates the transcription of PTP1b. An embodiment of the present invention is the use of the level of the mRNA for the phosphatase PTP1b as a surrogate measure of MRP-1/p-glycoprotein activity.

The gene SXR is also an activator of multidrug resistance, as it stimulates transcription of certain multidrug resistance factors.

The impact of multidrug resistance factors with respect to chemotherapeutic agents used in breast cancer is as follows. Beneficial response to doxorubicin is compromised when the mRNA levels of either MDR1, GSTα, GSTπ, SXR, BCRP YB-1, or LRP/MVP are in the upper four percentile. Beneficial response to methotrexate is inhibited if mRNA levels of any of MRP1, MRP2, MRP3, or MRP4 or gamma-glutamyl cysteine synthetase are in the upper four percentile.

3. Eukaryotic Translation Initiation Factor 4E [EIF4E]

EIF4E mRNA levels provides evidence of protein expression and so expands the capability of RT-PCR to indicate variation in gene expression. Thus, one claim of the present invention is the use of EIF4E as an added indicator of gene expression of certain genes [e.g., cyclinD1, mdm2, VEGF, and others]. For example, in two tissue specimens containing the same amount of normalized VEGF mRNA, it is likely that the tissue containing the higher normalized level of EIF4E exhibits the greater level of VEGF gene expression.

The background is as follows. A key point in the regulation of mRNA translation is selection of mRNAs by the EIF4G complex to bind to the 43S ribosomal subunit. The protein EIF4E [the m7G CAP-binding protein] is often limiting because more mRNAs than EIF4E copies exist in cells. Highly structured 5'UTRs or highly GC-rich ones are inefficiently translated, and these often code for genes that carry out functions relevant to cancer [e.g., cyclinD1, mdm2, and VEGF]. EIF4E is itself regulated at the transcriptional/mRNA level. Thus, expression of EIF4E provides added indication of increased activity of a number of proteins.

It is also noteworthy that overexpression of EIF4E transforms cultured cells, and hence is an oncogene. Overexpression of EIF4E occurs in several different types of carcinomas but is particularly significant in breast cancer. EIF4E is typically expressed at very low levels in normal breast tissue.

D. Prognostic Indicators

1. DNA Repair Enzymes

Loss of BRCA1 or BRCA2 activity via mutation represents the critical oncogenic step in the most common type[s] of familial breast cancer. The levels of mRNAs of these important enzymes are abnormal in subsets of sporadic breast cancer as well. Loss of signals from either [to within the lower ten percentile] heightens risk of short survival.

2. Cell Cycle Regulators

Cell cycle regulators include 14 genes: c-MYC; c-Src; Cyclin D1; Ha-Ras; mdm2; p14ARF; p21WAF1/CIP; p16INK4a/p14; p23; p27; p53; PI3K; PKC-epsilon; PKC-delta.

The gene for p53 [TP53] is mutated in a large fraction of breast cancers. Frequently p53 levels are elevated when loss of function mutation occurs. When the mutation is dominant-negative, it creates survival value for the cancer cell because growth is promoted and apoptosis is inhibited. Thousands of different p53 mutations have been found in human cancer, and the functional consequences of many of them are not clear. A large body of academic literature addresses the prognostic and predictive significance of mutated p53 and the results are highly conflicting. The present invention provides a functional genomic measure of p53 activity, as follows. The activated wild type p53 molecule triggers transcription of the cell cycle inhibitor p21. Thus, the ratio of p53 to p21. should be low when p53 is wild-type and activated. When p53 is detectable and the ratio of p53 to p21 is elevated in tumors relative to normal breast, it signifies nonfunctional or dominant negative p53. The cancer literature provides evidence for this as born out by poor prognosis.

Mdm2 is an important p53 regulator. Activated wildtype p53 stimulates transcription of mdm2. The mdm2 protein binds p53 and promotes its proteolytic destruction. Thus, abnormally low levels of mdm2 in the presence of normal or higher levels of p53 indicate that p53 is mutated and inactivated.

One aspect of the present invention is the use of ratios of mRNAs levels p53:p21 and p53:mdm2 to provide a picture of p53 status. Evidence for dominant negative mutation of p53 (as indicated by high p53:p21 and/or high p53:mdm2 mRNA ratios—specifically in the upper ten percentile) presages higher risk of recurrence in breast cancer and therefore weights toward a decision to use chemotherapy in node negative post surgery breast cancer.

Another important cell cycle regulator is p27, which in the activated form blocks cell cycle progression at the level of cdk4. The protein is regulated primarily via phosphorylation/dephosphorylation, rather than at the transcriptional level. However, levels of p27 mRNAs do vary. Therefore a level of p27 mRNA in the upper ten percentile indicates reduced risk of recurrence of breast cancer post surgery.

Cyclin D1 is a principle positive regulator of entry into S phase of the cell cycle. The gene for cyclin D1 is amplified in about 20% of breast cancer patients, and therefore promotes tumor promotes tumor growth in those cases. One aspect of the present invention is use of cyclin D1 mRNA levels for diagnostic purposes in breast cancer. A level of cyclin D1 mRNA in the upper ten percentile suggests high risk of recurrence in breast cancer following surgery and suggests particular benefit of adjuvant chemotherapy.

3. Other Tumor Suppressors and Related Proteins

These include APC and E-cadherin. It has long been known that the tumor suppressor APC is lost in about 50% of colon cancers, with concomitant transcriptional upregulation of E-cadherin, an important cell adhesion molecule and growth suppressor. Recently, it has been found that the APC gene silenced in 15–40% of breast cancers. Likewise, the E-cadherin gene is silenced [via CpG island methylation] in about 30% of breast cancers. An abnormally low level of APC and/or E-cadherin mRNA in the lower 5 percentile suggests high risk of recurrence in breast cancer following surgery and heightened risk of shortened survival.

4. Regulators of Apoptosis

These include BCl/BAX family members BCl2, Bcl-xl, Bak, Bax and related factors, NFκ-B and related factors, and also p53BP1/ASPP1 and p53BP2/ASPP2.

Bax and Bak are pro-apoptotic and BCl2 and Bcl-xl are anti-apoptotic. Therefore, the ratios of these factors influence the resistance or sensitivity of a cell to toxic (pro-apoptotic) drugs. In breast cancer, unlike other cancers, elevated level of BCl2 (in the upper ten percentile) correlates with good outcome. This reflects the fact that BCl2 has growth inhibitory activity as well as anti-apoptotic activity, and in breast cancer the significance of the former activity outweighs the significance of the latter. The impact of BCl2 is in turn dependent on the status of the growth stimulating transcription factor c-MYC. The gene for c-MYC is amplified in about 20% of breast cancers. When c-MYC message levels are abnormally elevated relative to BCl2 (such that this ratio is in the upper ten percentile), then elevated level of BCl2 mRNA is no longer a positive indicator.

NFκ-B is another important anti-apoptotic factor. Originally, recognized as a pro-inflammatory transcription factor, it is now clear that it prevents programmed cell death in response to several extracellular toxic factors [such as tumor necrosis factor]. The activity of this transcription factor is regulated principally via phosphorylation/dephosphorylation events. However, levels of NFκ-B nevertheless do vary from cell to cell, and elevated levels should correlate with increased resistance to apoptosis. Importantly for present purposes, NFκ-B, exerts its anti-apoptotic activity largely through its stimulation of transcription of mRNAs encoding certain members of the IAP [inhibitor of apoptosis] family of proteins, specifically cIAP1, cIAP2, XIAP, and Survivin. Thus, abnormally elevated levels of mRNAs for these IAPs and for NFκ-B any in the upper 5 percentile] signify activation of the NFκ-B anti-apoptotic pathway. This suggests high risk of recurrence in breast cancer following chemotherapy and therefore poor prognosis. One embodiment of the present invention is the inclusion in the gene set of the above apoptotic regulators, and the above-outlined use of combinations and ratios of the levels of their mRNAs for prognosis in breast cancer.

The proteins p53BP1 and 2 bind to p53 and promote transcriptional activation of pro-apoptotic genes. The levels of p53BP1 and 2 are suppressed in a significant fraction of breast cancers, correlating with poor prognosis. When either is expressed in the lower tenth percentile poor prognosis is indicated.

5. Factors that Control Cell Invasion and Angiogenesis

These include uPA, PAI1, cathepsinsB, G and L, scatter factor [HGF], c-met, KDR, VEGF, and CD31. The plasminogen activator uPA and its serpin regulator PAI1 promote breakdown of extracellular matrices and tumor cell invasion. Abnormally elevated levels of both mRNAs in malignant breast tumors (in the upper twenty percentile) signify an increased risk of shortened survival, increased recurrence in breast cancer patients post surgery, and increased importance of receiving adjuvant chemotherapy. On the other hand, node negative patients whose tumors do not express elevated levels of these mRNA species are less likely to have recurrence of this cancer and could more seriously consider whether the benefits of standard chemotherapy justifies the associated toxicity.

Cathepsins B or L, when expressed in the upper ten percentile, predict poor disease-free and overall survival. In particular, cathepsin L predicts short survival in node positive patients.

Scatter factor and its cognate receptor c-met promote cell motility and invasion, cell growth, and angiogenesis. In breast cancer elevated levels of mRNAs encoding these factors should prompt aggressive treatment with chemotherapeutic drugs, when expression of either, or the combination, is above the $90^{th}$ percentile.

VEGF is a central positive regulator of angiogenesis, and elevated levels in solid tumors predict short survival [note many references showing that elevated level of VEGF predicts short survival]. Inhibitors of VEGF therefore slow the growth of solid tumors in animals and humans. VEGF activity is controlled at the level of transcription. VEGF mRNA levels in the upper ten percentile indicate significantly worse than average prognosis. Other markers of vascularization, CD31 [PECAM], and KDR indicate high vessel density in tumors and that the tumor will be particularly malignant and aggressive, and hence that an aggressive therapeutic strategy is warranted.

6. Markers for Immune and Inflammatory Cells and Processes

These markers include the genes for Immunoglobulin light chain λ, CD18, CD3, CD68, Fas [CD95], and Fas Ligand.

Several lines of evidence suggest that the mechanisms of action of certain drugs used in breast cancer entail activation of the host immune/inflammatory response (For example, Herceptin®). One aspect of the present invention is the inclusion in the gene set of markers for inflammatory and immune cells, and markers that predict tumor resistance to immune surveillance. Immunoglobulin light chain lambda is a marker for immunoglobulin producing cells. CD18 is a marker for all white cells. CD3 is a marker for T-cells. CD68 is a marker for macrophages.

CD95 and Fas ligand are a receptor: ligand pair that mediate one of two major pathways by which cytotoxic T cells and NK cells kill targeted cells. Decreased expression of CD95 and increased expression of Fas Ligand indicates poor prognosis in breast cancer. Both CD95 and Fas Ligand are transmembrane proteins, and need to be membrane anchored to trigger cell death. Certain tumor cells produce a truncated soluble variant of CD95, created as a result of alternative splicing of the CD95 mRNA. This blocks NK cell and cytotoxic T cell Fas Ligand-mediated killing of the tumors cells. Presence of soluble CD95 correlates with poor survival in breast cancer. The gene set includes both soluble and full-length variants of CD95.

7. Cell Proliferation Markers

The gene set includes the cell proliferation markers Ki67/MiB1, PCNA, Pin1, and thymidine kinase. High levels of expression of proliferation markers associate with high histologic grade, and short survival. High levels of thymidine kinase in the upper ten percentile suggest in creased risk of short survival. Pin1 is a prolyl isomerase that stimulates cell growth, in part through the transcriptional activation of the cyclin D1 gene, and levels in the upper ten percentile contribute to a negative prognostic profile.

8. Other Growth Factors and Receptors

This gene set includes IGF1, IGF2, IGFBP3, IGF1R, FGF2, FGFR1, CSF-1R/fms, CSF-1, IL6 and IL8. All of these proteins are expressed in breast cancer. Most stimulate tumor growth. However, expression of the growth factor FGF2 correlates with good outcome. Some have anti-apoptotic activity, prominently IGF1. Activation of the IGF1 axis via elevated IGF1, IGF1R, or IGFBP3 (as indicated by the sum of these signals in the upper ten percentile) inhibits tumor cell death and strongly contributes to a poor prognostic profile.

9. Gene Expression Markers that Define Subclasses of Breast Cancer

These include: GRO1 oncogene alpha, Grb7, cytokeratins 5 and 17, retinal binding protein 4, hepatocyte nuclear factor 3, integrin alpha 7, and lipoprotein lipase. These markers subset breast cancer into different cell types that are phenotypically different at the level of gene expression. Tumors expressing signals for Bcl2, hepatocyte nuclear factor 3, LIV1 and ER above the mean have the best prognosis for disease free and overall survival following surgical removal of the cancer. Another category of breast cancer tumor type, characterized by elevated expression of lipoprotein lipase, retinol binding protein 4, and integrin α7, carry intermediate prognosis. Tumors expressing either elevated levels of cytokeratins 5, and 17, GRO oncogene at levels four-fold or greater above the mean, or ErbB2 and Grb7 at levels ten-fold or more above the mean, have worst prognosis.

Although throughout the present description, including the Examples below, various aspects of the invention are explained with reference to gene expression studies, the invention can be performed in a similar manner, and similar results can be reached by applying proteomics techniques that are well known in the art. The proteome is the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry and/or N-terminal sequencing, and (3) analysis of the data using bioinformatics. Proteomics methods are valuable supplements to other methods of gene expression profiling, and can be used, alone or in combination with other methods of the present invention, to detect the products of the gene markers of the present invention.

Further details of the invention will be described in the following non-limiting Examples.

EXAMPLE 1

Isolation of RNA from Formalin-Fixed, Paraffin-Embedded (FPET) Tissue Specimens

A. Protocols

I. EPICENTRE® Xylene Protocol

RNA Isolation (1) Cut 1–6 sections (each 10 μm thick) of paraffin-embedded tissue per sample using a clean microtome blade and place into a 1.5 ml eppendorf tube.

(2) To extract paraffin, add 1 ml of xylene and invert the tubes for 10 minutes by rocking on a nutator.

(3) Pellet the sections by centrifugation for 10 minutes at 14,000×g in an eppendorf microcentrifuge.

(4) Remove the xylene, leaving some in the bottom to avoid dislodging the pellet.

(5) Repeat steps 2–4.

(6) Add 1 ml of 100% ethanol and invert for 3 minutes by rocking on the nutator.

(7) Pellet the debris by centrifugation for 10 minutes at 14,000×g in an eppendorf microcentrifuge.

(8) Remove the ethanol, leaving some at the bottom to avoid the pellet.

(9) Repeat steps 6–8 twice.

(10) Remove all of the remaining ethanol.

(11) For each sample, add 2 µl of 50 µg/µl Proteinase K to 300 µl of Tissue and Cell Lysis Solution.

(12) Add 300 µl of Tissue and Cell Lysis Solution containing the Proteinase K to each sample and mix thoroughly.

(13) Incubate at 65° C. for 90 minutes (vortex mixing every 5 minutes). Visually monitor the remaining tissue fragment. If still visible after 30 minutes, add an additional 2 µl of 50 µg/µl Proteinase K and continue incubating at 65° C. until fragment dissolves.

(14) Place the samples on ice for 3–5 minutes and proceed with protein removal and total nucleic acid precipitation.

Protein Removal and Precipitation of Total Nucleic Acid (1) Add 150 µl of MPC Protein Precipitation Reagent to each lysed sample and vortex vigorously for 10 seconds.

(2) Pellet the debris by centrifugation for 10 minutes at 14,000×g in an eppendorf microcentrifuge.

(3) Transfer the supernatant into clean eppendorf tubes and discard the pellet.

(4) Add 500 µl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6) Remove all of the isopropanol with a pipet, being careful not to dislodge the pellet.

Removal of Contaminating DNA from RNA Preparations (1) Prepare 200 µl of DNase I solution for each sample by adding 5 µl of RNase-Free DNase I (1 U/µl) to 195 µl of 1×DNase Buffer.

(2) Completely resuspend the pelleted RNA in 200 µl of DNase I solution by vortexing.

(3) Incubate the samples at 37° C. for 60 minutes.

(4) Add 200 µl of 2×T and C Lysis Solution to each sample and vortex for 5 seconds.

(5) Add 200 µl of MPC Protein Precipitation Reagent, mix by vortexing for 10 seconds and place on ice for 3–5 minutes.

(6) Pellet the debris by centrifugation for 10 minutes at 14,000×g in an eppendorf microcentrifuge.

(7) Transfer the supernatant containing the RNA to clean eppendorf tubes and discard the pellet. (Be careful to avoid transferring the pellet.)

(8) Add 500 µl of isopropanol to each supernatant and rock samples on the nutator for 3 minutes.

(9) Pellet the RNA by centrifugation at 4° C. for 10 minutes at 14,000×g in an eppendorf microcentrifuge.

(10) Remove the isopropanol, leaving some at the bottom to avoid dislodging the pellet.

(11) Rinse twice with 1 ml of 75% ethanol. Centrifuge briefly if the RNA pellet is dislodged.

(12) Remove ethanol carefully.

(13) Set under fume hood for about 3 minutes to remove residual ethanol.

(14) Resuspend the RNA in 30 µl of TE Buffer and store at −30° C.

II. Hot Wax/Urea Protocol of the Invention

RNA Isolation (1) Cut 3 sections (each 10 µm thick) of paraffin-embedded tissue using a clean microtome blade and place into a 1.5 ml eppendorf tube.

(2) Add 300 µl of lysis buffer (10 mM Tris 7.5, 0.5% sodium lauroyl sarcosine, 0.1 mM EDTA pH 7.5, 4M Urea) containing 330 µg/ml Proteinase K (added freshly from a 50 µg/µl stock solution) and vortex briefly.

(3) Incubate at 65° C. for 90 minutes (vortex mixing every 5 minutes). Visually monitor the tissue fragment. If still visible after 30 minutes, add an additional 2 µl of 50 µg/µl Proteinase K and continue incubating at 65° C. until fragment dissolves.

(4) Centrifuge for 5 minutes at 14,000×g and transfer upper aqueous phase to new tube, being careful not to disrupt the paraffin seal.

(5) Place the samples on ice for 3–5 minutes and proceed with protein removal and total nucleic acid precipitation.

Protein Removal and Precipitation of Total Nucleic Acid (1) Add 150 µl of 7.5M NH$_4$OAc to each lysed sample and vortex vigorously for 10 seconds.

(2) Pellet the debris by centrifugation for 10 minutes at 14,000×g in an eppendorf microcentrifuge.

(3) Transfer the supernatant into clean eppendorf tubes and discard the pellet.

(4) Add 500 µl of isopropanol to the recovered supernatant and thoroughly mix by rocking on the nutator for 3 minutes.

(5) Pellet the RNA/DNA by centrifugation at 4° C. for 10 minutes at 14,000×g in an eppendorf microcentrifuge.

(6) Remove all of the isopropanol with a pipet, being careful not to dislodge the pellet.

Removal of Contaminating DNA from RNA Preparations (1) Add 45 µl of 1×DNase I buffer (10 mM Tris-Cl, pH 7,5, 2.5 mM MgCl$_2$, 0.1 mM CaCl$_2$) and 5 µl of RNase-Free DNase I (2 U/µl, Ambion) to each sample.

(2) Incubate the samples at 37° C. for 60 minutes. Inactivate the DNaseI by heating at 70° C. for 5 minutes.

B. Results

Experimental evidence demonstrates that the hot RNA extraction protocol of the invention does not compromise RNA yield. Using 19 FPE breast cancer specimens, extracting RNA from three adjacent sections in the same specimens, RNA yields were measured via capillary electrophoresis with fluorescence detection (Agilent Bioanalyzer). Average RNA yields in nanograms and standard deviations with the invented and commercial methods, respectively, were: 139+/−21 versus 141+/−34.

Also, it was found that the urea-containing lysis buffer of the present invention can be substituted for the EPICENTRE® T&C lysis buffer, and the 7.5 M NH$_4$OAc reagent used for protein precipitation in accordance with the present invention can be substituted for the EPICENTRE® MPC protein precipitation solution with neither significant compromise of RNA yield nor TaqMan® efficiency.

EXAMPLE 2

Amplification of mRNA Species Prior to RT-PCR

The method described in section 10 above was used with RNA isolated from fixed, paraffin-embedded breast cancer tissue. TaqMan® analyses were performed with first strand cDNA generated with the T7-GSP primer (unamplified (T7-GSPr)), T7 amplified RNA (amplified (T7-GSPr)).

RNA was amplified according to step 2 of FIG. 4. As a control, TaqMan® was also performed with cDNA generated with an unmodified GSPr (amplified (GSPr)). An equivalent amount of initial template (1 ng/well) was used in each TaqMan® reaction.

Figure 8:
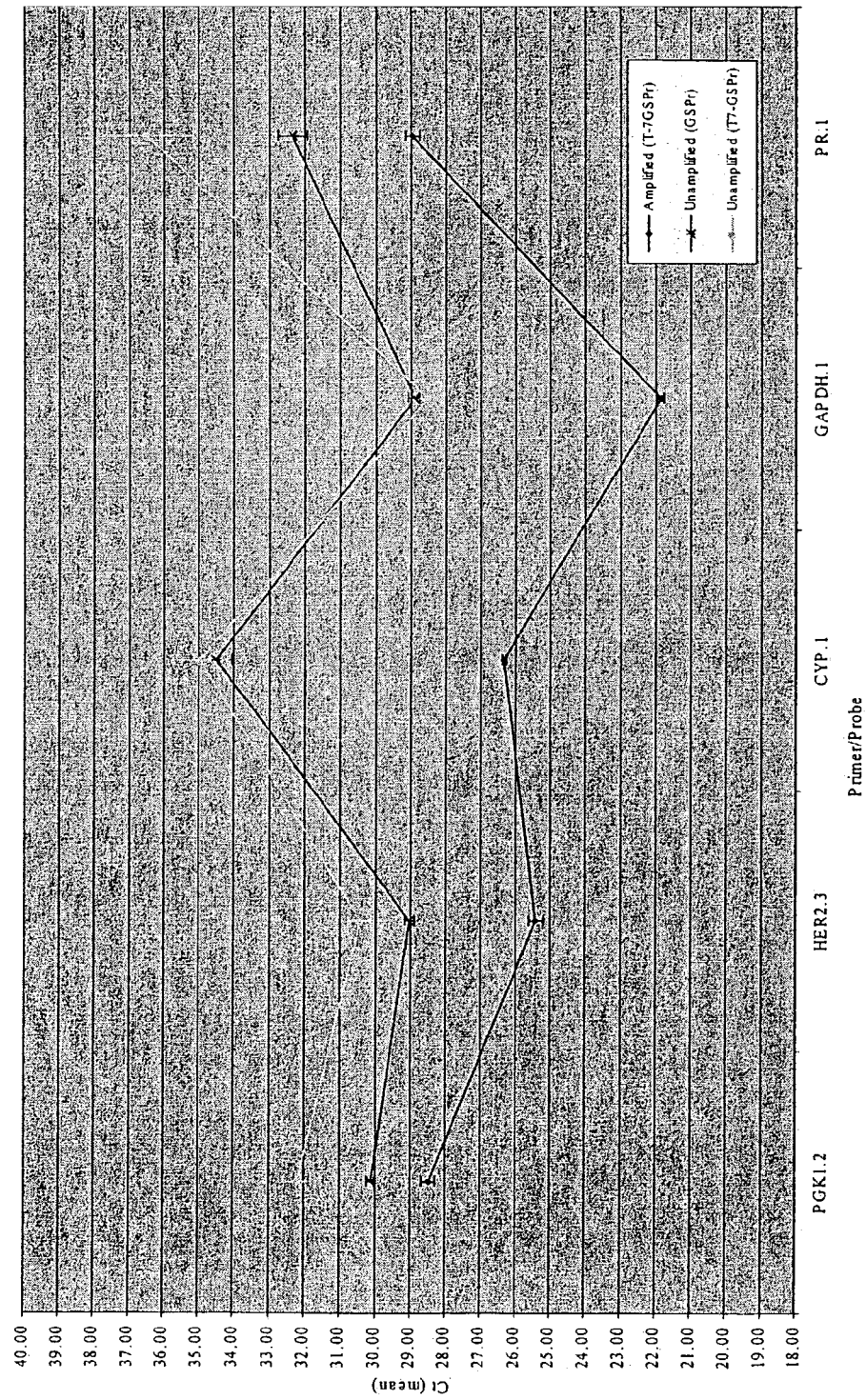
FIG. 8 shows results from an IVT/RT-PCR experiment.

The results are shown in FIG. 8. In vitro transcription increased RT-PCR signal intensity by more than 10 fold, and for certain genes by more than 100 fold relative to controls in which the RT-PCR primers were the same primers used in method 2 for the generation of double-stranded DNA for in vitro transcription (GSP-T7$_r$ and GSP$_f$). Also shown in FIG. 8 are RT-PCR data generated when standard optimized RT-PCR primers (i.e., lacking T7 tails) were used. As shown, compared to this control, the new method yielded substantial increases in RT-PCR signal (from 4 to 64 fold in this experiment).

The new method requires that each T7-GSP sequence be optimized so that the increase in the RT-PCR signal is the same for each gene, relative to the standard optimized RT-PCR (with non-T7 tailed primers).

EXAMPLE 3

A Study of Gene Expression in Premalignant and Malignant Breast Tumors

A gene expression study was designed and conducted with the primary goal to molecularly characterize gene expression in paraffin-embedded, fixed tissue samples of invasive breast ductal carcinoma, and to explore the correlation between such molecular profiles and disease-free survival. A further objective of the study was to compare the molecular profiles in tissue samples of invasive breast cancer with the molecular profiles obtained in ductal carcinoma in situ. The study was further designed to obtain data on the molecular profiles in lobular carcinoma in situ and in paraffin-embedded, fixed tissue samples of invasive lobular carcinoma.

Molecular assays were performed on paraffin-embedded, formalin-fixed primary breast tumor tissues obtained from 202 individual patients diagnosed with breast cancer. All patients underwent surgery with diagnosis of invasive ductal carcinoma of the breast, pure ductal carcinoma in situ (DCIS), lobular carcinoma of the breast, or pure lobular carcinoma in situ (LCIS). Patients were included in the study only if histopathologic assessment, performed as described in the Materials and Methods section, indicated adequate amounts of tumor tissue and homogeneous pathology.

The individuals participating in the study were divided into the following groups:

Group 1: Pure ductal carcinoma in situ (DCIS); n=18
Group 2: Invasive ductal carcinoma n=130
Group 3: Pure lobular carcinoma in situ (LCIS); n=7
Group 4: Invasive lobular carcinoma n=16

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, all tumor blocks were subjected to the same characterization, as described above, and the block most representative of the pathology was used for analysis.

Gene Expression Analysis mRNA was extracted and purified from fixed, paraffin-embedded tissue samples, and prepared for gene expression analysis as described in chapters 7–11 above. Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the median of all genes for that particular patient. Clinical outcome data were available for all patients from a review of registry data and selected patient charts.

Outcomes were classified as:
0 died due to breast cancer or to unknown cause or alive with breast cancer recurrence;
1 alive without breast cancer recurrence or died due to a cause other than breast cancer
Analysis was Performed By:
1. Analysis of the relationship between normalized gene expression and the binary outcomes of 0 or 1.
2. Analysis of the relationship between normalized gene expression and the time to outcome (0 or 1 as defined above) where patients who were alive without breast cancer recurrence or who died due to a cause other than breast cancer were censored. This approach was used to evaluate the prognostic impact of individual genes and also sets of multiple genes.

Analysis of 147 Patients with Invasive Breast Carcinoma by Binary Approach

In the first (binary) approach, analysis was performed on all 146 patients with invasive breast carcinoma. A t test was performed on the group of patients classified as 0 or 1 and the p-values for the differences between the groups for each gene were calculated.

The following Table 4 lists the 45 genes for which the p-value for the differences between the groups was <0.05.

TABLE 4

| Gene/SEQ ID NO: | Mean CT Alive | Mean CT Deceased | t-value | Degrees of freedom | p |
|---|---|---|---|---|---|
| FOXM1 | 33.66 | 32.52 | 3.92 | 144 | 0.0001 |
| PRAME | 35.45 | 33.84 | 3.71 | 144 | 0.0003 |
| Bcl2 | 28.52 | 29.32 | −3.53 | 144 | 0.0006 |
| STK15 | 30.82 | 30.10 | 3.49 | 144 | 0.0006 |
| CEGP1 | 29.12 | 30.86 | −3.39 | 144 | 0.0009 |
| Ki-67 | 30.57 | 29.62 | 3.34 | 144 | 0.0011 |
| GSTM1 | 30.62 | 31.63 | −3.27 | 144 | 0.0014 |
| CA9 | 34.96 | 33.54 | 3.18 | 144 | 0.0018 |
| PR | 29.56 | 31.22 | −3.16 | 144 | 0.0019 |
| BBC3 | 31.54 | 32.10 | −3.10 | 144 | 0.0023 |
| NME1 | 27.31 | 26.68 | 3.04 | 144 | 0.0028 |

TABLE 4-continued

| Gene/SEQ ID NO: | Mean CT Alive | Mean CT Deceased | t-value | Degrees of freedom | p |
|---|---|---|---|---|---|
| SURV | 31.64 | 30.68 | 2.92 | 144 | 0.0041 |
| GATA3 | 26.06 | 26.99 | -2.91 | 144 | 0.0042 |
| TFRC | 28.96 | 28.48 | 2.87 | 144 | 0.0047 |
| YB-1 | 26.72 | 26.41 | 2.79 | 144 | 0.0060 |
| DPYD | 28.51 | 28.84 | -2.67 | 144 | 0.0084 |
| GSTM3 | 28.21 | 29.03 | -2.63 | 144 | 0.0095 |
| RPS6KB1 | 31.18 | 30.61 | 2.61 | 144 | 0.0099 |
| Src | 27.97 | 27.69 | 2.59 | 144 | 0.0105 |
| Chk1 | 32.63 | 31.99 | 2.57 | 144 | 0.0113 |
| ID1 | 28.73 | 29.13 | -2.48 | 144 | 0.0141 |
| EstR1 | 24.22 | 25.40 | -2.44 | 144 | 0.0160 |
| p27 | 27.15 | 27.51 | -2.41 | 144 | 0.0174 |
| CCNB1 | 31.63 | 30.87 | 2.40 | 144 | 0.0176 |
| XIAP | 30.27 | 30.51 | -2.40 | 144 | 0.0178 |
| Chk2 | 31.48 | 31.11 | 2.39 | 144 | 0.0179 |
| CDC25B | 29.75 | 29.39 | 2.37 | 144 | 0.0193 |
| IGF1R | 28.85 | 29.44 | -2.34 | 144 | 0.0209 |
| AK055699 | 33.23 | 34.11 | -2.28 | 144 | 0.0242 |
| PI3KC2A | 31.07 | 31.42 | -2.25 | 144 | 0.0257 |
| TGFB3 | 28.42 | 28.85 | -2.25 | 144 | 0.0258 |
| BAGl1 | 28.40 | 28.75 | -2.24 | 144 | 0.0269 |
| CYP3A4 | 35.70 | 35.32 | 2.17 | 144 | 0.0317 |
| EpCAM | 28.73 | 28.34 | 2.16 | 144 | 0.0321 |
| VEGFC | 32.28 | 31.82 | 2.16 | 144 | 0.0326 |
| pS2 | 28.96 | 30.60 | -2.14 | 144 | 0.0341 |
| hENT1 | 27.19 | 26.91 | 2.12 | 144 | 0.0357 |
| WISP1 | 31.20 | 31.64 | -2.10 | 144 | 0.0377 |
| HNF3A | 27.89 | 28.64 | -2.09 | 144 | 0.0384 |
| NFKBp65 | 33.22 | 33.80 | -2.08 | 144 | 0.0396 |
| BRCA2 | 33.06 | 32.62 | 2.08 | 144 | 0.0397 |
| EGFR | 30.68 | 30.13 | 2.06 | 144 | 0.0414 |
| TK1 | 32.27 | 31.72 | 2.02 | 144 | 0.0453 |
| VDR | 30.08 | 29.73 | 1.99 | 144 | 0.0488 |

In the foregoing Table 4, lower (negative) t-values indicate higher expression (or lower CTs), associated with better outcomes, and, inversely, higher (positive) t-values indicate higher expression (lower CTs) associated with worse outcomes. Thus, for example, elevated expression of the FOXM1 gene (t-value=3.92, CT mean alive>CT mean deceased) indicates a reduced likelihood of disease free survival. Similarly, elevated expression of the CEGP1 gene (t-value=-3.39; CT mean alive<CT mean deceased) indicates an increased likelihood of disease free survival.

Based on the data set forth in Table 4, the overexpression of any of the following genes in breast cancer indicates a reduced likelihood of survival without cancer recurrence following surgery: FOXM1; PRAME; SKT15, Ki-67; CA9; NME1; SURV; TFRC; YB-1; RPS6KB1; Src; Chk1; CCNB1; Chk2; CDC25B; CYP3A4; EpCAM; VEGFC; hENT1; BRCA2; EGFR; TK1; VDR.

Based on the data set forth in Table 4, the overexpression of any of the following genes in breast cancer indicates a better prognosis for survival without cancer recurrence following surgery: Blc12; CEGP1; GSTM1; PR; BBC3; GATA3; DPYD; GSTM3; ID1; EstR1; p27; XIAP; IGF1R; AK055699; PI3KC2A; TGFB3; BAGI1; pS2; WISP1; HNF3A; NFKBp65.

Analysis of 108 ER Positive Patient by Binary Approach 108 patients with normalized CT for estrogen receptor (ER)<25.2 (i.e., ER positive patients) were subjected to separate analysis. A t test was performed on the groups of patients classified as 0 or 1 and the p-values for the differences between the groups for each gene were calculated. The following Table 5 lists the 12 genes where the p-value for the differences between the groups was <0.05.

TABLE 5

| Gene/SEQ ID NO: | Mean CT Alive | Mean CT Deceased | t-value | Degrees of freedom | p |
|---|---|---|---|---|---|
| PRAME | 35.54 | 33.88 | 3.03 | 106 | 0.0031 |
| Bcl2 | 28.24 | 28.87 | -2.70 | 106 | 0.0082 |
| FOXM1 | 33.82 | 32.85 | 2.66 | 106 | 0.089 |
| DIABLO | 30.33 | 30.71 | -2.47 | 106 | 0.0153 |
| EPHX1 | 28.62 | 28.03 | 2.44 | 106 | 0.0163 |
| HIF1A | 29.37 | 28.88 | 2.40 | 106 | 0.0180 |
| VEGFC | 32.39 | 31.69 | 2.39 | 106 | 0.0187 |
| Ki-67 | 30.73 | 29.82 | 2.38 | 106 | 0.0191 |
| IGF1R | 28.60 | 29.18 | -2.37 | 106 | 0.0194 |
| VDR | 30.14 | 29.60 | 2.17 | 106 | 0.0322 |
| NME1 | 27.34 | 26.80 | 2.03 | 106 | 0.0452 |
| GSTM3 | 28.08 | 28.92 | -2.00 | 106 | 0.0485 |

For each gene, a classification algorithm was utilized to identify the best threshold value (CT) for using each gene alone in predicting clinical outcome.

Based on the data set forth in Table 5, overexpression of the following genes in ER-positive cancer is indicative of a reduced likelihood of survival without cancer recurrence following surgery: PRAME; FOXM1; EPHX1; HIF1A; VEGFC; Ki-67; VDR; NME1. Some of these genes (PRAME; FOXM1; VEGFC; Ki-67; VDR; and NME1) were also identified as indicators of poor prognosis in the previous analysis, not limited to ER-positive breast cancer. The overexpression of the remaining genes (EPHX1 and HIF1A) appears to be negative indicator of disease free survival in ER-positive breast cancer only. Based on the data set forth in Table 5, overexpression of the following genes in ER-positive cancer is indicative of a better prognosis for survival without cancer recurrence following surgery: Bcl-2; DIABLO; IGF1R; GSTM3. Of the latter genes, Bcl-2; IGFR1; and GSTM3 have also been identified as indicators of good prognosis in the previous analysis, not limited to ER-positive breast cancer. The overexpression of DIABLO appears to be positive indicator of disease free survival in ER-positive breast cancer only.

Analysis of Multiple Genes and Indicators of Outcome

Two approaches were taken in order to determine whether using multiple genes would provide better discrimination between outcomes.

First, a discrimination analysis was performed using a forward stepwise approach. Models were generated that classified outcome with greater discrimination than was obtained with any single gene alone.

According to a second approach (time-to-event approach), for each gene a Cox Proportional Hazards model (see, e.g. Cox, D. R., and Oakes, D. (1984), *Analysis of Survival Data*, Chapman and Hall, London, N.Y.) was defined with time to recurrence or death as the dependent variable, and the expression level of the gene as the independent variable. The genes that have a p-value <0.05 in the Cox model were identified. For each gene, the Cox model provides the relative risk (RR) of recurrence or death for a unit change in the expression of the gene. One can choose to partition the patients into subgroups at any threshold value of the measured expression (on the CT scale), where all patients with expression values above the threshold have higher risk, and all patients with expression values below the threshold have lower risk, or vice versa, depending on whether the gene is an indicator of good (RR>1.01) or poor (RR<1.01) prognosis. Thus, any threshold value will define subgroups of patients with respectively increased or decreased risk. The results are summarized in the following Tables 6 and 7.

TABLE 6

Cox Model Results for 146 Patients with Invasive Breast Cancer

| Gene | Relative Risk (RR) | SE Relative Risk | p value |
|---|---|---|---|
| FOXM1 | 0.58 | 0.15 | 0.0002 |
| STK15 | 0.51 | 0.20 | 0.0006 |
| PRAME | 0.78 | 0.07 | 0.0007 |
| Bcl2 | 1.66 | 0.15 | 0.0009 |
| CEGP1 | 1.25 | 0.07 | 0.0014 |
| GSTM1 | 1.40 | 0.11 | 0.0014 |
| Ki67 | 0.62 | 0.15 | 0.0016 |
| PR | 1.23 | 0.07 | 0.0017 |
| Contig51037 | 0.81 | 0.07 | 0.0022 |
| NME1 | 0.64 | 0.15 | 0.0023 |
| YB-1 | 0.39 | 0.32 | 0.0033 |
| TFRC | 0.53 | 0.21 | 0.0035 |
| BBC3 | 1.72 | 0.19 | 0.0036 |
| GATA3 | 1.32 | 0.10 | 0.0039 |
| CA9 | 0.81 | 0.07 | 0.0049 |
| SURV | 0.69 | 0.13 | 0.0049 |
| DPYD | 2.58 | 0.34 | 0.0052 |
| RPS6KB1 | 0.60 | 0.18 | 0.0055 |
| GSTM3 | 1.36 | 0.12 | 0.0078 |
| Src.2 | 0.39 | 0.36 | 0.0094 |
| TGFB3 | 1.61 | 0.19 | 0.0109 |
| CDC25B | 0.54 | 0.25 | 0.0122 |
| XIAP | 3.20 | 0.47 | 0.0126 |
| CCNB1 | 0.68 | 0.16 | 0.0151 |
| IGF1R | 1.42 | 0.15 | 0.0153 |
| Chk1 | 0.68 | 0.16 | 0.0155 |
| ID1 | 1.80 | 0.25 | 0.0164 |
| p27 | 1.69 | 0.22 | 0.0168 |
| Chk2 | 0.52 | 0.27 | 0.0175 |
| EstR1 | 1.17 | 0.07 | 0.0196 |
| HNF3A | 1.21 | 0.08 | 0.206 |
| pS2 | 1.12 | 0.05 | 0.0230 |
| BAGI1 | 1.88 | 0.29 | 0.0266 |
| AK055699 | 1.24 | 0.10 | 0.0276 |
| pENT1 | 0.51 | 0.31 | 0.0293 |
| EpCAM | 0.62 | 0.22 | 0.0310 |
| WISP1 | 1.39 | 0.16 | 0.0338 |
| VEGFC | 0.62 | 0.23 | 0.0364 |
| TK1 | 0.73 | 0.15 | 0.0382 |
| NFKBp65 | 1.32 | 0.14 | 0.0384 |
| BRCA2 | 0.66 | 0.20 | 0.0404 |
| CYP3A4 | 0.60 | 0.25 | 0.0417 |
| EGFR | 0.72 | 0.16 | 0.0436 |

TABLE 7

Cox Model Results for 108 Patients wih ER + Invasive Breast Cancer

| Gene | Relative Risk (RR) | SE Relative Risk | p-value |
|---|---|---|---|
| PRAME | 0.75 | 0.10 | 0.0045 |
| Contig51037 | 0.75 | 0.11 | 0.0060 |
| Blc2 | 2.11 | 0.28 | 0.0075 |
| HIF1A | 0.42 | 0.34 | 0.0117 |
| IGF1R | 1.92 | 0.26 | 0.0117 |
| FOXM1 | 0.54 | 0.24 | 0.0119 |
| EPHX1 | 0.43 | 0.33 | 0.0120 |
| Ki67 | 0.60 | 0.21 | 0.0160 |
| CDC25B | 0.41 | 0.38 | 0.0200 |
| VEGFC | 0.45 | 0.37 | 0.0288 |
| CTSB | 0.32 | 0.53 | 0.0328 |
| DIABLO | 2.91 | 0.50 | 0.0328 |
| p27 | 1.83 | 0.28 | 0.0341 |
| CDH1 | 0.57 | 0.27 | 0.0352 |
| IGFBP3 | 0.45 | 0.40 | 0.0499 |

The binary and time-to-event analyses, with few exceptions, identified the same genes as prognostic markers. For example, comparison of Tables 4 and 6 shows that, with the exception of a single gene, the two analyses generated the same list of top 15 markers (as defined by the smallest p values). Furthermore, when both analyses identified the same gene, they were concordant with respect to the direction (positive or negative sign) of the correlation with survival/recurrence. Overall, these results strengthen the conclusion that the identified markers have significant prognostic value.

For Cox models comprising more than two genes (multivariate models), stepwise entry of each individual gene into the model is performed, where the first gene entered is pre-selected from among those genes having significant univariate p-values, and the gene selected for entry into the model at each subsequent step is the gene that best improves the fit of the model to the data. This analysis can be performed with any total number of genes. In the analysis the results of which are shown below, stepwise entry was performed for up to 10 genes.

Multivariate analysis is performed using the following equation:

$$RR=\exp[\text{coef}(geneA) \times Ct(geneA) + \text{coef}(geneB) \times Ct(geneB) + \text{coef}(geneC) \times Ct(geneC) + \ldots].$$

In this equation, coefficiencts for genes that are predictors of beneficial outcome are positive numbers and coefficients for genes that are predictors of unfavorable outcome are negative numbers. The "Ct" values in the equation are ΔCts, i.e. reflect the difference between the average normalized Ct value for a population and the normalized Ct measured for the patient in question. The convention used in the present analysis has been that ΔCts below and above the population average have positive signs and negative signs, respectively (reflecting greater or lesser mRNA abundance). The relative risk (RR) calculated by solving this equation will indicate if the patient has an enhanced or reduced chance of long-term survival without cancer recurrence.

Multivariate Gene Analysis of 147 Patients with Invasive Breast Carcinoma (a) A multivariate stepwise analysis, using the Cox Proportional Hazards Model, was performed on the gene expression data obtained for all 147 patients with invasive breast carcinoma. Genes CEGP1, FOXM1, STK15 and PRAME were excluded from this analysis. The following ten-gene sets have been identified by this analysis as having particularly strong predictive value of patient survival without cancer recurrence following surgical removal of primary tumor.

1. Bcl2, cyclinG1, NFKBp65, NME1, EPHX1, TOP2B, DR5, TERC, Src, DIABLO;
2. Ki67, XIAP, hENT1, TS, CD9, p27, cyclinG1, pS2, NFKBp65, CYP3A4;
3. GSTM1, XIAP, Ki67, TS, cyclinG1, p27, CYP3A4, pS2, NFKBp65, ErbB3;
4. PR, NME1, XIAP, upa, cyclinG1, Contig51037, TERC, EPHX1, ALDH1A3, CTSL;
5. CA9, NME1, TERC, cyclinG1, EPHX1, DPYD, Src, TOP2B, NFKBp65, VEGFC;
6. TFRC, XIAP, Ki67, TS, cyclinG1, p27, CYP3A4, pS2, ErbB3, NFKBp65.

(b) A multivariate stepwise analysis, using the Cox Proportional Hazards Model, was performed on the gene expression data obtained for all 147 patients with invasive breast carcinoma, using an interrogation set including a reduced number of genes. The following ten-gene sets have been identified by this analysis as having particularly strong predictive value of patient survival without cancer recurrence following surgical removal of primary tumor.

1. Bcl2, PRAME, cyclinG1, FOXM1, NFKBp65, TS, XIAP, Ki67, CYP3A4, p27;
2. FOXM1, cyclinG1, XIAP, Contig51037, PRAME, TS, Ki67, PDGFRa, p27, NFKBp65;
3. PRAME, FOXM1, cyclinG1, XIAP, Contig51037, TS, Ki6, PDGFRa, p27, NFKBp65;
4. Ki67, XIAP, PRAME, hENT1, contig51037, TS, CD9, p27, ErbB3, cyclinG1;
5. STK15, XIAP, PRAME, PLAUR, p27, CTSL, CD18, PREP, p53, RPS6KB1;
6. GSTM1, XIAP, PRAME, p27, Contig51037, ErbB3, GSTp, EREG, ID1, PLAUR;
7. PR, PRAME, NME1, XIAP, PLAUR, cyclinG1, Contig51037, TERC, EPHX1, DR5;
8. CA9, FOXM1, cyclinG1, XIAP, TS, Ki67, NFKBp65, CYP3A4, GSTM3, p27;
9. TFRC, XIAP, PRAME, p27, Contig51037, ErbB3, DPYD, TERC, NME1, VEGFC;
10. CEGP1, PRAME, hENT1, XIAP, Contig51037, ErbB3, DPYD, NFKBp65, ID1, TS.

Multivariate Analysis of Patients with ER Positive Invasive Breast Carcinoma

A multivariate stepwise analysis, using the Cox Proportional Hazards Model, was performed on the gene expression data obtained for patients with ER positive invasive breast carcinoma. The following ten-gene sets have been identified by this analysis as having particularly strong predictive value of patient survival without cancer recurrence following surgical removal of primary tumor.

1. PRAME, p27, IGFBP2, HIF1A, TIMP2, ILT2, CYP3A4, ID1, EstR1, DIABLO;
2. Contig51037, EPHX1, Ki67, TIMP2, cyclinG1, DPYD, CYP3A4, TP, AIB1, CYP2C8;
3. Bcl2, hENT1, FOXM1, Contig51037, cyclinG1, Contig46653, PTEN, CYP3A4, TIMP2, AREG;
4. HIF1A, PRAME, p27, IGFBP2, TIMP2, ILT2, CYP3A4, ID1, EstR1, DIABLO;
5. IGF1R, PRAME, EPHX1, Contig51037, cyclinG1, Bcl2, NME1, PTEN, TBP, TIMP2;
6. FOXM1, Contig51037, VEGFC, TBP, HIF1A, DPYD, RAD51C, DCR3, cyclinG1, BAG1;
7. EPHX1, Contig51037, Ki67, TIMP2, cyclinG1, DPYD, CYP3A4, TP, AIB1, CYP2C8;
8. Ki67, VEGFC, VDR, GSTM3, p27, upa, ITGA7, rhoC, TERC, Pin1;
9. CDC25B, Contig51037, hENT1, Bcl2, HLAG, TERC, NME1, upa, ID1, CYP;
10. VEGFC, Ki67, VDR, GSTM3, p27, upa, ITGA7, rhoC, TERC, Pin1;
11. CTSB, PRAME, p27, IGFBP2, EPHX1, CTSL, BAD, DR5, DCR3, XIAP;
12. DIABLO, Ki67, hENT1, TIMP2, ID1, p27, KRT19, IGFBP2, TS, PDGFB;
13. p27, PRAME, IGFBP2, HIF1A, TIMP2, ILT2, CYP3A4, ID1, EstR1, DIABLO;
14. CDH1; PRAME, VEGFC; HIF1A; DPYD, TIMP2, CYP3A4, EstR1, RBP4, p27;
15. IGFBP3, PRAME, p27, Bcl2, XIAP, EstR1, Ki67, TS, Src, VEGF;
16. GSTM3, PRAME, p27, IGFBP3, XIAP, FGF2, hENT1, PTEN, EstR1, APC;
17. hENT1, Bcl2, FOXM1, Contig51037, CyclinG1, Contig46653, PTEN, CYP3A4, TIMP2, AREG;
18. STK15, VEGFC, PRAME, p27, GCLC, hENT1, ID1, TIMP2, EstR1, MCP1;
19. NME1, PRAM, p27, IGFBP3, XIAP, PTEN, hENT1, Bcl2, CYP3A4, HLAG;
20. VDR, Bcl2, p27, hENT1, p53, PI3KC2A, EIF4E, TFRC, MCM3, ID1;
21. EIF4E, Contig51037, EPHX1, cyclinG1, Bcl2, DR5, TBP, PTEN, NME1, HER2;
22. CCNB1, PRAME, VEGFC, HIF1A, hENT1, GCLC, TIMP2, ID1, p27, upa;
23. ID1, PRAME, DIABLO, hENT1, p27, PDGFRa, NME1, BIN1, BRCA1, TP;
24. FBXO5, PRAME, IGFBP3, p27, GSTM3, hENT1, XIAP, FGF2, TS, PTEN;
25. GUS, HIA1A, VEGFC, GSTM3, DPYD, hENT1, FBXO5, CA9, CYP, KRT18;
26. Bclx, Bcl2, hENT1, Contig51037, HLAG, CD9, ID1, BRCA1, BIN1, HBEGF.

It is noteworthy that many of the foregoing gene sets include genes that alone did not have sufficient predictive value to qualify as prognostic markers under the standards discussed above, but in combination with other genes, their presence provides valuable information about the likelihood of long-term patient survival without cancer recurrence All references cited throughout the disclosure are hereby expressly incorporated by reference.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the diagnosis and treatment of breast cancer, similar genes, gene sets and methods concerning other types of cancer are specifically within the scope herein.

TABLE 1

| | | | |
|---|---|---|---|
| 1. | ADD3 (adducin 3 gamma)* | 96. | human kallikrein 10 |
| 2. | AKT1/Protein Kinase B | 97. | MLH1 |
| | | 98. | hsp27 |
| 3. | AKT 2 | 99. | humanchorionic gonadotropin/CGA |
| 4. | AKT 3 | 100. | Human Extracellular Protein S1-5 |
| 5. | Aldehyde dehydrogenase1A1 | 101. | Id-1 |
| 6. | Aldehyde dehydrogenase1A3 | 102. | Id-2 |
| | | 103. | Id-3 |
| 7. | amphiregulin | 104. | IGF-1 |
| 8. | APC | 105. | IGF2 |
| 9. | ARG | 106. | IGF1R |
| 10. | ATM | 107. | IGFBP3 |
| 11. | Bak | 108. | interstitial integrin alpha 7 |
| 12. | Bax | 109. | IL6 |
| 13. | Bcl2 | 110. | IL8 |
| 14. | Bcl-x1 | 111. | IRF-2* |
| 15. | BRK | 112. | IRF9 Protein |
| 16. | BCRP | 113. | Kalikrein 5 |
| 17. | BRCA-1 | 114. | Kalikrein 6 |
| 18. | BRCA-2 | 115. | KDR |
| 19. | Caspase-3 | 116. | Ki-67/MiB1 |
| 20. | Cathepsin B | 117. | lipoprotein lipase^ |
| 21. | Cathepsin G | 118. | LIV1 |
| 22. | Cathepsin L | 119. | LungResistance Protein/MVP |
| 23. | CD3 | | |
| 24. | CD9 | 120. | Lot1 |
| 25. | CD18 | 121. | Maspin |
| 26. | CD31 | 122. | MCM2 |
| 27. | CD44^ | 123. | MCM3 |
| 28. | CD68 | 124. | MCM7 |

TABLE 1-continued

| | |
|---|---|
| 29. CD82/K4I-1 | 125. MCP-1 |
| 30. Cdc25A | 126. microtubule-associated protein 4 |
| 31. Cdc25B | |
| 32. CGA | 127. MCJ |
| 33. COX2 | 128. mdm2 |
| 34. CSF-1 | 129. MDR-1 |
| 35. CSF-1R/fms | 130. microsomalepoxide hydrolase |
| 36. cIAP1 | |
| 37. cIAP2 | 131. MMP9 |
| 38. c-abl | 132. MRP1 |
| 39. c-kit | 133. MRP2 |
| 40. c-kitL | 134. MRP3 |
| 41. c-met | 135. MRP4 |
| 42. c-myc | 136. MSN (Moesin)* |
| 43. cN-1 | 137. mTOR |
| 44. cryptochrome1* | 138. Muc1/CA 15-3 |
| 45. c-Src | 139. NF-kB |
| 46. Cyclin D1 | 140. P14ARF |
| 47. CYP1B1 | 141. P16INK4a/p14 |
| 48. CYP2C9* | 142. p21wAF1/CIP1 |
| 49. Cytokeratin 5^ | 143. p23 |
| 50. Cytokeratin 17^ | 144. p27 |
| 51. Cytokeratin 18^ | 145. p311* |
| 52. DAP-Kinase-1 | 146. p53 |
| 53. DHFR | 147. PAI1 |
| 54. DIABLO | 148. PCNA |
| 55. Dihydropyrimidine dehydrogenase | 149. PDGF-A |
| | 150. PDGF-B |
| 56. EGF | 151. PDGF-C |
| 57. ECadherin/CDH1^ | 152. PDGF-D |
| 58. ELF 3* | 153. PDGFR-α |
| 59. Endothelin | 154. PDGFR-β |
| 60. Epiregulin | 155. PI3K |
| 61. ER-alpha | 156. Pin1 |
| 62. ErbB-1 | 157. PKC-ε |
| 63. ErbB-2 | 158. Pkc-δ |
| 64. ErbB-3 | 159. PLAG1(pleiomorphicadenoma 1)* |
| 65. ErbB-4 | |
| 66. ER-Beta | 160. PREPprolylendopeptidase*PEP |
| 67. Eukaryotic Translation Initiation Factor 4B*(EIF4B) | 161. Progesteronereceptor |
| | 162. pS2/trefoilfactor1 |
| | 163. PTEN |
| | 164. PTP1b |
| 68. E1F4E | 165. RAR-alpha |
| 69. farnesyl pyrolophosphate synthetase | 166. RAR-beta2 |
| | 167. RCP |
| | 168. ReducedFolateCarrier |
| 70. FAS (CD95) | 169. Retinol binding protein 4^ |
| 71. FasL | 170. STK15/BTAK |
| 72. FGF R 1* | 171. Survivin |
| 73. FGF2 [bFGF] | 172. SXR |
| 74. 53BP1 | 173. Syk |
| 75. 53BP2 | 174. TGD (thymine-DNA glycosylase)* |
| 76. GALC (galactosylcera-midase)* | |
| | 175. TGFalpha |
| | 176. Thymidine Kinase |
| | 177. Thymidinephosphorylase |
| 77. Gamma-GCS(glutamyl cysteinesynthetase) | 178. ThymidylateSynthase |
| | 179. TopoisomeraseII-α |
| 78. GATA3 | 180. TopoisomeraseII-β |
| 79. geranylgeranyl pyrophosphatesynthetase | 181. TRAMP |
| | 182. UPA |
| 80. G-CSF | 183. VEGF |
| 81. GPC3 | 184. Vimentin |
| 82. gravin* [AK AP258] | 185. WTH3 |
| 83. GRO1 oncogene alpha^ | 186. XAF1 |
| 84. Grb7 | 187. XIAP |
| 85. GST-alpha | 188. XIST |
| 86. GST-pi | 189. XPA |
| 87. Ha-Ras | 190. YB-1 |
| 88. HB-EGF | |
| 89. HE4-extracellular Proteinase Inhibitor Homologue* | |
| 90. hepatocyte nuclear factor 3^ | |
| 91. HER-2 | |
| 92. HGF/Scatter factor | |
| 93. hIAP1 | |
| 94. hIAP2 | |
| 95. HIF-1 | |

*NCI 60 drug Sens./Resist Marker
^In Cluster Defining tumor subclass
Jan. 19, 2002

TABLE 2

| Gene | Accession No. | Forward Primer SEQ ID NO. | Reverse Primer SEQ ID NO. | Amplicon SEQ ID NO. |
|---|---|---|---|---|
| ABCB1 | NM_000927 | 1 | 2 | 3 |
| ABCC1 | NM_004996 | 4 | 5 | 6 |
| ABCC2 | NM_000392 | 7 | 8 | 9 |
| ABCC3 | NM_003786 | 10 | 11 | 12 |
| ABCC4 | NM_005845 | 13 | 14 | 15 |
| ABL1 | NM_005157 | 16 | 17 | 18 |
| ABL2 | NM_005158 | 19 | 20 | 21 |
| ACTB | NM_001101 | 22 | 23 | 24 |
| AKT1 | NM_005163 | 25 | 26 | 27 |
| AKT3 | NM_005465 | 28 | 29 | 30 |
| ALDH1 | NM_000689 | 31 | 32 | 33 |
| ALDH1A3 | NM_000693 | 34 | 35 | 36 |
| APC | NM_000038 | 37 | 38 | 39 |
| AREG | NM_001657 | 40 | 41 | 42 |
| B2M | NM_004048 | 43 | 44 | 45 |
| BAK1 | NM_001188 | 46 | 47 | 48 |
| BAX | NM_004324 | 49 | 50 | 51 |
| BCL2 | NM_000633 | 52 | 53 | 54 |
| BCL2L1 | NM_001191 | 55 | 56 | 57 |
| BIRC3 | NM_001165 | 58 | 59 | 60 |
| BIRC4 | NM_001167 | 61 | 62 | 63 |
| BIRC5 | NM_001168 | 64 | 65 | 66 |
| BRCA1 | NM_007295 | 67 | 68 | 69 |
| BRCA2 | NM_000059 | 70 | 71 | 72 |
| CCND1 | NM_001758 | 73 | 74 | 75 |
| CD3Z | NM_000734 | 76 | 77 | 78 |
| CD68 | NM_001251 | 79 | 80 | 81 |
| CDC25A | NM_001789 | 82 | 83 | 84 |
| CDH1 | NM_004360 | 85 | 86 | 87 |
| CDKN1A | NM_000389 | 88 | 89 | 90 |
| CDKN1B | NM_004064 | 91 | 92 | 93 |
| CDKN2A | NM_000077 | 94 | 95 | 96 |
| CYP1B1 | NM_000104 | 97 | 98 | 99 |
| DHFR | NM_000791 | 100 | 101 | 102 |
| DPYD | NM_000110 | 103 | 104 | 105 |
| ECGF1 | NM_001953 | 106 | 107 | 108 |
| EGFR | NM_005228 | 109 | 110 | 111 |
| EIF4E | NM_001968 | 112 | 113 | 114 |
| ERBB2 | NM_004448 | 115 | 116 | 117 |
| ERBB3 | NM_001982 | 118 | 119 | 120 |
| ESR1 | NM_000125 | 121 | 122 | 123 |
| ESR2 | NM_001437 | 124 | 125 | 126 |
| GAPD | NM_002046 | 127 | 128 | 129 |
| GATA3 | NM_002051 | 130 | 131 | 132 |
| GRB7 | NM_005310 | 133 | 134 | 135 |
| GRO1 | NM_001511 | 136 | 137 | 138 |
| GSTP1 | NM_000852 | 139 | 140 | 141 |
| GUSB | NM_000181 | 142 | 143 | 144 |
| hHGF | M29145 | 145 | 146 | 147 |
| HNF3A | NM_004496 | 148 | 149 | 150 |
| ID2 | NM_002166 | 151 | 152 | 153 |
| IGF1 | NM_000618 | 154 | 155 | 156 |
| IGFBP3 | NM_000598 | 157 | 158 | 159 |
| ITGA7 | NM_002206 | 160 | 161 | 162 |
| ITGB2 | NM_000211 | 163 | 164 | 165 |
| KDR | NM_002253 | 166 | 167 | 168 |
| KIT | NM_000222 | 169 | 170 | 171 |
| KITLG | NM_000899 | 172 | 173 | 174 |
| KRT17 | NM_000422 | 175 | 176 | 177 |
| KRT5 | NM_000424 | 178 | 179 | 180 |
| LPL | NM_000237 | 181 | 182 | 183 |
| MET | NM_000245 | 184 | 185 | 186 |
| MKI67 | NM_002417 | 187 | 188 | 189 |
| MVP | NM_017458 | 190 | 191 | 192 |

TABLE 2-continued

| Gene | Accession No. | Forward Primer SEQ ID NO. | Reverse Primer SEQ ID NO. | Amplicon SEQ ID NO. |
|---|---|---|---|---|
| MYC | NM_002467 | 193 | 194 | 195 |
| PDGFA | NM_002607 | 196 | 197 | 198 |
| PDGFB | NM_002608 | 199 | 200 | 201 |
| PDGFC | NM_016205 | 202 | 203 | 204 |
| PDGFRA | NM_006206 | 205 | 206 | 207 |
| PDGFRB | NM_002609 | 208 | 209 | 210 |
| PGK1 | NM_000291 | 211 | 212 | 213 |
| PGR | NM_000926 | 214 | 215 | 216 |
| PIN1 | NM_006221 | 217 | 218 | 219 |
| PLAU | NM_002658 | 220 | 221 | 222 |
| PPIH | NM_006347 | 223 | 224 | 225 |
| PTEN | NM_000314 | 226 | 227 | 228 |
| PTGS2 | NM_000963 | 229 | 230 | 231 |
| RBP4 | NM_006744 | 232 | 233 | 234 |
| RELA | NM_021975 | 235 | 236 | 237 |
| RPL19 | NM_000981 | 238 | 239 | 240 |
| RPLP0 | NM_001002 | 241 | 242 | 243 |
| SCDGF-B | NM_025208 | 244 | 245 | 246 |
| SERPINE1 | NM_000602 | 247 | 248 | 249 |
| SLC19A1 | NM_003056 | 250 | 251 | 252 |
| TBP | NM_003194 | 253 | 254 | 255 |
| TFF1 | NM_003225 | 256 | 257 | 258 |
| TFRC | NM_003234 | 259 | 260 | 261 |
| TK1 | NM_003258 | 262 | 263 | 264 |
| TNFRSF6 | NM_000043 | 265 | 266 | 267 |
| TNFSF6 | NM_000639 | 268 | 269 | 270 |
| TOP2A | NM_001067 | 271 | 272 | 273 |
| TOP2B | NM_001068 | 274 | 275 | 276 |
| TP53 | NM_000546 | 277 | 278 | 279 |
| TYMS | NM_001071 | 280 | 281 | 282 |
| VEGF | NM_003376 | 283 | 284 | 285 |

TABLE 3

| GENE | ACCESSION NO. | SEQ ID NO: |
|---|---|---|
| AK055699 | AK055699 | 286 |
| BAG1 | NM_004323 | 287 |
| BBC3 | NM_014417 | 288 |
| Bcl2 | NM_000633 | 289 |
| BRCA2 | NM_000059 | 290 |
| CA9 | NM_001216 | 291 |
| CCNB1 | NM_031966 | 292 |
| CDC25B | NM_021874 | 293 |
| CEGP1 | NM_020974 | 294 |
| Chk1 | NM_001274 | 295 |
| Chk2 | NM_007194 | 296 |
| CYP3A4 | NM_017460 | 297 |
| DIABLO | NM_019887 | 298 |
| DPYD | NM_000110 | 299 |
| EGFR | NM_005228 | 300 |
| EpCAM | NM_002354 | 301 |
| EPHX1 | NM_000120 | 302 |
| EstR1 | NM_000125 | 303 |
| FOXM1 | NM_021953 | 304 |
| GATA3 | NM_002051 | 305 |
| GSTM1 | NM_000561 | 306 |
| GSTM3 | NM_000849 | 307 |
| hENT1 | NM_004955 | 308 |
| HIF1A | NM_001530 | 309 |
| HNF3A | NM_004496 | 310 |
| ID1 | NM_002165 | 311 |
| IGF1R | NM_000875 | 312 |
| Ki-67 | NM_002417 | 313 |
| NFKBp65 | NM_021975 | 314 |
| NME1 | NM_000269 | 315 |
| p27 | NM_004064 | 316 |
| PI3KC2A | NM_002645 | 317 |
| PR | NM_000926 | 318 |
| PRAME | NM_006115 | 319 |
| pS2 | NM_003225 | 320 |
| RPS6KB1 | NM_003161 | 321 |

TABLE 3-continued

| GENE | ACCESSION NO. | SEQ ID NO: |
|---|---|---|
| Src | NM_004383 | 322 |
| STK15 | NM_003600 | 323 |
| SURV | NM_001168 | 324 |
| TFRC | NM_003234 | 325 |
| TGFB3 | NM_003239 | 326 |
| TK1 | NM_003258 | 327 |
| VDR | NM_000376 | 328 |
| VEGFC | NM_005429 | 329 |
| WISP1 | NM_003882 | 330 |
| XIAP | NM_001167 | 331 |
| YB-1 | NM_004559 | 332 |
| ITGA7 | NM_002206 | 333 |
| PDGFB | NM_002608 | 334 |
| Upa | NM_002658 | 335 |
| TBP | NM_003194 | 336 |
| PDGFRa | NM_006206 | 337 |
| Pin1 | NM_006221 | 338 |
| CYP | NM_006347 | 339 |
| RBP4 | NM_006744 | 340 |
| BRCA1 | NM_007295 | 341 |
| APC | NM_000038 | 342 |
| GUS | NM_000181 | 343 |
| CD18 | NM_000211 | 344 |
| PTEN | NM_000314 | 345 |
| P53 | NM_000546 | 346 |
| ALDH1A3 | NM_000693 | 347 |
| GSTp | NM_000852 | 348 |
| TOP2B | NM_001068 | 349 |
| TS | NM_001071 | 350 |
| Bclx | NM_001191 | 351 |
| AREG | NM_001657 | 352 |
| TP | NM_001953 | 353 |
| EIF4E | NM_001968 | 354 |
| ErbB3 | NM_001982 | 355 |
| EREG | NM_001432 | 356 |
| GCLC | NM_001498 | 357 |
| CD9 | NM_001769 | 358 |
| HB-EGF | NM_001945 | 359 |
| IGFBP2 | NM_000597 | 360 |
| CTSL | NM_001912 | 361 |
| PREP | NM_002726 | 362 |
| CYP3A4 | NM_017460 | 363 |
| ILT-2 | NM_006669 | 364 |
| MCM3 | NM_002388 | 365 |
| KRT19 | NM_002276 | 366 |
| KRT18 | NM_000224 | 367 |
| TIMP2 | NM_003255 | 368 |
| BAD | NM_004322 | 369 |
| CYP2C8 | NM_030878 | 370 |
| DCR3 | NM_016434 | 371 |
| PLAUR | NM_002659 | 372 |
| PI3KC2A | NM_002645 | 373 |
| FGF2 | NM_002006 | 374 |
| HLA-G | NM_002127 | 375 |
| AIB1 | NM_006534 | 376 |
| MCP1 | NM_002982 | 377 |
| Contig46653 | Contig46653 | 378 |
| RhoC | NM_005167 | 379 |
| DR5 | NM_003842 | 380 |
| RAD51C | NM_058216 | 381 |
| BIN1 | NM_004305 | 382 |
| VDR | NM_000376 | 383 |
| TERC | U86046 | 384 |

What is claimed is:

1. A method of predicting the likelihood of long-term survival of a breast cancer patient without the recurrence of breast cancer, following surgical removal of the primary tumor, comprising determining the expression level of Bcl2, STK15, CEGP1, Ki-67, GSTM1, PR, SURV, TFRC, EstR1, CCNB1, BAGI1, and Her2, wherein overexpression of STK15, Ki-67, SURV, TFRC, CCNB1, and Her2, indicates a decreased likelihood of long-term survival without breast cancer recurrence, and the overexpression of Bcl2, CEGP1, GSTM1, PR, EstR1, BAGI1, indicates an increased likelihood of long-term survival without breast cancer recurrence.

2. The method of claim 1 wherein said RNA is isolated from a fixed, wax-embedded breast cancer tissue specimen of said patient.

3. The method of claim 1, wherein said RNA is fragmented RNA.

4. The method of claim 1, wherein said RNA is isolated from a fine needle biopsy sample.

5. The method of claim 1, further comprising creating a report summarizing the data obtained by the determination of said gene expression levels.

6. The method of claim 5, wherein said report includes prediction of the likelihood of long term survival of said patient without the recurrence of breast cancer following surgical removal of the primary tumor.

7. The method of claim 6, wherein said report includes recommendation for a treatment modality of said patient.

* * * * *

SEQUENCE LISTING

<160> NUMBER OF SEQ ID NOS: 384

<210> SEQ ID NO 1
<211> LENGTH: 18
<212> TYPE: DNA
<213> ORGANISM: Homo sapiens

<400> SEQUENCE: 1
gtcccaggag cccatcct                                                   18

<210> SEQ ID NO 2
<211> LENGTH: 19
<212> TYPE: DNA
<213> ORGANISM: Homo sapiens

<400> SEQUENCE: 2
cccggctgtt gtctccata                                                  19

<210> SEQ ID NO 3
<211> LENGTH: 68
<212> TYPE: DNA
<213> ORGANISM: Homo sapiens

<400> SEQUENCE: 3
gtcccaggag cccatcctgt tgactgcag cattgctgag aacattgcct atggagacaa      60
cagccggg                                                              68

<210> SEQ ID NO 4
<211> LENGTH: 18
<212> TYPE: DNA
<213> ORGANISM: Homo sapiens

<400> SEQUENCE: 4
tcatggtgcc cgtcaatg                                                   18

<210> SEQ ID NO 5
<211> LENGTH: 23
<212> TYPE: DNA
<213> ORGANISM: Homo sapiens

<400> SEQUENCE: 5
cgattgtctt tgctcttcat gtg                                             23

<210> SEQ ID NO 6
<211> LENGTH: 79
<212> TYPE: DNA
<213> ORGANISM: Homo sapiens

<400> SEQUENCE: 6
tcatggtgcc cgtcaatgct gtgatggcga tgaagaccaa gacgtatcag gtggcccaca     60
tgaagagcaa agacaatcg                                                  79

<210> SEQ ID NO 7
<211> LENGTH: 20
<212> TYPE: DNA
<213> ORGANISM: Homo sapiens

<400> SEQUENCE: 7 agggatgac ttggacacat                                                  20

<210> SEQ ID NO 8
<211> LENGTH: 20
<212> TYPE: DNA
<213> ORGANISM: Homo sapiens

<400> SEQUENCE: 8
aaaactgcat ggctttgtca                                            20

<210> SEQ ID NO 9
<211> LENGTH: 65
<212> TYPE: DNA
<213> ORGANISM: Homo sapiens

<400> SEQUENCE: 9 agggatgac ttggacacat ctgccattcg acatgactgc aattttgaca aagccatgca  60
gtttt                                                            65

<210> SEQ ID NO 10
<211> LENGTH: 22
<212> TYPE: DNA
<213> ORGANISM: Homo sapiens

<400> SEQUENCE: 10
tcatcctggc gatctacttc ct                                         22

<210> SEQ ID NO 11
<211> LENGTH: 20
<212> TYPE: DNA
<213> ORGANISM: Homo sapiens

<400> SEQUENCE: 11
ccgttgagtg gaatcagcaa                                            20

<210> SEQ ID NO 12
<211> LENGTH: 91
<212> TYPE: DNA
<213> ORGANISM: Homo sapiens

<400> SEQUENCE: 12
tcatcctggc gatctacttc ctctggcaga acctaggtcc ctctgtcctg gctggagtcg  60
ctttcatggt cttgctgatt ccactcaacg g                                91

<210> SEQ ID NO 13
<211> LENGTH: 20
<212> TYPE: DNA
<213> ORGANISM: Homo sapiens

<400> SEQUENCE: 13
agcgcctgga atctacaact                                            20

<210> SEQ ID NO 14
<211> LENGTH: 20
<212> TYPE: DNA
<213> ORGANISM: Homo sapiens

<400> SEQUENCE: 14
agagcccctg gagagaagat                                            20

<210> SEQ ID NO 15
<211> LENGTH: 66
<212> TYPE: DNA
<213> ORGANISM: Homo sapiens -continued

```
<400> SEQUENCE: 15
agcgcctgga atctacaact cggagtccag tgttttccca cttgtcatct tctctccagg      60
ggctct                                                                66

<210> SEQ ID NO 16
<211> LENGTH: 24
<212> TYPE: DNA
<213> ORGANISM: Homo sapiens

<400> SEQUENCE: 16
gcccagagaa ggtctatgaa ctca                                            24

<210> SEQ ID NO 17
<211> LENGTH: 22
<212> TYPE: DNA
<213> ORGANISM: Homo sapiens

<400> SEQUENCE: 17
gtttcaaagg cttggtggat tt                                              22

<210> SEQ ID NO 18
<211> LENGTH: 94
<212> TYPE: DNA
<213> ORGANISM: Homo sapiens

<400> SEQUENCE: 18
gcccagagaa ggtctatgaa ctcatgcgag catgttggca gtggaatccc tctgaccggc      60
cctcctttgc tgaaatccac caagcctttg aaac                                 94

<210> SEQ ID NO 19
<211> LENGTH: 21
<212> TYPE: DNA
<213> ORGANISM: Homo sapiens

<400> SEQUENCE: 19
cgcagtgcag ctgagtatct g                                               21

<210> SEQ ID NO 20
<211> LENGTH: 21
<212> TYPE: DNA
<213> ORGANISM: Homo sapiens

<400> SEQUENCE: 20
tgcccagggc tactctcact t                                               21

<210> SEQ ID NO 21
<211> LENGTH: 80
<212> TYPE: DNA
<213> ORGANISM: Homo sapiens

<400> SEQUENCE: 21
cgcagtgcag ctgagtatct gctcagcagt ctaatcaatg gcagcttcct ggtgcgagaa      60
agtgagagta gccctgggca                                                 80

<210> SEQ ID NO 22
<211> LENGTH: 21
<212> TYPE: DNA
<213> ORGANISM: Homo sapiens

<400> SEQUENCE: 22
cagcagatgt ggatcagcaa g                                               21
```

<210> SEQ ID NO 23
<211> LENGTH: 18
<212> TYPE: DNA
<213> ORGANISM: Homo sapiens

<400> SEQUENCE: 23
gcatttgcgg tggacgat                                                 18

<210> SEQ ID NO 24
<211> LENGTH: 66
<212> TYPE: DNA
<213> ORGANISM: Homo sapiens

<400> SEQUENCE: 24
cagcagatgt ggatcagcaa gcaggagtat gacgagtccg gcccctccat cgtccaccgc   60
aaatgc                                                              66

<210> SEQ ID NO 25
<211> LENGTH: 20
<212> TYPE: DNA
<213> ORGANISM: Homo sapiens

<400> SEQUENCE: 25
cgcttctatg gcgctgagat                                               20

<210> SEQ ID NO 26
<211> LENGTH: 20
<212> TYPE: DNA
<213> ORGANISM: Homo sapiens

<400> SEQUENCE: 26
tcccggtaca ccacgttctt                                               20

<210> SEQ ID NO 27
<211> LENGTH: 71
<212> TYPE: DNA
<213> ORGANISM: Homo sapiens

<400> SEQUENCE: 27
cgcttctatg gcgctgagat tgtgtcagcc ctggactacc tgcactcgga gaagaacgtg   60
gtgtaccggg a                                                        71

<210> SEQ ID NO 28
<211> LENGTH: 25
<212> TYPE: DNA
<213> ORGANISM: Homo sapiens

<400> SEQUENCE: 28
ttgtctctgc cttggactat ctaca                                         25

<210> SEQ ID NO 29
<211> LENGTH: 24
<212> TYPE: DNA
<213> ORGANISM: Homo sapiens

<400> SEQUENCE: 29
ccagcattag attctccaac ttga                                          24

<210> SEQ ID NO 30
<211> LENGTH: 75
<212> TYPE: DNA

```
<213> ORGANISM: Homo sapiens

<400> SEQUENCE: 30
ttgtctctgc cttggactat ctacattccg gaaagattgt gtaccgtgat ctcaagttgg    60
agaatctaat gctgg                                                    75

<210> SEQ ID NO 31
<211> LENGTH: 25
<212> TYPE: DNA
<213> ORGANISM: Homo sapiens

<400> SEQUENCE: 31
gaaggagata aggaggatgt tgaca                                         25

<210> SEQ ID NO 32
<211> LENGTH: 18
<212> TYPE: DNA
<213> ORGANISM: Homo sapiens

<400> SEQUENCE: 32
cgccacggag atccaatc                                                 18

<210> SEQ ID NO 33
<211> LENGTH: 74
<212> TYPE: DNA
<213> ORGANISM: Homo sapiens

<400> SEQUENCE: 33
gaaggagata aggaggatgt tgacaaggca gtgaaggccg caagacaggc ttttcagatt    60
ggatctccgt ggcg                                                     74

<210> SEQ ID NO 34
<211> LENGTH: 21
<212> TYPE: DNA
<213> ORGANISM: Homo sapiens

<400> SEQUENCE: 34
tggtgaacat tgtgccagga t                                             21

<210> SEQ ID NO 35
<211> LENGTH: 22
<212> TYPE: DNA
<213> ORGANISM: Homo sapiens

<400> SEQUENCE: 35
gaaggcgatc ttgttgatct ga                                            22

<210> SEQ ID NO 36
<211> LENGTH: 80
<212> TYPE: DNA
<213> ORGANISM: Homo sapiens

<400> SEQUENCE: 36
tggtgaacat tgtgccagga ttcgggccca cagtgggagc agcaatttct tctcaccctc    60
agatcaacaa gatcgccttc                                               80

<210> SEQ ID NO 37
<211> LENGTH: 20
<212> TYPE: DNA
<213> ORGANISM: Homo sapiens

<400> SEQUENCE: 37
```

```
ggacagcagg aatgtgtttc                                                    20

<210> SEQ ID NO 38
<211> LENGTH: 20
<212> TYPE: DNA
<213> ORGANISM: Homo sapiens

<400> SEQUENCE: 38
acccactcga tttgtttctg                                                    20

<210> SEQ ID NO 39
<211> LENGTH: 69
<212> TYPE: DNA
<213> ORGANISM: Homo sapiens

<400> SEQUENCE: 39
ggacagcagg aatgtgtttc tccatacagg tcacggggag ccaatggttc agaaacaaat        60
cgagtgggt                                                                69

<210> SEQ ID NO 40
<211> LENGTH: 27
<212> TYPE: DNA
<213> ORGANISM: Homo sapiens

<400> SEQUENCE: 40
tgtgagtgaa atgccttcta gtagtga                                            27

<210> SEQ ID NO 41
<211> LENGTH: 27
<212> TYPE: DNA
<213> ORGANISM: Homo sapiens

<400> SEQUENCE: 41
ttgtggttcg ttatcatact cttctga                                            27

<210> SEQ ID NO 42
<211> LENGTH: 82
<212> TYPE: DNA
<213> ORGANISM: Homo sapiens

<400> SEQUENCE: 42
tgtgagtgaa atgccttcta gtagtgaacc gtcctcggga gccgactatg actactcaga        60
agagtatgat aacgaaccac aa                                                 82

<210> SEQ ID NO 43
<211> LENGTH: 19
<212> TYPE: DNA
<213> ORGANISM: Homo sapiens

<400> SEQUENCE: 43
gtctcgctcc gtggcctta                                                     19

<210> SEQ ID NO 44
<211> LENGTH: 24
<212> TYPE: DNA
<213> ORGANISM: Homo sapiens

<400> SEQUENCE: 44
cgtgagtaaa cctgaatctt tgga                                               24

<210> SEQ ID NO 45
```

```
<211> LENGTH: 93
<212> TYPE: DNA
<213> ORGANISM: Homo sapiens

<400> SEQUENCE: 45
gtctcgctcc gtggccttag ctgtgctcgc gctactctct ctttctggcc tggaggctat     60
ccagcgtact ccaaagattc aggtttactc acg                                  93

<210> SEQ ID NO 46
<211> LENGTH: 20
<212> TYPE: DNA
<213> ORGANISM: Homo sapiens

<400> SEQUENCE: 46
ccattcccac cattctacct                                                 20

<210> SEQ ID NO 47
<211> LENGTH: 20
<212> TYPE: DNA
<213> ORGANISM: Homo sapiens

<400> SEQUENCE: 47
gggaacatag acccaccaat                                                 20

<210> SEQ ID NO 48
<211> LENGTH: 66
<212> TYPE: DNA
<213> ORGANISM: Homo sapiens

<400> SEQUENCE: 48
ccattcccac cattctacct gaggccagga cgtctggggt gtggggattg gtgggtctat     60
gttccc                                                                66

<210> SEQ ID NO 49
<211> LENGTH: 18
<212> TYPE: DNA
<213> ORGANISM: Homo sapiens

<400> SEQUENCE: 49
ccgccgtgga cacagact                                                   18

<210> SEQ ID NO 50
<211> LENGTH: 21
<212> TYPE: DNA
<213> ORGANISM: Homo sapiens

<400> SEQUENCE: 50
ttgccgtcag aaaacatgtc a                                               21

<210> SEQ ID NO 51
<211> LENGTH: 70
<212> TYPE: DNA
<213> ORGANISM: Homo sapiens

<400> SEQUENCE: 51
ccgccgtgga cacagactcc ccccgagagg tcttttttccg agtggcagct gacatgtttt    60
ctgacggcaa                                                            70

<210> SEQ ID NO 52
<211> LENGTH: 25
<212> TYPE: DNA
<213> ORGANISM: Homo sapiens
```

```
<400> SEQUENCE: 52
cagatggacc tagtacccac tgaga                                          25

<210> SEQ ID NO 53
<211> LENGTH: 24
<212> TYPE: DNA
<213> ORGANISM: Homo sapiens

<400> SEQUENCE: 53
cctatgattt aagggcattt ttcc                                           24

<210> SEQ ID NO 54
<211> LENGTH: 73
<212> TYPE: DNA
<213> ORGANISM: Homo sapiens

<400> SEQUENCE: 54
cagatggacc tagtacccac tgagatttcc acgccgaagg acagcgatgg gaaaaatgcc    60
cttaaatcat agg                                                       73

<210> SEQ ID NO 55
<211> LENGTH: 24
<212> TYPE: DNA
<213> ORGANISM: Homo sapiens

<400> SEQUENCE: 55
cttttgtgga actctatggg aaca                                           24

<210> SEQ ID NO 56
<211> LENGTH: 19
<212> TYPE: DNA
<213> ORGANISM: Homo sapiens

<400> SEQUENCE: 56
cagcggttga agcgttcct                                                 19

<210> SEQ ID NO 57
<211> LENGTH: 70
<212> TYPE: DNA
<213> ORGANISM: Homo sapiens

<400> SEQUENCE: 57
cttttgtgga actctatggg aacaatgcag cagccgagag ccgaaagggc caggaacgct    60
tcaaccgctg                                                           70

<210> SEQ ID NO 58
<211> LENGTH: 24
<212> TYPE: DNA
<213> ORGANISM: Homo sapiens

<400> SEQUENCE: 58
ggatatttcc gtggctctta ttca                                           24

<210> SEQ ID NO 59
<211> LENGTH: 25
<212> TYPE: DNA
<213> ORGANISM: Homo sapiens

<400> SEQUENCE: 59
cttctcatca aggcagaaaa atctt                                          25
```

<210> SEQ ID NO 60
<211> LENGTH: 86
<212> TYPE: DNA
<213> ORGANISM: Homo sapiens

<400> SEQUENCE: 60
ggatatttcc gtggctctta ttcaaactct ccatcaaatc ctgtaaactc cagagcaaat    60
caagattttt ctgccttgat gagaag    86

<210> SEQ ID NO 61
<211> LENGTH: 23
<212> TYPE: DNA
<213> ORGANISM: Homo sapiens

<400> SEQUENCE: 61
gcagttggaa gacacaggaa agt    23

<210> SEQ ID NO 62
<211> LENGTH: 21
<212> TYPE: DNA
<213> ORGANISM: Homo sapiens

<400> SEQUENCE: 62
tgcgtggcac tattttcaag a    21

<210> SEQ ID NO 63
<211> LENGTH: 77
<212> TYPE: DNA
<213> ORGANISM: Homo sapiens

<400> SEQUENCE: 63
gcagttggaa gacacaggaa agtatcccca aattgcagat ttatcaacgg cttttatctt    60
gaaaatagtg ccacgca    77

<210> SEQ ID NO 64
<211> LENGTH: 20
<212> TYPE: DNA
<213> ORGANISM: Homo sapiens

<400> SEQUENCE: 64
tgttttgatt cccgggctta    20

<210> SEQ ID NO 65
<211> LENGTH: 24
<212> TYPE: DNA
<213> ORGANISM: Homo sapiens

<400> SEQUENCE: 65
caaagctgtc agctctagca aaag    24

<210> SEQ ID NO 66
<211> LENGTH: 80
<212> TYPE: DNA
<213> ORGANISM: Homo sapiens

<400> SEQUENCE: 66
tgttttgatt cccgggctta ccaggtgaga agtgagggag gaagaaggca gtgtcccttt    60
tgctagagct gacagctttg    80

<210> SEQ ID NO 67
<211> LENGTH: 20

```
<212> TYPE: DNA
<213> ORGANISM: Homo sapiens

<400> SEQUENCE: 67 tcaggggggct agaaatctgt                                                  20

<210> SEQ ID NO 68
<211> LENGTH: 20
<212> TYPE: DNA
<213> ORGANISM: Homo sapiens

<400> SEQUENCE: 68
ccattccagt tgatctgtgg                                                   20

<210> SEQ ID NO 69
<211> LENGTH: 65
<212> TYPE: DNA
<213> ORGANISM: Homo sapiens

<400> SEQUENCE: 69 tcaggggggct agaaatctgt tgctatgggc ccttcaccaa catgcccaca gatcaactgg      60
aatgg                                                                   65

<210> SEQ ID NO 70
<211> LENGTH: 20
<212> TYPE: DNA
<213> ORGANISM: Homo sapiens

<400> SEQUENCE: 70
agttcgtgct ttgcaagatg                                                   20

<210> SEQ ID NO 71
<211> LENGTH: 20
<212> TYPE: DNA
<213> ORGANISM: Homo sapiens

<400> SEQUENCE: 71
aaggtaagct gggtctgctg                                                   20

<210> SEQ ID NO 72
<211> LENGTH: 70
<212> TYPE: DNA
<213> ORGANISM: Homo sapiens

<400> SEQUENCE: 72
agttcgtgct ttgcaagatg gtgcagagct ttatgaagca gtgaagaatg cagcagaccc      60
agcttacctt                                                              70

<210> SEQ ID NO 73
<211> LENGTH: 21
<212> TYPE: DNA
<213> ORGANISM: Homo sapiens

<400> SEQUENCE: 73
gcatgttcgt ggcctctaag a                                                 21

<210> SEQ ID NO 74
<211> LENGTH: 22
<212> TYPE: DNA
<213> ORGANISM: Homo sapiens

<400> SEQUENCE: 74
```
cggtgtagat gcacagcttc tc    22

<210> SEQ ID NO 75
<211> LENGTH: 69
<212> TYPE: DNA
<213> ORGANISM: Homo sapiens

<400> SEQUENCE: 75
gcatgttcgt ggcctctaag atgaaggaga ccatcccct gacggccgag aagctgtgca    60
tctacaccg    69

<210> SEQ ID NO 76
<211> LENGTH: 20
<212> TYPE: DNA
<213> ORGANISM: Homo sapiens

<400> SEQUENCE: 76
agatgaagtg gaaggcgctt    20

<210> SEQ ID NO 77
<211> LENGTH: 21
<212> TYPE: DNA
<213> ORGANISM: Homo sapiens

<400> SEQUENCE: 77
tgcctctgta atcggcaact g    21

<210> SEQ ID NO 78
<211> LENGTH: 65
<212> TYPE: DNA
<213> ORGANISM: Homo sapiens

<400> SEQUENCE: 78
agatgaagtg gaaggcgctt ttcaccgcgg ccatcctgca ggcacagttg ccgattacag    60
aggca    65

<210> SEQ ID NO 79
<211> LENGTH: 18
<212> TYPE: DNA
<213> ORGANISM: Homo sapiens

<400> SEQUENCE: 79
tggttcccag ccctgtgt    18

<210> SEQ ID NO 80
<211> LENGTH: 19
<212> TYPE: DNA
<213> ORGANISM: Homo sapiens

<400> SEQUENCE: 80
ctcctccacc ctgggttgt    19

<210> SEQ ID NO 81
<211> LENGTH: 74
<212> TYPE: DNA
<213> ORGANISM: Homo sapiens

<400> SEQUENCE: 81
tggttcccag ccctgtgtcc acctccaagc ccagattcag attcgagtca tgtacacaac    60
ccagggtgga ggag    74

```
<210> SEQ ID NO 82
<211> LENGTH: 20
<212> TYPE: DNA
<213> ORGANISM: Homo sapiens

<400> SEQUENCE: 82
tcttgctggc tacgcctctt                                                    20

<210> SEQ ID NO 83
<211> LENGTH: 21
<212> TYPE: DNA
<213> ORGANISM: Homo sapiens

<400> SEQUENCE: 83
ctgcattgtg gcacagttct g                                                  21

<210> SEQ ID NO 84
<211> LENGTH: 71
<212> TYPE: DNA
<213> ORGANISM: Homo sapiens

<400> SEQUENCE: 84
tcttgctggc tacgcctctt ctgtccctgt tagacgtcct ccgtccatat cagaactgtg        60
ccacaatgca g                                                             71

<210> SEQ ID NO 85
<211> LENGTH: 21
<212> TYPE: DNA
<213> ORGANISM: Homo sapiens

<400> SEQUENCE: 85
tgagtgtccc ccggtatctt c                                                  21

<210> SEQ ID NO 86
<211> LENGTH: 21
<212> TYPE: DNA
<213> ORGANISM: Homo sapiens

<400> SEQUENCE: 86
cagccgcttt cagattttca t                                                  21

<210> SEQ ID NO 87
<211> LENGTH: 81
<212> TYPE: DNA
<213> ORGANISM: Homo sapiens

<400> SEQUENCE: 87
tgagtgtccc ccggtatctt ccccgccctg ccaatcccga tgaaattgga aattttattg        60
atgaaaatct gaaagcggct g                                                  81

<210> SEQ ID NO 88
<211> LENGTH: 21
<212> TYPE: DNA
<213> ORGANISM: Homo sapiens

<400> SEQUENCE: 88
tggagactct cagggtcgaa a                                                  21

<210> SEQ ID NO 89
<211> LENGTH: 22
<212> TYPE: DNA
<213> ORGANISM: Homo sapiens
```

```
<400> SEQUENCE: 89
ggcgtttgga gtggtagaaa tc                                             22

<210> SEQ ID NO 90
<211> LENGTH: 65
<212> TYPE: DNA
<213> ORGANISM: Homo sapiens

<400> SEQUENCE: 90
tggagactct cagggtcgaa acggcggca gaccagcatg acagatttct accactccaa     60
acgcc                                                                65

<210> SEQ ID NO 91
<211> LENGTH: 21
<212> TYPE: DNA
<213> ORGANISM: Homo sapiens

<400> SEQUENCE: 91
cggtggacca cgaagagtta a                                              21

<210> SEQ ID NO 92
<211> LENGTH: 19
<212> TYPE: DNA
<213> ORGANISM: Homo sapiens

<400> SEQUENCE: 92
ggctcgcctc ttccatgtc                                                 19

<210> SEQ ID NO 93
<211> LENGTH: 66
<212> TYPE: DNA
<213> ORGANISM: Homo sapiens

<400> SEQUENCE: 93
cggtggacca cgaagagtta acccgggact tggagaagca ctgcagagac atggaagagg    60
cgagcc                                                               66

<210> SEQ ID NO 94
<211> LENGTH: 19
<212> TYPE: DNA
<213> ORGANISM: Homo sapiens

<400> SEQUENCE: 94
gcggaaggtc cctcagaca                                                 19

<210> SEQ ID NO 95
<211> LENGTH: 23
<212> TYPE: DNA
<213> ORGANISM: Homo sapiens

<400> SEQUENCE: 95
tctaagtttc ccgaggtttc tca                                            23

<210> SEQ ID NO 96
<211> LENGTH: 70
<212> TYPE: DNA
<213> ORGANISM: Homo sapiens

<400> SEQUENCE: 96
gcggaaggtc cctcagacat ccccgattga aagaaccaga gaggctctga gaaacctcgg    60
gaaacttaga                                                           70
```

<210> SEQ ID NO 97
<211> LENGTH: 22
<212> TYPE: DNA
<213> ORGANISM: Homo sapiens

<400> SEQUENCE: 97
ccagctttgt gcctgtcact at                                              22

<210> SEQ ID NO 98
<211> LENGTH: 20
<212> TYPE: DNA
<213> ORGANISM: Homo sapiens

<400> SEQUENCE: 98
gggaatgtgg tagcccaaga                                                 20

<210> SEQ ID NO 99
<211> LENGTH: 71
<212> TYPE: DNA
<213> ORGANISM: Homo sapiens

<400> SEQUENCE: 99
ccagctttgt gcctgtcact attcctcatg ccaccactgc caacacctct gtcttgggct     60
accacattcc c                                                          71

<210> SEQ ID NO 100
<211> LENGTH: 27
<212> TYPE: DNA
<213> ORGANISM: Homo sapiens

<400> SEQUENCE: 100
ttgctataac taagtgcttc tccaaga                                         27

<210> SEQ ID NO 101
<211> LENGTH: 22
<212> TYPE: DNA
<213> ORGANISM: Homo sapiens

<400> SEQUENCE: 101
gtggaatggc agctcactgt ag                                              22

<210> SEQ ID NO 102
<211> LENGTH: 73
<212> TYPE: DNA
<213> ORGANISM: Homo sapiens

<400> SEQUENCE: 102
ttgctataac taagtgcttc tccaagaccc caactgagtc cccagcacct gctacagtga     60
gctgccattc cac                                                        73

<210> SEQ ID NO 103
<211> LENGTH: 19
<212> TYPE: DNA
<213> ORGANISM: Homo sapiens

<400> SEQUENCE: 103
aggacgcaag gagggtttg                                                  19

<210> SEQ ID NO 104
<211> LENGTH: 21
<212> TYPE: DNA

<210> SEQ ID NO 105
<211> LENGTH: 87
<212> TYPE: DNA
<213> ORGANISM: Homo sapiens

<400> SEQUENCE: 104
gatgtccgcc gagtccttac t                                      21

<210> SEQ ID NO 105
<211> LENGTH: 87
<212> TYPE: DNA
<213> ORGANISM: Homo sapiens

<400> SEQUENCE: 105
aggacgcaag gagggtttgt cactggcaga ctcgagactg taggcactgc catggcccct     60
gtgctcagta aggactcggc ggacatc                                        87

<210> SEQ ID NO 106
<211> LENGTH: 24
<212> TYPE: DNA
<213> ORGANISM: Homo sapiens

<400> SEQUENCE: 106
ctatatgcag ccagagatgt gaca                                  24

<210> SEQ ID NO 107
<211> LENGTH: 24
<212> TYPE: DNA
<213> ORGANISM: Homo sapiens

<400> SEQUENCE: 107
ccacgagttt cttactgaga atgg                                  24

<210> SEQ ID NO 108
<211> LENGTH: 82
<212> TYPE: DNA
<213> ORGANISM: Homo sapiens

<400> SEQUENCE: 108
ctatatgcag ccagagatgt gacagccacc gtggacagcc tgccactcat cacagcctcc     60
attctcagta agaaactcgt gg                                            82

<210> SEQ ID NO 109
<211> LENGTH: 20
<212> TYPE: DNA
<213> ORGANISM: Homo sapiens

<400> SEQUENCE: 109
tgtcgatgga cttccagaac                                      20

<210> SEQ ID NO 110
<211> LENGTH: 19
<212> TYPE: DNA
<213> ORGANISM: Homo sapiens

<400> SEQUENCE: 110
attgggacag cttggatca                                       19

<210> SEQ ID NO 111
<211> LENGTH: 62
<212> TYPE: DNA
<213> ORGANISM: Homo sapiens

<400> SEQUENCE: 111
tgtcgatgga cttccagaac cacctgggca gctgccaaaa gtgtgatcca agctgtccca     60

```
at                                                                    62

<210> SEQ ID NO 112
<211> LENGTH: 23
<212> TYPE: DNA
<213> ORGANISM: Homo sapiens

<400> SEQUENCE: 112
gatctaagat ggcgactgtc gaa                                             23

<210> SEQ ID NO 113
<211> LENGTH: 25
<212> TYPE: DNA
<213> ORGANISM: Homo sapiens

<400> SEQUENCE: 113
ttagattccg ttttctcctc ttctg                                           25

<210> SEQ ID NO 114
<211> LENGTH: 82
<212> TYPE: DNA
<213> ORGANISM: Homo sapiens

<400> SEQUENCE: 114
gatctaagat ggcgactgtc gaaccggaaa ccacccctac tcctaatccc ccgactacag     60
aagaggagaa aacggaatct aa                                              82

<210> SEQ ID NO 115
<211> LENGTH: 20
<212> TYPE: DNA
<213> ORGANISM: Homo sapiens

<400> SEQUENCE: 115
cggtgtgaga agtgcagcaa                                                 20

<210> SEQ ID NO 116
<211> LENGTH: 19
<212> TYPE: DNA
<213> ORGANISM: Homo sapiens

<400> SEQUENCE: 116
cctctcgcaa gtgctccat                                                  19

<210> SEQ ID NO 117
<211> LENGTH: 70
<212> TYPE: DNA
<213> ORGANISM: Homo sapiens

<400> SEQUENCE: 117
cggtgtgaga agtgcagcaa gccctgtgcc cgagtgtgct atggtctggg catggagcac     60
ttgcgagagg                                                            70

<210> SEQ ID NO 118
<211> LENGTH: 23
<212> TYPE: DNA
<213> ORGANISM: Homo sapiens

<400> SEQUENCE: 118
cggttatgtc atgccagata cac                                             23

<210> SEQ ID NO 119
```

```
<211> LENGTH: 24
<212> TYPE: DNA
<213> ORGANISM: Homo sapiens

<400> SEQUENCE: 119
gaactgagac ccactgaaga aagg                                              24

<210> SEQ ID NO 120
<211> LENGTH: 81
<212> TYPE: DNA
<213> ORGANISM: Homo sapiens

<400> SEQUENCE: 120
cggttatgtc atgccagata cacacctcaa aggtactccc tcctcccggg aaggcaccct       60
ttcttcagtg ggtctcagtt c                                                 81

<210> SEQ ID NO 121
<211> LENGTH: 19
<212> TYPE: DNA
<213> ORGANISM: Homo sapiens

<400> SEQUENCE: 121
cgtggtgccc ctctatgac                                                    19

<210> SEQ ID NO 122
<211> LENGTH: 19
<212> TYPE: DNA
<213> ORGANISM: Homo sapiens

<400> SEQUENCE: 122
ggctagtggg cgcatgtag                                                    19

<210> SEQ ID NO 123
<211> LENGTH: 68
<212> TYPE: DNA
<213> ORGANISM: Homo sapiens

<400> SEQUENCE: 123
cgtggtgccc ctctatgacc tgctgctgga gatgctggac gcccaccgcc tacatgcgcc       60
cactagcc                                                                68

<210> SEQ ID NO 124
<211> LENGTH: 20
<212> TYPE: DNA
<213> ORGANISM: Homo sapiens

<400> SEQUENCE: 124
tggtccatcg ccagttatca                                                   20

<210> SEQ ID NO 125
<211> LENGTH: 23
<212> TYPE: DNA
<213> ORGANISM: Homo sapiens

<400> SEQUENCE: 125
tgttctagcg atcttgcttc aca                                               23

<210> SEQ ID NO 126
<211> LENGTH: 76
<212> TYPE: DNA
<213> ORGANISM: Homo sapiens

<400> SEQUENCE: 126
```

```
tggtccatcg ccagttatca catctgtatg cggaacctca aaagagtccc tggtgtgaag    60
caagatcgct agaaca                                                    76
```

<210> SEQ ID NO 127
<211> LENGTH: 24
<212> TYPE: DNA
<213> ORGANISM: Homo sapiens

<400> SEQUENCE: 127

```
catccatgac aactttggta tcgt                                           24
```

<210> SEQ ID NO 128
<211> LENGTH: 21
<212> TYPE: DNA
<213> ORGANISM: Homo sapiens

<400> SEQUENCE: 128

```
cagtcttctg ggtggcagtg a                                              21
```

<210> SEQ ID NO 129
<211> LENGTH: 74
<212> TYPE: DNA
<213> ORGANISM: Homo sapiens

<400> SEQUENCE: 129

```
catccatgac aactttggta tcgtggaagg actcatgacc acagtccatg ccatcactgc    60
cacccagaag actg                                                      74
```

<210> SEQ ID NO 130
<211> LENGTH: 23
<212> TYPE: DNA
<213> ORGANISM: Homo sapiens

<400> SEQUENCE: 130

```
caaaggagct cactgtggtg tct                                            23
```

<210> SEQ ID NO 131
<211> LENGTH: 26
<212> TYPE: DNA
<213> ORGANISM: Homo sapiens

<400> SEQUENCE: 131

```
gagtcagaat ggcttattca cagatg                                         26
```

<210> SEQ ID NO 132
<211> LENGTH: 75
<212> TYPE: DNA
<213> ORGANISM: Homo sapiens

<400> SEQUENCE: 132

```
caaaggagct cactgtggtg tctgtgttcc aaccactgaa tctggacccc atctgtgaat    60
aagccattct gactc                                                     75
```

<210> SEQ ID NO 133
<211> LENGTH: 20
<212> TYPE: DNA
<213> ORGANISM: Homo sapiens

<400> SEQUENCE: 133

```
ccatctgcat ccatcttgtt                                                20
```

<210> SEQ ID NO 134
<211> LENGTH: 20
<212> TYPE: DNA
<213> ORGANISM: Homo sapiens

<400> SEQUENCE: 134
ggccaccagg gtattatctg                                            20

<210> SEQ ID NO 135
<211> LENGTH: 67
<212> TYPE: DNA
<213> ORGANISM: Homo sapiens

<400> SEQUENCE: 135
ccatctgcat ccatcttgtt tgggctcccc acccttgaga agtgcctcag ataataccct    60
ggtggcc                                                          67

<210> SEQ ID NO 136
<211> LENGTH: 23
<212> TYPE: DNA
<213> ORGANISM: Homo sapiens

<400> SEQUENCE: 136
cgaaaagatg ctgaacagtg aca                                        23

<210> SEQ ID NO 137
<211> LENGTH: 20
<212> TYPE: DNA
<213> ORGANISM: Homo sapiens

<400> SEQUENCE: 137
tcaggaacag ccaccagtga                                            20

<210> SEQ ID NO 138
<211> LENGTH: 73
<212> TYPE: DNA
<213> ORGANISM: Homo sapiens

<400> SEQUENCE: 138
cgaaaagatg ctgaacagtg acaaatccaa ctgaccagaa gggaggagga agctcactgg    60
tggctgttcc tga                                                   73

<210> SEQ ID NO 139
<211> LENGTH: 20
<212> TYPE: DNA
<213> ORGANISM: Homo sapiens

<400> SEQUENCE: 139
gagaccctgc tgtcccagaa                                            20

<210> SEQ ID NO 140
<211> LENGTH: 23
<212> TYPE: DNA
<213> ORGANISM: Homo sapiens

<400> SEQUENCE: 140
ggttgtagtc agcgaaggag atc                                        23

<210> SEQ ID NO 141
<211> LENGTH: 76
<212> TYPE: DNA
<213> ORGANISM: Homo sapiens

```
<400> SEQUENCE: 141
gagaccctgc tgtcccagaa ccagggaggc aagaccttca ttgtgggaga ccagatctcc    60
ttcgctgact acaacc                                                    76

<210> SEQ ID NO 142
<211> LENGTH: 20
<212> TYPE: DNA
<213> ORGANISM: Homo sapiens

<400> SEQUENCE: 142
cccactcagt agccaagtca                                                20

<210> SEQ ID NO 143
<211> LENGTH: 20
<212> TYPE: DNA
<213> ORGANISM: Homo sapiens

<400> SEQUENCE: 143
cacgcaggtg gtatcagtct                                                20

<210> SEQ ID NO 144
<211> LENGTH: 73
<212> TYPE: DNA
<213> ORGANISM: Homo sapiens

<400> SEQUENCE: 144
cccactcagt agccaagtca caatgtttgg aaaacagccc gtttacttga gcaagactga    60
taccacctgc gtg                                                       73

<210> SEQ ID NO 145
<211> LENGTH: 24
<212> TYPE: DNA
<213> ORGANISM: Homo sapiens

<400> SEQUENCE: 145
catcaaatgt cagccctgga gttc                                           24

<210> SEQ ID NO 146
<211> LENGTH: 26
<212> TYPE: DNA
<213> ORGANISM: Homo sapiens

<400> SEQUENCE: 146
ttcctgtagg tctttacccc gatagc                                         26

<210> SEQ ID NO 147
<211> LENGTH: 85
<212> TYPE: DNA
<213> ORGANISM: Homo sapiens

<400> SEQUENCE: 147
catcaaatgt cagccctgga gttccatgat accacacgaa cacagctttt tgccttcgag    60
ctatcggggt aaagacctac aggaa                                          85

<210> SEQ ID NO 148
<211> LENGTH: 24
<212> TYPE: DNA
<213> ORGANISM: Homo sapiens

<400> SEQUENCE: 148
```

```
tccaggatgt taggaactgt gaag                                          24

<210> SEQ ID NO 149
<211> LENGTH: 22
<212> TYPE: DNA
<213> ORGANISM: Homo sapiens

<400> SEQUENCE: 149
gcgtgtctgc gtagtagctg tt                                            22

<210> SEQ ID NO 150
<211> LENGTH: 73
<212> TYPE: DNA
<213> ORGANISM: Homo sapiens

<400> SEQUENCE: 150
tccaggatgt taggaactgt gaagatggaa gggcatgaaa ccagcgactg aacagctac    60 tacgcagaca cgc                                                      73

<210> SEQ ID NO 151
<211> LENGTH: 23
<212> TYPE: DNA
<213> ORGANISM: Homo sapiens

<400> SEQUENCE: 151
aacgactgct actccaagct caa                                           23

<210> SEQ ID NO 152
<211> LENGTH: 22
<212> TYPE: DNA
<213> ORGANISM: Homo sapiens

<400> SEQUENCE: 152
ggatttccat cttgctcacc tt                                            22

<210> SEQ ID NO 153
<211> LENGTH: 76
<212> TYPE: DNA
<213> ORGANISM: Homo sapiens

<400> SEQUENCE: 153
aacgactgct actccaagct caaggagctg gtgcccagca tcccccagaa caagaaggtg   60
agcaagatgg aaatcc                                                   76

<210> SEQ ID NO 154
<211> LENGTH: 21
<212> TYPE: DNA
<213> ORGANISM: Homo sapiens

<400> SEQUENCE: 154
tccggagctg tgatctaagg a                                             21

<210> SEQ ID NO 155
<211> LENGTH: 20
<212> TYPE: DNA
<213> ORGANISM: Homo sapiens

<400> SEQUENCE: 155
cggacagagc gagctgactt                                               20

<210> SEQ ID NO 156
<211> LENGTH: 76
```

<212> TYPE: DNA
<213> ORGANISM: Homo sapiens

<400> SEQUENCE: 156
tccggagctg tgatctaagg aggctggaga tgtattgcgc acccctcaag cctgccaagt    60
cagctcgctc tgtccg    76

<210> SEQ ID NO 157
<211> LENGTH: 17
<212> TYPE: DNA
<213> ORGANISM: Homo sapiens

<400> SEQUENCE: 157
acgcaccggg tgtctga    17

<210> SEQ ID NO 158
<211> LENGTH: 24
<212> TYPE: DNA
<213> ORGANISM: Homo sapiens

<400> SEQUENCE: 158
tgccctttct tgatgatgat tatc    24

<210> SEQ ID NO 159
<211> LENGTH: 68
<212> TYPE: DNA
<213> ORGANISM: Homo sapiens

<400> SEQUENCE: 159
acgcaccggg tgtctgatcc caagttccac cccctccatt caaagataat catcatcaag    60
aaagggca    68

<210> SEQ ID NO 160
<211> LENGTH: 22
<212> TYPE: DNA
<213> ORGANISM: Homo sapiens

<400> SEQUENCE: 160
ccattcaccc tgtgtaacag ga    22

<210> SEQ ID NO 161
<211> LENGTH: 21
<212> TYPE: DNA
<213> ORGANISM: Homo sapiens

<400> SEQUENCE: 161
ccgaccctct aggttaaggc a    21

<210> SEQ ID NO 162
<211> LENGTH: 68
<212> TYPE: DNA
<213> ORGANISM: Homo sapiens

<400> SEQUENCE: 162
ccattcaccc tgtgtaacag gaccccaagg acctgcctcc ccggaagtgc cttaacctag    60
agggtcgg    68

<210> SEQ ID NO 163
<211> LENGTH: 20
<212> TYPE: DNA
<213> ORGANISM: Homo sapiens

<400> SEQUENCE: 163
cgtcaggacc caccatgtct                                              20

<210> SEQ ID NO 164
<211> LENGTH: 24
<212> TYPE: DNA
<213> ORGANISM: Homo sapiens

<400> SEQUENCE: 164
ggttaattgg tgacatcctc aaga                                         24

<210> SEQ ID NO 165
<211> LENGTH: 81
<212> TYPE: DNA
<213> ORGANISM: Homo sapiens

<400> SEQUENCE: 165
cgtcaggacc caccatgtct gccccatcac gcggccgaga catggcttgg ccacagctct   60
tgaggatgtc accaattaac c                                            81

<210> SEQ ID NO 166
<211> LENGTH: 23
<212> TYPE: DNA
<213> ORGANISM: Homo sapiens

<400> SEQUENCE: 166
caaacgctga catgtacggt cta                                          23

<210> SEQ ID NO 167
<211> LENGTH: 18
<212> TYPE: DNA
<213> ORGANISM: Homo sapiens

<400> SEQUENCE: 167
gctcgttggc gcactctt                                                18

<210> SEQ ID NO 168
<211> LENGTH: 88
<212> TYPE: DNA
<213> ORGANISM: Homo sapiens

<400> SEQUENCE: 168
caaacgctga catgtacggt ctatgccatt cctcccccgc atcacatcca ctggtattgg   60
cagttggagg aagagtgcgc caacgagc                                     88

<210> SEQ ID NO 169
<211> LENGTH: 25
<212> TYPE: DNA
<213> ORGANISM: Homo sapiens

<400> SEQUENCE: 169
gaggcaactg cttatggctt aatta                                        25

<210> SEQ ID NO 170
<211> LENGTH: 18
<212> TYPE: DNA
<213> ORGANISM: Homo sapiens

<400> SEQUENCE: 170
ggcactcggc ttgagcat                                                18

```
<210> SEQ ID NO 171
<211> LENGTH: 75
<212> TYPE: DNA
<213> ORGANISM: Homo sapiens

<400> SEQUENCE: 171
gaggcaactg cttatggctt aattaagtca gatgcggcca tgactgtcgc tgtaaagatg      60
ctcaagccga gtgcc                                                      75

<210> SEQ ID NO 172
<211> LENGTH: 18
<212> TYPE: DNA
<213> ORGANISM: Homo sapiens

<400> SEQUENCE: 172
gtccccggga tggatgtt                                                   18

<210> SEQ ID NO 173
<211> LENGTH: 25
<212> TYPE: DNA
<213> ORGANISM: Homo sapiens

<400> SEQUENCE: 173
gatcagtcaa gctgtctgac aattg                                           25

<210> SEQ ID NO 174
<211> LENGTH: 79
<212> TYPE: DNA
<213> ORGANISM: Homo sapiens

<400> SEQUENCE: 174
gtccccggga tggatgtttt gccaagtcat tgttggataa gcgagatggt agtacaattg      60
tcagacagct tgactgatc                                                  79

<210> SEQ ID NO 175
<211> LENGTH: 21
<212> TYPE: DNA
<213> ORGANISM: Homo sapiens

<400> SEQUENCE: 175
cgaggattgg ttcttcagca a                                               21

<210> SEQ ID NO 176
<211> LENGTH: 22
<212> TYPE: DNA
<213> ORGANISM: Homo sapiens

<400> SEQUENCE: 176
actctgcacc agctcactgt tg                                              22

<210> SEQ ID NO 177
<211> LENGTH: 73
<212> TYPE: DNA
<213> ORGANISM: Homo sapiens

<400> SEQUENCE: 177
cgaggattgg ttcttcagca agacagagga actgaaccgc gaggtggcca ccaacagtga      60
gctggtgcag agt                                                        73

<210> SEQ ID NO 178
<211> LENGTH: 20
<212> TYPE: DNA
```

```
<213> ORGANISM: Homo sapiens

<400> SEQUENCE: 178
tcagtggaga aggagttgga                                                    20

<210> SEQ ID NO 179
<211> LENGTH: 20
<212> TYPE: DNA
<213> ORGANISM: Homo sapiens

<400> SEQUENCE: 179
tgccatatcc agaggaaaca                                                    20

<210> SEQ ID NO 180
<211> LENGTH: 69
<212> TYPE: DNA
<213> ORGANISM: Homo sapiens

<400> SEQUENCE: 180
tcagtggaga aggagttgga ccagtcaaca tctctgttgt cacaagcagt gtttcctctg        60
gatatggca                                                                69

<210> SEQ ID NO 181
<211> LENGTH: 26
<212> TYPE: DNA
<213> ORGANISM: Homo sapiens

<400> SEQUENCE: 181
gtacaagaga gaaccagact ccaatg                                             26

<210> SEQ ID NO 182
<211> LENGTH: 18
<212> TYPE: DNA
<213> ORGANISM: Homo sapiens

<400> SEQUENCE: 182
gtgtagcccg cggacact                                                      18

<210> SEQ ID NO 183
<211> LENGTH: 87
<212> TYPE: DNA
<213> ORGANISM: Homo sapiens

<400> SEQUENCE: 183
gtacaagaga gaaccagact ccaatgtcat tgtggtggac tggctgtcac gggctcagga        60
gcattaccca gtgtccgcgg gctacac                                            87

<210> SEQ ID NO 184
<211> LENGTH: 22
<212> TYPE: DNA
<213> ORGANISM: Homo sapiens

<400> SEQUENCE: 184
gacatttcca gtcctgcagt ca                                                 22

<210> SEQ ID NO 185
<211> LENGTH: 20
<212> TYPE: DNA
<213> ORGANISM: Homo sapiens

<400> SEQUENCE: 185
ctccgatcgc acacatttgt                                                    20
```

<210> SEQ ID NO 186
<211> LENGTH: 86
<212> TYPE: DNA
<213> ORGANISM: Homo sapiens

<400> SEQUENCE: 186
gacatttcca gtcctgcagt caatgcctct ctgccccacc ctttgttcag tgtggctggt    60
gccacgacaa atgtgtgcga tcggag                                        86

<210> SEQ ID NO 187
<211> LENGTH: 24
<212> TYPE: DNA
<213> ORGANISM: Homo sapiens

<400> SEQUENCE: 187
gttttggagg aaatgtgttc ttca                                          24

<210> SEQ ID NO 188
<211> LENGTH: 26
<212> TYPE: DNA
<213> ORGANISM: Homo sapiens

<400> SEQUENCE: 188
ttctctaata cactgccgtc ttaagg                                        26

<210> SEQ ID NO 189
<211> LENGTH: 101
<212> TYPE: DNA
<213> ORGANISM: Homo sapiens

<400> SEQUENCE: 189
gttttggagg aaatgtgttc ttcagtgcac agaatgcagc aaaacagcca tctgataaat    60
gctctgcaag ccctccctta agacggcagt gtattagaga a                       101

<210> SEQ ID NO 190
<211> LENGTH: 22
<212> TYPE: DNA
<213> ORGANISM: Homo sapiens

<400> SEQUENCE: 190
acgagaacga gggcatctat gt                                            22

<210> SEQ ID NO 191
<211> LENGTH: 22
<212> TYPE: DNA
<213> ORGANISM: Homo sapiens

<400> SEQUENCE: 191
gcatgtaggt gcttccaatc ac                                            22

<210> SEQ ID NO 192
<211> LENGTH: 75
<212> TYPE: DNA
<213> ORGANISM: Homo sapiens

<400> SEQUENCE: 192
acgagaacga gggcatctat gtgcaggatg tcaagaccgg aaaggtgcgc gctgtgattg    60
gaagcaccta catgc                                                    75

<210> SEQ ID NO 193

```
<211> LENGTH: 21
<212> TYPE: DNA
<213> ORGANISM: Homo sapiens

<400> SEQUENCE: 193
tccctccact cggaaggact a                                              21

<210> SEQ ID NO 194
<211> LENGTH: 22
<212> TYPE: DNA
<213> ORGANISM: Homo sapiens

<400> SEQUENCE: 194
cggttgttgc tgatctgtct ca                                             22

<210> SEQ ID NO 195
<211> LENGTH: 84
<212> TYPE: DNA
<213> ORGANISM: Homo sapiens

<400> SEQUENCE: 195
tccctccact cggaaggact atcctgctgc caagagggtc aagttggaca gtgtcagagt    60
cctgagacag atcagcaaca accg                                           84

<210> SEQ ID NO 196
<211> LENGTH: 19
<212> TYPE: DNA
<213> ORGANISM: Homo sapiens

<400> SEQUENCE: 196
ttgttggtgt gccctggtg                                                 19

<210> SEQ ID NO 197
<211> LENGTH: 21
<212> TYPE: DNA
<213> ORGANISM: Homo sapiens

<400> SEQUENCE: 197
tgggttctgt ccaaacactg g                                              21

<210> SEQ ID NO 198
<211> LENGTH: 67
<212> TYPE: DNA
<213> ORGANISM: Homo sapiens

<400> SEQUENCE: 198
ttgttggtgt gccctggtgc cgtggtggcg gtcactccct ctgctgccag tgtttggaca    60
gaaccca                                                              67

<210> SEQ ID NO 199
<211> LENGTH: 20
<212> TYPE: DNA
<213> ORGANISM: Homo sapiens

<400> SEQUENCE: 199
actgaaggag acccttggag                                                20

<210> SEQ ID NO 200
<211> LENGTH: 20
<212> TYPE: DNA
<213> ORGANISM: Homo sapiens

<400> SEQUENCE: 200
```

```
taaataaccc tgcccacaca                                          20

<210> SEQ ID NO 201
<211> LENGTH: 62
<212> TYPE: DNA
<213> ORGANISM: Homo sapiens

<400> SEQUENCE: 201
actgaaggag acccttggag cctaggggca tcggcaggag agtgtgtggg cagggttatt    60
ta                                                             62

<210> SEQ ID NO 202
<211> LENGTH: 28
<212> TYPE: DNA
<213> ORGANISM: Homo sapiens

<400> SEQUENCE: 202
agttactaaa aataccacg aggtcctt                                  28

<210> SEQ ID NO 203
<211> LENGTH: 21
<212> TYPE: DNA
<213> ORGANISM: Homo sapiens

<400> SEQUENCE: 203
gtcggtgagt gatttgtgca a                                        21

<210> SEQ ID NO 204
<211> LENGTH: 79
<212> TYPE: DNA
<213> ORGANISM: Homo sapiens

<400> SEQUENCE: 204
agttactaaa aataccacg aggtccttca gttgagacca agaccggtg tcaggggatt     60 gcacaaatca ctcaccgac                                           79

<210> SEQ ID NO 205
<211> LENGTH: 20
<212> TYPE: DNA
<213> ORGANISM: Homo sapiens

<400> SEQUENCE: 205
gggagtttcc aagagatgga                                          20

<210> SEQ ID NO 206
<211> LENGTH: 20
<212> TYPE: DNA
<213> ORGANISM: Homo sapiens

<400> SEQUENCE: 206
cttcaaccac cttcccaaac                                          20

<210> SEQ ID NO 207
<211> LENGTH: 72
<212> TYPE: DNA
<213> ORGANISM: Homo sapiens

<400> SEQUENCE: 207
gggagtttcc aagagatgga ctagtgcttg gtcgggtctt gggtctgga gcgtttggga    60 aggtggttga ag                                                  72
```

```
<210> SEQ ID NO 208
<211> LENGTH: 23
<212> TYPE: DNA
<213> ORGANISM: Homo sapiens

<400> SEQUENCE: 208
aggtgtcatc catcaacgtc tct                                            23

<210> SEQ ID NO 209
<211> LENGTH: 20
<212> TYPE: DNA
<213> ORGANISM: Homo sapiens

<400> SEQUENCE: 209
tcccgatcac aatgcacatg                                                20

<210> SEQ ID NO 210
<211> LENGTH: 90
<212> TYPE: DNA
<213> ORGANISM: Homo sapiens

<400> SEQUENCE: 210
aggtgtcatc catcaacgtc tctgtgaacg cagtgcagac tgtggtccgc cagggtgaga    60
acatcaccct catgtgcatt gtgatcggga                                     90

<210> SEQ ID NO 211
<211> LENGTH: 24
<212> TYPE: DNA
<213> ORGANISM: Homo sapiens

<400> SEQUENCE: 211
agagccagtt gctgtagaac tcaa                                           24

<210> SEQ ID NO 212
<211> LENGTH: 21
<212> TYPE: DNA
<213> ORGANISM: Homo sapiens

<400> SEQUENCE: 212
ctgggcctac acagtccttc a                                              21

<210> SEQ ID NO 213
<211> LENGTH: 74
<212> TYPE: DNA
<213> ORGANISM: Homo sapiens

<400> SEQUENCE: 213
agagccagtt gctgtagaac tcaaatctct gctgggcaag gatgttctgt tcttgaagga    60
ctgtgtaggc ccag                                                      74

<210> SEQ ID NO 214
<211> LENGTH: 26
<212> TYPE: DNA
<213> ORGANISM: Homo sapiens

<400> SEQUENCE: 214
gaaatgactg catcgttgat aaaatc                                         26

<210> SEQ ID NO 215
<211> LENGTH: 19
<212> TYPE: DNA
<213> ORGANISM: Homo sapiens
```

<400> SEQUENCE: 215
tgccagcctg acagcactt                                                  19

<210> SEQ ID NO 216
<211> LENGTH: 78
<212> TYPE: DNA
<213> ORGANISM: Homo sapiens

<400> SEQUENCE: 216
gaaatgactg catcgttgat aaaatccgca gaaaaaactg cccagcatgt cgccttagaa     60
agtgctgtca ggctggca                                                   78

<210> SEQ ID NO 217
<211> LENGTH: 20
<212> TYPE: DNA
<213> ORGANISM: Homo sapiens

<400> SEQUENCE: 217
gatcaacggc tacatccaga                                                 20

<210> SEQ ID NO 218
<211> LENGTH: 20
<212> TYPE: DNA
<213> ORGANISM: Homo sapiens

<400> SEQUENCE: 218
tgaactgtga ggccagagac                                                 20

<210> SEQ ID NO 219
<211> LENGTH: 68
<212> TYPE: DNA
<213> ORGANISM: Homo sapiens

<400> SEQUENCE: 219
gatcaacggc tacatccaga agatcaagtc gggagaggag gactttgagt ctctggcctc     60
acagttca                                                              68

<210> SEQ ID NO 220
<211> LENGTH: 19
<212> TYPE: DNA
<213> ORGANISM: Homo sapiens

<400> SEQUENCE: 220
gtggatgtgc cctgaagga                                                  19

<210> SEQ ID NO 221
<211> LENGTH: 20
<212> TYPE: DNA
<213> ORGANISM: Homo sapiens

<400> SEQUENCE: 221
ctgcggatcc agggtaagaa                                                 20

<210> SEQ ID NO 222
<211> LENGTH: 70
<212> TYPE: DNA
<213> ORGANISM: Homo sapiens

<400> SEQUENCE: 222
gtggatgtgc cctgaaggac aagccaggcg tctacacgag agtctcacac ttcttaccct     60

```
-continued
ggatccgcag                                                              70

<210> SEQ ID NO 223
<211> LENGTH: 27
<212> TYPE: DNA
<213> ORGANISM: Homo sapiens

<400> SEQUENCE: 223
tggacttcta gtgatgagaa agattga                                           27

<210> SEQ ID NO 224
<211> LENGTH: 22
<212> TYPE: DNA
<213> ORGANISM: Homo sapiens

<400> SEQUENCE: 224
cactgcgaga tcaccacagg ta                                                22

<210> SEQ ID NO 225
<211> LENGTH: 84
<212> TYPE: DNA
<213> ORGANISM: Homo sapiens

<400> SEQUENCE: 225
tggacttcta gtgatgagaa agattgagaa tgttcccaca ggccccaaca ataagcccaa       60
gctacctgtg gtgatctcgc agtg                                              84

<210> SEQ ID NO 226
<211> LENGTH: 25
<212> TYPE: DNA
<213> ORGANISM: Homo sapiens

<400> SEQUENCE: 226
tggctaagtg aagatgacaa tcatg                                             25

<210> SEQ ID NO 227
<211> LENGTH: 25
<212> TYPE: DNA
<213> ORGANISM: Homo sapiens

<400> SEQUENCE: 227
tgcacatatc attacaccag ttcgt                                             25

<210> SEQ ID NO 228
<211> LENGTH: 81
<212> TYPE: DNA
<213> ORGANISM: Homo sapiens

<400> SEQUENCE: 228
tggctaagtg aagatgacaa tcatgttgca gcaattcact gtaaagctgg aaagggacga      60
actggtgtaa tgatatgtgc a                                                81

<210> SEQ ID NO 229
<211> LENGTH: 23
<212> TYPE: DNA
<213> ORGANISM: Homo sapiens

<400> SEQUENCE: 229
tctgcagagt tggaagcact cta                                               23

<210> SEQ ID NO 230
<211> LENGTH: 21
```

```
<212> TYPE: DNA
<213> ORGANISM: Homo sapiens

<400> SEQUENCE: 230
gccgaggctt ttctaccaga a                                           21

<210> SEQ ID NO 231
<211> LENGTH: 79
<212> TYPE: DNA
<213> ORGANISM: Homo sapiens

<400> SEQUENCE: 231
tctgcagagt tggaagcact ctatggtgac atcgatgctg tggagctgta tcctgccctt    60
ctggtagaaa agcctcggc                                                79

<210> SEQ ID NO 232
<211> LENGTH: 24
<212> TYPE: DNA
<213> ORGANISM: Homo sapiens

<400> SEQUENCE: 232
acgacacgta tgccgtacag tact                                        24

<210> SEQ ID NO 233
<211> LENGTH: 18
<212> TYPE: DNA
<213> ORGANISM: Homo sapiens

<400> SEQUENCE: 233
ccgggaaaac acgaagga                                               18

<210> SEQ ID NO 234
<211> LENGTH: 86
<212> TYPE: DNA
<213> ORGANISM: Homo sapiens

<400> SEQUENCE: 234
acgacacgta tgccgtacag tactcctgcc gcctcctgaa cctcgatggc acctgtgctg    60
acagctactc cttcgtgttt tcccgg                                      86

<210> SEQ ID NO 235
<211> LENGTH: 19
<212> TYPE: DNA
<213> ORGANISM: Homo sapiens

<400> SEQUENCE: 235
ctgccgggat ggcttctat                                              19

<210> SEQ ID NO 236
<211> LENGTH: 22
<212> TYPE: DNA
<213> ORGANISM: Homo sapiens

<400> SEQUENCE: 236
ccaggttctg gaaactgtgg at                                          22

<210> SEQ ID NO 237
<211> LENGTH: 68
<212> TYPE: DNA
<213> ORGANISM: Homo sapiens

<400> SEQUENCE: 237
```

```
ctgccgggat ggcttctatg aggctgagct ctgcccggac cgctgcatcc acagtttcca    60
gaacctgg                                                             68
```

<210> SEQ ID NO 238
<211> LENGTH: 20
<212> TYPE: DNA
<213> ORGANISM: Homo sapiens

<400> SEQUENCE: 238

```
ccacaagctg aaggcagaca                                                20
```

<210> SEQ ID NO 239
<211> LENGTH: 21
<212> TYPE: DNA
<213> ORGANISM: Homo sapiens

<400> SEQUENCE: 239

```
gcgtgcttcc ttggtcttag a                                              21
```

<210> SEQ ID NO 240
<211> LENGTH: 85
<212> TYPE: DNA
<213> ORGANISM: Homo sapiens

<400> SEQUENCE: 240

```
ccacaagctg aaggcagaca aggcccgcaa gaagctcctg gctgaccagg ctgaggcccg    60
caggtctaag accaaggaag cacgc                                          85
```

<210> SEQ ID NO 241
<211> LENGTH: 24
<212> TYPE: DNA
<213> ORGANISM: Homo sapiens

<400> SEQUENCE: 241

```
ccattctatc atcaacgggt acaa                                           24
```

<210> SEQ ID NO 242
<211> LENGTH: 23
<212> TYPE: DNA
<213> ORGANISM: Homo sapiens

<400> SEQUENCE: 242

```
tcagcaagtg ggaaggtgta atc                                            23
```

<210> SEQ ID NO 243
<211> LENGTH: 75
<212> TYPE: DNA
<213> ORGANISM: Homo sapiens

<400> SEQUENCE: 243

```
ccattctatc atcaacgggt acaaacgagt cctggccttg tctgtggaga cggattacac    60
cttcccactt gctga                                                     75
```

<210> SEQ ID NO 244
<211> LENGTH: 20
<212> TYPE: DNA
<213> ORGANISM: Homo sapiens

<400> SEQUENCE: 244

```
tatcgaggca ggtcatacca                                                20
```

```
<210> SEQ ID NO 245
<211> LENGTH: 20
<212> TYPE: DNA
<213> ORGANISM: Homo sapiens

<400> SEQUENCE: 245
taacgcttgg catcatcatt                                                   20

<210> SEQ ID NO 246
<211> LENGTH: 74
<212> TYPE: DNA
<213> ORGANISM: Homo sapiens

<400> SEQUENCE: 246
tatcgaggca ggtcatacca tgaccggaag tcaaaagttg acctggatag gctcaatgat       60
gatgccaagc gtta                                                         74

<210> SEQ ID NO 247
<211> LENGTH: 19
<212> TYPE: DNA
<213> ORGANISM: Homo sapiens

<400> SEQUENCE: 247
ccgcaacgtg gttttctca                                                    19

<210> SEQ ID NO 248
<211> LENGTH: 21
<212> TYPE: DNA
<213> ORGANISM: Homo sapiens

<400> SEQUENCE: 248
tgctgggttt ctcctcctgt t                                                 21

<210> SEQ ID NO 249
<211> LENGTH: 81
<212> TYPE: DNA
<213> ORGANISM: Homo sapiens

<400> SEQUENCE: 249
ccgcaacgtg gttttctcac cctatggggt ggcctcggtg ttggccatgc tccagctgac       60
aacaggagga gaaacccagc a                                                 81

<210> SEQ ID NO 250
<211> LENGTH: 25
<212> TYPE: DNA
<213> ORGANISM: Homo sapiens

<400> SEQUENCE: 250
tcaagaccat catcactttc attgt                                             25

<210> SEQ ID NO 251
<211> LENGTH: 27
<212> TYPE: DNA
<213> ORGANISM: Homo sapiens

<400> SEQUENCE: 251
ggatcaggaa gtacacggag tataact                                           27

<210> SEQ ID NO 252
<211> LENGTH: 96
<212> TYPE: DNA
<213> ORGANISM: Homo sapiens
```

```
<400> SEQUENCE: 252
tcaagaccat catcactttc attgtctcgg acgtgcgggg cctgggcctc ccggtccgca      60
agcagttcca gttatactcc gtgtacttcc tgatcc                                96

<210> SEQ ID NO 253
<211> LENGTH: 19
<212> TYPE: DNA
<213> ORGANISM: Homo sapiens

<400> SEQUENCE: 253
gcccgaaacg ccgaatata                                                   19

<210> SEQ ID NO 254
<211> LENGTH: 23
<212> TYPE: DNA
<213> ORGANISM: Homo sapiens

<400> SEQUENCE: 254
cgtggctctc ttatcctcat gat                                              23

<210> SEQ ID NO 255
<211> LENGTH: 65
<212> TYPE: DNA
<213> ORGANISM: Homo sapiens

<400> SEQUENCE: 255
gcccgaaacg ccgaatataa tcccaagcgg tttgctgcgg taatcatgag gataagagag      60
ccacg                                                                  65

<210> SEQ ID NO 256
<211> LENGTH: 19
<212> TYPE: DNA
<213> ORGANISM: Homo sapiens

<400> SEQUENCE: 256
gccctcccag tgtgcaaat                                                   19

<210> SEQ ID NO 257
<211> LENGTH: 25
<212> TYPE: DNA
<213> ORGANISM: Homo sapiens

<400> SEQUENCE: 257
cgtcgatggt attaggatag aagca                                            25

<210> SEQ ID NO 258
<211> LENGTH: 86
<212> TYPE: DNA
<213> ORGANISM: Homo sapiens

<400> SEQUENCE: 258
gccctcccag tgtgcaaata agggctgctg tttcgacgac accgttcgtg gggtcccctg      60
gtgcttctat cctaatacca tcgacg                                           86

<210> SEQ ID NO 259
<211> LENGTH: 27
<212> TYPE: DNA
<213> ORGANISM: Homo sapiens

<400> SEQUENCE: 259
caagctagat cagcattctc taacttg                                          27
```

<210> SEQ ID NO 260
<211> LENGTH: 25
<212> TYPE: DNA
<213> ORGANISM: Homo sapiens

<400> SEQUENCE: 260
cacatgactg ttatcgccat ctact    25

<210> SEQ ID NO 261
<211> LENGTH: 99
<212> TYPE: DNA
<213> ORGANISM: Homo sapiens

<400> SEQUENCE: 261
caagctagat cagcattctc taacttgttt ggtggagaac cattgtcata tacccggttc    60
agcctggctc ggcaagtaga tggcgataac agtcatgtg    99

<210> SEQ ID NO 262
<211> LENGTH: 22
<212> TYPE: DNA
<213> ORGANISM: Homo sapiens

<400> SEQUENCE: 262
cacaggaaca acagcatctt tc    22

<210> SEQ ID NO 263
<211> LENGTH: 20
<212> TYPE: DNA
<213> ORGANISM: Homo sapiens

<400> SEQUENCE: 263
agataagccc ctgggatcca    20

<210> SEQ ID NO 264
<211> LENGTH: 75
<212> TYPE: DNA
<213> ORGANISM: Homo sapiens

<400> SEQUENCE: 264
cacaggaaca acagcatctt tcaccaagat gggtggcacc aaccttgctg ggacttggat    60 cccagggct tatct    75

<210> SEQ ID NO 265
<211> LENGTH: 21
<212> TYPE: DNA
<213> ORGANISM: Homo sapiens

<400> SEQUENCE: 265
ggattgctca acaaccatgc t    21

<210> SEQ ID NO 266
<211> LENGTH: 24
<212> TYPE: DNA
<213> ORGANISM: Homo sapiens

<400> SEQUENCE: 266
ggcattaaca cttttggacg ataa    24

<210> SEQ ID NO 267
<211> LENGTH: 91
<212> TYPE: DNA

<213> ORGANISM: Homo sapiens

<400> SEQUENCE: 267

| ggattgctca acaaccatgc tgggcatctg gaccctccta cctctggttc ttacgtctgt | 60 |
| --- | --- |
| tgctagatta tcgtccaaaa gtgttaatgc c | 91 |

<210> SEQ ID NO 268
<211> LENGTH: 24
<212> TYPE: DNA
<213> ORGANISM: Homo sapiens

<400> SEQUENCE: 268

| gcactttggg attctttcca ttat | 24 |
| --- | --- |

<210> SEQ ID NO 269
<211> LENGTH: 24
<212> TYPE: DNA
<213> ORGANISM: Homo sapiens

<400> SEQUENCE: 269

| gcatgtaaga agaccctcac tgaa | 24 |
| --- | --- |

<210> SEQ ID NO 270
<211> LENGTH: 80
<212> TYPE: DNA
<213> ORGANISM: Homo sapiens

<400> SEQUENCE: 270

| gcactttggg attctttcca ttatgattct tgttacagg caccgagaat gttgtattca | 60 |
| --- | --- |
| gtgagggtct tcttacatgc | 80 |

<210> SEQ ID NO 271
<211> LENGTH: 20
<212> TYPE: DNA
<213> ORGANISM: Homo sapiens

<400> SEQUENCE: 271

| aatccaaggg ggagagtgat | 20 |
| --- | --- |

<210> SEQ ID NO 272
<211> LENGTH: 20
<212> TYPE: DNA
<213> ORGANISM: Homo sapiens

<400> SEQUENCE: 272

| gtacagattt tgcccgagga | 20 |
| --- | --- |

<210> SEQ ID NO 273
<211> LENGTH: 72
<212> TYPE: DNA
<213> ORGANISM: Homo sapiens

<400> SEQUENCE: 273

| aatccaaggg ggagagtgat gacttccata tggactttga ctcagctgtg gctcctcggg | 60 |
| --- | --- |
| caaaatctgt ac | 72 |

<210> SEQ ID NO 274
<211> LENGTH: 21
<212> TYPE: DNA
<213> ORGANISM: Homo sapiens

<400> SEQUENCE: 274

```
tgtggacatc ttcccctcag a                                              21

<210> SEQ ID NO 275
<211> LENGTH: 18
<212> TYPE: DNA
<213> ORGANISM: Homo sapiens

<400> SEQUENCE: 275
ctagcccgac cggttcgt                                                  18

<210> SEQ ID NO 276
<211> LENGTH: 66
<212> TYPE: DNA
<213> ORGANISM: Homo sapiens

<400> SEQUENCE: 276
tgtggacatc ttcccctcag acttccctac tgagccacct tctctgccac gaaccggtcg   60
ggctag                                                               66

<210> SEQ ID NO 277
<211> LENGTH: 20
<212> TYPE: DNA
<213> ORGANISM: Homo sapiens

<400> SEQUENCE: 277
ctttgaaccc ttgcttgcaa                                                20

<210> SEQ ID NO 278
<211> LENGTH: 18
<212> TYPE: DNA
<213> ORGANISM: Homo sapiens

<400> SEQUENCE: 278
cccgggacaa agcaaatg                                                  18

<210> SEQ ID NO 279
<211> LENGTH: 68
<212> TYPE: DNA
<213> ORGANISM: Homo sapiens

<400> SEQUENCE: 279
ctttgaaccc ttgcttgcaa taggtgtgcg tcagaagcac ccaggacttc catttgcttt   60
gtcccggg                                                             68

<210> SEQ ID NO 280
<211> LENGTH: 18
<212> TYPE: DNA
<213> ORGANISM: Homo sapiens

<400> SEQUENCE: 280
gcctcggtgt gcctttca                                                  18

<210> SEQ ID NO 281
<211> LENGTH: 19
<212> TYPE: DNA
<213> ORGANISM: Homo sapiens

<400> SEQUENCE: 281
cgtgatgtgc gcaatcatg                                                 19

<210> SEQ ID NO 282
```

```
<211> LENGTH: 65
<212> TYPE: DNA
<213> ORGANISM: Homo sapiens

<400> SEQUENCE: 282
gcctcggtgt gcctttcaac atcgccagct acgccctgct cacgtacatg attgcgcaca    60
tcacg                                                                65

<210> SEQ ID NO 283
<211> LENGTH: 20
<212> TYPE: DNA
<213> ORGANISM: Homo sapiens

<400> SEQUENCE: 283
ctgctgtctt gggtgcattg                                                20

<210> SEQ ID NO 284
<211> LENGTH: 18
<212> TYPE: DNA
<213> ORGANISM: Homo sapiens

<400> SEQUENCE: 284
gcagcctggg accacttg                                                  18

<210> SEQ ID NO 285
<211> LENGTH: 71
<212> TYPE: DNA
<213> ORGANISM: Homo sapiens

<400> SEQUENCE: 285
ctgctgtctt gggtgcattg gagccttgcc ttgctgctct acctccacca tgccaagtgg    60
tcccaggctg c                                                         71

<210> SEQ ID NO 286
<211> LENGTH: 1947
<212> TYPE: DNA
<213> ORGANISM: Homo sapiens

<400> SEQUENCE: 286
ttttccccag atatgggatt ctattcagcc atagataatc tagacagagg atttcagaat    60
gaaaggaaaa atgtgtggag attagtccta gttcattctg agggccgact aagtggctca   120
gccagcttct tactccatct gcagttcata ctgccaaaga gctcccactt ccaaatcccc   180
agtgacttta tggagaagat tctgcattaa attgtctttc gaatgatggg gaagcaaggc   240
ataatatgcg atgatgagga gaaagtagac cagtgaggtg attgcaagac taacaaggag   300
actcaatggg aagttttcct ttcttttaga tattgctttt gaagtagatg gtaaaatttt   360
tgtcatcctt cttgtatttt ttgtacccca agttacaatt tttcttcttc cttgtaaata   420
atttaaacag tatttatttt tgtaaggcat aactagaaac taaatatat tctaaaaaat    480 tcattattct gaacaaagtg atcaaattag aatacatatt tttcaacagt ggtagagctt   540
ttaatatatg tttattgaaa gttatctata atacttgcac cagtgttgaa aaaagttaac   600
atgtaggcaa gagcaatatg tttgtctcaa ggattttcc atggtttcct cagtgatggt    660
gtcctggaat tattcaggtg gtgaccatca ctggtctaag tttgtgtgca gggttttcag   720
acgtgttttt gtgaaacttg gtagaaccat ggctaataaa aggacagtg ttgtcagggt    780 ccatctgccc tccatagaaa aatgtctctg gctcataaaa tgagactccc tcagggacta   840
aatatgaact gacagcagta actctgatac agaataatct aaattgcatc aaatggcctt   900
```

-continued

```
aattcagagt ttgttaggct tatcagtatg ttgcttttaa ttggggtggg aaagtagagg       960
gagagaaagc aagacattta ttaagcacct cgtatgtgcc aggcactatg ctaagcactt      1020
tacataagtt aggattaatc cctgcaagaa tcctataaag aatgttacta gcatttacac      1080
ttcccaaatg aaggtaccaa agctcaaacg caatgttgtg aagctgtttc cttcagattt      1140
aggttatgtg ggatgatgtg ggattgaaga ggaaagaaag gtgggattat ccccctagga      1200
agactttcag gcctgacttc ataggaattc atccatctta tcatgtggag tttatctcac      1260
cctgctgttg caggatgcta tttgcatgtg tccccaggtg atgttttttc tttggggagt      1320
aggggtttgg cttcctcatt catccctctt gctaaaagag gagatagttg atgttgcatc      1380
taaagatgct ataagacaat gaaagtttga tgttgtacat acctacaagt accatttttg      1440
tgcatgatta cactccactg acatcttcca gtactgcat gtgattgaat aagaaacaag       1500
aaagtgacca caccaaagcc tccctggctg gtgtacaggg atcaggtcca cagtggtaca      1560
gattcaacca ccacccaggg agtgcttgca gactctgcat agatgttgct gcatgcgtcc      1620
catgtgcctg tcagaatggc agtgtttaat tctcttgaaa gaaagttatt tgctcactat      1680
ccccagcctc aaggagccaa ggaagagtca ttcacatgga aggtccgggt ctggtcagcc      1740
actctgactt ttctaccaca ttaaattctc cattacatct cactattggt aatggcttaa      1800
gtgtaaagag ccatgatgtg tatattaagc tatgtgccac atatttattt ttagactctc      1860
cacagcattc atgtcaatat gggattaatg cctaaacttt gtaaatattg tacagtttgt      1920
aaatcaatga ataaaggttt tgagtgt                                          1947

<210> SEQ ID NO 287
<211> LENGTH: 1311
<212> TYPE: DNA
<213> ORGANISM: Homo sapiens

<400> SEQUENCE: 287
tagtcgggcg gggttgtgag acgccgcgct cagcttccat cgctgggcgg tcaacaagtg        60
cgggcctggc tcagcgcggg ggggcgcgga gaccgcgagg cgaccgggag cggctgggtt       120
cccggctgcg cgcccttcgg ccaggccggg agccgcgcca gtcggagccc ccggcccagc       180
gtggtccgcc tccctctcgg cgtccacctg cccggagtac tgccagcggg catgaccgac       240
ccaccagggg cgccgccgcc ggcgctcgca ggccgcggat gaagaagaaa accggcgcc        300 gctcgacccg gagcgaggag ttgacccgga gcgaggagtt gaccctgagt gaggaagcga       360
cctggagtga agaggcgacc cagagtgagg aggcgaccca gggcgaagag atgaatcgga       420
gccaggaggt gacccgggac gaggagtcga cccggagcga ggaggtgacc agggaggaaa       480
tggcggcagc tgggctcacc gtgactgtca cccacagcaa tgagaagcac gaccttcatg       540
ttacctccca gcagggcagc agtgaaccag ttgtccaaga cctggcccag gttgttgaag       600
aggtcatagg ggttccacag tcttttcaga aactcatatt taagggaaaa tctctgaagg       660
aaatggaaac accgttgtca gcacttggaa tacaagatgg ttgccgggtc atgttaattg       720
ggaaaaagaa cagtccacag gaagaggttg aactaaagaa gttgaaacat ttggagaagt       780
ctgtggagaa gatagctgac cagctggaag agttgaataa agagcttact ggaatccagc       840
agggttttct gcccaaggat ttgcaagctg aagctctctg caaacttgat aggagagtaa       900
aagccacaat agagcagttt atgaagatct tggaggagat tgacacactg atcctgccag       960
aaaatttcaa agacagtaga ttgaaaagga aaggcttggt aaaaaaggtt caggcattcc      1020
```

```
tagccgagtg tgacacagtg gagcagaaca tctgccagga gactgagcgg ctgcagtcta    1080
caaactttgc cctggccgag tgaggtgtag cagaaaaagg ctgtgctgcc ctgaagaatg    1140
gcgccaccag ctctgccgtc tctggatcgg aatttacctg atttcttcag ggctgctggg    1200
ggcaactggc catttgccaa ttttcctact ctcacactgg ttctcaatga aaatagtgt    1260 ctttgtgatt tgagtaaagc tcctattctg ttttttcacaa aaaaaaaaa a            1311
```

<210> SEQ ID NO 288
<211> LENGTH: 582
<212> TYPE: DNA
<213> ORGANISM: Homo sapiens

<400> SEQUENCE: 288

```
atggcccgcg cacgccagga gggcagctcc ccggagcccg tagagggcct ggcccgcgac     60
ggcccgcgcc ccttcccgct cggccgcctg gtgccctcgg cagtgtcctg cggcctctgc    120
gagcccggcc tggctgccgc ccccgccgcc ccaccctgc tgcccgctgc ctacctctgc    180
gcccccaccg cccacccgc cgtcaccgcc gccctggggg gttcccgctg gcctgggggt    240
ccccgcagcc ggccccgagg cccgcgcccg gacggtcctc agccctcgct ctcgctggcg    300
gagcagcacc tggagtcgcc cgtgcccagc gccccggggg ctctggcggg cggtcccacc    360
caggcggccc cggagtccg cggggaggag gaacagtggg cccgggagat cggggcccag    420
ctgcggcgga tggcggacga cctcaacgca cagtacgagc ggcggagaca agaggagcag    480
cagcggcacc gcccctcacc ctggagggtc ctgtacaatc tcatcatggg actcctgccc    540
ttacccaggg gccacagagc ccccgagatg gagcccaatt ag                      582
```

<210> SEQ ID NO 289
<211> LENGTH: 6030
<212> TYPE: DNA
<213> ORGANISM: Homo sapiens

<400> SEQUENCE: 289

```
gttggccccc gttactttc ctctgggaaa tatggcgcac gctgggagaa cagggtacga     60
taaccgggag atagtgatga agtacatcca ttataagctg tcgcagaggg gctacgagtg    120
ggatgcggga gatgtgggcg ccgcgccccc ggggccgcc ccgcgccgg gcatcttctc     180 ctcgcagccc gggcacacgc cccatacagc cgcatcccgg acccggtcg ccaggacctc    240 gccgctgcag accccggctg ccccggcgc cgcgcggggg cctgcgctca gcccggtgcc    300
acctgtggtc cacctgaccc tccgccaggc cggcgacgac ttctccccgcc gctaccgccg    360 cgacttcgcc gagatgtcca ggcagctgca cctgacgccc ttcaccgcgc ggggacgctt    420
tgccacggtg gtggaggagc tcttcaggga cggggtgaac tgggggagga ttgtggcctt    480
ctttgagttc ggtggggtca tgtgtgtgga gagcgtcaac cgggagatgt cgcccctggt    540
ggacaacatc gccctgtgga tgactgagta cctgaaccgg cacctgcaca cctggatcca    600
ggataacgga ggctgggatg cctttgtgga actgtacggc ccagcatgc ggcctctgtt     660 tgatttctcc tggctgtctc tgaagactct gtcagtttg gccctggtgg agcttgcat     720 caccctgggt gcctatctgg ccacaagtg aagtcaacat gcctgcccca acaaatatg     780 caaaaggttc actaaagcag tagaaataat atgcattgtc agtgatgttc catgaaacaa    840
agctgcaggc tgtttaagaa aaaataacac acatataaac atcacacaca cagacagaca    900
cacacacaca caacaattaa cagtcttcag gcaaaacgtc gaatcagcta tttactgcca    960
aagggaaata tcatttattt tttacattat taagaaaaaa agatttattt atttaagaca    1020
```

-continued

```
gtcccatcaa aactcctgtc tttggaaatc cgaccactaa ttgccaagca ccgcttcgtg    1080
tggctccacc tggatgttct gtgcctgtaa acatagattc gctttccatg ttgttggccg    1140
gatcaccatc tgaagagcag acggatggaa aaggacctg atcattgggg aagctggctt     1200
tctggctgct ggaggctggg gagaaggtgt tcattcactt gcatttcttt gccctggggg    1260
ctgtgatatt aacagaggga gggttcctgt gggggaagt ccatgcctcc ctggcctgaa     1320
gaagagactc tttgcatatg actcacatga tgcatacctg gtgggaggaa aagagttggg    1380
aacttcagat ggacctagta cccactgaga tttccacgcc gaaggacagc gatgggaaaa    1440
atgcccttaa atcataggaa agtattttt taagctacca attgtgccga gaaaagcatt     1500
ttagcaattt atacaatatc atccagtacc ttaagccctg attgtgtata ttcatatatt    1560
ttggatacgc accccccaac tcccaatact ggctctgtct gagtaagaaa cagaatcctc    1620
tggaacttga ggaagtgaac atttcggtga cttccgcatc aggaaggcta gagttaccca    1680
gagcatcagg ccgccacaag tgcctgcttt taggagaccg aagtccgcag aacctgcctg    1740
tgtcccagct tggaggcctg gtcctggaac tgagccgggg ccctcactgg cctcctccag    1800
ggatgatcaa cagggcagtg tggtctccga atgtctggaa gctgatggag ctcagaattc    1860
cactgtcaag aaagagcagt agagggtgt ggctgggcct gtcaccctgg ggccctccag     1920
gtaggcccgt tttcacgtgg agcatgggag ccacgaccct tcttaagaca tgtatcactg    1980
tagagggaag gaacagaggc cctgggccct tcctatcaga aggacatggt gaaggctggg    2040
aacgtgagga gaggcaatgg ccacggccca ttttggctgt agcacatggc acgttggctg    2100
tgtggccttg gcccacctgt gagtttaaag caaggcttta aatgactttg gagagggtca    2160
caaatcctaa agaagcatt gaagtgaggt gtcatggatt aattgacccc tgtctatgga     2220
attacatgta aaacattatc ttgtcactgt agtttggttt tatttgaaaa cctgacaaaa    2280
aaaaagttcc aggtgtggaa tatgggggtt atctgtacat cctggggcat taaaaaaaaa    2340
atcaatggtg gggaactata agaagtaac aaaagaagtg acatcttcag caaataaact     2400
aggaaatttt ttttcttcc agtttagaat cagccttgaa acattgatgg ataactctg      2460 tggcattatt gcattatata ccatttatct gtattaactt tggaatgtac tctgttcaat    2520
gtttaatgct gtggttgata tttcgaaagc tgctttaaaa aaatacatgc atctcagcgt    2580
ttttttgttt ttaattgtat ttagttatgg cctatacact atttgtgagc aaaggtgatc    2640
gttttctgtt tgagattttt atctcttgat tcttcaaaag cattctgaga aggtgagata    2700
agccctgagt ctcagctacc taagaaaaac ctggatgtca ctggccactg aggagctttg    2760
tttcaaccaa gtcatgtgca tttccacgtc aacagaattt tttattgtga cagttatatc    2820
tgttgtccct ttgaccttgt ttcttgaagg tttcctcgtc cctgggcaat tccgcattta    2880
attcatggta ttcaggatta catgcatgtt tggttaaacc catgagattc attcagttaa    2940
aaatccagat ggcaaatgac cagcagattc aaatctatgg tggtttgacc tttagagagt    3000
tgctttacgt ggcctgtttc aacacagacc cacccagagc cctcctgccc tccttccgcg    3060
ggggctttct catggctgtc cttcagggtc ttcctgaaat gcagtggtgc ttacgctcca    3120
ccaagaaagc aggaaacctg tggtatgaag ccagacctcc ccggcgggcc tcagggaaca    3180
gaatgatcag acctttgaat gattctaatt tttaagcaaa atattatttt atgaaaggtt    3240
tacattgtca aagtgatgaa tatgaatat ccaatcctgt gctgctatcc tgccaaaatc     3300
attttaatgg agtcagtttg cagtatgctc cacgtggtaa gatcctccaa gctgctttag    3360
```

```
aagtaacaat gaagaacgtg gacgctttta atataaagcc tgttttgtct tctgttgttg    3420
ttcaaacggg attcacagag tatttgaaaa atgtatatat attaagaggt cacgggggct    3480
aattgctggc tggctgcctt ttgctgtggg gttttgttac ctggttttaa taacagtaaa    3540
tgtgcccagc ctcttggccc cagaactgta cagtattgtg gctgcacttg ctctaagagt    3600
agttgatgtt gcattttcct tattgttaaa aacatgttag aagcaatgaa tgtatataaa    3660
agcctcaact agtcattttt ttctcctctt cttttttttc attatatcta attattttgc    3720
agttgggcaa cagagaacca tccctatttt gtattgaaga gggattcaca tctgcatctt    3780
aactgctctt tatgaatgaa aaacagtcc tctgtatgta ctcctcttta cactggccag    3840
ggtcagagtt aaatagagta tatgcacttt ccaaattggg gacaagggct ctaaaaaaag    3900
ccccaaaagg agaagaacat ctgagaacct cctcggccct cccagtccct cgctgcacaa    3960
atactccgca agagaggcca gaatgacagc tgacagggtc tatggccatc gggtcgtctc    4020
cgaagatttg gcaggggcag aaaactctgg caggcttaag atttggaata aagtcacaga    4080
atcaaggaag cacctcaatt tagttcaaac aagacgccaa cattctctcc acagctcact    4140
tacctctctg tgttcagatg tggccttcca tttatatgtg atctttgttt tattagtaaa    4200
tgcttatcat ctaaagatgt agctctggcc cagtgggaaa aattaggaag tgattataaa    4260
tcgagaggag ttataataat caagattaaa tgtaaataat cagggcaatc ccaacacatg    4320
tctagctttc acctccagga tctattgagt gaacagaatt gcaaatagtc tctatttgta    4380
attgaactta tcctaaaaca aatagtttat aaatgtgaac ttaaactcta attaattcca    4440
actgtacttt taaggcagtg gctgttttta gactttctta tcacttatag ttagtaatgt    4500
acacctactc tatcagagaa aaacaggaaa ggctcgaaat acaagccatt ctaaggaaat    4560
tagggagtca gttgaaattc tattctgatc ttattctgtg gtgtcttttg cagcccagac    4620
aaatgtggtt acacactttt taagaaatac aattctacat tgtcaagctt atgaaggttc    4680
caatcagatc tttattgtta ttcaatttgg atctttcagg gatttttttt ttaaattatt    4740
atgggacaaa ggacatttgt tggaggggtg ggagggagga acaatttta aatataaaac    4800 attcccaagt ttggatcagg gagttggaag ttttcagaat aaccagaact aagggtatga    4860
aggacctgta ttggggtcga tgtgatgcct ctgcgaagaa ccttgtgtga caaatgagaa    4920
acattttgaa gtttgtggta cgacctttag attccagaga catcagcatg gctcaaagtg    4980
cagctccgtt tggcagtgca atggtataaa tttcaagctg gatatgtcta atgggtattt    5040
aaacaataaa tgtgcagttt taactaacag gatatttaat gacaaccttc tggttggtag    5100
ggacatctgt ttctaaatgt ttattatgta caatacagaa aaaaatttta taaaattaag    5160
caatgtgaaa ctgaattgga gagtgataat acaagtcctt tagtcttacc cagtgaatca    5220
ttctgttcca tgtctttgga caaccatgac cttggacaat catgaaatat gcatctcact    5280
ggatgcaaag aaaatcagat ggagcatgaa tggtactgta ccggttcatc tggactgccc    5340
cagaaaaata acttcaagca aacatcctat caacaacaag gttgttctgc ataccaagct    5400
gagcacagaa gatgggaaca ctggtggagg atggaaaggc tcgctcaatc aagaaaattc    5460
tgagactatt aataaataag actgtagtgt agatactgag taaatccatg cacctaaacc    5520
ttttggaaaa tctgccgtgg gccctccaga tagctcattt cattaagttt ttccctccaa    5580
ggtagaattt gcaagagtga cagtggattg catttctttt ggggaagctt tcttttggtg    5640
gttttgttta ttatacctcc ttaagttttc aaccaaggtt tgcttttgtt ttgagttact    5700 ggggttatt ttgtttttaaa taaaaataag tgtacaataa gtgttttgt attgaaagct    5760
```

-continued

```
tttgttatca agattttcat acttttacct tccatggctc tttttaagat tgatacttttt    5820 aagaggtggc tgatattctg caacactgta cacataaaaa atacggtaag gatactttac    5880
atggttaagg taaagtaagt ctccagttgg ccaccattag ctataatggc actttgtttg    5940
tgttgttgga aaaagtcaca ttgccattaa actttccttg tctgtctagt taatattgtg    6000
aagaaaaata aagtacagtg tgagatactg                                      6030

<210> SEQ ID NO 290
<211> LENGTH: 10987
<212> TYPE: DNA
<213> ORGANISM: Homo sapiens

<400> SEQUENCE: 290
ggtggcgcga gcttctgaaa ctaggcggca gaggcggagc cgctgtggca ctgctgcgcc      60
tctgctgcgc ctcgggtgtc ttttgcggcg gtgggtcgcc gccggagaa gcgtgagggg     120 acagatttgt gaccggcgcg ttttttgtca gcttactccg gccaaaaaag aactgcacct    180
ctggagcgga cttatttacc aagcattgga ggaatatcgt aggtaaaaat gcctattgga    240
tccaaagaga ggccaacatt ttttgaaatt tttaagacac gctgcaacaa agcagattta    300
ggaccaataa gtcttaattg gtttgaagaa cttctcttcag aagctccacc ctataattct    360
gaacctgcag aagaatctga acataaaaac aacaattacg aaccaaaccct atttaaaact    420 ccacaaagga aaccatctta taatcagctg gcttcaactc caataatatt caaagagcaa    480
gggctgactc tgccgctgta ccaatctcct gtaaaagaat tagataaatt caaattagac    540
ttaggaagga atgttcccaa tagtagacat aaaagtcttc gcacagtgaa aactaaaatg    600
gatcaagcag atgatgtttc ctgtccactt ctaaattctt gtcttagtga aagtcctgtt    660
gttctacaat gtacacatgt aacaccacaa agagataagt cagtggtatg tgggagtttg    720
tttcatacac caaagtttgt gaagggtcgt cagacaccaa acatatttc tgaaagtcta    780 ggagctgagg tggatcctga tatgtcttgg tcaagttctt tagctacacc acccacccctt    840 agttctactg tgctcatagt cagaaatgaa gaagcatctg aaactgtatt tcctcatgat    900
actactgcta atgtgaaaag ctattttttcc aatcatgatg aaagtctgaa gaaaaatgat    960
agatttatcg cttctgtgac agacagtgaa acacacaaatc aaagagaagc tgcaagtcat   1020
ggatttggaa aaacatcagg gaattcattt aaagtaaata gctgcaaaga ccacattgga    1080
aagtcaatgc caaatgtcct agaagatgaa gtatatgaaa cagttgtaga tacctctgaa    1140
gaagatagtt tttcattatg ttttttctaaa tgtagaacaa aaaatctaca aaaagtaaga    1200
actagcaaga ctaggaaaaa aatttttccat gaagcaaacg ctgatgaatg tgaaaaatct    1260
aaaaaccaag tgaaagaaaa atactcattt gtatctgaag tggaaccaaa tgatactgat    1320
ccattagatt caaatgtagc acatcagaag ccctttgaga gtggaagtga caaaatctcc    1380
aaggaagttg taccgtcttt ggcctgtgaa tggtctcaac taacccctttc aggtctaaat    1440 ggagcccaga tggagaaaat accctattg catatttctt catgtgacca aaatatttca    1500
gaaaaagacc tattagacac agagaacaaa agaaagaaag attttcttac ttcagagaat    1560
tctttgccac gtatttctag cctaccaaaa tcagagaagc cattaaatga ggaaacagtg    1620
gtaaataaga gagatgaaga gcagcatctt gaatctcata cagactgcat tcttgcagta    1680
aagcaggcaa tatctggaac ttctccagtg gcttcttcat ttcagggtat caaaagtct    1740 atattcagaa taagagaatc acctaaagag actttcaatg caagttttttc aggtcatatg    1800
```

-continued

```
actgatccaa actttaaaaa agaaactgaa gcctctgaaa gtggactgga aatacatact    1860
gtttgctcac agaaggagga ctccttatgt ccaaatttaa ttgataatgg aagctggcca    1920
gccaccacca cacagaattc tgtagctttg aagaatgcag gtttaatatc cactttgaaa    1980
aagaaaacaa ataagtttat ttatgctata catgatgaaa cattttataa aggaaaaaaa    2040
ataccgaaag accaaaaatc agaactaatt aactgttcag cccagtttga agcaaatgct    2100
tttgaagcac acttacatt tgcaaatgct gattcaggtt tattgcattc ttctgtgaaa    2160
agaagctgtt cacagaatga ttctgaagaa ccaactttgt ccttaactag ctcttttggg    2220
acaattctga ggaaatgttc tagaaatgaa acatgttcta ataatacagt aatctctcag    2280
gatcttgatt ataaagaagc aaaatgtaat aaggaaaaac tacagttatt tattacccca    2340
gaagctgatt ctctgtcatg cctgcaggaa ggacagtgtg aaaatgatcc aaaaagcaaa    2400
aaagtttcag atataaaaga agaggtcttg gctgcagcat gtcacccagt acaacattca    2460
aaagtggaat acagtgatac tgactttcaa tcccagaaaa gtcttttata tgatcatgaa    2520
aatgccagca ctcttatttt aactcctact tccaaggatg ttctgtcaaa cctagtcatg    2580
atttctagag gcaaagaatc atacaaaatg tcagacaagc tcaaaggtaa caattatgaa    2640
tctgatgttg aattaaccaa aaatattccc atggaaaaga tcaagatgt atgtgctta     2700
aatgaaaatt ataaaaacgt tgagctgttg ccacctgaaa atacatgag agtagcatca    2760
ccttcaagaa aggtacaatt caaccaaaac acaaatctaa gagtaatcca aaaaaatcaa    2820
gaagaaacta cttcaatttc aaaaataact gtcaatccag actctgaaga acttttctca    2880
gacaatgaga ataattttgt cttccaagta gctaatgaaa ggaataatct tgctttagga    2940
aatactaagg aacttcatga acagacttg acttgtgtaa acgaacccat tttcaagaac    3000
tctaccatgg ttttatatgg agacacaggt gataaacaag caacccaagt gtcaattaaa    3060
aaagatttgg tttatgttct tgcagaggag aacaaaaata gtgtaaagca gcatataaaa    3120
atgactctag gtcaagattt aaaatcggac atctccttga atatagataa aataccagaa    3180
aaaaataatg attacatgaa caatgggca ggactcttag gtccaatttc aaatcacagt    3240
tttggaggta gcttcagaac agcttcaaat aaggaaatca agctctctga acataacatt    3300
aagaagagca aaatgttctt caaagatatt gaagaacaat atcctactag tttagcttgt    3360
gttgaaattg taaataccctt ggcattagat aatcaaaaga aactgagcaa gcctcagtca    3420
attaatactg tatctgcaca tttacagagt agtgtagttg tttctgattg taaaaatagt    3480
catataaccc ctcagatgtt attttccaag caggatttta attcaaacca taatttaaca    3540
cctagccaaa aggcagaaat tacagaactt ctactatat tagaagaatc aggaagtcag    3600
tttgaattta ctcagtttag aaaaccaagc tacatattgc agaagagtac atttgaagtg    3660
cctgaaaacc agatgactat cttaaagacc acttctgagg aatgcagaga tgctgatctt    3720
catgtcataa tgaatgcccc atcgattggt caggtagaca gcagcaagca atttgaaggt    3780
acagttgaaa ttaaacggaa gtttgctggc ctgttgaaaa atgactgtaa caaaagtgct    3840
tctggttatt taacagatga aaatgaagtg gggtttaggg gcttttattc tgctcatggc    3900
acaaaactga atgtttctac tgaagctctg caaaaagctg tgaaactgtt tagtgatatt    3960
gagaatatta gtgaggaaac ttctgcagag gtacatccaa taagtttatc ttcaagtaaa    4020
tgtcatgatt ctgttgtttc aatgtttaag atagaaaatc ataatgataa aactgtaagt    4080
gaaaaaaata taaatgcca actgatatta caaataata ttgaaatgac tactggcact    4140
tttgttgaag aaattactga aaattacaag agaaatactg aaaatgaaga taacaaatat    4200
```

```
actgctgcca gtagaaattc tcataactta gaatttgatg gcagtgattc aagtaaaaat    4260
gatactgttt gtattcataa agatgaaacg gacttgctat ttactgatca gcacaacata    4320
tgtcttaaat tatctggcca gtttatgaag gagggaaaca ctcagattaa agaagatttg    4380
tcagatttaa cttttttgga agttgcgaaa gctcaagaag catgtcatgg taatacttca    4440
aataaagaac agttaactgc tactaaaacg gagcaaaata taaagatttt tgagacttct    4500
gatacatttt ttcagactgc aagtgggaaa atattagtg tcgccaaaga gtcatttaat    4560
aaaattgtaa atttctttga tcagaaacca gaagaattgc ataacttttc cttaaattct    4620
gaattacatt ctgacataag aaagaacaaa atggacattc taagttatga ggaaacagac    4680
atagttaaac acaaaatact gaaagaaagt gtcccagttg gtactggaaa tcaactagtg    4740
accttccagg gacaacccga acgtgatgaa aagatcaaag aacctactct gttgggtttt    4800
catacagcta gcgggaaaaa agttaaaatt gcaaaggaat cttttggacaa agtgaaaaac    4860 cttttttgatg aaaaagagca aggtactagt gaaatcacca gttttagcca tcaatgggca    4920
aagaccctaa agtacagaga ggcctgtaaa gaccttgaat tagcatgtga gaccattgag    4980
atcacagctg ccccaaagtg taaagaaatg cagaattctc tcaataatga taaaaaccctt    5040 gtttctattg agactgtggt gccacctaag ctcttaagtg ataatttatg tagacaaact    5100
gaaaatctca aaacatcaaa aagtatcttt ttgaaagtta aagtacatga aaatgtagaa    5160
aaagaaacag caaaaagtcc tgcaacttgt tacacaaatc agtcccctta ttcagtcatt    5220
gaaaattcag ccttagcttt ttacacaagt tgtagtagaa aaacttctgt gagtcagact    5280
tcattacttg aagcaaaaaa atggcttaga gaaggaatat ttgatggtca accagaaaga    5340
ataaatactg cagattatgt aggaaattat ttgtatgaaa ataattcaaa cagtactata    5400
gctgaaaatg acaaaaatca tctctccgaa aaacaagata cttatttaag taacagtagc    5460
atgtctaaca gctattccta ccattctgat gaggtatata tgattcagg atatctctca    5520 aaaaataaac ttgattctgg tattgagcca gtattgaaga atgttgaaga tcaaaaaaac    5580
actagttttt ccaaagtaat atccaatgta aaagatgcaa atgcataccc acaaactgta    5640
aatgaagata tttgcgttga ggaacttgtg actagctctt caccctgcaa aaataaaaat    5700
gcagccatta aattgtccat atctaatagt aataattttg aggtagggcc acctgcattt    5760
aggatagcca gtggtaaaat cgtttgtgtt tcacatgaaa caattaaaaa agtgaaagac    5820
atatttacag acagtttcag taaagtaatt aaggaaaaca acgagaataa atcaaaaatt    5880
tgccaaacga aaattatggc aggttgttac gaggcattgg atgattcaga ggatattctt    5940
cataactctc tagataatga tgaatgtagc acgcattcac ataaggtttt tgctgacatt    6000
cagagtgaag aaattttaca acataaccaa aatatgtctg gattggagaa agtttctaaa    6060
atatcacctt gtgatgttag tttggaaact tcagatatat gtaaatgtag tatagggaag    6120
cttcataagt cagtctcatc tgcaaatact tgtgggattt ttagcacagc aagtggaaaa    6180
tctgtccagg tatcagatgc ttcattacaa aacgcaagac aagtgttttc tgaaatagaa    6240
gatagtacca agcaagtctt ttccaaagta ttgtttaaaa gtaacgaaca ttcagaccag    6300
ctcacaagag aagaaatac tgctatacgt actccagaac atttaatatc ccaaaaaggc    6360
ttttcatata atgtggtaaa ttcatctgct ttctctggat ttagtacagc aagtggaaag    6420
caagtttcca ttttagaaag ttccttacac aaagttaagg gagtgttaga ggaatttgat    6480
ttaatcagaa ctgagcatag tcttcactat tcacctacgt ctagacaaaa tgtatcaaaa    6540
```

```
atacttcctc gtgttgataa gagaaaccca gagcactgtg taaactcaga aatggaaaaa    6600
acctgcagta aagaatttaa attatcaaat aacttaaatg ttgaaggtgg ttcttcagaa    6660
aataatcact ctattaaagt ttctccatat ctctctcaat ttcaacaaga caaacaacag    6720
ttggtattag gaaccaaagt ctcacttgtt gagaacattc atgttttggg aaaagaacag    6780
gcttcaccta aaaacgtaaa aatgaaaatt ggtaaaactg aaacttttc tgatgttcct    6840 gtgaaaacaa atatagaagt ttgttctact tactccaaag attcagaaaa ctactttgaa    6900
acagaagcag tagaaattgc taaagctttt atggaagatg atgaactgac agattctaaa    6960
ctgccaagtc atgccacaca ttctcttttt acatgtcccg aaaatgagga aatggttttg    7020
tcaaattcaa gaattggaaa aagaagagga gagccccctta tcttagtggg agaaccctca    7080
atcaaaagaa acttattaaa tgaatttgac aggataatag aaaatcaaga aaaatcctta    7140
aaggcttcaa aaagcactcc agatggcaca ataaaagatc gaagattgtt tatgcatcat    7200
gtttctttag agccgattac ctgtgtaccc tttcgcacaa ctaaggaacg tcaagagata    7260
cagaatccaa attttaccgc acctggtcaa gaatttctgt ctaaatctca tttgtatgaa    7320
catctgactt tggaaaaatc ttcaagcaat ttagcagttt caggacatcc attttatcaa    7380
gtttctgcta caagaaatga aaaaatgaga cacttgatta ctacaggcag accaaccaaa    7440
gtctttgttc caccttttaa aactaaatca cattttcaca gagttgaaca gtgtgttagg    7500
aatattaact tggaggaaaa cagacaaaag caaacattg atggacatgg ctctgatgat    7560
agtaaaaata agattaatga caatgagatt catcagttta acaaaaacaa ctccaatcaa    7620
gcagcagctg taactttcac aaagtgtgaa gaagaacctt tagatttaat tacaagtctt    7680
cagaatgcca gagatataca ggatatgcga attaagaaga acaaaggca acgcgtcttt    7740 ccacagccag gcagtctgta tcttgcaaaa acatccactc tgcctcgaat ctctctgaaa    7800
gcagcagtag gaggccaagt tccctctgcg tgttctcata acagctgta tacgtatggc    7860 gtttctaaac attgcataaa aattaacagc aaaaatgcag agtcttttca gtttcacact    7920
gaagattatt ttggtaagga aagtttatgg actggaaaag gaatacagtt ggctgatggt    7980
ggatggctca taccctccaa tgatggaaag gctggaaaag aagaatttta tagggctctg    8040
tgtgacactc caggtgtgga tccaaagctt atttctagaa tttgggttta taatcactat    8100
agatggatca tatggaaact ggcagctatg gaatgtgcct ttcctaagga atttgctaat    8160
agatgcctaa gcccagaaag ggtgcttctt caactaaaat acagatatga tacggaaatt    8220
gatagaagca gaagatcggc tataaaaaag ataatggaaa gggatgacac agctgcaaaa    8280
acacttgttc tctgtgtttc tgacataatt tcattgagcg caaatatatc tgaaacttct    8340
agcaataaaa ctagtagtgc agatacccaa aaagtggcca ttattgaact tacagatggg    8400
tggtatgctg ttaaggccca gttagatcct ccctcttag ctgtcttaaa gaatggcaga    8460
ctgacagttg gtcagaagat tattcttcat ggagcagaac tggtgggctc tcctgatgcc    8520
tgtacacctc ttgaagcccc agaatctctt atgttaaga tttctgctaa cagtactcgg    8580
cctgctcgct ggtataccaa acttggattc tttcctgacc ctagaccttt tcctctgccc    8640
ttatcatcgc ttttcagtga tggaggaaat gttggttgtg ttgatgtaat tattcaaaga    8700
gcatacccta tacagtggat ggagaagaca tcatctggat tatacatatt tcgcaatgaa    8760
agagaggaag aaaaggaagc agcaaaatat gtggaggccc aacaaaagag actagaagcc    8820
ttattcacta aaattcagga ggaatttgaa gaacatgaag aaaacacaac aaaaccatat    8880
ttaccatcac gtgcactaac aagacagcaa gttcgtgctt tgcaagatgg tgcagagctt    8940
```

```
tatgaagcag tgaagaatgc agcagaccca gcttaccttg agggttattt cagtgaagag    9000
cagttaagag ccttgaataa tcacaggcaa atgttgaatg ataagaaaca agctcagatc    9060
cagttggaaa ttaggaaggc catgaatct gctgaacaaa aggaacaagg tttatcaagg     9120
gatgtcacaa ccgtgtggaa gttgcgtatt gtaagctatt caaaaaaga aaaagattca    9180 gttatactga gtatttggcg tccatcatca gatttatatt ctctgttaac agaaggaaag    9240
agatacagaa tttatcatct tgcaacttca aaatctaaaa gtaaatctga agagctaac    9300 atacagttag cagcgacaaa aaaaactcag tatcaacaac taccggtttc agatgaaatt    9360
ttatttcaga tttaccagcc acgggagccc cttcacttca gcaattttt agatccagac    9420 tttcagccat cttgttctga ggtggaccta ataggatttg tcgtttctgt tgtgaaaaaa    9480
acaggacttg cccctttcgt ctatttgtca gacgaatgtt acaatttact ggcaataaag    9540
ttttggatag accttaatga ggacattatt aagcctcata tgttaattgc tgcaagcaac    9600
ctccagtggc gaccagaatc caaatcaggc cttcttactt tatttgctgg agatttttct    9660
gtgttttctg ctagtccaaa agagggccac tttcaagaga cattcaacaa atgaaaaat    9720 actgttgaga atattgacat actttgcaat gaagcagaaa acaagcttat gcatatactg    9780
catgcaaatg atcccaagtg gtccacccca actaaagact gtacttcagg gccgtacact    9840
gctcaaatca ttcctggtac aggaaacaag cttctgatgt cttctcctaa ttgtgagata    9900
tattatcaaa gtcctttatc actttgtatg gccaaaagga gtctgtttc cacacctgtc    9960 tcagcccaga tgacttcaaa gtcttgtaaa ggggagaaag agattgatga ccaaaagaac   10020
tgcaaaaaga gaagagcctt ggatttcttg agtagactgc ctttacctcc acctgttagt   10080
cccatttgta catttgtttc tccggctgca cagaaggcat tcagccacc aaggagttgt    10140 ggcaccaaat acgaaacacc cataaagaaa aaagaactga attctcctca gatgactcca   10200
tttaaaaaat tcaatgaaat ttctcttttg gaaagtaatt caatagctga cgaagaactt   10260
gcattgataa atacccaagc tcttttgtct ggttcaacag gagaaaaaca atttatatct   10320
gtcagtgaat ccactaggac tgctcccacc agttcagaag attatctcag actgaaacga   10380
cgttgtacta catctctgat caaagaacag gagagttccc aggccagtac ggaagaatgt   10440
gagaaaaata gcaggacac aattacaact aaaaaatata tctaagcatt tgcaaaggcg    10500
acaataaatt attgacgctt aaccttttca gtttataaga ctggaatata atttcaaacc   10560
acacattagt acttatgttg cacaatgaga aaagaaatta gtttcaaatt tacctcagcg   10620
tttgtgtatc gggcaaaaat cgttttgccc gattccgtat tggtatactt ttgcttcagt   10680
tgcatatctt aaaactaaat gtaatttatt aactaatcaa gaaaaacatc tttggctgag   10740
ctcggtggct catgcctgta atcccaacac tttgagaagc tgaggtggga ggagtgcttg   10800
aggccaggag ttcaagacca gcctgggcaa cataggagac ccccatcttc tacgaagaaa   10860 aaaaaaagg ggaaaagaaa atcttttaaa tctttggatt tgatcactac aagtattatt    10920
ttacaatcaa caaatggtca atccaaactc aaacttgaga aaatatcttg ctttcaaatt   10980
gacacta                                                             10987
```

<210> SEQ ID NO 291
<211> LENGTH: 1552
<212> TYPE: DNA
<213> ORGANISM: Homo sapiens

<400> SEQUENCE: 291

```
gcccgtacac accgtgtgct gggacacccc acagtcagcc gcatggctcc cctgtgcccc      60
agcccctggc tccctctgtt gatcccggcc cctgctccag gcctcactgt gcaactgctg     120
ctgtcactgc tgcttctgat gcctgtccat ccccagaggt tgccccggat gcaggaggat     180
tccccttgg  gaggaggctc ttctggggaa gatgacccca tgggcgagga ggatctgccc     240
agtgaagagg attcacccag agaggaggat ccacccggag aggaggatct acctggagag     300
gaggatctac ctggagagga ggatctacct gaagttaagc ctaaatcaga agaagagggc     360
tccctgaagt tagaggatct acctactgtt gaggctcctg agatcctca  gaacccccag     420
aataatgccc acagggacaa agaagggat  gaccagagtc attggcgcta tggaggcgac     480
ccgccctggc cccgggtgtc cccagcctgc gcgggccgct ccagtccccc ggtggatatc     540
cgcccccagc tcgccgcctt ctgcccggcc ctgcgccccc tggaactcct gggcttccag     600
ctcccgccgc tcccagaact gcgcctgcgc aacaatggcc acagtgtgca actgaccctg     660
cctcctgggg tagagatggc tctggtcccc gggcgggagt accgggctct gcagctgcat     720
ctgcactggg gggctgcagg tcgtccgggc tcggagcaca ctgtggaagg ccaccgtttc     780
cctgccgaga tccacgtggt tcacctcagc accgcctttg ccagagttga cgaggccttg     840
gggcgcccgg gaggcctggc cgtgttggcc gcctttctgg aggagggccc ggaagaaaac     900
agtgcctatg agcagttgct gtctcgcttg aagaaaatcg ctgaggaagg ctcagagact     960
caggtcccag gactggacat atctgcactc ctgccctctg acttcagccg ctacttccaa    1020
tatgaggggt ctctgactac accgcccgtt gcccagggtg tcatctggac tgtgtttaac    1080
cagacagtga tgctgagtgc taagcagctc cacacccctct ctgacaccct gtggggacct   1140
ggtgactctc ggctacagct gaacttccga gcgacgcagc cttttgaatgg gcgagtgatt   1200
gaggcctcct tccctgctgg agtggacagc agtcctcggg ctgctgagcc agtccagctg    1260
aattcctgcc tggctgctgg tgacatccta gccctggttt ttggcctcct ttttgctgtc    1320
accagcgtcg cgttccttgt gcagatgaga aggcagcaca aagggggaac caaagggggt    1380
gtgagctacc gcccagcaga ggtagccgag actggagcct agaggctgga tcttggagaa    1440
tgtgagaagc cagccagagg catctgaggg ggagccggta actgtcctgt cctgctcatt    1500
atgccacttc cttttaactg ccaagaaatt ttttaaaata aatatttata at             1552
```

<210> SEQ ID NO 292
<211> LENGTH: 1578
<212> TYPE: DNA
<213> ORGANISM: Homo sapiens

<400> SEQUENCE: 292

```
acgaacaggc caataaggag ggagcagtgc ggggtttaaa tctgaggcta ggctggctct      60
tctcggcgtg ctgcggcgga acggctgttg gtttctgctg gttgtaggtc cttggctggt    120
cgggcctccg tgttctgct  tctccccgct gagctgctgc ctggtgaaga ggaagccatg    180
gcgctccgag tcaccaggaa ctcgaaaatt aatgctgaaa ataaggcgaa gatcaacatg    240
gcaggcgcaa agcgcgttcc tacgcccct  gctgcaacct ccaagcccgg actgaggcca    300
agaacagctc ttggggacat tggtaacaaa gtcagtgaac aactgcaggc caaaatgcct    360
atgaagaagg aagcaaaacc ttcagctact ggaaagtca  ttgataaaaa actaccaaaa    420
cctcttgaaa aggtacctat gctggtgcca gtgccagtgt ctgagccagt gccagagcca    480
gaacctgagc cagaacctga gcctgttaaa gaagaaaaac tttcgcctga gcctattttg    540
gttgatactg cctctccaag cccaatggaa acatctggat gtgcccctgc agaagaagac    600
```

-continued

```
ctgtgtcagg ctttctctga tgtaattctt gcagtaaatg atgtggatgc agaagatgga      660
gctgatccaa acctttgtag tgaatatgtg aaagatattt atgcttatct gagacaactt      720
gaggaagagc aagcagtcag accaaaatac ctactgggtc gggaagtcac tggaaacatg      780
agagccatcc taattgactg gctagtacag gttcaaatga aattcaggtt gttgcaggag      840
accatgtaca tgactgtctc cattattgat cggttcatgc agaataattg tgtgcccaag      900
aagatgctgc agctggttgg tgtcactgcc atgtttattg caagcaaata tgaagaaatg      960
taccctccag aaattggtga ctttgctttt gtgactgaca acacttatac taagcaccaa     1020
atcagacaga tggaaatgaa gattctaaga gctttaaact ttggtctggg tcggcctcta     1080
cctttgcact ccttcggag agcatctaag attggagagg ttgatgtcga gcaacatact     1140
ttggccaaat acctgatgga actaactatg ttggactatg acatggtgca ctttcctcct     1200
tctcaaattg cagcaggagc ttttttgctta gcactgaaaa ttctggataa tggtgaatgg     1260
acaccaactc tacaacatta cctgtcatat actgaagaat ctcttcttcc agttatgcag     1320
cacctggcta agaatgtagt catggtaaat caaggactta caaagcacat gactgtcaag     1380
aacaagtatg ccacatcgaa gcatgctaag atcagcactc taccacagct gaattctgca     1440
ctagttcaag atttagccaa ggctgtggca aaggtgtaac ttgtaaactt gagttggagt     1500
actatattta caaataaaat tggcaccatg tgccatctgt aaaaaaaaaa aaaaaaaaaa     1560
aaaaaaaaaa aaaaaaa                                                   1578
```

<210> SEQ ID NO 293
<211> LENGTH: 3195
<212> TYPE: DNA
<213> ORGANISM: Homo sapiens

<400> SEQUENCE: 293

```
agaggcttcc ctggctggtg cctgagcccg gcgtccctcg cccccgccc tccccgcatc       60 cctctcctcc ctcgcgcctg gccctgtggc tcttcctccc tccctccttc ccccccccc      120 caccctcgc ccgctgcctc cctcggccca gccagctgtg ccggcgtttg ttggctgccc      180
tgcgcccggc cctccagcca gccttctgcc ggccccgccg cgatggaggt gccccagccg      240
gagcccgcgc caggctcggc tctcagtcca gcaggcgtgt gcggtggcgc ccagcgtccg      300
ggccacctcc cgggcctcct gctgggatct catggcctcc tggggtcccc ggtgcgggcg      360
gccgcttcct cgccggtcac caccctcacc cagaccatgc acgacctcgc cgggctcggc      420
agccgcagcc gcctgacgca cctatccctg tctcgacggg catccgaatc ctccctgtcg      480
tctgaatcct ccgaatcttc tgatgcaggt ctctgcatgg attccccag ccctatggac      540 ccccacatgg cggagcagac gtttgaacag gccatccagg cagccagccg gatcattcga      600
aacgagcagt ttgccatcag acgcttccag tctatgccgg tgaggctgct gggccacagc      660
cccgtgcttc ggaacatcac caactcccag gcgcccgacg gccggaggaa gagcgaggcg      720
ggcagtggag ctgccagcag ctctggggaa gacaaggaga atgtgcgctt ctggaaggcc      780
ggggtgggag ctctccggga agaggagggg gcatgctggg gtggttccct ggcatgtgag      840
gaccctcctc tcccatcttg gctgcaggat ggatttgtct tcaagatgcc atggaagccc      900
acacatccca gctccaccca tgctctggca gagtgggcca gccgcaggga agcctttgcc      960
cagagaccca gctcggcccc cgacctgatg tgtctcagtc ctgaccggaa gatggaagtg     1020
gaggagctca gcccctggc cctaggtcgc ttctctctga cccctgcaga ggggatact     1080
```

-continued

```
gaggaagatg atggatttgt ggacatccta gagagtgact taaaggatga tgatgcagtt    1140
cccccaggca tggagagtct cattagtgcc ccactggtca agaccttgga aaaggaagag    1200
gaaaaggacc tcgtcatgta cagcaagtgc cagcggctct tccgctctcc gtccatgccc    1260
tgcagcgtga tccggcccat cctcaagagg ctggagcggc cccaggacag ggacacgccc    1320
gtgcagaata gcggaggcg gagcgtgacc cctcctgagg agcagcagga ggctgaggaa    1380
cctaaagccc gcgtcctccg ctcaaaatca ctgtgtcacg atgagatcga gaacctcctg    1440
gacagtgacc accgagagct gattggagat tactctaagg ccttcctcct acagacagta    1500
gacgaaaagc accaagacct caagtacatc tcaccagaaa cgatggtggc cctattgacg    1560
ggcaagttca gcaacatcgt ggataagttt gtgattgtag actgcagata cccctatgaa    1620
tatgaaggcg ggcacatcaa gactgcggtg aacttgcccc tggaacgcga cgccgagagc    1680
ttcctactga agagccccat cgcgccctgt agcctggaca agagagtcat cctcattttc    1740
cactgtgaat tctcatctga gcgtgggccc cgcatgtgcc gtttcatcag ggaacgagac    1800
cgtgctgtca acgactaccc cagcctctac taccctgaga tgtatatcct gaaaggcggc    1860
tacaaggagt tcttccctca gcacccgaac ttctgtgaac cccaggacta ccggcccatg    1920
aaccacgagg ccttcaagga tgagctaaag accttccgcc tcaagactcg cagctgggct    1980
ggggagcgga gccggcggga gctcgtagcc cggctgcagg accagtgagg ggcctgcgcc    2040
agtcctgcta cctcccttgc cttcgaggc ctgaagccag ctgccctatg ggcctgccgg    2100
gctgagggcc tgctggaggc ctcaggtgct gtccatggga aagatggtgt ggtgtcctgc    2160
ctgtctgccc cagcccagat tccctgtgt catcccatca ttttccatat cctggtgccc    2220 cccaccctg gaaagagccca gtctgttgag ttagttaagt tgggttaata ccagcttaaa    2280
ggcagtattt tgtgtcctcc aggagcttct tgtttccttg ttagggttaa cccttcatct    2340
tcctgtgtcc tgaaacgctc ctttgtgtgt gtgtcagctg aggctgggga gagccgtggt    2400
ccctgaggat gggtcagagc taaactcctt cctggcctga gagtcagctc tctgccctgt    2460
gtacttcccg ggccagggct gcccctaatc tctgtaggaa ccgtggtatg tctgccatgt    2520 tgccccttc tcttttcccc tttcctgtcc caccatacga gcacctccag cctgaacaga    2580
agctcttact ctttcctatt tcagtgttac ctgtgtgctt ggtctgtttg actttacgcc    2640
catctcagga cacttccgta gactgtttag gttcccctgt caaatatcag ttacccactc    2700
ggtcccagtt ttgttgcccc agaaagggat gttattatcc ttgggggctc ccagggcaag    2760
ggttaaggcc tgaatcatga gcctgctgga agccagccc ctactgctgt gaaccctggg    2820
gcctgactgc tcagaacttg ctgctgtctt gttgcggatg gatggaaggt tggatggatg    2880
ggtggatggc cgtggatggc cgtggatgcg cagtgccttg catacccaaa ccaggtggga    2940
gcgttttgtt gagcatgaca cctgcagcag gaatatatgt gtgcctattt gtgtggacaa    3000
aaatatttac acttagggtt tggagctatt caagaggaaa tgtcacagaa gcagctaaac    3060
caaggactga gcaccctctg gattctgaat ctcaagatgg gggcagggct gtgcttgaag    3120
gccctgctga gtcatctgtt agggccttgg ttcaataaag cactgagcaa gttgagaaaa    3180
aaaaaaaaaa aaaaa                                                     3195
```

<210> SEQ ID NO 294
<211> LENGTH: 3737
<212> TYPE: DNA
<213> ORGANISM: Homo sapiens

<400> SEQUENCE: 294

-continued

```
ggcgtccgcg cacacctccc cgcgccgccg ccgccaccgc ccgcactccg ccgcctctgc    60
ccgcaaccgc tgagccatcc atgggggtcg cgggccgcaa ccgtcccggg gcggcctggg   120
cggtgctgct gctgctgctg ctgctgccgc cactgctgct gctggcgggg gccgtcccgc   180
cgggtcgggg ccgtgccgcg gggccgcagg aggatgtaga tgagtgtgcc caagggctag   240
atgactgcca tgccgacgcc ctgtgtcaga acacacccac ctcctacaag tgctcctgca   300
agcctggcta ccaaggggaa ggcaggcagt gtgaggacat cgatgaatgt ggaaatgagc   360
tcaatggagg ctgtgtccat gactgtttga atattccagg caattatcgt tgcacttgtt   420
ttgatggctt catgttggct catgacggtc ataattgtct tgatgtggac gagtgcctgg   480
agaacaatgg cggctgccag catacctgtg tcaacgtcat ggggagctat gagtgctgct   540
gcaaggaggg gttttcctg agtgacaatc agcacacctg cattcaccgc tcggaagagg   600
gcctgagctg catgaataag gatcacggct gtagtcacat ctgcaaggag gccccaaggg   660
gcagcgtcgc ctgtgagtgc aggcctggtt ttgagctggc caagaaccag agagactgca   720
tcttgacctg taaccatggg aacgtgtgggt gccagcactc ctgtgacgat acagccgatg   780
gcccagagtg cagctgccat ccacagtaca agatgcacac agatgggagg agctgccttg   840
agcgagagga cactgtcctg gaggtgacag agagcaacac cacatcagtg gtggatgggg   900
ataaacgggt gaaacggcgg ctgctcatgg aaacgtgtgc tgtcaacaat ggaggctgtg   960
accgcacctg taaggatact tcgacaggtg tccactgcag ttgtcctgtt ggattcactc  1020
tccagttgga tgggaagaca tgtaaagata ttgatgagtg ccagacccgc aatggaggtt  1080
gtgatcattt ctgcaaaaac atcgtgggca gttttgactg cggctgcaag aaaggattta  1140
aattattaac agatgagaag tcttgccaag atgtggatga gtgctctttg gataggacct  1200
gtgaccacag ctgcatcaac caccctggca catttgcttg tgcttgcaac cgagggtaca  1260
ccctgtatgc cttcacccac tgtggagaca ccaatgagtg cagcatcaac aacgaggct  1320 gtcagcaggt ctgtgtgaac acagtgggca gctatgaatg ccagtgccac cctgggtaca  1380
agctccactg gaataaaaaa gactgtgtgg aagtgaaggg gctcctgccc acaagtgtgt  1440
caccccgtgt gtccctgcac tgcggtaaga gtggtggagg agacgggtgc ttcctcagat  1500
gtcactctgg cattcacctc tcttcagatg tcaccaccat caggacaagt gtaaccttta  1560
agctaaatga aggcaagtgt agtttgaaaa atgctgagct gtttcccgag ggtctgcgac  1620
cagcactacc agagaagcac agctcagtaa aagagagctt ccgctacgta aaccttacat  1680
gcagctctgg caagcaagtc ccaggagccc ctggccgacc aagcaccccct aaggaaatgt  1740 ttatcactgt tgagtttgag cttgaaacta ccaaaaggga ggtgacagct tcttgtgacc  1800
tgagctgcat cgtaaagcga accgagaagc ggctccgtaa agccatccgc acgctcagaa  1860
aggccgtcca cagggagcag tttcacctcc agctctcagg catgaacctc gacgtggcta  1920
aaaagcctcc cagaacatct gaacgccagg cagagtcctg tggagtgggc cagggtcatg  1980
cagaaaacca atgtgtcagt tgcagggctg ggacctatta tgatggagca cgagaacgct  2040
gcattttatg tccaaatgga accttccaaa atgaggaagg acaaatgact tgtgaaccat  2100
gcccaagacc aggaaattct ggggccctga gacccccaga agcttggaat atgtctgaat  2160
gtggaggtct gtgtcaacct ggtgaatatt ctgcagatgg ctttgcacct tgccagctct  2220
gtgccctggg cacgttccag cctgaagctg gtcgaacttc ctgcttcccc tgtggaggag  2280
gccttgccac caaacatcag ggagctactt cctttcagga ctgtgaaacc agagttcaat  2340
```

| | |
|---|---:|
| gttcacctgg acatttctac aacaccacca ctcaccgatg tattcgttgc ccagtgggaa | 2400 |
| cataccagcc tgaatttgga aaaataatt gtgtttcttg cccaggaaat actacgactg | 2460 |
| actttgatgg ctccacaaac ataacccagt gtaaaaacag aagatgtgga ggggagctgg | 2520 |
| gagatttcac tgggtacatt gaatccccaa actacccagg caattaccca gccaacaccg | 2580 |
| agtgtacgtg gaccatcaac ccacccccca agcgccgcat cctgatcgtg gtccctgaga | 2640 |
| tcttcctgcc catagaggac gactgtgggg actatctggt gatgcggaaa acctcttcat | 2700 |
| ccaattctgt gacaacatat gaaacctgcc agacctacga acgccccatc gccttcacct | 2760 |
| ccaggtcaaa gaagctgtgg attcagttca gtccaatga agggaacagc gctagagggt | 2820 |
| tccaggtccc atacgtgaca tatgatgagg actaccagga actcattgaa gacatagttc | 2880 |
| gagatggcag gctctatgca tctgagaacc atcaggaaat acttaaggat aagaaactta | 2940 |
| tcaaggctct gtttgatgtc ctggcccatc ccagaacta tttcaagtac acagcccagg | 3000 |
| agtcccgaga gatgtttcca agatcgttca tccgattgct acgttccaaa gtgtccaggt | 3060 |
| ttttgagacc ttacaaatga ctcagcccac gtgccactca atacaaatgt tctgctatag | 3120 |
| ggttggtggg acagagctgt cttccttctg catgtcagca cagtcgggta ttgctgcctc | 3180 |
| ccgtatcagt gactcattag agttcaattt ttatagataa tacagatatt ttggtaaatt | 3240 |
| gaacttggtt tttctttccc agcatcgtgg atgtagactg agaatggctt tgagtggcat | 3300 |
| cagcttctca ctgctgtggg cggatgtctt ggatagatca cgggctggct gagctggact | 3360 |
| ttggtcagcc taggtgagac tcacctgtcc ttctggggtc ttactcctcc tcaaggagtc | 3420 |
| tgtagtggaa aggaggccac agaataagct gcttattctg aaacttcagc ttcctctagc | 3480 |
| ccggccctct ctaagggagc cctctgcact cgtgtgcagg ctctgaccag gcagaacagg | 3540 |
| caagagggga gggaaggaga cccctgcagg ctccctccac ccaccttgag acctgggagg | 3600 |
| actcagtttc tccacagcct tctccagcct gtgtgataca agtttgatcc caggaacttg | 3660 |
| agttctaagc agtgctcgtg aaaaaaaaaa gcagaaagaa ttagaaataa ataaaaacta | 3720 |
| agcacttctg gagacat | 3737 |

<210> SEQ ID NO 295
<211> LENGTH: 2042
<212> TYPE: DNA
<213> ORGANISM: Homo sapiens

<400> SEQUENCE: 295

| | |
|---|---:|
| ggggccagtc gttcgccgga aagcatttgt ctcccacctc atcataacaa caattaattt | 60 |
| cctctgggc ctgaggaggg cagaatttca accttcggtg tgcttgggag tggcgattgt | 120 |
| gatttacacg acaaaatgcc gaggtgctcg gtggagtcat ggcagtgccc tttgtggaag | 180 |
| actgggactt ggtgcaaacc ctgggagaag gtgcctatgg agaagttcaa cttgctgtga | 240 |
| atagagtaac tgaagaagca gtcgcagtga agattgtaga tatgaagcgt gccgtagact | 300 |
| gtccagaaaa tattaagaaa gagatctgta tcaataaaat gctaaatcat gaaaatgtag | 360 |
| taaaattcta tggtcacagg agagaaggca atatccaata tttatttctg gagtactgta | 420 |
| gtggaggaga gcttttgac agaatagagc cagacatagg catgcctgaa ccagatgctc | 480 |
| agagattctt ccatcaactc atggcagggg tggtttatct gcatggtatt ggaataactc | 540 |
| acagggatat taaaccagaa aatcttctgt tggatgaaag ggataacctc aaaatctcag | 600 |
| actttggctt ggcaacagta tttcggtata ataatcgtga gcgtttgttg aacaagatgt | 660 |
| gtggtactt accatatgtt gctccagaac ttctgaagag aagagaattt catgcagaac | 720 |

```
cagttgatgt tggtcctgt ggaatagtac ttactgcaat gctcgctgga gaattgccat      780
gggaccaacc cagtgacagc tgtcaggagt attctgactg gaaagaaaaa aaaacatacc      840
tcaacccttg gaaaaaaatc gattctgctc ctctagctct gctgcataaa atcttagttg      900
agaatccatc agcaagaatt accattccag acatcaaaaa agatagatgg tacaacaaac      960
ccctcaagaa aggggcaaaa aggccccgag tcacttcagg tggtgtgtca gagtctccca     1020 gtggatttc taagcacatt caatccaatt tggacttctc tccagtaaac agtgcttcta     1080
gtgaagaaaa tgtgaagtac tccagttctc agccagaacc ccgcacaggt ctttccttat     1140
gggataccag cccctcatac attgataaat tggtacaagg gatcagcttt tcccagccca     1200
catgtcctga tcatatgctt ttgaatagtc agttacttgg cacccaggga tcctcacaga     1260 accctggca gcggttggtc aaaagaatga cacgattctt taccaaattg gatgcagaca     1320
aatcttatca atgcctgaaa gagacttgtg agagttggg ctatcaatgg aagaaaagtt     1380
gtatgaatca ggttactata tcaacaactg ataggagaaa caataaactc attttcaaag     1440
tgaatttgtt agaaatggat gataaaatat tggttgactt ccggctttct aagggtgatg     1500
gattggagtt caagagacac ttcctgaaga ttaaaggaa gctgattgat attgtgagca     1560
gccagaaggt ttggcttcct gccacatgat cggaccatcg gctctgggga atcctggtga     1620
atatagtgct gctatgttga cattattctt cctagagaag attatcctgt cctgcaaact     1680
gcaaatagta gttcctgaag tgttcacttc cctgtttatc caaacatctt ccaatttatt     1740
ttgtttgttc ggcatacaaa taatacctat atcttaattg taagcaaaac tttggggaaa     1800
ggatgaatag aattcatttg attatttctt catgtgtgtt tagtatctga atttgaaact     1860
catctggtgg aaaccaagtt tcaggggaca tgagttttcc agcttttata cacacgtatc     1920
tcatttttat caaaacattt tgtttaattc aaaagtaca tatttcttcc atgttgattt     1980
aattctaaga tgaaccaata aagacataat tcttgcaaaa aaaaaaaaaa aaaaaaaaa     2040 aa                                                                    2042
```

<210> SEQ ID NO 296
<211> LENGTH: 2547
<212> TYPE: DNA
<213> ORGANISM: Homo sapiens

<400> SEQUENCE: 296

```
cttacaaggt acagtcctct gctcaggggg gccaggaggg tcttataggc atcattcacc       60
agggtcgaat gcttctctga gaagtccttt tcagtctgag acctctggct gaagaaatct      120
gggtggacaa gacgctgcag ttgctggtac ctgtgctgga gcttcgctgt atcaactctg      180
aaggaacggt tgcagtccat aaggctgaag tagtctcgag tggggtcagg tgcctgcagc      240
gctcggcact gtgggcagaa gaacctgtcc tcccgcccgg ggccccatgg gccgccgcag      300
ttccaacagc ggggataatt gcttcccgcc tgcgacgcag catcgcagct agcggtctc      360 cttctgggaa cccctgtcgg ccaaaacccc cacaccgga gcaaagcccc ggctctcccc       420
cgccacatct ggccggcggc ctatctagcc gtggtcactc gtggggaaaa gcaaagagag      480
cgtctaacca gactaatgtt gctgattggc tggggagtcg agggggcggg atcacccgag      540
gggaacccgg gttctaagtt ccgctctccc ttctaaacta caactcccag gaggcattga      600
ggcggcgcct gacggccaca tctgctgctc ctcattggtc cggcggcagg gggggggtt      660 ttgattggct gagggtggag tttgtatctg caggtttagc gccactctgc tggctgaggc      720
```

-continued

```
tgcggagagt gtgcggctcc aggtgggctc acgcggtcgt gatgtctcgg gagtcggatg      780
ttgaggctca gcagtctcat ggcagcagtg cctgttcaca gccccatggc agcgttaccc      840
agtcccaagg ctcctcctca cagtcccagg gcatatccag ctcctctacc agcacgatgc      900
caaactccag ccagtcctct cactccagct ctgggacact gagctcctta gagacagtgt      960
ccactcagga actctattct attcctgagg accaagaacc tgaggaccaa gaacctgagg     1020
agcctacccc tgcccctgg gctcgattat gggcccttca ggatggattt gccaatcttg      1080
aatgtgtgaa tgacaactac tggtttggga gggacaaaag ctgtgaatat tgctttgatg     1140
aaccactgct gaaagaaca gataaatacc gaacatacag caagaaacac tttcggattt      1200
tcagggaagt gggtcctaaa aactcttaca ttgcatacat agaagatcac agtggcaatg     1260
gaacctttgt aaatacagag cttgtaggga aggaaaacg ccgtcctttg aataacaatt     1320
ctgaaattgc actgtcacta agcagaaata agttttttgt cttttttgat ctgactgtag     1380
atgatcagtc agtttatcct aaggcattaa gagatgaata catcatgtca aaaactcttg    1440
gaagtggtgc ctgtggagag gtaaagctgg ctttcgagag gaaaacatgt aagaaagtag    1500
ccataaagat catcagcaaa aggaagtttg ctattggttc agcaagagag gcagacccag     1560
ctctcaatgt tgaaacagaa atagaaattt tgaaaaagct aaatcatcct tgcatcatca    1620
agattaaaaa cttttttgat gcagaagatt attatattgt tttggaattg atggaagggg    1680
gagagctgtt tgacaaagtg gtggggaata acgcctgaa agaagctacc tgcaagctct     1740 attttttacca gatgctcttg gctgtgcagt accttcatga aacggtatt atacaccgtg     1800 acttaaagcc agagaatgtt ttactgtcat ctcaagaaga ggactgtctt ataaagatta     1860
ctgattttgg gcactccaag attttgggag agacctctct catgagaacc ttatgtggaa    1920 ccccccaccta cttggcgcct gaagttcttg tttctgttgg gactgctggg tataaccgtg    1980
ctgtggactg ctggagttta ggagttattc tttttatctg ccttagtggg tatccacctt     2040
tctctgagca taggactcaa gtgtcactga aggatcagat caccagtgga aaatacaact     2100
tcattcctga agtctgggca gaagtctcag agaaagctct ggaccttgtc aagaagttgt     2160
tggtagtgga tccaaaggca cgttttacga cagaagaagc cttaagacac ccgtggcttc    2220
aggatgaaga catgaagaga aagtttcaag atcttctgtc tgaggaaaat gaatccacag     2280 ctctaccccca ggttctagcc cagccttcta ctagtcgaaa gcggcccgt gaagggggaag    2340 ccgagggtgc cgagaccaca aagcgcccag ctgtgtgtgc tgctgtgttg tgaactccgt     2400
ggtttgaaca cgaaagaaat gtaccttctt tcactctgtc atctttcttt tctttgagtc     2460
tgttttttta tagtttgtat tttaattatg ggataattg cttttttcaca gtcactgatg     2520 tacaattaaa aacctgatgg aacctgg                                         2547
```

<210> SEQ ID NO 297
<211> LENGTH: 2768
<212> TYPE: DNA
<213> ORGANISM: Homo sapiens

<400> SEQUENCE: 297

```
cactgctgtg cagggcagga aagctccatg cacatagccc agcaaagagc aacacagagc       60
tgaaaggaag actcagagga gagagataag taaggaaagt agtgatggct ctcatcccag      120
acttggccat ggaaacctgg cttctcctgg ctgtcagcct ggtgctcctc tatctatatg      180
gaacccattc acatggactt tttaagaagc ttggaattcc agggcccaca cctctgcctt      240
ttttgggaaa tattttgtcc taccataagg gcttttgtat gtttgacatg gaatgtcata      300
```

-continued

```
aaaagtatgg aaaagtgtgg ggcttttatg atggtcaaca gcctgtgctg gctatcacag      360
atcctgacat gatcaaaaca gtgctagtga agaatgtta ttctgtcttc acaaaccgga       420
ggccttttgg tccagtggga tttatgaaaa gtgccatctc tatagctgag gatgaagaat     480
ggaagagatt acgatcattg ctgtctccaa ccttcaccag tggaaaactc aaggagatgg     540
tccctatcat tgcccagtat ggagatgtgt tggtgagaaa tctgaggcgg aagcagaga     600 caggcaagcc tgtcaccttg aaagacgtct ttggggccta cagcatggat gtgatcacta    660
gcacatcatt tggagtgaac atcgactctc tcaacaatcc acaagacccc tttgtggaaa    720
acaccaagaa gcttttaaga tttgattttt tggatccatt ctttctctca ataacagtct    780
ttccattcct catcccaatt cttgaagtat aaaatatctg tgtgtttcca agagaagtta    840 caaattttt aagaaaatct gtaaaaagga tgaaagaaag tcgcctcgaa gatacacaaa    900
agcaccgagt ggatttcctt cagctgatga ttgactctca gaattcaaaa gaaactgagt   960
cccacaaagc tctgtccgat ctggagctcg tggcccaatc aattatcttt attttgctg   1020 gctatgaaac cacgagcagt gttctctcct tcattatgta tgaactggcc actcaccctg   1080
atgtccagca gaaactgcag gaggaaattg atgcagtttt acccaataag gcaccaccca   1140
cctatgatac tgtgctacag atggagtatc ttgacatggt ggtgaatgaa acgctcagat   1200
tattcccaat tgctatgaga cttgagaggg tctgcaaaaa agatgttgag atcaatggga   1260
tgttcattcc caaggggtg tgtggtgatga ttccaagcta tgctcttcac cgtgacccaa   1320
agtactggac agagcctgag aagttcctcc ctgaaagatt cagcaagaag aacaaggaca   1380
acatagatcc ttacatatac acacccttttg gaagtggacc cagaaactgc attggcatga   1440
ggtttgctct catgaacatg aaacttgctc taatcagagt ccttcagaac ttctccttca   1500
aaccttgtaa agaaacacag atcccctga aattaagctt aggaggactt cttcaaccag   1560
aaaaacccgt tgttctaaag gttgagtcaa gggatgcac cgtaagtgga gcctgaattt   1620
tcctaaggac ttctgctttg ctcttcaaga aatctgtgcc tgagaacacc agagacctca   1680
aattactttg tgaatagaac tctgaaatga agatgggctt catccaatgg actgcataaa   1740
taaccgggga ttctgtacat gcattgagct ctctcattgt ctgtgtagag tgttatactt   1800
gggaatataa aggaggtgac caaatcagtg tgaggaggta gatttggctc ctctgcttct   1860
cacgggacta tttccaccac ccccagttag caccattaac tcctcctgag ctctgataag   1920
agaatcaaca tttctcaata atttcctcca caaattatta atgaaaataa gaattatttt   1980
gatggctcta acaatgacat ttatatcaca tgttttctct ggagtattct ataagtttta   2040
tgttaaatca ataaagacca ctttacaaaa gtattatcag atgctttcct gcacattaag   2100
gagaaatcta tagaactgaa tgagaaccaa caagtaaata ttttttggtca ttgtaatcac   2160 tgttggcgtg gggcctttgt cagaactaga atttgattat taacataggt gaaagttaat   2220
ccactgtgac tttgcccatt gtttagaaag aatattcata gtttaattat gcctttttg    2280 atcaggcaca gtggctcacg cctgtaatcc tagcagtttg ggaggctgag ccgggtggat   2340
cgcctgaggt caggagttca agacaagcct ggcctacatg gttgaaaccc catctctact   2400
aaaaatacac aaaattagcta ggcatggtgg actcgcctgt aatctcacta cacaggaggc   2460
tgaggcagga gaatcacttg aacctgggag gcggatgttg aagtgagctg agattgcacc   2520
actgcactcc agtctgggtg agagtgagac tcagtcttaa aaaatatgc ctttttgaag   2580 cacgtacatt ttgtaacaaa gaactgaagc tcttattata ttattagttt tgatttaatg   2640
```

-continued

| | |
|---|---|
| ttttcagccc atctcctttc atatttctgg gagacagaaa acatgtttcc ctacacctct | 2700 |
| tgcattccat cctcaacacc caactgtctc gatgcaatga acacttaata aaaaacagtc | 2760 |
| gattggtc | 2768 |

<210> SEQ ID NO 298
<211> LENGTH: 1358
<212> TYPE: DNA
<213> ORGANISM: Homo sapiens

<400> SEQUENCE: 298

| | |
|---|---|
| ggcgtccgcg cgctgcacaa tggcggctct gaagagttgg ctgtcgcgca gcgtaacttc | 60 |
| attcttcagg tacagacagt gtttgtgtgt tcctgttgtg gctaacttta agaagcggtg | 120 |
| tttctcagaa ttgataagac catggcacaa aactgtgacg attggctttg gagtaaccct | 180 |
| gtgtgcggtt cctattgcac agaaatcaga gcctcattcc cttagtagtg aagcattgat | 240 |
| gaggagagca gtgtctttgg taacagatag cacctctacc tttctctctc agaccacata | 300 |
| tgcgttgatt gaagctatta ctgaatatac taaggctgtt tataccttaa cttctcttta | 360 |
| ccgacaatat acaagtttac ttgggaaaat gaattcagag gaggaagatg aagtgtggca | 420 |
| ggtgatcata ggagccagag ctgagatgac ttcaaaacac caagagtact gaagctgga | 480 |
| aaccacttgg atgactgcag ttggtctttc agagatggca gcagaagctg catatcaaac | 540 |
| tggcgcagat caggcctcta taaccgccag gaatcacatt cagctggtga actgcaggt | 600 |
| ggaagaggtg caccagctct cccggaaagc agaaaccaag ctggcagaag cacagataga | 660 |
| agagctccgt cagaaaacac aggaggaagg ggaggagcgg gctgagtcgg agcaggaggc | 720 |
| ctacctgcgt gaggattgag ggcctgagca cactgccctg tctccccact cagtggggaa | 780 |
| agcaggggca gatgccaccc tgcccagggt tggcatgact gtctgtgcac cgagaagagg | 840 |
| cggcaggtcc tgccctggcc aatcaggcga gacgcctttg tgagctgtga gtgcctcctg | 900 |
| tggtctcagg cttcgctgg acctggttct tagcccttgg gcactgcacc ctgtttaaca | 960 |
| tttcacccca ctctgtacag ctgctcttac ccatttttt tacctcacac ccaaagcatt | 1020 |
| ttgcctacct gggtcagaga gaggagtcct ttttgtcatg cccttaagtt cagcaactgt | 1080 |
| ttaacctgtt ttcagtctta tttacgtcgt caaaaatgat ttagtacttg ttccctctgt | 1140 |
| tgggatgcca gttgtggcag ggggagggga acctgtccag tttgtacgat ttctttgtat | 1200 |
| gtatttctga tgtgttctct gatctgcccc cactgtcctg tgaggacagc tgaggccaag | 1260 |
| gagtgaaaaa cctattacta ctaagagaag gggtgcagag tgtttacctg gtgctctcaa | 1320 |
| caggacttaa catcaacagg acttaacaca gaaaaaaa | 1358 |

<210> SEQ ID NO 299
<211> LENGTH: 4407
<212> TYPE: DNA
<213> ORGANISM: Homo sapiens

<400> SEQUENCE: 299

| | |
|---|---|
| tttcgactcg cgctccggct gctgtcactt ggctctctgg ctggagcttg aggacgcaag | 60 |
| gagggtttgt cactggcaga ctcgagactg taggcactgc catggcccct gtgctcagta | 120 |
| aggactcggc ggacatcgag agtatcctgg ctttaaatcc tcgaacacaa actcatgcaa | 180 |
| ctctgtgttc cacttcggcc aagaaattag acaagaaaca ttggaaaaga atcctgata | 240 |
| agaactgctt taattgtgag aagctggaga ataattttga tgacatcaag cacacgactc | 300 |
| ttggtgagcg aggagctctc cgagaagcaa tgagatgcct gaaatgtgca gatgccccgt | 360 |

-continued

```
gtcagaagag ctgtccaact aatcttgata ttaaatcatt catcacaagt attgcaaaca    420
agaactatta tggagctgct aagatgatat tttctgacaa cccacttggt ctgacttgtg    480
gaatggtatg tccaacctct gatctatgtg taggtggatg caatttatat gccactgaag    540
agggacccat taatattggt ggattgcagc aatttgctac tgaggtattc aaagcaatga    600
gtatcccaca gatcagaaat ccttcgctgc ctcccccaga aaaatgtct gaagcctatt     660 ctgcaaagat tgctcttttt ggtgctgggc ctgcaagtat aagttgtgct tccttttgg    720 ctcgattggg gtactctgac atcactatat ttgaaaaaca agaatatgtt ggtggtttaa    780
gtacttctga aattcctcag ttccggctgc cgtatgatgt agtgaatttt gagattgagc    840
taatgaagga ccttggtgta aagataattt gcggtaaaag cctttcagtg aatgaaatga    900
ctcttagcac tttgaaagaa aaaggctaca agctgctttt cattggaata ggtttgccag    960
aacccaataa agatgccatc ttccaaggcc tgacgcagga ccaggggttt tatacatcca   1020
aagacttttt gccacttgta gccaaaggca gtaaagcagg aatgtgcgcc tgtcactctc   1080
cattgccatc gatacgggga gtcgtgattg tacttggagc tggagacact gccttcgact   1140
gtgcaacatc tgctctacgt tgtggagctc gccgagtgtt catcgtcttc agaaaaggct   1200
ttgttaatat aagagctgtc cctgaggaga tggagcttgc taaggaagaa aagtgtgaat   1260
ttctgccatt cctgtcccca cggaaggtta tagtaaaagg tgggagaatt gttgctatgc   1320
agtttgttcg gacagagcaa gatgaaactg gaaaatggaa tgaagatgaa gatcagatgg   1380
tccatctgaa agccgatgtg gtcatcagtg cctttggttc agttctgagt gatcctaaag   1440
taaaagaagc cttgagccct ataaaattta acagatgggg tctcccagaa gtagatccag   1500
aaactatgca aactagtgaa gcatgggtat ttgcaggtgg tgatgtcgtt ggtttggcta   1560
acactacagt ggaatcggtg aatgatggaa agcaagcttc ttggtacatt cacaaatacg   1620
tacagtcaca atatgagct tccgtttctg ccaagcctga actaccctc ttttacactc     1680 ctattgatct ggtggacatt agtgtagaaa tggccggatt gaagtttata aatcctttg     1740 gtcttgctag cgcaactcca gccaccagca catcaatgat tcgaagagct tttgaagctg   1800
gatggggttt tgccctcacc aaaactttct ctcttgataa ggacattgtg acaaatgttt   1860
cccccagaat catccgggga accacctctg gccccatgta tggccctgga caaagctcct   1920
ttctgaatat tgagctcatc agtgagaaaa cggctgcata ttggtgtcaa agtgtcactg   1980
aactaaaggc tgacttccca gacaacattg tgattgctag cattatgtgc agttacaata   2040
aaaatgactg gacggaactt gccaagaagt ctgaggattc tggagcagat gccctggagt   2100
taaatttatc atgtccacat ggcatgggag aaagaggaat gggcctggcc tgtgggcagg   2160
atccagagct ggtgcggaac atctgccgct gggttaggca agctgttcag attccttttt   2220
ttgccaagct gaccccaaat gtcactgata ttgtgagcat cgcaagagct gcaaaggaag   2280
gtggtgccaa tggcgttaca gccaccaaca ctgtctcagg tctgatggga ttaaaatctg   2340
atggcacacc ttggccagca gtggggattg caaagcgaac tacatatgga ggagtgtctg   2400
ggacagcaat cagacctatt gctttgagag ctgtgacctc cattgctcgt gctctgcctg   2460
gatttcccat tttggctact ggtggaattg actctgctga aagtggtctt cagtttctcc   2520
atagtggtgc ttccgtcctc caggtatgca gtgccattca gaatcaggat ttcactgtga   2580
tcgaagacta ctgcactggc ctcaaagccc tgctttatct gaaaagcatt gaagaactac   2640
aagactggga tggacagagt ccagctactg tgagtcacca gaaagggaaa ccagttccac   2700
```

-continued

| | |
|---|---|
| gtatagctga actcatggac aagaaactgc caagttttgg accttatctg gaacagcgca | 2760 |
| agaaaatcat agcagaaaac aagattagac tgaaagaaca aaatgtagct ttttcaccac | 2820 |
| ttaagagaag ctgttttatc cccaaaaggc ctattcctac catcaaggat gtaataggaa | 2880 |
| aagcactgca gtaccttgga acatttggtg aattgagcaa cgtagagcaa gttgtggcta | 2940 |
| tgattgatga agaaatgtgt atcaactgtg gtaaatgcta catgacctgt aatgattctg | 3000 |
| gctaccaggc tatacagttt gatccagaaa cccacctgcc caccataacc gacacttgta | 3060 |
| caggctgtac tctgtgtctc agtgtttgcc ctattgtcga ctgcatcaaa atggtttcca | 3120 |
| ggacaacacc ttatgaacca aagagaggcg taccctatc tgtgaatccg gtgtgttaag | 3180 |
| gtgatttgtg aaacagttgc tgtgaacttt catgtcacct acatatgctg atctcttaaa | 3240 |
| atcatgatcc ttgtgttcag ctcttttccaa attaaaacaa atatacattt tctaaataaa | 3300 |
| aatatgtaat ttcaaaatac atttgtaagt gtaaaaaatg tctcatgtca atgaccattc | 3360 |
| aattagtggc ataaaataga ataattcttt tctgaggata gtagttaaat aactgtgtgg | 3420 |
| cagttaattg gatgttcact gccagttgtc ttatgtgaaa aattaacttt ttgtgtggca | 3480 |
| attagtgtga cagtttccaa attgccctat gctgtgctcc atatttgatt tctaattgta | 3540 |
| agtgaaatta agcattttga aacaaagtac tctttaacat acaagaaaat gtatccaagg | 3600 |
| aaacatttta tcaataaaaa ttacctttaa ttttaatgct gtttctaaga aaatgtagtt | 3660 |
| agctccataa agtacaaatg aagaaagtca aaaattattt gctatggcag gataagaaag | 3720 |
| cctaaaattg agtttgtgga ctttattaag taaaatcccc ttcgctgaaa ttgcttattt | 3780 |
| ttggtgttgg atagaggata gggagaatat ttactaacta aataccattc actactcatg | 3840 |
| cgtgagatgg gtgtacaaac tcatcctctt taatggcat ttctctttaa actatgttcc | 3900 |
| taaccaaatg agatgatagg atagatcctg gttaccactc ttttactgtg cacatatggg | 3960 |
| ccccggaatt ctttaatagt caccttcatg attatagcaa ctaatgtttg aacaaagctc | 4020 |
| aaagtatgca atgcttcatt attcaagaat gaaaaatata atgttgataa tatatattaa | 4080 |
| gtgtgccaaa tcagtttgac tactctctgt tttagtgttt atgtttaaaa gaaatatatt | 4140 |
| ttttgttatt attagataat atttttgtat ttctctattt tcataatcag taaatagtgt | 4200 |
| catataaact catttatctc ctcttcatgg catcttcaat atgaatctat aagtagtaaa | 4260 |
| tcagaaagta acaatctatg gcttatttct atgacaaatt caagagctag aaaaataaaa | 4320 |
| tgtttcatta tgcacttttta gaaatgcata tttgccacaa aacctgtatt actgaataat | 4380 |
| atcaaataaa atatcataaa gcattttt | 4407 |

<210> SEQ ID NO 300
<211> LENGTH: 5532
<212> TYPE: DNA
<213> ORGANISM: Homo sapiens

<400> SEQUENCE: 300

| | |
|---|---|
| gccgcgctgc gccggagtcc cgagctagcc ccggcgccgc cgccgcccag accggacgac | 60 |
| aggccacctc gtcggcgtcc gcccgagtcc ccgcctcgcc gccaacgcca caaccaccgc | 120 |
| gcacggcccc ctgactccgt ccagtattga tcgggagagc cggagcgagc tcttcgggga | 180 |
| gcagcgatgc gaccctccgg gacggccggg gcagcgctcc tggcgctgct ggctgcgctc | 240 |
| tgcccggcga gtcgggctct ggaggaaaag aaagtttgcc aaggcacgag taacaagctc | 300 |
| acgcagttgg gcactttga agatcatttt ctcagcctcc agaggatgtt caataactgt | 360 |
| gaggtggtcc ttgggaattt ggaaattacc tatgtgcaga ggaattatga tctttccttc | 420 |

-continued

```
ttaaagacca tccaggaggt ggctggttat gtcctcattg ccctcaacac agtggagcga    480
attcctttgg aaaacctgca gatcatcaga ggaaatatgt actacgaaaa ttcctatgcc    540
ttagcagtct tatctaacta tgatgcaaat aaaaccggac tgaaggagct gcccatgaga    600
aatttacagg aaatcctgca tggcgccgtg cggttcagca caaccctgc cctgtgcaac     660 gtggagagca tccagtggcg ggacatagtc agcagtgact ttctcagcaa catgtcgatg    720
gacttccaga accacctggg cagctgccaa aagtgtgatc caagctgtcc caatgggagc    780
tgctggggtg caggagagga gaactgccag aaactgacca aaatcatctg tgcccagcag    840
tgctccgggc gctgccgtgg caagtccccc agtgactgct gccacaacca gtgtgctgca    900
ggctgcacag gcccccggga gagcgactgc ctggtctgcc gcaaattccg agacgaagcc    960
acgtgcaagg acacctgccc cccactcatg ctctacaacc ccaccacgta ccagatggat   1020
gtgaaccccg agggcaaata cagctttggt gccacctgcg tgaagaagtg tccccgtaat   1080
tatgtggtga cagatcacgg ctcgtgcgtc cgagcctgtg gggccgacag ctatgagatg   1140
gaggaagacg gcgtccgcaa gtgtaagaag tgcgaagggc cttgccgcaa agtgtgtaac   1200
ggaataggta ttggtgaatt taaagactca ctctccataa atgctacgaa tattaaacac   1260
ttcaaaaact gcacctccat cagtggcgat ctccacatcc tgccggtggc atttagggt    1320 gactccttca cacatactcc tcctctggat ccacaggaac tggatattct gaaaaccgta   1380
aaggaaatca caggttttt gctgattcag gcttggcctg aaaacaggac ggacctccat    1440
gcctttgaga acctagaaat catacgcggc aggaccaagc aacatggtca gttttctctt   1500
gcagtcgtca gcctgaacat aacatccttg ggattacgct ccctcaagga gataagtgat   1560
ggagatgtga taatttcagg aaacaaaaat ttgtgctatg caaatacaat aaactggaaa   1620
aaactgtttg ggacctccgg tcagaaaacc aaaattataa gcaacagagg tgaaaacagc   1680
tgcaaggcca caggccaggt ctgccatgcc ttgtgctccc cgagggctg ctggggcccg     1740 gagcccaggg actgcgtctc ttgccggaat gtcagccgag caggaatg cgtggacaag     1800 tgcaagcttc tggagggtga gccaagggag tttgtggaga actctgagtg catacagtgc   1860
cacccagagt gcctgcctca ggccatgaac atcacctgca caggacgggg accagacaac   1920
tgtatccagt gtgcccacta cattgacggc ccccactgcg tcaagacctg cccggcagga   1980
gtcatgggag aaaacaacac cctggtctgg aagtacgcag acgccggcca tgtgtgccac   2040
ctgtgccatc caaactgcac ctacggatgc actgggccag tcttgaagg ctgtccaacg    2100 aatgggccta agatcccgtc catcgccact gggatggtgg gggcctcct cttgctgctg    2160 gtggtggccc tggggatcgg cctcttcatg cgaaggcgcc acatcgttcg gaagcgcacg   2220
ctgcggaggc tgctgcagga gagggagctt gtggagcctc ttacacccag tggagaagct   2280
cccaaccaag ctctcttgag gatcttgaag gaaactgaat tcaaaaagat caaagtgctg   2340
ggctccggtg cgttcggcac ggtgtataag ggactctgga tcccagaagg tgagaaagtt   2400
aaaattcccg tcgctatcaa ggaattaaga gaagcaacat ctcgaaagc caacaaggaa    2460 atcctcgatg aagcctacgt gatggccagc gtggacaacc cccacgtgtg ccgcctgctg   2520
ggcatctgcc tcacctccac cgtgcaactc atcacgcagc tcatgccctt cggctgcctc   2580
ctggactatg tccgggaaca caaagacaat attggctccc agtacctgct caactggtgt   2640
gtgcagatcg caaagggcat gaactacttg gaggaccgtc gcttggtgca ccgcgacctg   2700
gcagccagga acgtactggt gaaaacaccg cagcatgtca gatcacaga ttttgggctg    2760
```

-continued

```
gccaaactgc tgggtgcgga agagaaagaa taccatgcag aaggaggcaa agtgcctatc    2820
aagtggatgg cattggaatc aattttacac agaatctata cccaccagag tgatgtctgg    2880
agctacgggg tgaccgtttg ggagttgatg acctttggat ccaagccata tgacggaatc    2940
cctgccagcg agatctcctc catcctggag aaaggagaac gcctccctca gccacccata    3000
tgtaccatcg atgtctacat gatcatggtc aagtgctgga tgatagacgc agatagtcgc    3060
ccaaagttcc gtgagttgat catcgaattc tccaaaatgg cccgagaccc ccagcgctac    3120
cttgtcattc aggggatga aagaatgcat ttgccaagtc ctacagactc caacttctac    3180
cgtgccctga tggatgaaga agacatggac gacgtggtgg atgccgacga gtacctcatc    3240
ccacagcagg gcttcttcag cagcccctcc acgtcacgga ctcccctcct gagctctctg    3300
agtgcaacca gcaacaattc caccgtggct tgcattgata gaaatgggct gcaaagctgt    3360
cccatcaagg aagacagctt cttgcagcga tacagctcag accccacagg cgccttgact    3420
gaggacagca tagacgacac cttcctccca gtgcctgaat acataaacca gtccgttccc    3480
aaaaggcccg ctggctctgt gcagaatcct gtctatcaca atcagcctct gaaccccgcg    3540
cccagcagag acccacacta ccaggacccc cacagcactg cagtgggcaa ccccgagtat    3600
ctcaacactg tccagcccac ctgtgtcaac agcacattcg acagccctgc ccactgggcc    3660
cagaaaggca gccaccaaat tagcctggac aaccctgact accagcagga cttcttccc     3720 aaggaagcca agccaaatgg catctttaag ggctccacag ctgaaaatgc agaataccta    3780
agggtcgcgc cacaaagcag tgaatttatt ggagcatgac cacggaggat agtatgagcc    3840
ctaaaaatcc agactctttc gatacccagg accaagccac agcaggtcct ccatcccaac    3900
agccatgccc gcattagctc ttagacccac agactggttt tgcaacgttt acaccgacta    3960
gccaggaagt acttccacct cgggcacatt ttgggaagtt gcattccttt gtcttcaaac    4020
tgtgaagcat ttacagaaac gcatccagca agaatattgt ccctttgagc agaaatttat    4080 cttcaaaga ggtatatttg aaaaaaaaa aaaagtata tgtgaggatt tttattgatt       4140
ggggatcttg gagtttttca ttgtcgctat tgattttac ttcaatgggc tcttccaaca     4200
aggaagaagc ttgctggtag cacttgctac cctgagttca tccaggccca actgtgagca    4260
aggagcacaa gccacaagtc ttccagagga tgcttgattc cagtggttct gcttcaaggc    4320
ttccactgca aaacactaaa gatccaagaa ggccttcatg gccccagcag gccggatcgg    4380
tactgtatca agtcatggca ggtacagtag gataagccac tctgtccctt cctgggcaaa    4440
gaagaaacgg aggggatgaa ttcttcctta gacttacttt tgtaaaaatg tccccacggt    4500
acttactccc cactgatgga ccagtggttt ccagtcatga gcgttagact gacttgtttg    4560
tcttccattc cattgttttg aaactcagta tgccgcccct gtcttgctgt catgaaatca    4620
gcaagagagg atgacacatc aaataataac tcggattcca gcccacattg gattcatcag    4680
catttggacc aatagcccac agctgagaat gtggaatacc taaggataac accgcttttg    4740
ttctcgcaaa aacgtatctc ctaatttgag gctcagatga aatgcatcag gtcctttggg    4800
gcatagatca gaagactaca aaaatgaagc tgctctgaaa tctcctttag ccatcacccc    4860
aaccccccaa aattagtttg tgttacttat ggaagatagt tttctccttt tacttcactt    4920
caaaagcttt ttactcaaag agtatatgtt ccctccaggt cagctgcccc caaacccccct   4980 ccttacgctt tgtcacacaa aaagtgtctc tgccttgagt catctattca agcacttaca    5040
gctctgccca acagggca ttttacaggt gcgaatgaca gtagcattat gagtagtgtg       5100
aattcaggta gtaaatatga aactagggtt tgaaattgat aatgctttca caacatttgc    5160
```

-continued

```
agatgtttta gaaggaaaaa agttccttcc taaaataatt tctctacaat tggaagattg      5220
gaagattcag ctagttagga gcccattttt tcctaatctg tgtgtgccct gtaacctgac      5280
tggttaacag cagtcctttg taaacagtgt tttaaactct cctagtcaat atccacccca      5340
tccaatttat caaggaagaa atggttcaga aatatttttc agcctacagt tatgttcagt      5400
cacacacaca tacaaaatgt tcctttttgct tttaaagtaa ttttttgactc ccagatcagt     5460 cagagcccct acagcattgt taagaaagta tttgattttt gtctcaatga aaataaaact      5520
atattcattt cc                                                          5532

<210> SEQ ID NO 301
<211> LENGTH: 1528
<212> TYPE: DNA
<213> ORGANISM: Homo sapiens

<400> SEQUENCE: 301
cggcgagcga gcaccttcga cgcggtccgg ggaccccctc gtcgctgtcc tcccgacgcg        60
gacccgcgtg ccccaggcct cgcgctgccc ggccggctcc tcgtgtccca ctccccgcgc       120
acgccctccc gcgagtcccg ggcccctccc gcgcccctct tctcggcgcg cgcgcagcat       180
ggcgcccccg caggtcctcg cgttcgggct tctgcttgcc gcggcgacgg cgacttttgc       240
cgcagctcag gaagaatgtg tctgtgaaaa ctacaagctg gccgtaaact gctttgtgaa       300
taataatcgt caatgccagt gtacttcagt tggtgcacaa aatactgtca tttgctcaaa       360
gctggctgcc aaatgtttgg tgatgaaggc agaaatgaat ggctcaaaac ttgggagaag       420
agcaaaacct gaaggggccc tccagaacaa tgatgggctt tatgatcctg actgcgatga       480
gagcgggctc tttaaggcca agcagtgcaa cggcacctcc acgtgctggt gtgtgaacac       540
tgctggggtc agaagaacag acaaggacac tgaaataacc tgctctgagc gagtgagaac       600
ctactggatc atcattgaac taaaacacaa agcaagagaa aaaccttatg atagtaaaag       660
tttgcggact gcacttcaga aggagatcac aacgcgttat caactggatc caaaatttat       720
cacgagtatt ttgtatgaga ataatgttat cactattgat ctggttcaaa attcttctca       780
aaaaactcag aatgatgtgg acatagctga tgtggcttat tattttgaaa aagatgttaa       840
aggtgaatcc ttgtttcatt ctaagaaaat ggacctgaca gtaaatgggg aacaactgga       900
tctggatcct ggtcaaactt taatttatta tgttgatgaa aaagcacctg aattctcaat       960
gcagggtcta aaagctggtg ttattgctgt tattgtggtt gtggtgatag cagttgttgc      1020
tggaattgtt gtgctggtta tttccagaaa gaagagaatg gcaaagtatg agaaggctga      1080
gataaaggag atgggtgaga tgcataggga actcaatgca taactatata atttgaagat      1140
tatagaagaa gggaaatagc aaatggacac aaattacaaa tgtgtgtgcg tgggacgaag      1200
acatctttga aggtcatgag tttgttagtt taacatcata tatttgtaat agtgaaacct      1260
gtactcaaaa tataagcagc ttgaaactgg ctttaccaat cttgaaattt gaccacaagt      1320
gtcttatata tgcagatcta atgtaaaatc cagaacttgg actccatcgt taaaattatt      1380
tatgtgtaac attcaaatgt gtgcattaaa tatgcttcca cagtaaaatc tgaaaaactg      1440
atttgtgatt gaaagctgcc tttctatttta cttgagtctt gtacatacat actttttat      1500 gagctatgaa ataaaacatt ttaaactg                                         1528

<210> SEQ ID NO 302
<211> LENGTH: 1856
<212> TYPE: DNA
```

<213> ORGANISM: Homo sapiens

<400> SEQUENCE: 302

| | | | | | |
|---|---|---|---|---|---|
| ctgacttggc | aggactgtgc | aattgtcaga | aggccgtggg | gagtgggggc | cagtgcctgc | 60 |
| agcctgccct | gcctctctca | caggccctta | gagcatcgcc | aggtgcagag | ctccacagct | 120 |
| ctctttccca | aggagtaatc | agagggtgag | aacgtggagc | ctggtggaca | ggtgaaagca | 180 |
| ctgggatctt | tctgcccaga | aagggaaag | ttgcacattt | atatcctaga | gggaagcgac | 240 |
| agcagtgctt | ctccctgtgc | tgaggtacag | gagccatgtg | gctagaaatc | ctcctcactt | 300 |
| cagtgctggg | ctttgccatc | tactggttca | tctcccggga | caaagaggaa | actttgccac | 360 |
| ttgaagatgg | gtggtggggg | ccaggcacga | ggtccgcagc | cagggaggac | gacagcatcc | 420 |
| gcccttcaa | ggtggaaacg | tcagatgagg | agatccacga | cttacaccag | aggatcgata | 480 |
| agttccgttt | caccccacct | ttggaggaca | gctgcttcca | ctatggcttc | aactccaact | 540 |
| acctgaagaa | agtcatctcc | tactggcgga | atgaatttga | ctggaagaag | caggtggaga | 600 |
| ttctcaacag | ataccctcac | ttcaagacta | agattgaagg | gctggacatc | cacttcatcc | 660 |
| acgtgaagcc | cccccagctg | cccgcaggcc | ataccccgaa | gcccttgctg | atggtgcacg | 720 |
| gctggcccgg | ctctttctac | gagttttata | agatcatccc | actcctgact | gaccccaaga | 780 |
| accatggcct | gagcgatgag | cacgtttttg | aagtcatctg | cccttccatc | cctggctatg | 840 |
| gcttctcaga | ggcatcctcc | aagaagggt | tcaactcggt | ggccaccgcc | aggatctttt | 900 |
| acaagctgat | gctgcggctg | ggcttccagg | aattctacat | tcaaggaggg | gactgggggt | 960 |
| ccctgatctg | cactaatatg | gcccagctgg | tgcccagcca | cgtgaaaggc | ctgcacttga | 1020 |
| acatggcttt | ggttttaagc | aacttctcta | ccctgaccct | cctcctggga | cagcgtttcg | 1080 |
| ggaggtttct | tggcctcact | gagagggatg | tggagctgct | gtaccccgtc | aaggagaagg | 1140 |
| tattctacag | cctgatgagg | gagagcggct | acatgcacat | ccagtgcacc | aagcctgaca | 1200 |
| ccgtaggctc | tgctctgaat | gactctcctg | tgggtctggc | tgcctatatt | ctagagaagt | 1260 |
| tttccacctg | gaccaatacg | gaattccgat | acctggagga | tggaggcctg | gaaaggaagt | 1320 |
| tctccctgga | cgacctgctg | accaacgtca | tgctctactg | gacaacaggc | accatcatct | 1380 |
| cctcccagcg | cttctacaag | gagaacctgg | gacagggctg | gatgacccag | aagcatgagc | 1440 |
| ggatgaaggt | ctatgtgccc | actggcttct | ctgccttccc | ttttgagcta | ttgcacacgc | 1500 |
| ctgaaaagtg | ggtgaggttc | aagtacccaa | agctcatctc | ctattcctac | atggttcgtg | 1560 |
| ggggccactt | tgcggccttt | gaggagccgg | agctgctcgc | ccaggacatc | cgcaagttcc | 1620 |
| tgtcggtgct | ggagcggcaa | tgacccaccc | ctctccccc | gcctgccacc | tcccccaca | 1680 |
| agtgccctcc | aggcttttct | tggggaagat | acccctttc | tgaggaatga | gtttgcctcc | 1740 |
| gtcccctgcc | catgctggga | gcccacgctc | accccctcac | ccctccaagc | tcactcccca | 1800 |
| accccccaact | ccgtgtggta | agcaacatgg | ctttgatgat | aaacgacttt | actcta | 1856 |

<210> SEQ ID NO 303
<211> LENGTH: 6450
<212> TYPE: DNA
<213> ORGANISM: Homo sapiens

<400> SEQUENCE: 303

| | | | | | |
|---|---|---|---|---|---|
| gagttgtgcc | tggagtgatg | tttaagccaa | tgtcagggca | aggcaacagt | ccctggccgt | 60 |
| cctccagcac | ctttgtaatg | catatgagct | cgggagacca | gtacttaaag | ttggaggccc | 120 |
| gggagcccag | gagctggcgg | agggcgttcg | tcctgggagc | tgcacttgct | ccgtcgggtc | 180 |

-continued

```
gccggcttca ccggaccgca ggctcccggg gcagggccgg ggccagagct cgcgtgtcgg      240
cgggacatgc gctgcgtcgc ctctaacctc gggctgtgct cttttccag gtggcccgcc       300 ggtttctgag ccttctgccc tgcggggaca cggtctgcac cctgcccgcg ccacggacc       360 atgaccatga ccctccacac caaagcatct gggatggccc tactgcatca gatccaaggg     420
aacgagctgg agcccctgaa ccgtccgcag ctcaagatcc ccctggagcg gcccctgggc     480
gaggtgtacc tggacagcag caagcccgcc gtgtacaact accccgaggg cgccgcctac    540
gagttcaacg ccgcggccgc cgccaacgcg caggtctacg gtcagaccgg cctcccctac    600
ggccccgggt ctgaggctgc ggcgttcggc tccaacggcc tgggggtttt ccccccactc    660
aacagcgtgt ctccgagccc gctgatgcta ctgcacccgc cgccgcagct gtcgcctttc    720
ctgcagcccc acggccagca ggtgccctac tacctggaga cgagcccag cggctacacg     780 gtgcgcgagg ccgccccgcc ggcattctac aggccaaatt cagataatcg acgccagggt   840
ggcagagaaa gattggccag taccaatgac aagggaagta tggctatgga atctgccaag   900
gagactcgct actgtgcagt gtgcaatgac tatgcttcag gctaccatta tggagtctgg   960
tcctgtgagg gctgcaaggc cttcttcaag agaagtattc aaggacataa cgactatatg  1020
tgtccagcca ccaaccagtg caccattgat aaaaacagga ggaagagctg ccaggcctgc  1080
cggctccgca aatgctacga agtgggaatg atgaaaggtg ggatacgaaa agaccgaaga   1140
ggagggagaa tgttgaaaca caagcgccag agagatgatg gggagggcag gggtgaagtg  1200
gggtctgctg gagacatgag agctgccaac ctttggccaa gccgctcat gatcaaacgc    1260 tctaagaaga acagcctggc cttgtccctg acggccgacc agatggtcag tgccttgttg  1320
gatgctgagc ccccatact ctattccgag tatgatccta ccagacctt cagtgaagct    1380 tcgatgatgg gcttactgac caacctggca gacagggagc tggttcacat gatcaactgg  1440
gcgaagaggg tgccaggctt tgtggatttg accctccatg atcaggtcca ccttctagaa   1500
tgtgcctggc tagagatcct gatgattggt ctcgtctggc gctccatgga gcacccagtg  1560
aagctactgt ttgctcctaa cttgctcttg gacaggaacc agggaaaatg tgtagagggc   1620
atggtggaga tcttcgacat gctgctggct acatcatctc ggttccgcat gatgaatctg  1680
cagggagagg agtttgtgtg cctcaaatct attattttgc ttaattctgg agtgtacaca   1740
tttctgtcca gcaccctgaa gtctctggaa gagaaggacc atatccaccg agtcctggac   1800
aagatcacag acactttgat ccacctgatg gccaaggcag gcctgaccct gcagcagcag   1860
caccagcggc tggcccagct cctcctcatc ctctcccaca tcaggcacat gagtaacaaa   1920
ggcatggagc atctgtacag catgaagtgc aagaacgtgg tgccctcta tgacctgctg   1980 ctggagatgc tggacgccca ccgcctacat gcgcccacta gccgtggagg ggcatccgtg   2040
gaggagacgg accaaagcca cttggccact gcgggctcta cttcatcgca ttccttgcaa  2100
aagtattaca tcacggggga ggcagagggt ttccctgcca cagtctgaga gctccctggc   2160
tcccacacgg ttcagataat ccctgctgca ttttaccctc atcatgcacc actttagcca   2220
aattctgtct cctgcataca ctccggcatg catccaacac caatggcttt ctagatgagt   2280
ggccattcat ttgcttgctc agttcttagt ggcacatctt ctgtcttctg ttgggaacag   2340
ccaaagggat tccaaggcta aatctttgta acagctctct ttccccttg ctatgttact   2400 aagcgtgagg attcccgtag ctcttcacag ctgaactcag tctatgggtt ggggctcaga   2460
taactctgtg catttaagct acttgtagag acccaggcct ggagagtaga cattttgcct   2520
```

```
ctgataagca cttttaaaat ggctctaaga ataagccaca gcaaagaatt taaagtggct    2580
cctttaattg gtgacttgga gaaagctagg tcaagggttt attatagcac cctcttgtat    2640
tcctatggca atgcatcctt ttatgaaagt ggtacacctt aaagctttta tatgactgta    2700
gcagagtatc tggtgattgt caattcactt cccctatag gaatacaagg ggccacacag    2760
ggaaggcaga tccctagtt ggccaagact tattttaact tgatacactg cagattcaga    2820
gtgtcctgaa gctctgcctc tggctttccg gtcatgggtt ccagttaatt catgcctccc    2880
atggacctat ggagagcaac aagttgatct tagttaagtc tccctatatg agggataagt    2940
tcctgatttt tgttttttatt tttgtgttac aaaagaaagc cctccctccc tgaacttgca    3000
gtaaggtcag cttcaggacc tgttccagtg ggcactgtac ttggatcttc ccggcgtgtg    3060
tgtgccttac acaggggtga actgttcact gtggtgatgc atgatgaggg taaatggtag    3120
ttgaaaggag caggggccct ggtgttgcat ttagccctgg ggcatggagc tgaacagtac    3180
ttgtgcagga ttgttgtggc tactagagaa caagagggaa agtagggcag aaactggata    3240
cagttctgag cacagccaga cttgctcagg tggccctgca caggctgcag ctacctagga    3300
acattccttg cagaccccgc attgcctttg ggggtgccct gggatccctg ggtagtccca    3360
gctcttattc atttcccagc gtggccctgg ttggaagaag cagctgtcaa gttgtagaca    3420
gctgtgttcc tacaattggc ccagcaccct ggggcacggg agaagggtgg ggaccgttgc    3480
tgtcactact caggctgact ggggcctggt cagattacgt atgcccttgg tggtttagag    3540
ataatccaaa atcagggttt ggtttgggga agaaaatcct cccccttcct cccccgcccc    3600
gttccctacc gcctccactc ctgccagctc atttccttca atttcctttg acctataggc    3660 taaaaagaa aggctcattc cagccacagg gcagccttcc ctgggccttt gcttctctag    3720
cacaattatg ggttacttcc tttttcttaa caaaaagaa tgtttgattt cctctgggtg    3780
accttattgt ctgtaattga aaccctattg agaggtgatg tctgtgttag ccaatgaccc    3840
aggtagctgc tcgggcttct cttggtatgt cttgtttgga aaagtggatt tcattcattt    3900
ctgattgtcc agttaagtga tcaccaaagg actgagaatc tgggagggca aaaaaaaaa    3960 aaaaagtttt tatgtgcact taaatttggg gacaatttta tgtatctgtg ttaaggatat    4020
gcttaagaac ataattcttt tgttgctgtt tgtttaagaa gcaccttagt ttgtttaaga    4080
agcaccttat atagtataat atatattttt ttgaaattac attgcttgtt tatcagacaa    4140
ttgaatgtag taattctgtt ctggatttaa tttgactggg ttaacatgca aaaaccaagg    4200
aaaaatattt agttttttt tttttttttg tatacttttc aagctacctt gtcatgtata    4260
cagtcattta tgcctaaagc ctggtgatta ttcatttaaa tgaagatcac atttcatatc    4320
aacttttgta tccacagtag acaaaatagc actaatccag atgcctattg ttggatattg    4380
aatgacagac aatcttatgt agcaaagatt atgcctgaaa aggaaaatta ttcagggcag    4440
ctaattttgc ttttaccaaa atatcagtag taatatttt ggacagtagc taatgggtca    4500
gtgggttctt tttaatgttt atacttagat tttctttaa aaaattaaa ataaacaaa    4560 aaaaatttct aggactagac gatgtaatac cagctaaagc caaacaatta tacagtggaa    4620
ggttttacat tattcatcca atgtgtttct attcatgtta agatactact acatttgaag    4680
tgggcagaga acatcagatg attgaaatgt tcgcccaggg gtctccagca actttggaaa    4740
tctctttgta ttttttacttg aagtgccact aatggacagc agatattttc tggctgatgt    4800
tggtattggg tgtaggaaca tgatttaaaa aaaaaactct tgcctctgct ttcccccact    4860
ctgaggcaag ttaaaatgta aaagatgtga tttatctggg gggctcaggt atggtgggga    4920
```

| | |
|---|---|
| agtggattca ggaatctggg gaatggcaaa tatattaaga agagtattga aagtatttgg | 4980 |
| aggaaaatgg ttaattctgg gtgtgcacca aggttcagta gagtccactt ctgccctgga | 5040 |
| gaccacaaat caactagctc catttacagc catttctaaa atggcagctt cagttctaga | 5100 |
| gaagaaagaa caacatcagc agtaaagtcc atggaatagc tagtggtctg tgtttctttt | 5160 |
| cgccattgcc tagcttgccg taatgattct ataatgccat catgcagcaa ttatgagagg | 5220 |
| ctaggtcatc caaagagaag accctatcaa tgtaggttgc aaaatctaac ccctaaggaa | 5280 |
| gtgcagtctt tgatttgatt tccctagtaa ccttgcagat atgtttaacc aagccatagc | 5340 |
| ccatgccttt tgagggctga acaaataagg gacttactga taatttactt ttgatcacat | 5400 |
| taaggtgttc tcaccttgaa atcttataca ctgaaatggc cattgattta ggccactggc | 5460 |
| ttagagtact ccttcccctg catgacactg attacaaata ctttcctatt catactttcc | 5520 |
| aattatgaga tggactgtgg gtactgggag tgatcactaa caccatagta atgtctaata | 5580 |
| ttcacaggca gatctgcttg gggaagctag ttatgtgaaa ggcaaataaa gtcatacagt | 5640 |
| agctcaaaag gcaaccataa ttctctttgg tgcaagtctt gggagcgtga tctagattac | 5700 |
| actgcaccat tcccaagtta atcccctgaa aacttactct caactgggagc aaatgaactt | 5760 |
| tggtcccaaa tatccatctt ttcagtagcg ttaattatgc tctgttttcca actgcatttc | 5820 |
| ctttccaatt gaattaaagt gtggcctcgt ttttagtcat ttaaaattgt tttctaagta | 5880 |
| attgctgcct ctattatggc acttcaattt tgcactgtct tttgagattc aagaaaaatt | 5940 |
| tctattcatt tttttgcatc caattgtgcc tgaactttta aaatatgtaa atgctgccat | 6000 |
| gttccaaacc catcgtcagt gtgtgtgttt agagctgtgc accctagaaa caacatactt | 6060 |
| gtcccatgag caggtgcctg agacacagac ccctttgcat tcacagagag gtcattggtt | 6120 |
| atagagactt gaattaataa gtgacattat gccagtttct gttctctcac aggtgataaa | 6180 |
| caatgctttt tgtgcactac atactcttca gtgtagagct cttgtttttat gggaaaaggc | 6240 |
| tcaaatgcca aattgtgttt gatggattaa tatgcccttt tgccgatgca tactattact | 6300 |
| gatgtgactc ggttttgtcg cagctttgct ttgtttaatg aaacacactt gtaaacctct | 6360 |
| tttgcacttt gaaaagaat ccagcgggat gctcgagcac ctgtaaacaa ttttctcaac | 6420 |
| ctatttgatg ttcaaataaa gaattaaact | 6450 |

<210> SEQ ID NO 304
<211> LENGTH: 3336
<212> TYPE: DNA
<213> ORGANISM: Homo sapiens
<220> FEATURE:
<221> NAME/KEY: unsure
<222> LOCATION: (0)...(0)
<223> OTHER INFORMATION: n = A, T, C or G

<400> SEQUENCE: 304

| | |
|---|---|
| cggcggcgac tgcagtctgg agggtccaca cttgtgattc tcaatggaga gtgaaaacgc | 60 |
| agattcataa tgaaagctag cccccgtcgg ccactgattc tcaaaagacg gaggctgccc | 120 |
| cttcctgttc aaaatgcccc aagtgaaaca tcagaggagg aacctaagag atcccctgcc | 180 |
| caacaggagt ctaatcaagc agaggcctcc aaggaagtgg cggagtccaa ctcttgcaag | 240 |
| tttccagctg ggatcaagat tattaaccac cccaccatgc caacacgca agtagtggcc | 300 |
| atccccaaca atgctaatat tcacagcatc atcacagcac tgactgccaa gggaaaagag | 360 |
| agtggcagta gtgggcccaa caaattcatc ctcatcagct gtgggggagc cccaactcag | 420 |

-continued

```
cctccaggac tccggcctca aacccaaacc agctatgatg ccaaaaggac agaagtgacc      480
ctggagacct tgggaccaaa acctgcagct agggatgtga atcttcctag accacctgga      540 gcccttttgcg agcagaaacg ggagacctgt gcagatggtg aggcagcagg ctgcactatc     600
aacaatagcc tatccaacat ccagtggctt cgaaagatga gttctgatgg actgggctcc     660
cgcagcatca agcaagagat ggaggaaaag gagaattgtc acctggagca gcgacaggtt     720
aaggttgagg agccttcgag accatcagcg tcctggcaga actctgtgtc tgagcggcca     780
ccctactctt acatggccat gatacaattc gccatcaaca gcactgagag gaagcgcatg     840
actttgaaag acatctatac gtggattgag gaccactttc cctactttaa gcacattgcc     900
aagccaggct ggaagaactc catccgccac aacctttccc tgcacgacat gtttgtccgg     960
gagacgtctg ccaatggcaa ggtctccttc tggaccattc accccagtgc caaccgctac    1020
ttgacattgg accaggtgtt taagccactg acccagggt ctccacaatt gcccgagcac     1080
ttggaatcac agcagaaacg accgaatcca gagctccgcc ggaacatgac catcaaaacc    1140
gaactccccc tgggcgcacg gcggaagatg aagccactgc taccacgggt cagctcatac    1200
ctggtaccta tccagttccc ggtgaaccag tcactggtgt tgcagccctc ggtgaaggtg    1260
ccattgcccc tggcggcttc cctcatgagc tcagagcttg cccgccatag caagcgagtc    1320
cgcattgccc ccaaggtgct gctagctgag gagggatag ctcctctttc ttctgcagga     1380
ccagggaaag aggagaaact cctgtttgga aagggttttt ctcctttgct tccagttcag    1440
actatcaagg aggaagaaat ccagcctggg gaggaaatgc cacacttagc gagacccatc    1500
aaagtggaga gccctccctt ggaagagtgg ccctccccgg ccccatcttt caaagaggaa    1560
tcatctcact cctgggagga ttcgtcccaa tctcccaccc caagacccaa gaagtcctac    1620
agtgggctta ggtccccaac ccggtgtgtc tcggaaatgc ttgtgattca acacagggag    1680
aggagggaga ggagccggtc tcggaggaaa cagcatctac tgcctccctg tgtggatgag    1740
ccggagctgc tcttctcaga ggggcccagt acttcccgct gggccgcaga gctcccgttc    1800
ccagcagact cctctgaccc tgcctcccag ctcagctact cccaggaagt gggaggacct    1860
tttaagacac ccattaagga aacgctgccc atctcctcca ccccgagcaa atctgtcctc    1920
cccagaaccc ctgaatcctg gaggctcacg ccccagcca agtaggggg actggatttc      1980 agcccagtac aaacctccca gggtgcctct gaccccttgc ctgaccccct ggggctgatg    2040
gatctcagca ccactccctt gcaaagtgct cccccccttg aatcaccgca aaggctcctc    2100
agttcagaac ccttagacct catctccgtc ccctttggca actcttctcc ctcagatata    2160
gacgtcccca agccaggctc cccggagcca caggtttctg gccttgcagc caatcgttct    2220
ctgacagaag gcctggtcct ggacacaatg aatgacagcc tcagcaagat cctgctggac    2280
atcagctttc ctggcctgga cgaggaccca ctgggccctg acaacatcaa ctggtcccag    2340
tttattcctg agctacagta gagccctgcc cttgcccctg tgctcaagct gtccaccatc    2400
ccgggcactc aaggctcag tgcaccccaa gcctctgagt gaggacagca ggcagggact     2460
gttctgctcc tcatagctcc ctgctgcctg attatgcaaa agtagcagtc acaccctagc    2520
cactgctggg accttgtgtt ccccaagagt atctgattcc tctgctgtcc ctgccaggag    2580
ctgaagggtg ggaacaacaa aggcaatggt gaaaagagat taggaacccc ccagcctgtt    2640
tccattctct gcccagcagt ctcttacctt ccctgatctt tgcagggtgg tccgtgtaaa    2700
tagtataaat tctccaaatt atcctctaat tataaatgta agcttatttc cttagatcat    2760
tatccagaga ctgccagaag gtgggtagga tgacctgggg tttcaattga cttctgttcc    2820
```

-continued

| | |
|---|---|
| ttgcttttag ttttgataga agggaagacc tgcagtgcac ggtttcttcc aggctgaggt | 2880 |
| acctggatct tgggttcttc actgcaggga cccagacaag tggatctgct tgccagagtc | 2940 |
| cttttgccc ctccctgcca cctccccgtg tttccaagtc agctttcctg caagaagaaa | 3000 |
| tcctggttaa aaaagtcttt tgtattgggt caggagttga atttggggtg ggaggatgga | 3060 |
| tgcaactgaa gcagagtgtg ggtgcccaga tgtgcgctat tagatgtttc tctgataatg | 3120 |
| tccccaatca taccagggag actggcattg acgagaactc aggtggaggc ttgagaaggc | 3180 |
| cgaaagggcc cctgacctgc ctggcttcct tagcttgccc ctcagctttg caaagagcca | 3240 |
| ccctaggccc cagctgaccg catgggtgtg agccagcttg agaacactaa ctactcaata | 3300 |
| aaagcgaagg tggaccnaaa aaaaaaaaaa aaaaaa | 3336 |

<210> SEQ ID NO 305
<211> LENGTH: 2365
<212> TYPE: DNA
<213> ORGANISM: Homo sapiens

<400> SEQUENCE: 305

| | |
|---|---|
| tcccagcctt cccatccccc caccgaaagc aaatcattca acgaccccg accctccgac | 60 |
| ggcaggagcc ccccgacctc ccaggcggac cgcccttccc tccccgcgcg ggttccgggc | 120 |
| ccggcgagag ggcgcgacga cagccgaggc catggaggtg acggcggacc agccgcgctg | 180 |
| ggtgagccac caccaccccg ccgtgctcaa cgggcagcac ccggacacgc accacccggg | 240 |
| cctcagccac tcctacatgg acgcggcgca gtacccgctg ccgaggagg tggatgtgct | 300 |
| ttttaacatc gacggtcaag gcaaccacgt cccgccctac tacggaaaact cggtcagggc | 360 |
| cacggtgcag aggtaccctc cgaccccacca cgggagccag gtgtgccgcc cgcctctgct | 420 |
| tcatggatcc ctaccctggc tggacggcgg caaagccctg ggcagccacc acaccgcctc | 480 |
| cccctggaat ctcagcccct tctccaagac gtccatccac cacggctccc cggggcccct | 540 |
| ctccgtctac cccccggcct cgtcctcctc cttgtcgggg ggccacgcca gcccgcacct | 600 |
| cttcaccttc ccgcccaccc cgccgaagga cgtctcccg gacccatcgc tgtccacccc | 660 |
| aggctcggcc ggctcggccc ggcaggacga gaaagagtgc ctcaagtacc aggtgcccct | 720 |
| gcccgacagc atgaagctgg agtcgtccca ctcccgtggc agcatgaccg ccctgggtgg | 780 |
| agcctcctcg tcgacccacc accccatcac cacctacccg ccctacgtgc ccgagtacag | 840 |
| ctccggactc ttcccccca gcagcctgct gggcggctcc cccaccggct cggatgcaa | 900 |
| gtccaggccc aaggcccggt ccagcacagg cagggagtgt gtgaactgtg ggcaacctc | 960 |
| gaccccactg tggcggcgag atggcacggg acactacctg tgcaacgcct gcgggctcta | 1020 |
| tcacaaaatg aacggacaga accggcccct cattaagccc aagcgaaggc tgtctgcagc | 1080 |
| caggagagca gggacgtcct gtgcgaactg tcagaccacc acaaccacac tctgaggag | 1140 |
| gaatgccaat ggggaccctg tctgcaatgc ctgtgggctc tactacaagc ttcacaatat | 1200 |
| taacagaccc ctgactatga agaaggaagg catccagacc agaaccgaa aaatgtctag | 1260 |
| caaatccaaa aagtgcaaaa aagtgcatga ctcactggag gacttcccca agaacagctc | 1320 |
| gtttaacccg gccgccctct ccagacacat gtcctccctg agccacatct cgccctcag | 1380 |
| ccactccagc cacatgctga ccacgcccac gccgatgcac ccgccatcca gcctgtcctt | 1440 |
| tggaccacac cacccctcca gcatggtcac cgccatgggt tagagccctg ctcgatgctc | 1500 |
| acagggcccc cagcgagagt ccctgcagtc cctttcgact tgcattttg caggagcagt | 1560 |

-continued

```
atcatgaagc ctaaacgcga tggatatatg tttttgaagg cagaaagcaa aattatgttt      1620
gccactttgc aaaggagctc actgtggtgt ctgtgttcca accactgaat ctggacccca      1680
tctgtgaata agccattctg actcatatcc cctatttaac agggtctcta gtgctgtgaa      1740
aaaaaaaaat cctgaacatt gcatataact tatattgtaa gaaatactgt acaatgactt      1800
tattgcatct gggtagctgt aaggcatgaa ggatgccaag aagtttaagg aatatgggag      1860
aaatagtgtg gaaattaaga agaaactagg tctgatattc aaatggacaa actgccagtt      1920
ttgtttcctt tcactggcca cagttgtttg atgcattaaa agaaataaaa aaaagaaaa      1980 aagagaaaag aaaaaaaaag aaaaaagttg taggcgaatc atttgttcaa agctgttggc      2040
cctctgcaaa ggaaatacca gttctgggca atcagtgtta ccgttcacca gttgccattg      2100
agggtttcag agagcctttt tctaggccta catgctttgt gaacaagtcc ctgtaattgt      2160
tgtttgtatg tataattcaa agcaccaaaa taagaaaaga tgtagattta tttcatcata      2220
ttatacagac cgaactgttg tataaattta tttactgcta gtcttaagaa ctgctttctt      2280
tcgtttgttt gtttcaatat tttccttctc tctcaattt cggttgaata aactagatta      2340
cattcagttg gcaaaaaaaa aaaaa                                            2365
```

<210> SEQ ID NO 306
<211> LENGTH: 1117
<212> TYPE: DNA
<213> ORGANISM: Homo sapiens

<400> SEQUENCE: 306

```
gcaccaacca gcaccatgcc catgatactg gggtactggg acatccgcgg gctggcccac       60
gccatccgcc tgctcctgga atacacagac tcaagctatg aggaaaagaa gtacacgatg      120
ggggacgctc ctgattatga cagaagccag tggctgaatg aaaaattcaa gctgggcctg      180
gactttccca atctgcccta cttgattgat ggggctcaca agatcaccca gagcaacgcc      240
atcttgtgct acattgcccg caagcacaac ctgtgtgggg agacagaaga ggagaagatt      300
cgtgtggaca ttttggagaa ccagaccatg gacaaccata tgcagctggg catgatctgc      360
tacaatccag aatttgagaa actgaagcca agtacttgg aggaactccc tgaaaagcta      420
aagctctact cagagtttct ggggaagcgg ccatggtttg caggaaacaa gatcactttt      480
gtagattttc tcgtctatga tgtccttgac ctccaccgta tatttgagcc caactgcttg      540
gacgccttcc caaatctgaa ggacttcatc tcccgctttg agggcttgga gaagatctct      600
gcctacatga agtccagccg cttcctccca agacctgtgt tctcaaagat ggctgtctgg      660
ggcaacaagt agggcttga aggcaggagg tgggagtgag gagcccatac tcagcctgct      720
gcccaggctg tgcagcgcag ctggactctg catcccagca cctgcctcct cgttcctttc      780
tcctgtttat tcccatcttt actcccaaga cttcattgtc cctcttcact cccctaaac      840 ccctgtccca tgcaggccct tgaagcctc agctacccac tatccttgt gaacatcccc      900 tcccatcatt acccttccct gcactaaagc cagcctgacc ttccttcctg ttagtggttg      960
tgtctgcttt aaagcctgcc tggccccctcg cctgtggagc tcagcccga gctgtccccg     1020 tgttgcatga aggagcagca ttgactggtt tacaggccct gctcctgcag catggtccct     1080
gcctaggcct acctgatgga agtaaagcct caaccac                              1117
```

<210> SEQ ID NO 307
<211> LENGTH: 1266
<212> TYPE: DNA
<213> ORGANISM: Homo sapiens

<400> SEQUENCE: 307

```
ctcggaagcc cgtcaccatg tcgtgcgagt cgtctatggt tctcgggtac tgggatattc        60
gtgggctggc gcacgccatc cgcctgctcc tggagttcac ggatacctct tatgaggaga       120
aacggtacac gtgcggggaa gctcctgact atgatcgaag ccaatggctg gatgtgaaat       180
tcaagctaga cctggacttt cctaatctgc cctacctcct ggatgggaag aacaagatca       240
cccagagcaa tgccatcttg cgctacatcg ctcgcaagca aacatgtgt ggtgagactg        300
aagaagaaaa gattcgagtg gacatcatag agaaccaagt aatggatttc cgcacacaac       360
tgataaggct ctgttacagc tctgaccacg aaaaactgaa gcctcagtac ttggaagagc       420
tacctggaca actgaaacaa ttctccatgt ttctgtggaa attctcatgg tttgccgggg       480
aaaagctcac ctttgtggat tttctcacct atgatatctt ggatcagaac cgtatatttg       540
acccccaagtg cctggatgag ttcccaaacc tgaaggcttt catgtgccgt tttgaggctt       600
tggagaaaat cgctgcctac ttacagtctg atcagttctg caagatgccc atcaacaaca       660
agatggccca gtgggcaac aagcctgtat gctgagcagg aggcagactt gcagagcttg        720
ttttgtttca tcctgtccgt aagggggtcag cgctcttgct ttgctctttt caatgaatag       780
cacttatgtt actggtgtcc agctgagttt ctcttgggta taaaggctaa aagggaaaaa       840
ggatatgtgg agaatcatca agatatgaat tgaatcgctg cgatactgtg gcatttccct       900
actccccaac tgagttcaag ggctgtaggt tcatgcccaa gccctgagag tgggtactag       960
aaaaaacgag attgcacagt tggagagagc aggtgtgtta aatggactgg agtccctgtg      1020
aagactggt gaggataaca caagtaaaac tgtggtactg atggacttaa ccggagttcg       1080
gaaaccgtcc tgtgtacaca tgggagttta gtgtgataaa ggcagtattt cagactggtg      1140
ggctagccaa tagagttggc aattgcttat tgaaactcat taaaaataat agagccccac      1200
ttgacactat tcactaaaat taatctggaa tttaaggccc aacattaaac acaaagctgt      1260
attgat                                                                 1266
```

<210> SEQ ID NO 308
<211> LENGTH: 2162
<212> TYPE: DNA
<213> ORGANISM: Homo sapiens

<400> SEQUENCE: 308

```
gggctgcgct gtccagctgt ggctatggcc ccagccccga gatgaggagg gagagaacta        60
ggggcccgca ggcctgggaa tttccgtccc ccaccaagtc cggatgctca ctccaaagtc       120
tcagcaggcc cctgagggag ggagctgtca gccagggaaa accgagaaca ccatcaccat       180
gacaaccagt caccagcctc aggacagata caaagctgtc tggcttatct tcttcatgct       240
gggtctggga acgctgctcc cgtggaattt tttcatgacg gccactcagt atttcacaaa       300
ccgcctggac atgtcccaga atgtgtcctt ggtcactgct gaactgagca aggacgccca       360
ggcgtcagcc gcccctgcag cacccttgcc tgagcggaac tctctcagtg ccatcttcaa       420
caatgtcatg accctatgtg ccatgctgcc cctgctgtta ttcacctacc tcaactcctt       480
cctgcatcag aggatccccc agtccgtacg gatcctgggc agcctggtgg ccatcctgct       540
ggtgtttctg atcactgcca tcctggtgaa ggtgcagctg gatgctctgc ccttctttgt       600
catcaccatg atcaagatcg tgctcattaa ttcatttggt gccatcctgc agggcagcct       660
gtttggtctg gctggccttc tgcctgccag ctacacggcc cccatcatga gtggccaggg       720
```

```
cctagcaggc ttctttgcct ccgtggccat gatctgcgct attgccagtg gctcggaact      780
atcagaaagt gccttcggct actttatcac agcctgtgct gttatcattt tgaccatcat      840
ctgttacctg ggcctgcccc gcctggaatt ctaccgctac taccagcagc tcaagcttga      900
aggacccggg gagcaggaga ccaagttgga cctcattagc aaaggagagg agccaagagc      960
aggcaaagag gaatctggag tttcagtctc caactctcag cccaccaatg aaagccactc     1020
tatcaaagcc atcctgaaaa atatctcagt cctggctttc tctgtctgct tcatcttcac     1080
tatcaccatt gggatgtttc agccgtgac tgttgaggtc aagtccagca tcgcaggcag     1140
cagcacctgg gaacgttact tcattcctgt gtcctgtttc ttgactttca atatctttga     1200
ctggttgggc cggagcctca cagctgtatt catgtggcct gggaaggaca gccgctggct     1260
gccaagcctg tgctggcccc ggctggtgtt tgtgccactg ctgctgctgt gcaacattaa     1320
gccccgccgc tacctgactg tggtcttcga gcacgatgcc tggttcatct tcttcatggc     1380
tgcctttgcc ttctccaacg gctacctcgc cagcctctgc atgtgcttcg ggcccaagaa     1440
agtgaagcca gctgaggcag agaccgcagg agccatcatg gccttcttcc tgtgtctggg     1500
tctggcactg ggggctgttt tctccttcct gttccgggca attgtgtgac aaaggatgga     1560
cagaaggact gcctgcctcc ctccctgtct gcctcctgcc ccttccttct gccaggggtg     1620
atcctgagtg gtctggcggt ttttctttct aactgacttc tgctttccac ggcgtgtgct     1680
gggcccggat ctccaggccc tggggaggga gcctctggac ggacagtggg gacattgtgg     1740
gtttggggct cagagtcgag ggacggggtg tagcctcggc atttgcttga gtttctccac     1800
tcttggctct gactgatccc tgcttgtgca ggccagtgga ggctcttggg cttggagaac     1860
acgtgtgtct ctgtgtatgt gtctgtgtgt ctgcgtccgt gtctgtcaga ctgtctgcct     1920
gtcctggggt ggctaggagc tgggtctgac cgttgtatgg tttgacctga tatactccat     1980
tctcccctgc gcctcctcct ctgtgttttt tccatgtccc cctcccaact ccccatgccc     2040 agttttacc catcatgcac cctgtacagt tgccacgtta ctgcctttt taaaaatata     2100 tttgacagaa accaggtgcc ttcagaggct ctctgattta aataaacctt tcttgttttt     2160
tt                                                                   2162
```

<210> SEQ ID NO 309
<211> LENGTH: 3933
<212> TYPE: DNA
<213> ORGANISM: Homo sapiens

<400> SEQUENCE: 309

```
cacgaggcag cactctcttc gtcgcttcgg ccagtgtgtc gggctgggcc ctgacaagcc       60
acctgaggag aggctcggag ccgggcccgg accccggcga ttgccgcccg cttctctcta      120
gtctcacgag gggtttcccg cctcgcaccc ccacctctgg acttgccttt ccttctcttc      180
tccgcgtgtg gagggagcca gcgcttaggc cggagcgagc ctgggggccg ccgcgcgtga      240
agacatcgcg gggaccgatt caccatggag ggcgccggcg gcgcgaacga caagaaaaag      300
ataagttctg aacgtcgaaa agaaaagtct cgagatgcag ccagatctcg gcgaagtaaa      360
gaatctgaag ttttttatga gcttgctcat cagttgccac ttccacataa tgtgagttcg      420
catcttgata aggcctctgt gatgaggctt accatcagct atttgcgtgt gaggaaactt      480
ctggatgctg gtgatttgga tattgaagat gacatgaaag cacagatgaa ttgcttttat      540
ttgaaagcct tggatggttt tgttatggtt ctcacagatg atggtgacat gatttacatt      600
tctgataatg tgaacaaata catgggatta actcagtttg aactaactgg acacagtgtg      660
```

-continued

```
tttgatttta ctcatccatg tgaccatgag gaaatgagag aaatgcttac acacagaaat      720
ggccttgtga aaagggtaa agaacaaaac acacagcgaa gctttttct cagaatgaag        780
tgtaccctaa ctagccgagg aagaactatg aacataaagt ctgcaacatg gaaggtattg     840
cactgcacag gccacattca cgtatatgat accaacagta accaacctca gtgtgggtat    900
aagaaaccac ctatgacctg cttggtgctg atttgtgaac ccattcctca cccatcaaat    960
attgaaattc ctttagatag caagactttc ctcagtcgac acagcctgga tatgaaattt   1020
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttcgttgtg agtggtatta ttcagcacga cttgattttc    1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtg ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgttttat gtggatagtg atatggtcaa tgaattcaag   1860
ttggaattgg tagaaaaact ttttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagcccaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580
ttaataccct ctgatttagc atgtagactg ctggggcaat caatggatga agtggattta   2640
ccacagctga ccagttatga ttgtgaagtt aatgctccta caaggcag cagaaaccta   2700
ctgcagggtg aagaattact cagagctttg gatcaagtta actgagcttt ttcttaattt   2760
cattcctttt tttggacact ggtggctcac tacctaaagc agtctattta tattttctac   2820
atctaatttt agaagcctgg ctacaatact gcacaaactt ggttagttca attttttgatc   2880
cccttttctac ttaattaca ttaatgctct ttttagtat gttctttaat gctggatcac   2940
agacagctca ttttctcagt ttttggtat ttaaaccatt gcattgcagt agcatcattt   3000
```

```
taaaaaatgc accttttat ttatttattt ttggctaggg agtttatccc tttttcgaat    3060
tatttttaag aagatgccaa tataattttt gtaagaaggc agtaaccttt catcatgatc    3120
ataggcagtt gaaaaatttt tacaccttt ttttcacatt ttacataaat aataatgctt    3180
tgccagcagt acgtggtagc cacaattgca caatatattt tcttaaaaaa taccagcagt    3240
tactcatgga atatattctg cgtttataaa actagttttt aagaagaaat ttttttggc     3300
ctatgaaatt gttaaacctg aacatgaca ttgttaatca tataataatg attcttaaat     3360
gctgtatggt ttattattta aatgggtaaa gccatttaca taatatagaa agatatgcat    3420
atatctagaa ggtatgtggc atttatttgg ataaaattct caattcagag aaatcatctg    3480
atgtttctat agtcactttg ccagctcaaa agaaacaat accctatgta gttgtggaag     3540
tttatgctaa tattgtgtaa ctgatattaa acctaaatgt tctgcctacc ctgttggtat    3600
aaagatattt tgagcagact gtaaacaaga aaaaaaaat catgcattct tagcaaaatt    3660
gcctagtatg ttaatttgct caaaatacaa tgtttgattt tatgcacttt gtcgctatta    3720
acatccttt tttcatgtag atttcaataa ttgagtaatt ttagaagcat tatttagga     3780
atatatagtt gtcacagtaa atatcttgtt ttttctatgt acattgtaca aatttttcat    3840
tcctttgct ctttgtggtt ggatctaaca ctaactgtat tgttttgtta catcaaataa    3900
acatcttctg tggaaaaaaa aaaaaaaaa aaa                                  3933

<210> SEQ ID NO 310
<211> LENGTH: 2872
<212> TYPE: DNA
<213> ORGANISM: Homo sapiens

<400> SEQUENCE: 310
tccaggaatc gatagtgcat tcgtgcgcgc ggccgcccgt cgcttcgcac agggctggat      60
ggttgtattg ggcagggtgg ctccaggatg ttaggaactg tgaagatgga agggcatgaa     120
accagcgact ggaacagcta ctacgcagac acgcaggagg cctactcctc ggtcccggtc     180
agcaacatga actcaggcct gggctccatg aactccatga acacctacat gaccatgaac    240
accatgacta cgagcggcaa catgacccg cgtccttca acatgtccta tgccaacccg       300
gccttagggg ccggcctgag tcccggcgca gtagccggca tgccgggggg ctcggcgggc    360
gccatgaaca gcatgactgc ggccggcgtg acggccatgg gtacggcgct gagcccgagc    420
ggcatgggcg ccatgggtgc gcagcaggcg gcctccatga tgaatggcct gggcccctac    480
gcggccgcca tgaacccgtg catgagcccc atggcgtacg cgccgtccaa cctgggccgc    540
agccgcgcgg gcggcggcgg cgacgccaag acgttcaagc gcagttaccc gcacgccaag    600
ccgcccactc cgtacatctc gctcatcacc atggccatcc agcgggcgcc cagcaagatg    660
ctcacgctga gcgagatcta ccagtggatc atggacctct tcccctatta ccggcagaac    720
cagcagcgct ggcagaactc catccgccac tgctgtcct tcaatgactg cttcgtcaag    780
gtggcacgct ccccggacaa gccgggcaag ggctcctact ggacgctgca cccggactcc    840
ggcaacatgt tcgagaacgg ctgctacttg cgccgccaga gcgcttcaa gtgcgagaag    900
cagccgggg ccggcggcgg gggcgggagc ggaagcgggg gcagcggcgc caagggcggc    960
cctgagagcc gcaaggaccc ctctggcgcc tctaacccca gcgccgactc gccccctccat    1020
cggggtgtgc acgggaagac cggccagcta gagggcgcgc cggccccggg cccggccgcc    1080
agcccccaga ctctggacca cagtggggcg acggcgacag gggcgcctc ggagttgaag    1140
actccagcct cctcaactgc gcccccata agctccgggc ccggggcgct ggcctctgtg    1200
```

```
cccgcctctc acccggcaca cggcttggca ccccacgagt cccagctgca cctgaaaggg      1260
gaccccacct actccttcaa ccacccgttc tccatcaaca acctcatgtc ctcctcggag      1320
cagcagcata agctggactt caaggcatac gaacaggcac tgcaatactc gccttacggc      1380
tctacgttgc ccgccagcct gcctctaggc agcgcctcgg tgaccaccag gagccccatc      1440
gagccctcag ccctggagcc ggcgtactac caaggtgtgt attccagacc cgtcctaaac      1500
acttcctagc tcccgggact gggggtttg tctggcatag ccatgctggt agcaagagag       1560
aaaaaatcaa cagcaaacaa aaccacacaa accaaaccgt caacagcata ataaaatcca      1620
acaactattt ttatttcatt tttcatgcac aaccttgccc ccagtgcaaa agactgttac      1680
tttattattg tattcaaaat tcattgtgta tattactaca aagacggccc caaaccaatt      1740
tttttcctgc gaagtttaat gatccacaag tgtatatatg aaattctcct ccttccttgc      1800 cccctctct ttcttccctc ttggccctcc agacattcta gtttgtggag ggttatttaa       1860
aaaacaaaaa ggaagatggt caagtttgta aaatatttgt ttgtgctttt ccccctcct      1920 tacctgaccc cctacgagtt tacaggcttg tggcaatact cttaaccata agaattgaaa      1980
tggtgaagaa acaagtatac actagaggct cttaaaagta ttgaaaagac aatactgctg      2040
ttatatagca agacataaac agattataaa catcagagcc atttgcttct cagtttacat      2100
ttctgataca tgcagatagc agatgtcttt aaatgaaata catgtatatt gtgtatggac      2160
ttaattatgc acatgctcag atgtgtagac atcctccgta tatttacata acatatagag      2220
gtaatagata ggtgatatac gtgatacgtt ctcaagagtt gcttgaccga aagttacaag      2280
gaccccaacc cctttgctct ctacccacag atggccctgg gaacaatcct caggaattgc      2340
cctcaagaac tcgcttcttt gctttgagag tgccatggtc atgtcattct gagtacata      2400 acacataaat tagtttctat gagtgtatac catttaaaga tttttcagt aaagggaata      2460 ttacatgttg ggaggaggag ataagttata gggagctgga tttcaaacgg tggtccaaga      2520
ttcaaaaatc ctattgatag tggccatttt aatcattgcc atcgtgtgct tgtttcatcc      2580
agtgttatgc actttccaca gttggtgtta gtatagccag agggtttcat tattatttct      2640
ctttgctttc tcaatgttaa tttattgcat ggtttattct ttttctttac agctgaaatt      2700
gctttaaatg atggttaaaa ttacaaatta aattgggaat ttttatcaat gtgattgtaa      2760
ttaaaaatat tttgatttaa ataacaaaaa taataccaga ttttaagccg cggaaaatgt      2820
tcttgatcat ttgcagttaa ggactttaaa taaatcaaat gttaacaaaa aa             2872
```

<210> SEQ ID NO 311
<211> LENGTH: 926
<212> TYPE: DNA
<213> ORGANISM: Homo sapiens

<400> SEQUENCE: 311

```
ggggcccatt ctgtttcagc cagtcgccaa gaatcatgaa agtcgccagt ggcagcaccg       60
ccaccgccgc cgcgggcccc agctgcgcgc tgaaggccgg caagacagcg agcggtgcgg      120
gcgaggtggt gcgctgtctg tctgagcaga gcgtggccat ctcgcgctgc cggggcgccg      180
gggcgcgcct gcctgccctg ctggacgagc agcaggtaaa cgtgctgctc tacgacatga      240
acggctgtta ctcacgcctc aaggagctgg tgcccaccct gccccagaac cgcaaggtga      300
gcaaggtgga gattctccag cacgtcatcg actacatcag ggaccttcag ttggagctga      360
actcggaatc cgaagttggg accccgggg ccgagggct gccggtccgg gctccgctca        420
```

| | |
|---|---|
| gcaccctcaa cggcgagatc agcgccctga cggccgaggc ggcatgcgtt cctgcggacg | 480 |
| atcgcatctt gtgtcgctga agcgcctccc ccagggaccg gcggacccca gccatccagg | 540 |
| gggcaagagg aattacgtgc tctgtgggtc tcccccaacg cgcctcgccg gatctgaggg | 600 |
| agaacaagac cgatcggcgg ccactgcgcc cttaactgca tccagcctgg ggctgaggct | 660 |
| gaggcactgg cgaggagagg cgctcctct ctgcacacct actagtcacc agagacttta | 720 |
| gggggtggga ttccactcgt gtgtttctat tttttgaaaa gcagacattt taaaaaatgg | 780 |
| tcacgtttgg tgcttctcag atttctgagg aaattgcttt gtattgtata ttacaatgat | 840 |
| caccgactga gaatattgtt ttacaatagt tctgtggggc tgttttttttg ttattaaaca | 900 |
| ataatttag atggtgaaaa aaaaaa | 926 |

<210> SEQ ID NO 312
<211> LENGTH: 4989
<212> TYPE: DNA
<213> ORGANISM: Homo sapiens

<400> SEQUENCE: 312

| | |
|---|---|
| tttttttttt ttttgagaaa gggaatttca tcccaaataa aaggaatgaa gtctggctcc | 60 |
| ggaggagggt ccccgacctc gctgtggggg ctcctgtttc tctccgccgc gctctcgctc | 120 |
| tggccgacga gtggagaaat ctgcgggcca ggcatcgaca tccgcaacga ctatcagcag | 180 |
| ctgaagcgcc tggagaactg cacggtgatc gagggctacc tccacatcct gctcatctcc | 240 |
| aaggccgagg actaccgcag ctaccgcttc cccaagctca cggtcattac cgagtacttg | 300 |
| ctgctgttcc gagtggctgg cctcgagagc ctcggagacc tcttccccaa cctcacggtc | 360 |
| atccgcggct ggaaactctt ctacaactac gccctggtca tcttcgagat gaccaatctc | 420 |
| aaggatattg gctttacaa cctgaggaac attactcggg gggccatcag gattgagaaa | 480 |
| aatgctgacc tctgttacct ctccactgtg gactggtccc tgatcctgga tgcggtgtcc | 540 |
| aataactaca ttgtggggaa taagcccccca aaggaatgtg gggacctgtg tccagggacc | 600 |
| atggaggaga agccgatgtg tgagaagacc accatcaaca atgagtacaa ctaccgctgc | 660 |
| tggaccacaa accgctgcca gaaaatgtgc ccaagcacgt gtgggaagcg ggcgtgcacc | 720 |
| gagaacaatg agtgctgcca ccccgagtgc ctgggcagct gcagcgcgcc tgacaacgac | 780 |
| acggcctgtg tagcttgccg ccactactac tatgccggtg tctgtgtgcc tgcctgcccg | 840 |
| cccaacacct acaggtttga gggctggcgc tgtgtggacc gtgacttctg cgccaacatc | 900 |
| ctcagcgccg agagcagcga ctccgagggg tttgtgatcc acgacggcga gtgcatgcag | 960 |
| gagtgcccct cgggcttcat ccgcaacggc agccagagca tgtactgcat cccttgtgaa | 1020 |
| ggtccttgcc cgaaggtctg tgaggaagaa agaaaacaa agaccattga ttctgttact | 1080 |
| tctgctcaga tgctccaagg atgcaccatc ttcaagggca atttgctcat taacatccga | 1140 |
| cgggggaata acattgcttc agagctggag aacttcatgg ggctcatcga ggtggtgacg | 1200 |
| ggctacgtga agatccgcca ttctcatgcc ttggtctcct tgtccttcct aaaaaacctt | 1260 |
| cgcctcatcc taggagagga gcagctagaa gggaattact ccttctacgt cctcgacaac | 1320 |
| cagaacttgc agcaactgtg ggactgggac caccgcaacc tgaccatcaa gcagggaaa | 1380 |
| atgtactttt ctttcaatcc caattatgt gtttccgaaa tttaccgcat ggaggaagtg | 1440 |
| acggggacta aagggcgcca agcaaaggg gacataaaca ccaggaacaa cggggagaga | 1500 |
| gcctcctgtg aaagtgacgt cctgcatttc acctccacca ccacgtcgaa gaatcgcatc | 1560 |
| atcataaccct ggcaccggta ccggcccct gactacaggg atctcatcag cttcaccgtt | 1620 |

```
tactacaagg aagcaccctt taagaatgtc acagagtatg atgggcagga tgcctgcggc    1680
tccaacagct ggaacatggt ggacgtggac ctcccgccca acaaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctccctct ctgcccaacg gcaacctgag ttactacatt    1980
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aaccccaaga ctgaggtgtg tggtggggag aaagggcctt gctgcgcctg ccccaaaact    2160
gaagccgaga agcaggccga aaggaggagg gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga gacagagtac ccttcttttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct tttaaagtg gccggaacct gagaatccca atggattgat tctaatgtat    2640
gaaataaaat acgatcaca gttgaggat cagcgagaat gtgtgtccag acaggaatac    2700
aggaagtatg gagggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
gtgtacgttc ctgatgagtg ggaggtggct cgggagaaga tcaccatgag ccggaacntt    3060 gggcagggt cgtttgggat ggtctatgaa ggagttgcca agggtgtggt gaaagatgaa    3120 cctgaaaccca gagtggccat taaaacagtg aacgaggccg caagcatgcg tgagaggatt    3180
gagtttctca cgaagcttc tgtgatgaag gagttcaatt gtcaccatgt ggtgcgattg    3240
ctgggtgtgg tgtcccaagg ccagccaaca ctggtcatca tggaactgat gacacggggc    3300
gatctcaaaa gttatctccg gtctctgagg ccagaaatgg agaataatcc agtcctagca    3360 cctcaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga cagactat    3540 taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccagggc ttgtccaacg agcaagtcct tcgcttcgtc    3720 atggaggcg gccttctgga caagccagac aactgtcctg acatgctgtt tgaactgatg    3780
cgcatgtgct ggcagtataa ccccaagatg aggccttcct tcctggagat catcagcagc    3840
atcaaagagg agatggagcc tggcttccgg gaggtctcct tctactacag cgaggagaac    3900
aagctgcccg agcggaggaa gctggacctg agccagagaa acatggagag cgtccccctg    3960
```

```
gacccctcgg cctcctcgtc ctccctgcca ctgcccgaca gacactcagg acacaaggcc    4020
gagaacggcc ccggccctgg ggtgctggtc ctccgcgcca gcttcgacga gagacagcct    4080
tacgcccaca tgaacggggg ccgcaagaac gagcgggcct tgccgctgcc ccagtcttcg    4140
acctgctgat ccttggatcc tgaatctgtg caaacagtaa cgtgtgcgca cgcgcagcgg    4200 ggtgggggg gagagagagt tttaacaatc cattcacaag cctcctgtac ctcagtggat    4260
cttcagttct gcccttgctg cccgcgggag acagcttctc tgcagtaaaa cacatttggg    4320
atgttccttt tttcaatatg caagcagctt tttattccct gcccaaaccc ttaactgaca    4380
tgggccttta agaaccttaa tgacaacact taatagcaac agagcacttg agaaccagtc    4440
tcctcactct gtccctgtcc ttccctgttc tcccttctc tctcctctct gcttcataac    4500
ggaaaaataa ttgccacaag tccagctggg aagccctttt tatcagtttg aggaagtggc    4560
tgtccctgtg gccccatcca accactgtac acccgcct gacaccgtgg gtcattacaa    4620
aaaaacacgt ggagatggaa attttacct ttatctttca cctttctagg gacatgaaat    4680
ttacaaaggg ccatcgttca tccaaggctg ttaccatttt aacgctgcct aattttgcca    4740
aaatcctgaa ctttctccct catcggcccg gcgctgattc ctcgtgtccg gaggcatggg    4800
tgagcatggc agctggttgc tccatttgag agacacgctg gcgacacact ccgtccatcc    4860
gactgcccct gctgtgctgc tcaaggccac aggcacacag gtctcattgc ttctgactag    4920
attattattt gggggaactg gacacaatag gtctttctct cagtgaaggt ggggagaagc    4980
tgaaccggc                                                            4989
```

<210> SEQ ID NO 313
<211> LENGTH: 12515
<212> TYPE: DNA
<213> ORGANISM: Homo sapiens

<400> SEQUENCE: 313

```
ctaccgggcg gaggtgagcg cggcgccggc tcctcctgcg gcggactttg ggtgcgactt      60
gacgagcggt ggttcgacaa gtggccttgc gggccggatc gtcccagtgg aagagttgta     120
aatttgcttc tggccttccc ctacggatta tacctggcct tcccctacgg attatactca     180
acttactgtt tagaaaatgt ggcccacgag acgcctggtt actatcaaaa ggagcgggt     240 cgacggtccc cactttcccc tgagcctcag cacctgcttg tttggaaggg gtattgaatg     300
tgacatccgt atccagcttc ctgttgtgtc aaaacaacat tgcaaaattg aaatccatga     360
gcaggaggca atattacata atttcagttc cacaaatcca acacaagtaa atgggtctgt     420
tattgatgag cctgtacggc taaaacatgg agatgtaata actattattg atcgttcctt     480
caggtatgaa aatgaaagtc ttcagaatgg aaggaagtca actgaatttc caagaaaaat     540
acgtgaacag gagccagcac gtcgtgtctc aagatctagc ttctcttctg accctgatga     600
gaaagctcaa gattccaagg cctattcaaa atcactgaa ggaaaagttt caggaaatcc     660
tcaggtacat atcaagaatg tcaaagaaga cagtaccgca gatgactcaa agacagtgt     720 tgctcaggga acaactaatg ttcattcctc agaaacatgct ggacgtaatg cagaaatgc     780 agctgatccc atttctgggg attttaaaga aatttccagc gttaaattag tgagccgtta     840
tggagaattg aagtctgttc ccactacaca atgtcttgac aatagcaaaa aaatgaatc     900 tccctttgg aagctttatg agtcagtgaa gaaagagttg gatgtaaat cacaaaaaga     960 aaatgtccta cagtattgta gaaaatctgg attacaaact gattacgcaa cagagaaga    1020 aagtgctgat ggtttacagg gggagaccca actgttggtc tcgcgtaagt caagaccaaa    1080
```

-continued

| | |
|---|---|
| atctggtggg agcggccacg ctgtggcaga gcctgcttca cctgaacaag agcttgacca | 1140 |
| gaacaagggg aagggaagag acgtggagtc tgttcagact cccagcaagg ctgtgggcgc | 1200 |
| cagctttcct ctctatgagc cggctaaaat gaagacccct gtacaatatt cacagcaaca | 1260 |
| aaattctcca caaaacata agaacaaaga cctgtatact actggtagaa gagaatctgt | 1320 |
| gaatctgggt aaaagtgaag gcttcaaggc tggtgataaa actcttactc ccaggaagct | 1380 |
| ttcaactaga aatcgaacac cagctaaagt tgaagatgca gctgactctg ccactaagcc | 1440 |
| agaaaatctc tcttccaaaa ccagaggaag tattcctaca gatgtggaag ttctgcctac | 1500 |
| ggaaactgaa attcacaatg agccattttt aactctgtgg ctcactcaag ttgagaggaa | 1560 |
| gatccaaaag gattccctca gcaagcctga gaaattgggc actacagctg acagatgtg | 1620 |
| ctctggggtta cctggtctta gttcagttga tatcaacaac tttggtgatt ccattaatga | 1680 |
| gagtgaggga atacctttga aaagaaggcg tgtgtccttt ggtgggcacc taagacctga | 1740 |
| actatttgat gaaaacttgc ctcctaatac gcctctcaaa aggggagaag ccccaaccaa | 1800 |
| aagaaagtct ctggtaatgc acactccacc tgtcctgaag aaaatcatca aggaacagcc | 1860 |
| tcaaccatca ggaaaacaag agtcaggttc agaaatccat gtggaagtga aggcacaaag | 1920 |
| cttggtttata gcccctccag ctcctagtcc taggaaaaact ccagttgcca gtgatcaacg | 1980 |
| ccgtaggtcc tgcaaaacag cccctgcttc cagcagcaaa tctcagacag aggttcctaa | 2040 |
| gagaggagga gaaagagtgg caacctgcct tcaaaagaga gtgtctatca gccgaagtca | 2100 |
| acatgatatt ttacagatga tatgttccaa agaagaagt ggtgcttcgg aagcaaatct | 2160 |
| gattgttgca aaatcatggg cagatgtagt aaaacttggt gcaaaacaaa cacaaactaa | 2220 |
| agtcataaaa catggtcctc aaaggtcaat gaacaaaagg caaagaagac ctgctactcc | 2280 |
| aaagaagcct gtgggcgaag ttcacagtca atttagtaca ggccacgcaa actctccttg | 2340 |
| taccataata atagggaaag ctcatactga aaaagtacat gtgcctgctc gaccctacag | 2400 |
| agtgctcaac aacttcattt ccaaccaaaa aatggacttt aaggaagatc tttcaggaat | 2460 |
| agctgaaatg ttcaagaccc cagtgaagga gcaaccgcag ttgacaagca catgtcacat | 2520 |
| cgctatttca aattcagaga atttgcttgg aaaacagttt caaggaactg attcaggaga | 2580 |
| agaacctctg ctccccacct cagagagttt tggaggaaat gtgttcttca gtgcacagaa | 2640 |
| tgcagcaaaa cagccatctg ataaatgctc tgcaagccct cccttaagac ggcagtgtat | 2700 |
| tagagaaaat ggaaacgtag caaaaacgcc caggaacacc tacaaaatga cttctctgga | 2760 |
| gacaaaaact tcagatactg agacagagcc ttcaaaaaca gtatccactg taaacaggtc | 2820 |
| aggaaggtct acagagttca ggaatataca gaagctacct gtggaaagta agagtgaaga | 2880 |
| aacaaataca gaaattgttg agtgcatcct aaaaagaggt cagaaggcaa cactactaca | 2940 |
| acaaggagaa gaaggagaga tgaaggaaat agaaagacct tttgagacat ataaggaaaa | 3000 |
| tattgaatta aagaaaacg atgaaaagat gaaagcaatg aagagatcaa gaacttgggg | 3060 |
| gcagaaatgt gcaccaatgt ctgacctgac agacctcaag agcttgcctg atacagaact | 3120 |
| catgaaagac acggcacgtg gccagaatct cctccaaacc caagatcatg ccaaggcacc | 3180 |
| aaagagtgag aaaggcaaaa tcactaaaat gcccctgccag tcattacaac cagaaccaat | 3240 |
| aaacacccca acacacacaa aacaacagtt gaaggcatcc ctggggaaag taggtgtgaa | 3300 |
| agaagagctc ctagcagtcg gcaagttcac acgacgtca ggggagacca cgcacacgca | 3360 |
| cagagagcca gcaggagatg gcaagagcat cagaacgttt aaggagtctc caaagcagat | 3420 |

```
cctggaccca gcagcccgtg taactggaat gaagaagtgg ccaagaacgc ctaaggaaga    3480
ggcccagtca ctagaagacc tggctggctt caaagagctc ttccagacac caggtccctc    3540
tgaggaatca atgactgatg agaaaactac caaaatagcc tgcaaatctc caccaccaga    3600
atcagtggac actccaacaa gcacaaagca atggcctaag agaagtctca ggaaagcaga    3660
tgtagaggaa gaattcttag cactcaggaa actaacacca tcagcaggga aagccatgct    3720
tacgcccaaa ccagcaggag gtgatgagaa agacattaaa gcatttatgg gaactccagt    3780
gcagaaactg gacctggcag gaactttacc tggcagcaaa agacagctac agactcctaa    3840
ggaaaaggcc caggctctag aagacctggc tggctttaaa gagctcttcc agactcctgg    3900
tcacaccgag gaattagtgg ctgctggtaa aaccactaaa ataccctgcg actctccaca    3960
gtcagaccca gtggacaccc caacaagcac aaagcaacga cccaagagaa gtatcaggaa    4020
agcagatgta gagggagaac tcttagcgtg caggaatcta atgccatcag caggcaaagc    4080
catgcacacg cctaaaccat cagtaggtga agagaaagac atcatcatat ttgtgggaac    4140
tccagtgcag aaactggacc tgacagagaa cttaaccggc agcaagagac ggccacaaac    4200
tcctaaggaa gaggcccagg ctctggaaga cctgactggc tttaaagagc tcttccagac    4260
ccctggtcat actgaagaag cagtggctgc tggcaaaaact actaaaatgc cctgcgaatc    4320
ttctccacca gaatcagcag acaccccaac aagcacaaga aggcagccca agacaccttt    4380
ggagaaaagg gacgtacaga aggagctctc agccctgaag aagctcacac agacatcagg    4440
ggaaaccaca cacacagata aagtaccagg aggtgaggat aaaagcatca acgcgtttag    4500
ggaaactgca aaacagaaac tggacccagc agcaagtgta actggtagca agaggcaccc    4560
aaaaactaag gaaaaggccc aaccctaga agacctggct ggctggaaag agctcttcca    4620
gacaccagta tgcactgaca agcccacgac tcacgagaaa actaccaaaa tagcctgcag    4680
atcacaacca gacccagtgg acacaccaac aagctccaag ccacagtcca agagaagtct    4740
caggaaagtg gacgtagaag aagaattctt cgcactcagg aaacgaacac catcagcagg    4800
caaagccatg cacacaccca accagcagt aagtggtgag aaaaacatct acgcatttat    4860
gggaactcca gtgcagaaac tggacctgac agagaactta actggcagca agagacggct    4920
acaaactcct aaggaaaagg cccaggctct agaagacctg gctggcttta aagagctctt    4980
ccagacacga ggtcacactg aggaatcaat gactaacgat aaaactgcca aagtagcctg    5040
caaatcttca caaccagacc tagacaaaaa cccagcaagc tccaagcgac ggctcaagac    5100
atccctgggg aaagtgggcg tgaaagaaga gctcctagca gttggcaagc tcacacagac    5160
atcaggagag actacacaca cacacacaga gccaacagga gatggtaaga gcatgaaagc    5220
atttatggag tctccaaagc agatcttaga ctcagcagca agtctaactg gcagcaagag    5280
gcagctgaga actcctaagg gaaagtctga agtccctgaa gacctggccg gcttcatcga    5340
gctcttccag acaccaagtc acactaagga atcaatgact aatgaaaaaa ctaccaaagt    5400
atcctacaga gcttcacagc cagacctagt ggacacccca acaagctcca agccacagcc    5460
caagagaagt ctcaggaaag cagacactga agaagaattt ttagcattta ggaaacaaac    5520
gccatcagca ggcaaagcca tgcacacacc caaaccagca gtaggtgaag agaaagacat    5580 caaacacgttt tgggaactc cagtgcagaa actggaccag ccaggaaatt tacctggcag    5640
caatagacgg ctacaaactc gtaaggaaaa ggcccaggct ctagaagaac tgactggctt    5700
cagagagctt ttccagacac catgcactga taaccccaca gctgatgaga aaactaccaa    5760
aaaaatactc tgcaaatctc cgcaatcaga cccagcggac accccaacaa acacaaagca    5820
```

-continued

```
acggcccaag agaagcctca agaaagcaga cgtagaggaa gaattttag cattcaggaa      5880 actaacacca tcagcaggca aagccatgca cacgcctaaa gcagcagtag gtgaagagaa      5940
agacatcaac acatttgtgg ggactccagt ggagaaactg gacctgctag gaaatttacc      6000
tggcagcaag agacggccac aaactcctaa agaaaaggcc aaggctctag aagatctggc      6060
tggcttcaaa gagctcttcc agacaccagg tcacactgag gaatcaatga ccgatgacaa      6120
aatcacagaa gtatcctgca atctccaca accagaccca gtcaaaaccc caacaagctc      6180
caagcaacga ctcaagatat ccttggggaa agtaggtgtg aaagaagagg tcctaccagt      6240
cggcaagctc acacagacgt cagggaagac cacacagaca cacagagaga cagcaggaga      6300
tggaaagagc atcaaagcgt ttaaggaatc tgcaaagcag atgctggacc cagcaaacta      6360
tggaactggg atggagaggt ggccaagaac acctaaggaa gaggcccaat cactagaaga      6420
cctggccggc ttcaaagagc tcttccagac accagaccac actgaggaat caacaactga      6480
tgacaaaact accaaaatag cctgcaaatc tccaccacca gaatcaatgg acactccaac      6540
aagcacaagg aggcggccca aaacaccttt ggggaaaagg gatatagtgg aagagctctc      6600
agccctgaag cagctcacac agaccacaca cacagacaaa gtaccaggag atgaggataa      6660
aggcatcaac gtgttcaggg aaactgcaaa acagaaactg gacccagcag caagtgtaac      6720
tggtagcaag aggcagccaa gaactcctaa gggaaaagcc caaccctag aagacttggc       6780 tggcttgaaa gagctcttcc agacaccagt atgcactgac aagcccacga ctcacgagaa      6840
aactaccaaa atagcctgca gatctccaca accagaccca gtgggtaccc caacaatctt      6900
caagccacag tccaagagaa gtctcaggaa agcagacgta gaggaagaat ccttagcact      6960
caggaaacga acaccatcag tagggaaagc tatggacaca cccaaaccag caggaggtga      7020
tgagaaagac atgaaagcat ttatgggaac tccagtgcag aaattggacc tgccaggaaa      7080
tttacctggc agcaaaagat ggccacaaac tcctaaggaa aaggcccagg ctctagaaga      7140
cctggctggc ttcaaagagc tcttccagac accaggcact gacaagccca cgactgatga      7200
gaaaactacc aaaatagcct gcaaatctcc acaaccagac ccagtggaca ccccagcaag      7260
cacaaagcaa cggcccaaga gaaacctcag gaaagcagac gtagaggaag aattttttagc      7320 actcaggaaa cgaacaccat cagcaggcaa agccatggac accccaaaac cagcagtaag      7380
tgatgagaaa aatatcaaca catttgtgga aactccagtg cagaaactgg acctgctagg      7440
aaatttacct ggcagcaaga gacagccaca gactcctaag gaaaaggctg aggctctaga      7500
ggacctggtt ggcttcaaag aactcttcca gacaccaggt cacactgagg aatcaatgac      7560
tgatgacaaa atcacagaag tatcctgtaa atctccacag ccagagtcat tcaaaacctc      7620
aagaagctcc aagcaaaggc tcaagatacc cctggtgaaa gtggacatga agaagagcc      7680 cctagcagtc agcaagctca cacggacatc aggggagact acgcaaacac acacagagcc      7740
aacaggagat agtaagagca tcaaagcgtt taaggagtct ccaaagcaga tcctggaccc      7800
agcagcaagt gtaactggta gcaggaggca gctgagaact cgtaaggaaa aggcccgtgc      7860
tctagaagac ctggttgact tcaaagagct cttctcagca ccaggtcaca ctgaagagtc      7920
aatgactatt gacaaaaaca caaaaattcc ctgcaaatct cccccaccag aactaacaga      7980
cactgccacg agcacaaaga gatgccccaa gacacgtccc aggaaagaag taaagagga      8040 gctctcagca gttgagaggc tcacgcaaac atcagggcaa agcacacaca cacacaaga      8100 accagcaagc ggtgatgagg gcatcaaagt attgaagcaa cgtgcaaaga agaaaccaaa      8160
```

```
cccagtagaa gaggaaccca gcaggagaag gccaagagca cctaaggaaa aggcccaacc    8220
cctggaagac ctggccggct tcacagagct ctctgaaaca tcaggtcaca ctcaggaatc    8280
actgactgct ggcaaagcca ctaaaatacc ctgcgaatct cccccactag aagtggtaga    8340
caccacagca agcacaaaga ggcatctcag gacacgtgtg cagaaggtac aagtaaaaga    8400
agagccttca gcagtcaagt tcacacaaac atcaggggaa accacggatg cagacaaaga    8460
accagcaggt gaagataaag gcatcaaagc attgaaggaa tctgcaaaac agacaccggc    8520
tccagcagca agtgtaactg gcagcaggag acggccaaga gcacccaggg aaagtgccca    8580
agccatagaa gacctagctg gcttcaaaga cccagcagca ggtcacactg aagaatcaat    8640
gactgatgac aaaaccacta aaatacgctg caaatcatca ccagaactag aagacaccgc    8700
aacaagctca aagagacggc ccaggacacg tgcccagaaa gtagaagtga aggaggagct    8760
gttagcagtt ggcaagctca cacaaacctc aggggagacc acgcacaccg acaaagagcc    8820
ggtaggtgag ggcaaaggca cgaaagcatt taagcaacct gcaaagcgga acgtggacgc    8880
agaagatgta attggcagca ggagacagcc aagagcacct aaggaaaagg cccaaccctc    8940
ggaagacctg gccagcttcc aagagctctc tcaaacacca ggccacactg aggaactggc    9000
aaatggtgct gctgatagct ttacaagcgc tccaaagcaa acacctgaca gtggaaaacc    9060
tctaaaaata tccagaagag ttcttcgggc ccctaaagta gaaccgtgg gagacgtggt     9120 aagcaccaga gaccctgtaa aatcacaaag caaaagcaac acttccctgc ccccactgcc    9180
cttcaagagg ggaggtggca agatggaag cgtcacggga accaagaggc tgcgctgcat     9240
gccagcacca gaggaaattg tggaggagct gccagccagc aagaagcaga gggttgctcc    9300
cagggcaaga ggcaaatcat ccgaacccgt ggtcatcatg aagagaagtt tgaggacttc    9360
tgcaaaaaga attgaacctg cggaagagct gaacagcaac gacatgaaaa ccaacaaaga    9420
ggaacacaaa ttacaagact cggtccctga aaataaggga atatccctgc gctccagacg    9480
ccaagataag actgaggcag aacagcaaat aactgaggtc tttgtattag cagaaagaat    9540
agaaataaac agaaatgaaa agaagcccat gaagacctcc ccagagatgg acattcagaa    9600
tccagatgat ggagcccgga aacccatacc tagagacaaa gtcactgaga acaaaaggtg    9660
cttgaggtct gctagacaga atgagagctc ccagcctaag gtggcagagg agagcggagg    9720
gcagaagagt gcgaaggttc tcatgcagaa tcagaaaggg aaaggagaag caggaaattc    9780
agactccatg tgcctgagat caagaaagac aaaaagccag cctgcagcaa gcactttgga    9840
gagcaaatct gtgcagagag taacgcggag tgtcaagagg tgtgcagaaa atccaaagaa    9900
ggctgaggac aatgtgtgtg tcaagaaaat aacaaccaga agtcataggg acagtgaaga    9960
tatttgacag aaaaatcgaa ctgggaaaaa tataataaag ttagttttgt gataagttct   10020
agtgcagttt ttgtcataaa ttacaagtga attctgtaag taaggctgtc agtctgctta   10080
agggaagaaa actttggatt tgctgggtct gaatcggctt cataaactcc actgggagca   10140
ctgctgggct cctggactga gaatagttga acaccggggg ctttgtgaag gagtctgggc   10200
caaggtttgc cctcagcttt gcagaatgaa gccttgaggt ctgtcaccac ccacagccac   10260
cctacagcag ccttaactgt gacacttgcc acactgtgtc gtcgtttgtt tgcctatgtt   10320
ctccagggca cggtggcagg aacaactatc ctcgtctgtc ccaacactga gcaggcactc   10380
ggtaaacacg aatgaatgga taagcgcacg gatgaatgga gcttacaaga tctgtctttc   10440
caatggccgg gggcatttgg tccccaaatt aaggctattg acatctgca caggacagtc    10500 ctatttttga tgtcctttcc tttctgaaaa taaagttttg tgctttggag aatgactcgt   10560
```

```
gagcacatct ttagggacca agagtgactt tctgtaagga gtgactcgtg gcttgccttg      10620
gtctcttggg aatacttttc taactagggt tgctctcacc tgagacattc tccacccgcg      10680
gaatctcagg gtcccaggct gtgggccatc acgacctcaa actggctcct aatctccagc      10740
tttcctgtca ttgaaagctt cggaagttta ctggctctgc tcccgcctgt tttctttctg      10800
actctatctg gcagcccgat gccacccagt acaggaagtg acaccagtac tctgtaaagc      10860
atcatcatcc ttggagagac tgagcactca gcaccttcag ccacgatttc aggatcgctt      10920
ccttgtgagc cgctgcctcc gaaatctcct ttgaagccca gacatctttc tccagcttca      10980
gacttgtaga tataactcgt tcatcttcat ttactttcca ctttgccccc tgtcctctct      11040
gtgttcccca aatcagagaa tagcccgcca tcccccagat cacctgtctg gattcctccc      11100 cattcacccca ccttgccagg tgcaggtgag gatggtgcac cagacagggt agctgtcccc      11160
caaaatgtgc cctgtgcggg cagtgccctg tctccacgtt tgtttcccca gtgtctggcg      11220
gggagccagg tgacatcata aatacttgct gaatgaatgc agaaatcagc ggtactgact      11280
tgtactatat tggctgccat gatagggttc tcacagcgtc atccatgatc gtaagggaga      11340
atgacattct gcttgaggga gggaatagaa aggggcaggg aggggacatc tgagggcttc      11400
acagggctgc aaagggtaca gggattgcac cagggcagaa caggggaggg tgttcaagga      11460
agagtggctc ttagcagagg cactttggaa ggtgtgaggc ataaatgctt ccttctacgt      11520
aggccaacct caaaactttc agtaggaatg ttgctatgat caagttgttc taacacttta      11580
gacttagtag taattatgaa cctcacatag aaaaatttca tccagccata tgcctgtgga      11640
gtggaatatt ctgtttagta gaaaaatcct ttagagttca gctctaacca gaaatcttgc      11700
tgaagtatgt cagcaccttt tctcaccctg gtaagtacag tatttcaaga gcacgctaag      11760
ggtggttttc attttacagg gctgttgatg atgggttaaa aatgttcatt taagggctac      11820
ccccgtgttt aatagatgaa caccacttct acacaaccct ccttggtact gggggaggga      11880
gagatctgac aaatactgcc cattcccta ggctgactgg atttgagaac aaatacccac      11940
ccatttccac catggtatgg taacttctct gagcttcagt ttccaagtga atttccatgt      12000
aataggacat tcccattaaa tacaagctgt ttttactttt tcgcctccca gggcctgtgc      12060
gatctggtcc cccagcctct cttgggcttt cttacactaa ctctgtacct accatctcct      12120 gcctcccctta ggcaggcacc tccaaccacc acacactccc tgctgttttc cctgcctgga      12180
actttcccac cagcccccacc aagatcattt catccagtcc tgagctcagc ttaagggagg      12240
cttcttgcct gtgggttccc tcaccccat gcctgtcctc caggctgggg caggttctta      12300
gtttgcctgg aattgttctg tacctctttg tagcacgtag tgttgtgaaa ctaagccact      12360
aattgagttt ctggctcccc tcctggggtt gtaagttttg ttcattcatg agggccgact      12420
gtatttcctg gttactgtat cccagtgacc agccacagga gatgtccaat aaagtatgtg      12480
atgaaatggt cttaaaaaaa aaaaaaaaaa aaaaa                                 12515
```

<210> SEQ ID NO 314
<211> LENGTH: 2444
<212> TYPE: DNA
<213> ORGANISM: Homo sapiens
<400> SEQUENCE: 314

```
ggcacgaggc ggggccgggt cgcagctggg cccgcggcat ggacgaactg ttccccctca        60
tcttcccggc agagcagccc aagcagcggg gcatgcgctt ccgctacaag tgcgaggggc       120
```

-continued

| | |
|---|---|
| gctccgcggg cagcatccca ggcgagagga gcacagatac caccaagacc caccccacca | 180 |
| tcaagatcaa tggctacaca ggaccaggga cagtgcgcat ctccctggtc accaaggacc | 240 |
| ctcctcaccg gcctcacccc cacgagcttg taggaaagga ctgccgggat ggcttctatg | 300 |
| aggctgagct ctgcccggac cgctgcatcc acagtttcca gaacctggga atccagtgtg | 360 |
| tgaagaagcg ggacctggag caggctatca gtcagcgcat ccagaccaac aacaacccct | 420 |
| tccaagttcc tatagaagag cagcgtgggg actacgacct gaatgctgtg cggctctgct | 480 |
| tccaggtgac agtgcgggac ccatcaggca ggcccctccg cctgccgcct gtcctttctc | 540 |
| atcccatctt tgacaatcgt gcccccaaca ctgccgagct caagatctgc cgagtgaacc | 600 |
| gaaactctgg cagctgcctc ggtggggatg agatcttcct actgtgtgac aaggtgcaga | 660 |
| agaggacat tgaggtgtat ttcacgggac caggctggga ggcccgaggc tccttttcgc | 720 |
| aagctgatgt gcaccgacaa gtggccattg tgttccggac ccctccctac gcagacccca | 780 |
| gcctgcaggc tcctgtgcgt gtctccatgc agctgcggcg gccttccgac cgggagctca | 840 |
| gtgagcccat ggaattccag tacctgccag atacagacga tcgtcaccgg attgaggaga | 900 |
| aacgtaaaag gacatatgag accttcaaga gcatcatgaa gaagagtcct ttcagcggac | 960 |
| ccaccgaccc ccggcctcca cctcgacgca ttgctgtgcc ttcccgcagc tcagcttctg | 1020 |
| tccccaagcc agcaccccag ccctatccct ttacgtcatc cctgagcacc atcaactatg | 1080 |
| atgagtttcc caccatggtg tttccttctg ggcagatcag ccaggcctcg gccttggccc | 1140 |
| cggccctcc ccaagtcctg ccccaggctc cagcccctgc ccctgctcca gccatggtat | 1200 |
| cagctctggc ccaggcccca gcccctgtcc cagtcctagc cccaggccct cctcaggctg | 1260 |
| tggccccacc tgcccccaag cccacccagg ctggggaagg aacgctgtca gaggccctgc | 1320 |
| tgcagctgca gtttgatgat gaagacctgg gggccttgct tggcaacagc acagacccag | 1380 |
| ctgtgttcac agacctggca tccgtcgaca actccgagtt tcagcagctg ctgaaccagg | 1440 |
| gcatacctgt ggccccccac acaactgagc ccatgctgat ggagtaccct gaggctataa | 1500 |
| ctcgcctagt gacagcccag aggcccccg acccagctcc tgctccactg ggggccccgg | 1560 |
| ggctccccaa tggcctcctt tcaggagatg aagacttctc ctccattgcg gacatggact | 1620 |
| tctcagccct gctgagtcag atcagctcct aaggggtga cgcctgccct ccccagagca | 1680 |
| ctggttgcag gggattgaag ccctccaaaa gcacttacgg attctggtgg ggtgtgttcc | 1740 |
| aactgccccc aactttgtgg atgtcttcct tggagggggg agccatattt tattcttta | 1800 |
| ttgtcagtat ctgtatctct ctctcttttt ggaggtgctt aagcagaagc attaacttct | 1860 |
| ctggaaaggg gggagctggg gaaactcaaa cttttcccct gtcctgatgg tcagctccct | 1920 |
| tctctgtagg gaactgtggg gtcccccatc cccatcctcc agcttctggt actctcctag | 1980 |
| agacagaagc aggctggagg taaggccttt gagcccacaa agccttatca agtgtcttcc | 2040 |
| atcatggatt cattacagct taatcaaaat aacgccccag ataccagccc ctgtatggca | 2100 |
| ctggcattgt ccctgtgcct aacaccagcg tttgaggggc tgccttcctg ccctacagag | 2160 |
| gtctctgccg gctctttcct tgctcaacca tggctgaagg aaacagtgca acagcactgg | 2220 |
| ctctctccag gatccagaag gggtttggtc tggacttcct tgctctcccc tcttctcaag | 2280 |
| tgccttaata gtaggtaag ttgttaagag tgggggagag caggctggca gctctccagt | 2340 |
| caggaggcat agttttagt gaacaatcaa agcacttgga ctcttgctct ttctactctg | 2400 |
| aactaataaa gctgttgcca agctggacgg cacgagctcg tgcc | 2444 |

<210> SEQ ID NO 315
<211> LENGTH: 732
<212> TYPE: DNA
<213> ORGANISM: Homo sapiens

<400> SEQUENCE: 315

| | | | | | |
|---|---|---|---|---|---|
| tgctgcgaac | cacgtgggtc | ccgggcgcgt | ttcgggtgct | ggcggctgca | gccggagttc | 60 |
| aaacctaagc | agctggaagg | aaccatggcc | aactgtgagc | gtaccttcat | tgcgatcaaa | 120 |
| ccagatgggg | tccagcgggg | tcttgtggga | gagattatca | agcgttttga | gcagaaagga | 180 |
| ttccgccttg | ttggtctgaa | attcatgcaa | gcttccgaag | atcttctcaa | ggaacactac | 240 |
| gttgacctga | aggaccgtcc | attctttgcc | ggcctggtga | atacatgca | ctcagggccg | 300 |
| gtagttgcca | tggtctggga | ggggctgaat | gtggtgaaga | cgggccgagt | catgctcggg | 360 |
| gagaccaacc | ctgcagactc | caagcctggg | accatccgtg | gagacttctg | catacaagtt | 420 |
| ggcaggaaca | ttatacatgg | cagtgattct | gtggagagtg | cagagaagga | gatcggcttg | 480 |
| tggtttcacc | ctgaggaact | ggtagattac | acgagctgtg | ctcagaactg | gatctatgaa | 540 |
| tgacaggagg | gcagaccaca | ttgcttttca | catccatttc | ccctcctcc | catgggcaga | 600 |
| ggaccaggct | gtaggaaatc | tagttattta | caggaacttc | atcataattt | ggagggaagc | 660 |
| tcttggagct | gtgagttctc | cctgtacagt | gttaccatcc | cgaccatct | gattaaaatg | 720 |
| cttcctccca | gc | | | | | 732 |

<210> SEQ ID NO 316
<211> LENGTH: 2422
<212> TYPE: DNA
<213> ORGANISM: Homo sapiens

<400> SEQUENCE: 316

| | | | | | |
|---|---|---|---|---|---|
| gtcagcctcc | cttccaccgc | catattgggc | cactaaaaaa | aggggctcg | tcttttcggg | 60 |
| gtgtttttct | ccccctcccc | tgtccccgct | tgctcacggc | tctgcgactc | cgacgccggc | 120 |
| aaggtttgga | gagcggctgg | gttcgcggga | cccgcgggct | tgcacccgcc | cagactcgga | 180 |
| cgggctttgc | caccctctcc | gcttgcctgg | tcccctctcc | tctccgccct | ccgctcgcc | 240 |
| agtccatttg | atcagcggag | actcggcggc | cgggccgggg | cttccccgca | gcccctgcgc | 300 |
| gctcctagag | ctcgggccgt | ggctcgtcgg | ggtctgtgtc | ttttggctcc | gagggcagtc | 360 |
| gctgggcttc | cgagaggggt | tcgggccgcg | tagggggcgct | ttgttttgtt | cggttttgtt | 420 |
| tttttgagag | tgcgagagag | gcggtcgtgc | agacccggga | gaaagatgtc | aaacgtgcga | 480 |
| gtgtctaacg | ggagccctag | cctggagcgg | atggacgcca | ggcaggcgga | gcaccccaag | 540 |
| ccctcggcct | gcaggaacct | cttcggcccg | gtggaccacg | aagagttaac | ccggacttg | 600 |
| gagaagcact | gcagagacat | ggaagaggcg | agccagcgca | agtggaattt | cgattttcag | 660 |
| aatcacaaac | ccctagaggg | caagtacgag | tggcaagagg | tggagaaggg | cagcttgccc | 720 |
| gagttctact | acagacccc | gcggccccc | aaaggtgcct | gcaaggtgcc | ggcgcaggag | 780 |
| agccaggatg | tcagcgggag | ccgccggcg | gcgccttaa | ttggggctcc | ggctaactct | 840 |
| gaggacacgc | atttggtgga | cccaaagact | gatccgtcgg | acagccagac | ggggttagcg | 900 |
| gagcaatgcg | caggaataag | gaagcgacct | gcaaccgacg | attcttctac | tcaaaacaaa | 960 |
| agagccaaca | gaacagaaga | aaatgtttca | gacggttccc | caaatgccgg | ttctgtggag | 1020 |
| cagacgccca | agaagcctgg | cctcagaaga | cgtcaaacgt | aaacagctcg | aattaagaat | 1080 |
| atgtttcctt | gtttatcaga | tacatcactg | cttgatgaag | caaggaagat | atacatgaaa | 1140 |

-continued

```
attttaaaaa tacatatcgc tgacttcatg gaatggacat cctgtataag cactgaaaaa       1200
caacaacaca ataacactaa aattttaggc actcttaaat gatctgcctc taaaagcgtt       1260
ggatgtagca ttatgcaatt aggttttttcc ttatttgctt cattgtacta cctgtgtata       1320
tagtttttac cttttatgta gcacataaac tttggggaag ggagggcagg gtggggctga       1380
ggaactgacg tggagcgggg tatgaagagc ttgctttgat ttacagcaag tagataaata       1440
tttgacttgc atgaagagaa gcaattttgg ggaagggttt gaattgtttt ctttaaagat       1500
gtaatgtccc tttcagagac agctgatact tcatttaaaa aaatcacaaa aatttgaaca       1560
ctggctaaag ataattgcta tttattttta caagaagttt attctcattt gggagatctg       1620
gtgatctccc aagctatcta agtttgtta gatagctgca tgtggctttt ttaaaaaagc       1680
aacagaaacc tatcctcact gccctcccca gtctctctta agttggaat ttaccagtta       1740 attactcagc agaatggtga tcactccagg tagtttgggg caaaaatccg aggtgcttgg       1800
gagttttgaa tgttaagaat tgaccatctg ctttttattaa atttgttgac aaaattttct       1860 catttttcttt tcacttcggg ctgtgtaaac acagtcaaaa taattctaaa tccctcgata       1920
tttttaaaga tctgtaagta acttcacatt aaaaaatgaa atatttttta atttaaagct       1980
tactctgtcc atttatccac aggaaagtgt tatttttaaa ggaaggttca tgtagagaaa       2040
agcacacttg taggataagt gaatggata ctacatcttt aaacagtatt tcattgcctg       2100
tgtatggaaa aaccatttga agtgtacctg tgtacataac tctgtaaaaa cactgaaaaa       2160
ttatactaac ttatttatgt taaaagattt ttttttaatct agacaatata caagccaaag       2220
tggcatgttt tgtgcatttg taaatgctgt gttgggtaga ataggtttc ccctcttttg       2280 ttaaataata tggctatgct taaaaggttg catactgagc caagtataat tttttgtaat       2340
gtgtgaaaaa gatgccaatt attgttacac attaagtaat caataaagaa aacttccata       2400
gctaaaaaaa aaaaaaaaaa aa                                                2422
```

<210> SEQ ID NO 317
<211> LENGTH: 5061
<212> TYPE: DNA
<213> ORGANISM: Homo sapiens

<400> SEQUENCE: 317

```
atggctcaga tatttagcaa cagcggattt aaagaatgtc catttttcaca tccggaacca       60 acaagagcaa aagatgtgga caaagaagaa gcattacaga tggaagcaga ggctttagca       120
aaactgcaaa aggatagaca agtgactgac aatcagagag gctttgagtt gtcaagcagc       180
accagaaaaa aagcacaggt ttataacaag caggattatg atctcatggt gtttcctgaa       240
tcagattccc aaaaaagagc attagatatt gatgtagaaa agctcaccca agctgaactt       300
gagaaactat tgctggatga cagtttcgag actaaaaaaa cacctgtatt accagttact       360
cctattctga gcccttcctt ttcagcacag ctctatttta gacctactat tcagagagga       420
cagtggccac ctggattacc tgggccttcc acttatgctt taccttctat ttatccttct       480
acttacagta acaggctgc attccaaaat ggcttcaatc caagaatgcc cacttttcca       540
tctacagaac ctatatattt aagtcttccg ggacaatctc catatttctc atatccttttg       600 acacctgcca cacccttttca tccacaagga agcttaccta tctatcgtcc agtagtcagt       660
actgacatgg caaaactatt tgacaaaata gctagtacat cagaattttt aaaaaatggg       720
aaagcaagga ctgatttgga gataacagat tcaaagtca gcaatctaca ggtatctcca       780
aagtctgagg atatcagtaa atttgactgg ttagacttgg atcctctaag taagcctaag       840
```

```
gtggataatg tggaggtatt agaccatgag gaagagaaaa atgtttcaag tttgctagca    900
aaggatcctt gggatgctgt tcttcttgaa gagagatcga cagcaaattg tcatcttgaa    960
agaaaggtga atgaaaatc cctttctgtg gcaactgtta caagaagcca gtctttaaat   1020
attcgaacaa ctcagcttgc aaaagcccag ggccatatat ctcagaaaga cccaaatggg   1080
accagtagtt tgccaactgg aagttctctt cttcaagaag ttgaagtaca gaatgaggag   1140
atggcagctt tttgtcgatc cattacaaaa ttgaagacca aatttccata taccaatcac   1200
cgcacaaacc caggctattt gttaagtcca gtcacagcgc aaagaaacat atgcggagaa   1260
aatgctagtg tgaaggtctc cattgacatt gaaggatttc agctaccagt tacttttacg   1320
tgtgatgtga gttctactgt agaaatcatt ataatgcaag ccctttgctg ggtacatgat   1380
gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta acaaacacc tgtatcaaat agaaaaacct   1620
tgcaaagaag ccatgacgag cacccctgtt gaagaactct tagattctta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca gagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
cctggaacag ttaccaaaaa aggatatgtc atggaaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
aaagactcat cacttggact ttctaaagaa gataaagctt ttttatggga gaaacgttat   2700
tattgcttca acacccaaa ttgtcttcct aaaatattag caagcgcccc aaactggaaa   2760
tggggtaatc ttgccaaaac ttactcattg cttcaccagt ggcctgcatt gtacccacta   2820
attgcattgg aacttcttga ttcaaaattt gctgatcagg aagtaagatc cctagctgtg   2880
acctggattg aggccattag tgatgatgag ctaacagatc ttcttccaca gtttgtacaa   2940
gctttgaaat atgaaattta cttgaatagt tcattagtgc aattccttt gtccagggca   3000
ttgggaaata tccagatagc acacaattta tattggcttc tcaaagatgc cctgcatgat   3060
gtacagtttta gtacccgata cgaacatgtt ttgggtgctc tcctgtcagt aggaggaaaa   3120
cgacttagag aagaacttct aaaacagacg aaacttgtac agcttttagg aggagtagca   3180
```

| | |
|---|---:|
| gaaaaagtaa ggcaggctag tggatcagcc agacaggttg ttctccaaag aagtatggaa | 3240 |
| cgagtacagt ccttttttca gaaaataaa tgccgtctcc ctctcaagcc aagtctagtg | 3300 |
| gcaaaagaat taaatattaa gtcgtgttcc ttcttcagtt ctaatgctgt ccccctaaaa | 3360 |
| gtcacaatgg tgaatgctga ccctctggga gaagaaatta atgtcatgtt taaggttggt | 3420 |
| gaagatcttc ggcaagatat gttagcttta cagatgataa agattatgga taagatctgg | 3480 |
| cttaagaag gactagatct gaggatggta attttcaaat gtctctcaac tggcagagat | 3540 |
| cgaggcatgg tggagctggt tcctgcttcc gatacccctca ggaaaatcca agtggaatat | 3600 |
| ggtgtgacag gatcctttaa agataaacca cttgcagagt ggctaaggaa atacaatccc | 3660 |
| tctgaagaag aatatgaaaa ggcttcagag aactttatct attcctgtgc tggatgctgt | 3720 |
| gtagccacct atgttttagg catctgtgat cgacacaatg acaatataat gcttcgaagc | 3780 |
| acgggacaca tgtttcacat tgactttgga agttttttgg gacatgcaca gatgtttggc | 3840 |
| agcttcaaaa gggatcgggc tccttttgtg ctgacctctg atatggcata tgtcattaat | 3900 |
| gggggtgaaa agcccaccat tcgttttcag ttgtttgtgg acctctgctg tcaggcctac | 3960 |
| aacttgataa gaaagcagac aaaccttttt cttaacctcc tttcactgat gattccttca | 4020 |
| gggttaccag aacttacaag tattcaagat ttgaaatacg ttagagatgc acttcaaccc | 4080 |
| caaactacag acgcagaagc tacaattttc tttactaggc ttattgaatc aagtttggga | 4140 |
| agcattgcca caaagtttaa cttcttcatt cacaaccttg ctcagcttcg ttttctggt | 4200 |
| cttccttcta atgatgagcc catcctttca ttttcaccta aaacatactc ctttagacaa | 4260 |
| gatggtcgaa tcaaggaagt ctctgttttt acatatcata agaaatacaa cccagataaa | 4320 |
| cattatatttt atgtagtccg aattttgtgg gaaggacaga ttgaaccatc atttgtcttc | 4380 |
| cgaacatttg tcgaatttca ggaacttcac aataagctca gtattatttt tccactttgg | 4440 |
| aagttaccag gctttcctaa taggatggtt ctaggaagaa cacacataaa agatgtagca | 4500 |
| gccaaaagga aaattgagtt aaacagttac ttacagagtt tgatgaatgc ttcaacggat | 4560 |
| gtagcagagt gtgatcttgt ttgtactttc ttccacccctt tacttcgtga tgagaaagct | 4620 |
| gaagggatag ctaggtctgc agatgcaggt tccttcagtc ctactccagg ccaaatagga | 4680 |
| ggagctgtga aattatccat ctcttaccga aatggtactc ttttcatcat ggtgatgcat | 4740 |
| atcaaagatc ttgttactga agatggagct gacccaaatc catatgtcaa acataccta | 4800 |
| cttccagata accacaaaac atccaaacgt aaaaccaaaa tttcacgaaa aacgaggaat | 4860 |
| ccgacattca atgaaatgct tgtatacagt ggatatagca agaaaccct aagacagcga | 4920 |
| gaacttcaac taagtgtact cagtgcagaa tctctgcggg agaattttt cttgggtgga | 4980 |
| gtaaccctgc ctttgaaaga tttcaacttg agcaaagaga cggttaaatg gtatcagctg | 5040 |
| actgcggcaa catacttgta a | 5061 |

<210> SEQ ID NO 318
<211> LENGTH: 3014
<212> TYPE: DNA
<213> ORGANISM: Homo sapiens

<400> SEQUENCE: 318

| | |
|---|---:|
| ctgaccagcg ccgccctccc ccgccccga cccaggaggt ggagatccct ccggtccagc | 60 |
| cacattcaac acccactttc tcctcccctct gcccctatat tcccgaaacc ccctcctcct | 120 |
| tccctttttcc ctcctcccctg gagacggggg aggagaaaag gggagtccag tcgtcatgac | 180 |
| tgagctgaag gcaaagggtc cccgggctcc ccacgtggcg ggcggcccgc cctcccccga | 240 |

```
ggtcggatcc ccactgctgt gtcgcccagc cgcaggtccg ttcccgggga gccagacctc    300
ggacaccttg cctgaagttt cggccatacc tatctccctg gacgggctac tcttccctcg    360
gccctgccag ggacaggacc cctccgacga aagacgcag gaccagcagt cgctgtcgga     420
cgtggagggc gcatattcca gagctgaagc tacaaggggt gctggaggca gcagttctag    480
tcccccagaa aaggacagcg gactgctgga cagtgtcttg gacactctgt tggcgccctc    540
aggtcccggg cagagccaac ccagccctcc cgcctgcgag gtcaccagct cttggtgcct    600
gtttggcccc gaacttcccg aagatccacc ggctgccccc gccacccagc gggtgttgtc    660
cccgctcatg agccggtccg ggtgcaaggt tggagacagc tccgggacgg cagctgccca    720
taaagtgctg ccccggggcc tgtcaccagc ccggcagctg ctgctcccgg cctctgagag    780
ccctcactgg tccggggccc cagtgaagcc gtctccgcag gccgctgcgg tggaggttga    840
ggaggaggat ggctctgagt ccgaggagtc tgcgggtccg cttctgaagg gcaaacctcg    900
ggctctgggt ggcgcggcgg ctggaggagg agccgcggct gtcccgccgg gggcggcagc    960
aggaggcgtc gccctggtcc ccaaggaaga ttcccgcttc tcagcgccca gggtcgccct   1020
ggtggagcag gacgcgccga tggcgcccgg gcgctccccg ctggccacca cggtgatgga   1080
tttcatccac gtgcctatcc tgcctctcaa tcacgcctta ttggcagccc gcactcggca   1140
gctgctggaa gacgaaagtt acgacggcgg ggccggggct gccagcgcct ttgccccgcc   1200
gcggagttca ccctgtgcct cgtccacccc ggtcgctgta ggcgacttcc ccgactgcgc   1260
gtaccccgcc gacgccgagc caaggacga cgcgtaccct ctctatagcg acttccagcc   1320
gcccgctcta aagataaagg aggaggagga aggcgcggag gcctccgcgc gctccccgcg   1380
ttcctacctt gtggccggtg ccaaccccgc agccttcccg gatttcccgt tggggccacc   1440
gcccccgctg ccgccgcgag cgaccccatc cagacccggg gaagcggcgg tgacggccgc   1500
acccgccagt gcctcagtct cgtctgcgtc ctcctcgggg tcgaccctgg agtgcatcct   1560
gtacaaagcg gagggcgcgc cgccccagca gggcccgttc gcgccgccgc cctgcaaggc   1620
gccgggcgcg agcggctgcc tgctcccgcg ggacggcctg ccctccacct ccgcctctgc   1680
cgccgccgcc ggggcggccc ccgcgctcta ccctgcactc ggcctcaacg ggctcccgca   1740
gctcggctac caggccgccg tgctcaagga gggcctgccg caggtctacc cgccctatct   1800
caactacctg aggccggatt cagaagccag ccagagccca aatacagct tcgagtcatt    1860
acctcagaag atttgtttaa tctgtgggga tgaagcatca ggctgtcatt atggtgtcct   1920
tacctgtggg agctgtaagg tcttctttaa gagggcaatg gaagggcagc acaactactt   1980
atgtgctgga agaaatgact gcatcgttga taaaatccgc agaaaaaact gcccagcatg   2040
tcgccttaga aagtgctgtc aggctggcat ggtccttgga ggtcgaaaat ttaaaaagtt   2100
caataaagtc agagttgtga gagcactgga tgctgttgct ctcccacagc cagtgggcgt   2160
tccaaatgaa agccaagccc taagccagag attcactttt tcaccaggtc aagacataca   2220
gttgattcca ccactgatca acctgttaat gagcattgaa ccagatgtga tctatgcagg   2280
acatgacaac acaaaacctg cacctccag ttctttgctg acaagtctta atcaactagg   2340
cgagaggcaa cttctttcag tagtcaagtg gtctaaatca ttgccaggtt tcgaaactt    2400
acatattgat gaccagataa ctctcattca gtattcttgg atgagcttaa tggtgtttgg   2460
tctaggatgg agatcctaca acacgtcag tgggcagatg ctgtattttg cacctgatct    2520
aatactaaat gaacagcgga tgaaagaatc atcattctat tcattatgcc ttaccatgtg   2580
```

```
gcagatccca caggagtttg tcaagcttca agttagccaa gaagagttcc tctgtatgaa    2640
agtattgtta cttcttaata caattccttt ggaagggcta cgaagtcaaa cccagtttga    2700
ggagatgagg tcaagctaca ttagagagct catcaaggca attggtttga ggcaaaaagg    2760
agttgtgtcg agctcacagc gtttctatca acttacaaaa cttcttgata acttgcatga    2820
tcttgtcaaa caacttcatc tgtactgctt gaatacattt atccagtccc gggcactgag    2880
tgttgaattt ccagaaatga tgtctgaagt tattgctgca caattaccca agatattggc    2940
agggatggtg aaaccccttc tctttcataa aaagtgaatg tcatctttttt cttttaaaga    3000 attaaatttt gtgg                                                      3014

<210> SEQ ID NO 319
<211> LENGTH: 2148
<212> TYPE: DNA
<213> ORGANISM: Homo sapiens

<400> SEQUENCE: 319
gcttcagggt acagctcccc cgcagccaga agccgggcct gcagcgcctc agcaccgctc      60
cgggacaccc cacccgcttc ccaggcgtga cctgtcaaca gcaacttcgc ggtgtggtga     120
actctctgag gaaaaaccat tttgattatt actctcagac gtgcgtggca acaagtgact     180
gagacctaga aatccaagcg ttggaggtcc tgaggcagc ctaagtcgct tcaaaatgga     240
acgaaggcgt ttgtggggtt ccattcagag ccgatacatc agcatgagtg tgtggacaag     300
cccacggaga cttgtggagc tggcagggca gagcctgctg aaggatgagg ccctggccat     360
tgccgccctg gagttgctgc ccagggagct cttcccgcca ctcttcatgg cagcctttga     420
cgggagacac agccagaccc tgaaggcaat ggtgcaggcc tggcccttca cctgcctccc     480
tctgggagtg ctgatgaagg acaacatct tcacctggag accttcaaag ctgtgcttga     540
tggacttgat gtgctccttg cccaggaggt tcgccccagg aggtggaaac ttcaagtgct     600
ggatttacgg aagaactctc atcaggactt ctggactgta tggtctggaa acagggccag     660
tctgtactca tttccagagc cagaagcagc tcagcccatg acaaagaagc gaaaagtaga     720
tggtttgagc acagaggcag agcagcccctt cattccagta gaggtgctcg tagacctgtt     780
cctcaaggaa ggtgcctgtg atgaattgtt ctcctacctc attgagaaag tgaagcgaaa     840
gaaaaatgta ctacgcctgt gctgtaagaa gctgaagatt tttgcaatgc ccatgcagga     900
tatcaagatg atcctgaaaa tggtgcagct ggactctatt gaagatttgg aagtgacttg     960
tacctggaag ctacccacct tggcgaaatt ttctccttac ctgggccaga tgattaatct    1020
gcgtagactc ctcctctccc acatccatgc atcttcctac atttcccgg agaaggaaga    1080 gcagtatatc gcccagttca cctctcagtt cctcagtctg cagtgcctgc aggctctcta    1140
tgtggactct ttatttttcc ttagaggccg cctggatcag ttgctcaggc acgtgatgaa    1200
cccccttgga accctctcaa taactaactg ccggcttttcg gaaggggatg tgatgcatct    1260
gtcccagagt cccagcgtca gtcagctaag tgtcctgagt ctaagtgggg tcatgctgac    1320
cgatgtaagt cccgagcccc tccaagctct gctggagaga gcctctgcca ccctccagga    1380
cctggtcttt gatgagtgtg ggatcacgga tgatcagctc cttgccctcc tgccttccct    1440
gagccactgc tccagcttacaaccttaag cttctacggg aattccatct ccatatctgc    1500
cttgcagagt ctcctgcagc acctcatcgg gctgagcaat ctgacccacg tgctgtatcc    1560 tgtcccctg gagagttatg aggacatcca tggtaccctc cacctggaga ggcttgccta    1620
tctgcatgcc aggctcaggg agttgctgtg tgagttgggg cggcccagca tggtctggct    1680
```

-continued

```
tagtgccaac ccctgtcctc actgtgggga cagaaccttc tatgacccgg agcccatcct    1740
gtgcccctgt ttcatgccta actagctggg tgcacatatc aaatgcttca ttctgcatac    1800
ttggacacta aagccaggat gtgcatgcat cttgaagcaa caaagcagcc acagtttcag    1860
acaaatgttc agtgtgagtg aggaaaacat gttcagtgag gaaaaaacat tcagacaaat    1920
gttcagtgag gaaaaaaagg ggaagttggg gataggcaga tgttgacttg aggagttaat    1980
gtgatctttg gggagataca tcttatagag ttagaaatag aatctgaatt tctaaaggga    2040
gattctggct tgggaagtac atgtaggagt taatccctgt gtagactgtt gtaaagaaac    2100
tgttgaaaat aaagagaagc aatgtgaagc aaaaaaaaaa aaaaaaaa                 2148
```

<210> SEQ ID NO 320
<211> LENGTH: 540
<212> TYPE: DNA
<213> ORGANISM: Homo sapiens

<400> SEQUENCE: 320

```
atccctgact cggggtcgcc tttggagcag agaggaggca atggccacca tggagaacaa     60
ggtgatctgc gccctggtcc tggtgtccat gctggccctc ggcaccctgg ccgaggccca    120
gacagagacg tgtacagtgg cccccgtga aagacagaat tgtggttttc ctggtgtcac     180
gccctcccag tgtgcaaata agggctgctg tttcgacgac accgttcgtg gggtcccctg    240
gtgcttctat cctaatacca tcgacgtccc tccagaagag gagtgtgaat tttagacact    300
tctgcaggga tctgcctgca tcctgacggg gtgccgtccc cagcacggtg attagtccca    360
gagctcggct gccacctcca ccggacacct cagacacgct tctgcagctg tgcctcggct    420
cacaacacag attgactgct ctgactttga ctactcaaaa ttggcctaaa aattaaaaga    480
gatcgatatt aaaaaaaaaa aaaaaaaaaa aaaaaaaaaa aaaaaaaaaa aaaaaaaaaa    540
```

<210> SEQ ID NO 321
<211> LENGTH: 2346
<212> TYPE: DNA
<213> ORGANISM: Homo sapiens

<400> SEQUENCE: 321

```
gcacgaggct gcggcgggtc cgggcccatg aggcgacgaa ggaggcggga cggcttttac     60
ccagccccgg acttccgaga cagggaagct gaggacatgg caggagtgtt tgacatagac    120
ctggaccagc cagaggacgc gggctctgag gatgagctgg aggaggggg tcagttaaat    180 gaaagcatgg accatggggg agttggacca tatgaacttg gcatggaaca ttgtgagaaa    240
tttgaaatct cagaaactag tgtgaacaga gggccagaaa aaatcagacc agaatgtttt    300
gagctacttc gggtacttgg taaaggggc tatggaaagg ttttttcaagt acgaaaagta    360 acaggagcaa atactgggaa atatttgcc atgaaggtgc ttaaaaaggc aatgatagta    420
agaaatgcta agatacagc tcatacaaaa gcagaacgga atattctgga ggaagtaaag    480
catcccttca tcgtggattt aatttatgcc tttcagactg gtggaaaact ctacctcatc    540
cttgagtatc tcagtggagg agaactattt atgcagttag aaagagaggg aatatttatg    600
gaagacactg cctgctttta cttggcagaa atctccatgg cttttgggca tttacatcaa    660
aaggggatca tctacagaga cctgaagccg gagaatatca tgcttaatca ccaaggtcat    720
gtgaaactaa cagactttgg actatgcaaa gaatctattc atgatggaac agtcacacac    780
acattttgtg gaacaataga atacatggcc cctgaaatct tgatgagaag tggccacaat    840
```

-continued

| | |
|---|---|
| cgtgctgtgg attggtggag tttgggagca ttaatgtatg acatgctgac tggagcaccc | 900 |
| ccattcactg gggagaatag aaagaaaaca attgacaaaa tcctcaaatg taaactcaat | 960 |
| ttgcctccct acctcacaca agaagccaga gatctgctta aaaagctgct gaaaagaaat | 1020 |
| gctgcttctc gtctgggagc tggtcctggg gacgctggag aagttcaagc tcatccattc | 1080 |
| tttagacaca ttaactggga agaacttctg gctcgaaagg tggagccccc ctttaaacct | 1140 |
| ctgttgcaat ctgaagagga tgtaagtcag tttgattcca agtttacacg tcagacacct | 1200 |
| gtcgacagcc cagatgactc aactctcagt gaaagtgcca atcaggtctt tctgggtttt | 1260 |
| acatatgtgg ctccatctgt acttgaaagt gtgaaagaaa agttttcctt tgaaccaaaa | 1320 |
| atccgatcac ctcgaagatt tattggcagc ccacgaacac ctgtcagccc agtcaaattt | 1380 |
| tctcctgggg atttctgggg aagaggtgct tcggccagca cagcaaatcc tcagacacct | 1440 |
| gtggaatacc caatggaaac aagtggcata gagcagatgg atgtgacaat gagtggggaa | 1500 |
| gcatcggcac cacttccaat acgacagccg aactctgggc catacaaaaa acaagctttt | 1560 |
| cccatgatct ccaaacggcc agagcacctg cgtatgaatc tatgacagag caatgctttt | 1620 |
| aatgaattta aggcaaaaag gtggagaggg agatgtgtga gcatcctgca aggtgaaaca | 1680 |
| agactcaaaa tgacagtttc agagagtcaa tgtcattaca tagaacactt cggacacagg | 1740 |
| aaaaataaac gtggatttta aaaaatcaat caatggtgca aaaaaaaact taagcaaaa | 1800 |
| tagtattgct gaactcttag gcacatcaat taattgattc ctcgcgacat ctttctcaac | 1860 |
| cttatcaagg attttcatgt tgatgactcg aaactgacag tattaagggt aggatgttgc | 1920 |
| tctgaatcac tgtgagtctg atgtgtgaag aagggtatcc tttcattagg caagtacaaa | 1980 |
| ttgcctataa tacttgcaac taaggacaaa ttagcatgca agcttggtca aacttttccc | 2040 |
| aggcaaaatg ggaaggcaaa gacaaaagaa acttaccaat tgatgtttta cgtgcaaaca | 2100 |
| acctgaatct ttttttttata taaatatata ttttttcaaat agattttga ttcagctcat | 2160 |
| tatgaaaaac atcccaaact ttaaaatgcg aaattattgg ttggtgtgaa gaaagccaga | 2220 |
| caacttctgt ttcttctctt ggtgaaataa taaaatgcaa atgaatcatt gttaacacag | 2280 |
| ctgtggctcg tttgagggat tggggtggac ctggggttta ttttcagtaa cccagctgcg | 2340 |
| gagcct | 2346 |

<210> SEQ ID NO 322
<211> LENGTH: 2420
<212> TYPE: DNA
<213> ORGANISM: Homo sapiens

<400> SEQUENCE: 322

| | |
|---|---|
| tccggggcgg cccccggcag ccagcgcgac gttccaaaat cgaacctcag tggcggcgct | 60 |
| cggaagcgga actctgccgg ggccgcgccg gctacattgt ttcctccccc cgactccctc | 120 |
| ccgcccccctt cccccgcctt tcttccctcc gcgacccggg ccgtgcgtcc gtcccctgc | 180 |
| ctctgcctgg cggtccctcc tcccctctcc ttgcacccat acctctttgt accgcacccc | 240 |
| ctggggaccc ctgcgcccct cccctccccc ctgaccgcat ggaccgtccc gcaggccgct | 300 |
| gatgccgccc gcggcgaggt ggccggacc gcagtgcccc aagagagctc taatggtacc | 360 |
| aagtgacagg ttggctttac tgtgactcgg ggacgccaga gctcctgaga agatgtcagc | 420 |
| aatacaggcc gcctggccat ccggtacaga atgtattgcc aagtacaact tccacggcac | 480 |
| tgccgagcag gacctgccct tctgcaaagg agacgtgctc accattgtgg ccgtcaccaa | 540 |
| ggaccccaac tggtacaaag ccaaaaacaa ggtgggccgt gagggcatca tcccagccaa | 600 |

```
ctacgtccag aagcgggagg gcgtgaaggc gggtaccaaa ctcagcctca tgccttggtt      660
ccacggcaag atcacacggg agcaggctga gcggcttctg tacccgccgg agacaggcct      720
gttcctggtg cgggagagca ccaactaccc cggagactac acgctgtgcg tgagctgcga      780
cggcaaggtg gagcactacc gcatcatgta ccatgccagc aagctcagca tcgacgagga      840
ggtgtacttt gagaacctca tgcagctggt ggagcactac acctcagacg cagatggact      900
ctgtacgcgc tcattaaac caaaggtcat ggagggcaca gtggcggccc aggatgagtt       960
ctaccgcagc ggctgggccc tgaacatgaa ggagctgaag ctgctgcaga ccatcgggaa     1020
gggggagttc ggagacgtga tgctgggcga ttaccgaggg aacaaagtcg ccgtcaagtg     1080
cattaagaac gacgccactg cccaggcctt cctggctgaa gcctcagtca tgacgcaact     1140
gcggcatagc aacctggtgc agctcctggg cgtgatcgtg gaggagaagg gcgggctcta     1200
catcgtcact gagtacatgg ccaaggggag ccttgtggac tacctgcggt ctaggggtcg     1260
gtcagtgctg ggcggagact gtctcctcaa gttctcgcta gatgtctgcg aggccatgga     1320
atacctggag gcaacaatt tcgtgcatcg agacctggct gcccgcaatg tgctggtgtc      1380
tgaggacaac gtggccaagg tcagcgactt tggtctcacc aaggaggcgt ccagcaccca     1440
ggacacgggc aagctgccag tcaagtggac agccctgag gccctgagag aagaaaatt      1500 ctccactaag tctgacgtgt ggagtttcgg aatccttctc tgggaaatct actcctttgg     1560
gcgagtgcct tatccaagaa ttcccctgaa ggacgtcgtc cctcgggtgg agaagggcta     1620
caagatggat gcccccgacg gctgcccgcc cgcagtctat gaagtcatga gaactgctg      1680 gcacctggac gccgccatgc ggccctcctt cctacagctc cgagagcagc ttgagcacat     1740
caaaacccac gagctgcacc tgtgacggct ggcctccgcc tgggtcatgg gcctgtgggg     1800
actgaacctg gaagatcatg gacctggtgc ccctgctcac tgggcccgag cctgaactga     1860
gccccagcgg gctggcgggc cttttcctg cgtcccagcc tgcacccctc cggccccgtc      1920
tctcttggac ccacctgtgg ggcctgggga gcccactgag gggccaggga ggaaggaggc     1980
cacggagcgg gcggcagcgc cccaccacgt cgggcttccc tggcctcccg ccactcgcct     2040
tcttagagtt ttattccttt cctttttga gattttttt ccgtgtgttt attttttatt       2100
atttttcaag ataaggagaa agaaagtacc cagcaaatgg gcattttaca agaagtacga     2160
atcttatttt tcctgtcctg cccgtgaggt gggggggacc gggcccctct ctagggaccc     2220
ctcgccccag cctcattccc cattctgtgt cccatgtccc gtgtctcctc ggtcgccccg     2280
tgtttgcgct tgaccatgtt gcactgtttg catgcgcccg aggcagacgt ctgtcagggg     2340
cttggatttc gtgtgccgct gccacccgcc caccgccctt gtgagatgga atcgtaataa     2400
accacgccat gaggaaaaaa                                                 2420
```

<210> SEQ ID NO 323
<211> LENGTH: 2253
<212> TYPE: DNA
<213> ORGANISM: Homo sapiens

<400> SEQUENCE: 323

```
ggaagacttg ggtccttggg tcgcaggtgg gagccgacgg gtgggtagac cgtgggggat       60
atctcagtgg cggacgagga cggcggggac aaggggcggc tggtcggagt ggcggagcgt      120
caagtcccct gtcggttcct ccgtcccctga gtgtccttgg cgctgccttg tgcccgccca     180
gcgcctttgc atccgctcct gggcaccgag gcgccctgta ggatactgct tgttacttat     240
```

-continued

```
tacagctaga ggcatcatgg accgatctaa agaaaactgc atttcaggac ctgttaaggc        300
tacagctcca gttggaggtc caaaacgtgt tctcgtgact cagcaaattc cttgtcagaa        360
tccattacct gtaaatagtg gccaggctca gcgggtcttg tgtccttcaa attcttccca        420
gcgcgttcct ttgcaagcac aaaagcttgt ctccagtcac aagccggttc agaatcagaa        480
gcagaagcaa ttgcaggcaa ccagtgtacc tcatcctgtc tccaggccac tgaataacac        540
ccaaaagagc aagcagcccc tgccatcggc acctgaaaat aatcctgagg aggaactggc        600
atcaaaacag aaaaatgaag aatcaaaaaa gaggcagtgg gctttggaag actttgaaat        660
tggtcgccct ctgggtaaag aaagtttgg taatgtttat ttggcaagag aaaagcaaag         720
caagtttatt ctggctctta agtgttatt taaagctcag ctggagaaag ccggagtgga         780
gcatcagctc agaagagaag tagaaataca gtcccacctt cggcatccta atattcttag        840
actgtatggt tatttccatg atgctaccag agtctaccta attctggaat atgcaccact        900
tggaacagtt tatagagaac ttcagaaact ttcaaagttt gatgagcaga gaactgctac        960
ttatataaca gaattggcaa atgccctgtc ttactgtcat cgaagagag ttattcatag        1020 agacattaag ccagagaact tacttcttgg atcagctgga gagcttaaaa ttgcagattt       1080
tgggtggtca gtacatgctc catcttccag gaggaccact ctctgtggca ccctggacta       1140
cctgccccct gaaatgattg aaggtcggat gcatgatgag aaggtggatc tctgagcct        1200 tggagttctt tgctatgaat ttttagttgg gaagcctcct tttgaggcaa acacatacca       1260
agagacctac aaaagaatat cacgggttga attcacattc cctgactttg taacagaggg       1320
agccagggac ctcatttcaa gactgttgaa gcataatccc agccagaggc caatgctcag       1380
agaagtactt gaacacccct ggatcacagc aaattcatca aaaccatcaa attgccaaaa       1440
caaagaatca gctagcaaac agtcttagga atcgtgcagg gggagaaatc cttgagccag       1500
ggctgccata taacctgaca ggaacatgct actgaagttt attttaccat tgactgctgc       1560
cctcaatcta gaacgctaca aagaaatat ttgtttact cagcaggtgt gccttaacct        1620
ccctattcag aaagctccac atcaataaac atgacactct gaagtgaaag tagccacgag       1680
aattgtgcta cttatactgg ttcataatct ggaggcaagg ttcgactgca gccgccccgt       1740
cagcctgtgc taggcatggt gtcttcacag gaggcaaatc cagagcctgg ctgtggggaa       1800
agtgaccact ctgccctgac cccgatcagt taaggagctg tgcaataacc ttcctagtac       1860
ctgagtgagt gtgtaactta ttgggttggc gaagcctggt aaagctgttg gaatgagtat       1920
gtgattcttt ttaagtatga aaataaagat atatgtacag acttgtattt tttctctggt       1980
ggcattcctt taggaatgct gtgtgtctgt ccggcacccc ggtaggcctg attgggtttc       2040
tagtcctcct taaccactta tctcccatat gagagtgtga aaaataggaa cacgtgctct       2100
acctccattt agggatttgc ttgggataca gaagaggcca tgtgtctcag agctgttaag       2160
ggcttatttt tttaaaacat tggagtcata gcatgtgtg aaactttaaa tatgcaaata        2220
aataagtatc tatgtctaaa aaaaaaaaaa aaa                                     2253
```

<210> SEQ ID NO 324
<211> LENGTH: 1619
<212> TYPE: DNA
<213> ORGANISM: Homo sapiens

<400> SEQUENCE: 324

```
ccgccagatt tgaatcgcgg gacccgttgg cagaggtggc ggcggcggca tgggtgcccc         60
gacgttgccc cctgcctggc agcccttct caaggaccac cgcatctcta cattcaagaa        120
```

```
ctggcccttc ttggagggct gcgcctgcac cccggagcgg atggccgagg ctggcttcat      180
ccactgcccc actgagaacg agccagactt ggcccagtgt ttcttctgct tcaaggagct      240
ggaaggctgg gagccagatg acgacccat  agaggaacat aaaaagcatt cgtccggttg      300
cgctttcctt tctgtcaaga agcagtttga agaattaacc cttggtgaat ttttgaaact      360
ggacagagaa agagccaaga acaaaattgc aaaggaaacc aacaataaga agaaagaatt      420
tgaggaaact gcgaagaaag tgcgccgtgc catcgagcag ctggctgcca tggattgagg      480
cctctggccg gagctgcctg gtcccagagt ggctgcacca cttccagggt ttattccctg      540
gtgccaccag ccttcctgtg ggccccttag caatgtctta ggaaaggaga tcaacatttt      600
caaattagat gtttcaactg tgctcctgtt ttgtcttgaa agtggcacca gaggtgcttc      660
tgcctgtgca gcgggtgctg ctggtaacag tggctgcttc tctctctctc tctctttttt      720
gggggctcat ttttgctgtt ttgattcccg ggcttaccag gtgagaagtg agggaggaag      780
aaggcagtgt ccctttttgct agagctgaca gctttgttcg cgtgggcaga gccttccaca     840
gtgaatgtgt ctggacctca tgttgttgag gctgtcacag tcctgagtgt ggacttggca      900
ggtgcctgtt gaatctgagc tgcaggttcc ttatctgtca cacctgtgcc tcctcagagg      960
acagtttttt tgttgttgtg tttttttgtt tttttttttt ggtagatgca tgacttgtgt     1020
gtgatgagag aatggagaca gagtccctgg ctcctctact gtttaacaac atggctttct     1080
tattttgttt gaattgttaa ttcacagaat agcacaaact acaattaaaa ctaagcacaa     1140
agccattcta agtcattggg gaaacggggt gaacttcagg tggatgagga gacagaatag     1200
agtgatagga agcgtctggc agatactcct tttgccactg ctgtgtgatt agacaggccc     1260
agtgagccgc ggggcacatg ctggccgctc ctccctcaga aaaaggcagt ggcctaaatc     1320 cttttttaaat gacttggctc gatgctgtgg gggactggct gggctgctgc aggccgtgtg    1380
tctgtcagcc caaccttcac atctgtcacg ttctccacac gggggagaga cgcagtccgc     1440
ccaggtcccc gctttctttg gaggcagcag ctcccgcagg gctgaagtct ggcgtaagat     1500
gatggatttg attcgccctc ctccctgtca tagagctgca gggtggattg ttacagcttc     1560
gctggaaacc tctggaggtc atctcggctg ttcctgagaa ataaaaagcc tgtcatttc      1619
```

<210> SEQ ID NO 325
<211> LENGTH: 5010
<212> TYPE: DNA
<213> ORGANISM: Homo sapiens

<400> SEQUENCE: 325

```
ggcggctcgg gacggaggac gcgctagtgt gagtgcgggc ttctagaact acaccgaccc       60
tcgtgtcctc ccttcatcct gcggggctgg ctggagcggc cgctccggtg ctgtccagca      120
gccataggga gccgcacggg gagcgggaaa gcggtcgcgg ccccaggcgg ggcggccggg      180
atggagcggg gccgcgagcc tgtggggaag gggctgtggc ggcgcctcga gcggctgcag      240
gttcttctgt gtggcagttc agaatgatgg atcaagctag atcagcattc tctaacttgt      300
ttggtggaga accattgtca tatacccggt tcagcctggc tcggcaagta gatggcgata      360
acagtcatgt ggagatgaaa cttgctgtag atgaagaaga aaatgctgac aataacacaa      420
aggccaatgt cacaaaacca aaaaggtgta gtggaagtat ctgctatggg actattgctg      480
tgatcgtctt tttcttgatt ggatttatga ttggctactt gggctattgt aaagggggtag     540 aaccaaaaac tgagtgtgag agactggcag gaaccgagtc tccagtgagg gaggagccag      600
```

```
gagaggactt ccctgcagca cgtcgcttat attgggatga cctgaagaga aagttgtcgg     660
agaaactgga cagcacagac ttcaccagca ccatcaagct gctgaatgaa aattcatatg     720
tccctcgtga ggctggatct caaaaagatg aaaatcttgc gttgtatgtt gaaaatcaat     780
ttcgtgaatt taaactcagc aaagtctggc gtgatcaaca ttttgttaag attcaggtca     840
aagacagcgc tcaaaactcg gtgatcatag ttgataagaa cggtagactt gtttacctgg     900
tggagaatcc tgggggttat gtggcgtata gtaaggctgc aacagttact ggtaaactgg     960
tccatgctaa ttttggtact aaaaaagatt ttgaggattt atacactcct gtgaatggat    1020
ctatagtgat tgtcagagca gggaaaatca cctttgcaga aaaggttgca aatgctgaaa    1080
gcttaaatgc aattggtgtg ttgatataca tggaccagac taaatttccc attgttaacg    1140
cagaactttc attctttgga catgctcatc tggggacagg tgacccttac acacctggat    1200
tcccttcctt caatcacact cagtttccac catctcggtc atcaggattg cctaatatac    1260
ctgtccagac aatctccaga gctgctgcag aaaagctgtt tgggaatatg gaaggagact    1320
gtccctctga ctggaaaaca gactctacat gtaggatggt aacctcagaa agcaagaatg    1380
tgaagctcac tgtgagcaat gtgctgaaag agataaaaat tcttaacatc tttggagtta    1440
ttaaaggctt tgtagaacca gatcactatg ttgtagttgg ggcccagaga gatgcatggg    1500
gccctggagc tgcaaaatcc ggtgtaggca cagctctcct attgaaactt gcccagatgt    1560
tctcagatat ggtcttaaaa gatgggtttc agcccagcag aagcattatc tttgccagtt    1620
ggagtgctgg agactttgga tcggttggtg ccactgaatg gctagaggga tacctttcgt    1680
ccctgcattt aaaggctttc acttatatta atctggataa agcggttctt ggtaccagca    1740
acttcaaggt ttctgccagc ccactgttgt atacgcttat tgagaaaaca atgcaaaatg    1800
tgaagcatcc ggttactggg caatttctat atcaggacag caactgggcc agcaaagttg    1860
agaaactcac tttagacaat gctgctttcc ctttccttgc atattctgga atcccagcag    1920
tttctttctg ttttttgcgag gacacagatt atccttattt gggtaccacc atggacacct    1980
ataaggaact gattgagagg attcctgagt tgaacaaagt ggcacgagca gctgcagagg    2040
tcgctggtca gttcgtgatt aaactaaccc atgatgttga attgaacctg gactatgaga    2100
ggtacaacag ccaactgctt tcatttgtga gggatctgaa ccaatacaga gcagacataa    2160
aggaaatggg cctgagttta cagtggctgt attctgctcg tggagacttc ttccgtgcta    2220
cttccagact aacaacagat ttcgggaatg ctgagaaaac agacagattt gtcatgaaga    2280
aactcaatga tcgtgtcatg agagtggagt atcacttcct ctctccctac gtatctccaa    2340
aagagtctcc tttccgacat gtcttctggg gctccggctc tcacacgctg ccagctttac    2400
tggagaactt gaaactgcgt aaacaaaata acggtgcttt taatgaaacg ctgttcagaa    2460
accagttggc tctagctact tggactattc agggagctgc aaatgccctc tctggtgacg    2520
tttgggacat tgacaatgag tttttaaatgt gatacccata gcttccatga aacagcagg    2580 gtagtctggt ttctagactt gtgctgatcg tgctaaattt tcagtagggc tacaaaacct    2640
gatgttaaaa ttccatccca tcatcttggt actactagat gtctttaggc agcagctttt    2700
aatacagggt agataacctg tacttcaagt taaagtgaat aaccacttaa aaaatgtcca    2760
tgatggaata ttcccctatc tctagaattt taagtgcttt gtaatgggaa ctgcctcttt    2820
cctgttgttg ttaatgaaaa tgtcagaaac cagttatgtg aatgatctct ctgaatccta    2880
agggctggtc tctgctgaag gttgtaagtg gttcgcttac tttgagtgat cctccaactt    2940
catttgatgc taaataggag ataccaggtt gaaagacctc tccaaatgag atctaagcct    3000
```

-continued

| | | |
|---|---|---|
| ttccataagg aatgtagcag gtttcctcat tcctgaaaga aacagttaac tttcagaaga | 3060 |
| gatgggcttg ttttcttgcc aatgaggtct gaaatggagg tccttctgct ggataaaatg | 3120 |
| aggttcaact gttgattgca ggaataaggc cttaatatgt taacctcagt gtcatttatg | 3180 |
| aaagaggggg accagaagcc aaagacttag tatattttct tttcctctgt cccttccccc | 3240 |
| ataagcctcc atttagttct tgttattttt tgtttcttcc aaagcacatt gaaagagaac | 3300 |
| cagtttcagg tgtttagttg cagactcagt tgtcagact ttaaagaata atatgctgcc | 3360 |
| aaattttggc caaagtgtta atcttagggg agagctttct gtccttttgg cactgagata | 3420 |
| tttattgttt atttatcagt gacagagttc actataaatg gtgttttttt aatagaatat | 3480 |
| aattatcgga agcagtgcct tccataatta tgacagttat actgtcggtt tttttttaaat | 3540 |
| aaaagcagca tctgctaata aaacccaaca gatactggaa gttttgcatt tatggtcaac | 3600 |
| acttaagggt tttagaaaac agccgtcagc caaatgtaat tgaataaagt tgaagctaag | 3660 |
| atttagagat gaattaaatt taattagggg ttgctaagaa gcgagcactg accagataag | 3720 |
| aatgctggtt ttcctaaatg cagtgaattg tgaccaagtt ataaatcaat gtcacttaaa | 3780 |
| ggctgtggta gtactcctgc aaaatttat agctcagttt atccaaggtg taactctaat | 3840 |
| tcccatttgc aaaatttcca gtacctttgt cacaatccta acacattatc gggagcagtg | 3900 |
| tcttccataa tgtataaaga acaaggtagt ttttacctac cacagtgtct gtatcggaga | 3960 |
| cagtgatctc catatgttac actaagggtg taagtaatta tcgggaacag tgtttcccat | 4020 |
| aattttcttc atgcaatgac atcttcaaag cttgaagatc gttagtatct aacatgtatc | 4080 |
| ccaactccta taattcccta tcttttagtt ttagttgcag aaacattttg tggtcattaa | 4140 |
| gcattgggtg ggtaaattca accactgtaa aatgaaatta ctacaaaatt tgaaatttag | 4200 |
| cttgggttt tgttacctttt atggtttctc caggtcctct acttaatgag atagcagcat | 4260 |
| acatttataa tgtttgctat tgacaagtca ttttaattta tcacattatt tgcatgttac | 4320 |
| ctcctataaa cttagtgcgg acaagtttta atccagaatt gaccttttga cttaaagcag | 4380 |
| agggactttg tatagaaggt ttgggggctg tgggaagga gagtcccctg aaggtctgac | 4440 |
| acgtctgcct acccattcgt ggtgatcaat taaatgtagg tatgaataag ttcgaagctc | 4500 |
| cgtgagtgaa ccatcatata aacgtgtagt acagctgttt gtcataggc agttggaaac | 4560 |
| ggcctcctag ggaaaagttc atagggtctc ttcaggttct tagtgtcact tacctagatt | 4620 |
| tacagcctca cttgaatgtg tcactactca cagtctcttt aatcttcagt tttatcttta | 4680 |
| atctcctctt ttatcttgga ctgacattta gcgtagctaa gtgaaaaggt catagctgag | 4740 |
| attcctggtt cggtgttac gcacacgtac ttaaatgaaa gcatgtggca tgttcatcgt | 4800 |
| ataacacaat atgaatacag ggcatgcatt ttgcagcagt gagtctcttc agaaaaccct | 4860 |
| tttctacagt tagggttgag ttacttccta tcaagccagt acgtgctaac aggctcaata | 4920 |
| ttcctgaatg aaatatcaga ctagtgacaa gctcctggtc ttgagatgtc ttctcgttaa | 4980 |
| ggagtagggc cttttggagg taaaggtata | 5010 |

<210> SEQ ID NO 326
<211> LENGTH: 2574
<212> TYPE: DNA
<213> ORGANISM: Homo sapiens

<400> SEQUENCE: 326
cctgtttaga cacatggaca acaatcccag cgctacaagg cacacagtcc gcttcttcgt      60

-continued

| | |
|---|---|
| cctcagggtt gccagcgctt cctggaagtc ctgaagctct cgcagtgcag tgagttcatg | 120 |
| caccttcttg ccaagcctca gtctttggga tctgggagg ccgcctggtt ttcctccctc | 180 |
| cttctgcacg tctgctgggg tctcttcctc tccaggcctt gccgtccccc tggcctctct | 240 |
| tcccagctca cacatgaaga tgcacttgca aagggctctg gtggtcctgg ccctgctgaa | 300 |
| ctttgccacg gtcagcctct ctctgtccac ttgcaccacc ttggacttcg gccacatcaa | 360 |
| gaagaagagg gtggaagcca ttaggggaca gatcttgagc aagctcaggc tcaccagccc | 420 |
| ccctgagcca acggtgatga cccacgtccc ctatcaggtc ctggccctttt acaacagcac | 480 |
| ccgggagctg ctggaggaga tgcatgggga gggaggaa ggctgcaccc aggaaaacac | 540 |
| cgagtcggaa tactatgcca aagaaatcca taaattcgac atgatccagg ggctggcgga | 600 |
| gcacaacgaa ctggctgtct gccctaaagg aattacctcc aaggttttcc gcttcaatgt | 660 |
| gtcctcagtg gagaaaaata gaaccaacct attccgagca gaattccggg tcttgcgggt | 720 |
| gcccaacccc agctctaagc ggaatgagca gaggatcgag ctcttccaga tccttcggcc | 780 |
| agatgagcac attgccaaac agcgctatat cggtggcaag aatctgccca cgggggcac | 840 |
| tgccgagtgg ctgtccttg atgtcactga cactgtgcgt gagtggctgt tgagaagaga | 900 |
| gtccaactta ggtctagaaa tcagcattca ctgtccatgt cacacctttc agcccaatgg | 960 |
| agatatcctg gaaaacattc acgaggtgat ggaaatcaaa ttcaaaggcg tggacaatga | 1020 |
| ggatgaccat ggccgtggag atctggggcg cctcaagaag cagaaggatc accacaaccc | 1080 |
| tcatctaatc ctcatgatga ttcccccaca ccggctcgac aacccgggcc aggggggtca | 1140 |
| gaggaagaag cgggctttgg acaccaatta ctgcttccgc aacttggagg agaactgctg | 1200 |
| tgtgcgcccc ctctacattg acttccgaca ggatctgggc tggaagtggg tccatgaacc | 1260 |
| taagggctac tatgccaact tctgctcagg cccttgccca tacctccgca gtgcagacac | 1320 |
| aacccacagc acggtgctgg gactgtacaa cactctgaac cctgaagcat ctgcctcgcc | 1380 |
| ttgctgcgtg ccccaggacc tggagcccct gaccatcctg tactatgttg ggaggacccc | 1440 |
| caaagtggag cagctctcca acatggtggt gaagtcttgt aaatgtagct gagaccccac | 1500 |
| gtgcgacaga gagaggggag agagaaccac cactgcctga ctgcccgctc ctcgggaaac | 1560 |
| acacaagcaa caaacctcac tgagaggcct ggagcccaca accttcggct ccgggcaaat | 1620 |
| ggctgagatg gaggtttcct tttggaacat ttctttcttg ctggctctga gaatcacggt | 1680 |
| ggtaaagaaa gtgtgggttt ggttagagga aggctgaact cttcagaaca cacagacttt | 1740 |
| ctgtgacgca gacagagggg atgggatag aggaaaggga tggtaagttg agatgttgtg | 1800 |
| tggcaatggg atttgggcta ccctaaaggg agaaggaagg gcagagaatg gctgggtcag | 1860 |
| ggccagactg gaagacactt cagatctgag gttggatttg ctcattgctg taccacatct | 1920 |
| gctctaggga atctggatta tgttatacaa ggcaagcatt ttttttttta aagacaggtt | 1980 |
| acgaagacaa agtcccagaa ttgtatctca tactgtctgg gattaagggc aaatctatta | 2040 |
| cttttgcaaa ctgtcctcta catcaattaa catcgtgggt cactacaggg agaaaatcca | 2100 |
| ggtcatgcag ttcctggccc atcaactgta ttgggccttt tggatatgct gaacgcagaa | 2160 |
| gaaagggtgg aaatcaaccc tctcctgtct gccctctggg tccctcctct cacctctccc | 2220 |
| tcgatcatat ttccccttgg acacttggtt agacgccttc caggtcagga tgcacatttc | 2280 |
| tggattgtgg ttccatgcag ccttggggca ttatgggtct tccccccactt ccccctccaag | 2340 |
| accctgtgtt catttggtgt tcctggaagc aggtgctaca acatgtgagg cattcgggga | 2400 |
| agctgcacat gtgccacaca gtgacttggc cccagacgca tagactgagg tataaagaca | 2460 |

```
agtatgaata ttactctcaa aatctttgta taaataaata ttttttggggc atcctggatg    2520 atttcatctt ctggaatatt gtttctagaa cagtaaaagc cttattctaa ggtg          2574
```

<210> SEQ ID NO 327
<211> LENGTH: 1421
<212> TYPE: DNA
<213> ORGANISM: Homo sapiens

<400> SEQUENCE: 327

```
acttactgcg ggacggcctt ggagagtact cgggttcgtg aacttcccgg aggcgcaatg      60
agctgcatta acctgcccac tgtgctgccc ggctccccca gcaagacccg ggggcagatc     120
caggtgattc tcgggccgat gttctcagga aaaagcacag agttgatgag acgcgtccgt     180
cgcttccaga ttgctcagta caagtgcctg gtgatcaagt atgccaaaga cactcgctac     240
agcagcagct tctgcacaca tgaccggaac accatggagg cgctgcccgc ctgcctgctc     300
cgagacgtgg cccaggaggc cctgggcgtg gctgtcatag gcatcgacga ggggcagttt     360
ttccctgaca tcatggagtt ctgcgaggcc atgccaacg ccgggaagac cgtaattgtg      420
gctgcactgg atgggacctt ccagaggaag ccatttgggg ccatcctgaa cctggtgccg     480
ctggccgaga gcgtggtgaa gctgacggcg gtgtgcatgg agtgcttccg ggaagccgcc     540
tataccaaga ggctcggcac agagaaggag gtcgaggtga ttgggggagc agacaagtac     600
cactccgtgt gtcggctctg ctacttcaag aaggcctcag gccagcctgc cgggccggac     660
aacaaagaga actgcccagt gccaggaaag ccaggggaag ccgtggctgc caggaagctc     720
tttgccccac agcagattct gcaatgcagc cctgccaact gagggacctg caagggccgc     780 ccgctcccctt cctgccactg ccgcctactg gacgctgccc tgcatgctgc ccagccactc     840
caggaggaag tcgggaggcg tggagggtga ccacaccttg gccttctggg aactctcctt     900 tgtgtgctg ccccacctgc cgcatgctcc ctcctctcct acccactggt ctgcttaaag       960
cttccctctc agctgctggg acgatcgccc aggctggagc tggccccgct tggtggcctg    1020
ggatctggca cactccctct ccttgggtg agggacagag ccccacgctg ttgacatcag     1080
cctgcttctt cccctctgcg gctttcactg ctgagtttct gttctccctg ggaagcctgt    1140
gccagcacct ttgagccttg gcccacactg aggcttaggc ctctctgcct gggatgggct    1200
cccaccctcc cctgaggatg gcctggattc acgccctctt gtttccttttt gggctcaaag    1260 cccttcctac ctctggtgat ggtttccaca ggaacaacag catctttcac caagatgggt    1320
ggcaccaacc ttgctgggac ttggatccca ggggcttatc tcttcaagtg tggagagggc    1380
agggtccacg cctctgctgt agcttatgaa attaactaat t                         1421
```

<210> SEQ ID NO 328
<211> LENGTH: 4604
<212> TYPE: DNA
<213> ORGANISM: Homo sapiens

<400> SEQUENCE: 328

```
ggaacagctt gtccacccgc cggccggacc agaagccttt gggtctgaag tgtctgtgag      60
acctcacaga agagcacccc tgggctccac ttacctgccc cctgctcctt cagggatgga    120
ggcaatggcg gccagcactt ccctgcctga ccctggagac tttgaccgga acgtgccccg    180
gatctgtggg gtgtgtggag accgagccac tggctttcac ttcaatgcta tgacctgtga    240
aggctgcaaa ggcttcttca ggcgaagcat gaagcggaag gcactattca cctgcccctt    300
```

-continued

```
caacggggac tgccgcatca ccaaggacaa ccgacgccac tgccaggcct gccggctcaa      360
acgctgtgtg gacatcggca tgatgaagga gttcattctg acagatgagg aagtgcagag      420
gaagcgggag atgatcctga agcggaagga ggaggaggcc ttgaaggaca gtctgcggcc      480
caagctgtct gaggagcagc agcgcatcat tgccatactg ctggacgccc accataagac      540
ctacgacccc acctactccg acttctgcca gttccggcct ccagttcgtg tgaatgatgg      600
tggagggagc catccttcca ggcccaactc cagacacact cccagcttct ctggggactc      660
ctcctcctcc tgctcagatc actgtatcac ctcttcagac atgatggact cgtccagctt      720
ctccaatctg gatctgagtg aagaagattc agatgaccct tctgtgaccc tagagctgtc      780
ccagctctcc atgctgcccc acctggctga cctggtcagt tacagcatcc aaaaggtcat      840
tggctttgct aagatgatac caggattcag agacctcacc tctgaggacc agatcgtact      900
gctgaagtca agtgccattg aggtcatcat gttgcgctcc aatgagtcct tcaccatgga      960
cgacatgtcc tggacctgtg caaccaaga ctacaagtac cgcgtcagtg acgtgaccaa     1020
agccggacac agcctggagc tgattgagcc cctcatcaag ttccaggtgg gactgaagaa     1080
gctgaacttg catgaggagg agcatgtcct gctcatggcc atctgcatcg tctccccaga     1140
tcgtcctggg gtgcaggacg ccgcgctgat tgaggccatc caggaccgcc tgtccaacac     1200
actgcagacg tacatccgct gccgccaccc gcccccgggc agccacctgc tctatgccaa     1260
gatgatccag aagctagccg acctgcgcag cctcaatgag gagcactcca gcagtaccg     1320 ctgcctctcc ttccagcctg agtgcagcat gaagctaacg cccccttgtgc tcgaagtgtt     1380 tggcaatgag atctcctgac taggacagcc tgtgcggtgc ctgggtgggg ctgctcctcc     1440
agggccacgt gccaggcccg ggctggcgg ctactcagca gccctcctca cccgtctggg     1500
gttcagcccc tcctctgcca cctcccctat ccacccagcc cattctctct cctgtccaac     1560
ctaacccctt tcctgcgggc ttttcccgg tcccttgaga cctcagccat gaggagttgc     1620
tgtttgtttg acaaagaaac ccaagtgggg gcagagggca gaggctggag gcaggccttg     1680
cccagagatg cctccaccgc tgcctaagtg gctgctgact gatgttgagg gaacagacag     1740
gagaaatgca tccattcctc agggacagag acacctgcac ctcccccccac tgcaggcccc     1800 gcttgtccag cgcctagtgg ggtctccctc tcctgcctta ctcacgataa ataatcggcc     1860
cacagctccc accccacccc cttcagtgcc caccaacatc ccattgccct ggttatattc     1920
tcacgggcag tagctgtggt gaggtgggtt ttcttcccat cactggagca ccaggcacga     1980
acccacctgc tgagagaccc aaggaggaaa aacagacaaa aacagcctca cagaagaata     2040
tgacagctgt ccctgtcacc aagctcacag ttcctcgccc tgggtctaag gggttggttg     2100
aggtggaagc cctccttcca cggatccatg tagcaggact gaattgtccc cagttttgcag     2160 aaaagcacct gccgacctcg tcctccccct gccagtgcct tacctcctgc caggagagc      2220 cagccctccc tgtcctcctc ggatcaccga gagtagccga gagcctgctc ccccacccc      2280 tccccagggg agagggtctg gagaagcagt gagccgcatc ttctccatct ggcagggtgg     2340
gatggaggag aagaattttc agaccccagc ggctgagtca tgatctccct gccgcctcaa     2400
tgtggttgca aggccgctgt tcaccacagg gctaagagct aggctgccgc accccagagt     2460
gtgggaaggg agagcgggc agtctcgggt ggctagtcag agagagtgtt tgggggttcc     2520
gtgatgtagg gtaaggtgcc ttcttattct cactccacca cccaaaagtc aaaaggtgcc     2580
tgtgaggcag gggcggagtg atacaacttc aagtgcatgc tctctgcagg tcgagcccag     2640
cccagctggt gggaagcgtc tgtccgttta ctccaaggtg ggtctttgtg agagtgagct     2700
```

-continued

```
gtaggtgtgc gggaccggta cagaaaggcg ttcttcgagg tggatcacag aggcttcttc    2760
agatcaatgc ttgagtttgg aatcggccgc attccctgag tcaccaggaa tgttaaagtc    2820
agtgggaacg tgactgcccc aactcctgga agctgtgtcc ttgcacctgc atccgtagtt    2880
ccctgaaaac ccagagagga atcagacttc acactgcaag agccttggtg tccacctggc    2940
cccatgtctc tcagaattct tcaggtggaa aacatctga agccacgtt ccttactgca      3000 gaatagcata tatatcgctt aatcttaaat ttattagata tgagttgttt tcagactcag    3060
actccatttg tattatagtc taatatacag ggtagcaggt accactgatt tggagatatt    3120
tatgggggga gaacttacat tgtgaaactt ctgtacatta attattattg ctgttgttat    3180
tttacaaggg tctagggaga gacccttgtt tgattttagc tgcagaactg tattggtcca    3240
gcttgctctt cagtgggaga aaaacacttg taagttgcta aacgagtcaa tcccctcatt    3300
caggaaaact gacagaggag ggcgtgactc acccaagcca tataactca gctagaagtg     3360 ggccaggaca ggccgggcgc ggtggctcac gcctgtaatc ccagcagttt gggaggtcga    3420
ggtaggtgga tcacctgagg tcgggagttc gagaccaacc tgaccaacat ggagaaaccc    3480
tgtctctatt aaaaatacaa aaaaaaaaa aaaaaaaat agccgggcat ggtggcgcaa      3540
gcctgtaatc ccagctactc aggaggctga ggcagaagaa ttgaacccag gaggtggagg    3600
ttgcagtgag ctgagatcgt gccgttactc tccaacctgg acaacaagag cgaaactccg    3660
tcttagaagt ggaccaggac aggaccagat tttggagtca tggtccggtg tccttttcac    3720
tacaccatgt ttgagctcag acccccactc tcattcccca ggtggctgac ccagtccctg    3780
ggggaagccc tggatttcag aaagagccaa gtctggatct gggaccctt ccttccttcc    3840 ctggcttgta actccaccaa gcccatcaga aggagaagga aggagactca cctctgcctc    3900
aatgtgaatc agaccctacc ccaccacgat gtgccctggc tgctgggctc tccacctcag    3960
gccttggata atgctgttgc ctcatctata acatgcattt gtctttgtaa tgtcaccacc    4020
ttcccagctc tccctctggc cctgcttctt cggggaactc ctgaaatatc agttactcag    4080
ccctgggccc caccacctag gccactcctc caaggaagt ctaggagctg ggaggaaaag      4140
aaaagagggg aaaatgagtt tttatggggc tgaacgggga gaaaaggtca tcatcgattc    4200
tactttagaa tgagagtgtg aaatagacat ttgtaaatgt aaaacttta aggtatatca     4260 ttataactga aggagaaggt gccccaaaat gcaagatttt ccacaagatt cccagagaca    4320
ggaaaatcct ctggctggct aactggaagc atgtaggaga atccaagcga ggtcaacaga    4380
gaaggcagga atgtgtggca gatttagtga agctagaga tatggcagcg aaaggatgta     4440
aacagtgcct gctgaatgat ttccaaagag aaaaaagtt tgccagaagt ttgtcaagtc     4500
aaccaatgta gaaagctttg cttatggtaa taaaaatggc tcatacttat atagcactta    4560
ctttgtttgc aagtactgct gtaaataaat gctttatgca aacc                    4604
```

<210> SEQ ID NO 329
<211> LENGTH: 2076
<212> TYPE: DNA
<213> ORGANISM: Homo sapiens

<400> SEQUENCE: 329

```
cggggaaggg gagggaggag ggggacgagg gctctggcgg gtttggaggg gctgaacatc     60
gcggggtgtt ctggtgtccc ccgccccgcc tctccaaaaa gctacaccga cgcggaccgc    120
ggcggcgtcc tccctcgccc tcgcttcacc tcgcgggctc cgaatgcggg gagctcggat    180
```

```
gtccggtttc ctgtgaggct tttacctgac acccgccgcc tttccccggc actggctggg      240
agggcgccct gcaaagttgg gaacgcggag ccccggaccc gctcccgccg cctccggctc      300
gcccaggggg ggtcgccggg aggagcccgg gggagaggga ccaggagggg cccgcggcct      360
cgcagggccg cccgcgcccc caccccctgcc cccgccagcg gaccggtccc ccaccccccgg    420 tccttccacc atgcacttgc tgggcttctt ctctgtggcg tgttctctgc tcgccgctgc      480
gctgctcccg gtcctcgcg aggcgcccgc cgccgccgcc gccttcgagt ccggactcga       540
cctctcggac gcggagcccg acgcgggcga ggccacggct tatgcaagca agatctggga      600
ggagcagtta cggtctgtgt ccagtgtaga tgaactcatg actgtactct acccagaata     660
ttggaaaatg tacaagtgtc agctaaggaa aggaggctgg caacataaca gagaacaggc     720
caacctcaac tcaaggacag aagagactat aaaatttgct gcagcacatt ataatacaga     780
gatcttgaaa agtattgata atgagtggag aaagactcaa tgcatgccac gggaggtgtg     840
tatagatgtg gggaaggagt ttggagtcgc gacaaacacc ttctttaaac ctccatgtgt     900
gtccgtctac agatgtgggg gttgctgcaa tagtgagggg ctgcagtgca tgaacaccag     960
cacgagctac ctcagcaaga cgttatttga aattacagtg cctctctctc aaggccccaa    1020
accagtaaca atcagttttg ccaatcacac ttcctgccga tgcatgtcta aactggatgt    1080
ttacagacaa gttcattcca ttattagacg ttccctgcca gcaacactac cacagtgtca    1140
ggcagcgaac aagacctgcc ccaccaatta catgtggaat aatcacatct gcagatgcct    1200
ggctcaggaa gattttatgt tttcctcgga tgctggagat gactcaacag atggattcca    1260
tgacatctgt ggaccaaaca aggagctgga tgaagagacc tgtcagtgtg tctgcagagc    1320
ggggcttcgg cctgccagct gtggacccca caaagaacta cagaaaact catgccagtg    1380 tgtctgtaaa acaaactct tccccagcca atgtggggcc aaccgagaat tgatgaaaa     1440 cacatgccag tgtgtatgta aagaacctg cccagaaaat caacccctaa atcctggaaa    1500
atgtgcctgt gaatgtacag aaagtccaca gaaatgcttg ttaaaaggaa agaagttcca    1560
ccaccaaaca tgcagctgtt acagacggc atgtacgaac cgccagaagg cttgtgagcc    1620
aggattttca tatagtgaag aagtgtgtcg ttgtgtccct tcatattgga aaagaccaca    1680
aatgagctaa gattgtactg ttttccagtt catcgatttt ctattatgga aaactgtgtt    1740
gccacagtag aactgtctgt gaacagagag acccttgtgg gtccatgcta acaaagacaa    1800
aagtctgtct ttcctgaacc atgtggataa ctttacagaa atggactgga gctcatctgc    1860
aaaaggcctc ttgtaaagac tggttttctg ccaatgacca aacagccaag attttcctct    1920
tgtgatttct ttaaaagaat gactatataa tttatttcca ctaaaaatat tgtttctgca    1980
ttcattttta tagcaacaac aattggtaaa actcactgtg atcaatattt ttatatcatg    2040
caaaatatgt ttaaataaa atgaaaattg tattat                              2076
```

<210> SEQ ID NO 330
<211> LENGTH: 2819
<212> TYPE: DNA
<213> ORGANISM: Homo sapiens

<400> SEQUENCE: 330

```
ctgggcccag ctcccccgag aggtggtcgg atcctctggg ctgctcggtc gatgcctgtg       60
ccactgacgt ccaggcatga ggtggttcct gccctggacg ctggcagcag tgacagcagc     120
agccgccagc accgtcctgg ccacggccct ctctccagcc cctacgacca tggactttac     180
cccagctcca ctgcaggaca cctcctcacg cccccaattc tgcaagtggc catgtgagtg    240
```

-continued

| | |
|---|---|
| cccgccatcc ccaccccgct gcccgctggg ggtcagcctc atcacagatg gctgtgagtg | 300 |
| ctgtaagatg tgcgctcagc agcttgggga caactgcacg gaggctgcca tctgtgaccc | 360 |
| ccaccggggc ctctactgtg actacagcgg ggaccgcccg aggtacgcaa taggagtgtg | 420 |
| tgcacaggtg gtcggtgtgg gctgcgtcct ggatggggtg cgctacaaca acggccagtc | 480 |
| cttccagcct aactgcaagt acaactgcac gtgcatcgac ggcgcggtgg gctgcacacc | 540 |
| actgtgcctc cgagtgcgcc cccgcgtct ctggtgcccc cacccgcggc gcgtgagcat | 600 |
| acctggccac tgctgtgagc agtgggtatg tgaggacgac gccaagaggc cacgcaagac | 660 |
| cgcaccccgt gacacaggag ccttcgatgc tgtgggtgag gtggaggcat ggcacaggaa | 720 |
| ctgcatagcc tacacaagcc cctggagccc ttgctccacc agctgcggcc tgggggtctc | 780 |
| cactcggatc tccaatgtta acgcccagtg ctggcctgag caagagagcc gcctctgcaa | 840 |
| cttgcggcca tgcgatgtgg acatccatac actcattaag gcaggaagaa agtgtctggc | 900 |
| tgtgtaccag ccagaggcat ccatgaactt cacacttgcg ggctgcatca gcacacgctc | 960 |
| ctatcaaccc aagtactgtg gagtttgcat ggacaatagg tgctgcatcc cctacaagtc | 1020 |
| taagactatc gacgtgtcct tccagtgtcc tgatgggctt ggcttctccc gccaggtcct | 1080 |
| atggattaat gcctgcttct gtaacctgag ctgtaggaat cccaatgaca tctttgctga | 1140 |
| cttggaatcc taccctgact tctcagaaat tgccaactag gcaggcacaa atcttgggtc | 1200 |
| ttggggacta acccaatgcc tgtgaagcag tcagcccta tggccaataa cttttcacca | 1260 |
| atgagcctta gttaccctga tctggaccct tggcctccat ttctgtctct aaccattcaa | 1320 |
| atgacgcctg atggtgctgc tcaggcccat gctatgagtt ttctccttga tatcattcag | 1380 |
| catctactct aaagaaaaat gcctgtctct agctgttctg gactacaccc aagcctgatc | 1440 |
| cagccttttcc aagtcactag aagtcctgct ggatcttgcc taaatcccaa gaaatggaat | 1500 |
| caggtagact tttaatatca ctaatttctt ctttagatgc caaaccacaa gactctttgg | 1560 |
| gtccattcag atgaatagat ggaatttgga acaatagaat aatctattat ttggagcctg | 1620 |
| ccaagaggta ctgtaatggg taattctgac gtcagcgcac caaaactatc ctgattccaa | 1680 |
| atatgtatgc acctcaaggt catcaaacat ttgccaagtg agttgaatag ttgcttaatt | 1740 |
| ttgattttta atgaaagtt gtatccatta acctgggcat tgttgaggtt aagtttctct | 1800 |
| tcacccctac actgtgaagg gtacagatta ggtttgtccc agtcagaaat aaaatttgat | 1860 |
| aaacattcct gttgatggga aaagccccca gttaatactc cagagacagg gaaaggtcag | 1920 |
| cccgtttcag aaggaccaat tgactctcac actgaatcag ctgctgactg gcagggcttt | 1980 |
| gggcagttgg ccaggctctt ccttgaatct tctcccttgt cctgcttggg gttcatagga | 2040 |
| attggtaagg cctctggact ggcctgtctg gcccctgaga gtggtgccct ggaacactcc | 2100 |
| tctactctta cagagccttg agagacccag ctgcagacca tgccagaccc actgaaatga | 2160 |
| ccaagacagg ttcaggtagg ggtgtgggtc aaaccaagaa gtgggtgccc ttggtagcag | 2220 |
| cctggggtga cctctagagc tggaggctgt gggactccag gggcccccgt gttcaggaca | 2280 |
| catctattgc agagactcat ttcacagcct ttcgttctgc tgaccaaatg gccagttttc | 2340 |
| tggtaggaag atggaggttt accggttgtt tagaaacaga aatagactta ataaaggttt | 2400 |
| aaagctgaag aggttgaagc taaaaggaaa aggttgttgt taatgaatat caggctatta | 2460 |
| tttattgtat taggaaaata taatatttac tgttagaatt ctttatttta gggccttttc | 2520 |
| tgtgccagac attgctctca gtgctttgca tgtattagct cactgaatct tcacgacaat | 2580 |

```
gttgagaagt tcccattatt atttctgttc ttacaaatgt gaaacggaag ctcatagagg    2640
tgagaaaact caaccagagt cacccagttg gtgactggga agttaggat tcagatcgaa     2700 attggactgt ctttataacc catatttcc ccctgtttt  agagcttcca aatgtgtcag     2760
aataggaaaa cattgcaata aatggcttga ttttttaaaa aaaaaaaaaa aaaaaaaa      2819

<210> SEQ ID NO 331
<211> LENGTH: 2540
<212> TYPE: DNA
<213> ORGANISM: Homo sapiens

<400> SEQUENCE: 331
gaaaaggtgg acaagtccta ttttcaagag aagatgactt ttaacagttt tgaaggatct      60
aaaacttgtg tacctgcaga catcaataag gaagaagaat ttgtagaaga gtttaataga     120
ttaaaaactt tgctaatttt tccaagtggt agtcctgttt cagcatcaac actggcacga     180
gcagggtttc tttatactgg tgaaggagat accgtgcggt gctttagttg tcatgcagct     240
gtagatagat ggcaatatgg agactcagca gttggaagac acaggaaagt atccccaaat     300
tgcagattta tcaacggctt ttatcttgaa aatagtgcca cgcagtctac aaattctggt     360
atccagaatg gtcagtacaa agttgaaaac tatctgggaa gcagagatca ttttgcctta     420
gacaggccat ctgagacaca tgcagactat cttttgaaaa ctgggcaggt tgtagatata     480
tcagacacca tatcccgag gaaccctgcc atgtattgtg aagaagctag attaaagtcc      540
tttcagaact ggccagacta tgctcaccta accccaagag agttagcaag tgctggactc     600
tactacacag gtattggtga ccaagtgcag tgcttttgtt gtggtggaaa actgaaaaat     660
tgggaacctt gtgatcgtgc ctggtcagaa cacaggcgac actttcctaa ttgcttcttt     720
gttttgggcc ggaatcttaa tattcgaagt gaatctgatg ctgtgagttc tgataggaat     780
ttcccaaatt caacaaatct tccaagaaat ccatccatgg cagattatga agcacggatc     840 tttactttg ggacatggat atactcagtt aacaaggagc agcttgcaag agctggattt      900
tatgctttag gtgaaggtga taaagtaaag tgctttcact gtggaggagg ctaactgat      960 tggaagccca gtgaagaccc ttgggaacaa catgctaaat ggtatccagg gtgcaaatat     1020
ctgttagaac agaagggaca agaatatata aacaatattc atttaactca ttcacttgag     1080
gagtgtctgg taagaactac tgagaaaaca ccatcactaa ctagaagaat tgatgatacc     1140
atcttccaaa atcctatggt acaagaagct atacgaatgg ggttcagttt caaggacatt     1200
aagaaaataa tggaggaaaa aattcagata tctgggagca actataaatc acttgaggtt     1260
ctggttgcag atctagtgaa tgctcagaaa gacagtatgc aagatgagtc aagtcagact     1320
tcattacaga aagagattag tactgaagag cagctaaggc gcctgcaaga ggagaagctt     1380
tgcaaaatct gtatggatag aaatattgct atcgttttg ttccttgtgg acatctagtc     1440
acttgtaaac aatgtgctga agcagttgac aagtgtccca tgtgctacac agtcattact     1500
ttcaagcaaa aaatttttat gtcttaatct aactctatag taggcatgtt atgttgttct     1560
tattaccctg attgaatgtg tgatgtgaac tgacttaag taatcaggat tgaattccat      1620
tagcatttgc taccaagtag gaaaaaaaat gtacatggca gtgttttagt tggcaatata     1680
atctttgaat tcttgatttt ttcagggtat tagctgtatt atccatttt tttactgtta     1740 tttaattgaa accatagact aagaataaga agcatcatac tataactgaa cacaatgtgt     1800
attcatagta tactgatta atttctaagt gtaagtgaat taatcatctg gattttttat      1860
tcttttcaga taggcttaac aaatggagct ttctgtatat aaatgtggag attagagtta     1920
```

| | |
|---|---|
| atctccccaa tcacataatt tgttttgtgt gaaaaaggaa taaattgttc catgctggtg | 1980 |
| gaaagataga gattgttttt agaggttggt tgttgtgttt taggattctg tccattttct | 2040 |
| tgtaaaggga taaacacgga cgtgtgcgaa atatgtttgt aaagtgattt gccattgttg | 2100 |
| aaagcgtatt taatgataga atactatcga gccaacatgt actgacatgg aaagatgtca | 2160 |
| gagatatgtt aagtgtaaaa tgcaagtggc gggacactat gtatagtctg agccagatca | 2220 |
| aagtatgtat gttgttaata tgcatagaac gagagatttg gaaagatata caccaaactg | 2280 |
| ttaaatgtgg tttctcttcg gggagggggg gattggggga ggggcccag aggggtttta | 2340 |
| gagggccctt ttcactttcg acttttttca ttttgttctg ttcggatttt ttataagtat | 2400 |
| gtagaccccg aagggttta tgggaactaa catcagtaac ctaaccccg tgactatcct | 2460 |
| gtgctcttcc tagggagctg tgttgtttcc cacccaccac ccttccctct gaacaaatgc | 2520 |
| ctgagtgctg gggcactttg | 2540 |

<210> SEQ ID NO 332
<211> LENGTH: 1474
<212> TYPE: DNA
<213> ORGANISM: Homo sapiens

<400> SEQUENCE: 332

| | |
|---|---|
| aaaaagaaat caagaatgca attttatta caatagtcac gccggaaata cctagaaata | 60 |
| aatttaactg aggatgtaaa agacctctac aaggagagtt caatgcgtag cgggagcgga | 120 |
| gagctgaccc cagagagccc tgggcagccc cacctccgcc gccggcctag ttaccatcac | 180 |
| accccggaga gcccgcagct gccgcagccg gccccagtca ccatcaccgc aaccatgagc | 240 |
| agcgaggcca agacccagca gccgcccgcc gcccccccg ccgccccgc cctcagcgcc | 300 |
| gccgacacca gcccggcac taccggagcg gcgcagggag cggtggcccg gcggctcac | 360 |
| atcggcggcg ctggcgcggg cgacaagaag gtcatcgcaa cgaaggtttt gggaacagta | 420 |
| aaatggttca atgtaaggaa cggatatggt ttcatcaaca ggaatgacac caaggaagat | 480 |
| gtatttgtac accagactgc cataaagaag aataacccca ggaagtacct tcgcagtgta | 540 |
| ggagatggag agactgtgga gtttgatgtt gttgaaggag aaaagggtgc ggaggcagca | 600 |
| aatgttacag gtcctggtgg tgttccagtt caaggcagta aatatgcagc agaccgtaac | 660 |
| cattatagac gctatccacg tcgtagggt cctccacgca attaccagca aaattaccag | 720 |
| aatagtgaga gtggggaaaa gaacgaggga tcggagagtc ctcccgaagc caggcccaac | 780 |
| aacgccggcc ctacgcaggc gaaggttccc accttactac atgcggagac ctatgggcgt | 840 |
| cgaccacagt attccaaccc tcctgtgcag ggagaagtga tggagggtgc tgacaaccag | 900 |
| ggtgcaggag aacaaggtag accagtgagg cagatatgta tcgggatat agaccacgat | 960 |
| tccgcagggg ccctcctcgc caaaagacag cctagagagg acggcaatga agaagataaa | 1020 |
| gaaaatcaag gagatgagac ccaaggtcag cagccacctc aagctcggta ccgccgcaac | 1080 |
| ttcaattacc gacgcagacg cccagaaaac cctaaccac aagatggcaa agagacaaaa | 1140 |
| gcagccgatc caccagctga gaattcgtcc gctcccgagg ctgagcaggg cggggctgag | 1200 |
| taaatgccgg cttaccatct ctaccatcat ccggtttagt catccaacaa gaagaaatat | 1260 |
| gaaattccag caataagaaa tgaacaaaag attggagctg aagacctaaa gtgcttgctt | 1320 |
| tttgcccgtt gaccagataa atagaactat ctgcattatc tatgcagcat gggggtttta | 1380 |
| ttatgttttta cctaaagacg tctcttttg gtaataacaa accgtgtttt ttaaaaaagc | 1440 |

-continued

```
ctggtttttc tcaatacgcc tttaaaggaa ttcc                         1474
```

<210> SEQ ID NO 333
<211> LENGTH: 4079
<212> TYPE: DNA
<213> ORGANISM: Homo sapiens

<400> SEQUENCE: 333

```
ggagcggcgg gcgggcggga gggctggcgg ggcgaacgtc tgggagacgt ctgaaagacc    60
aacgagactt tggagaccag agacgcgcct gggggggacct ggggcttggg gcgtgcgaga   120
tttcccttgc attcgctggg agctcgcgca gggatcgtcc catggccggg gctcggagcc   180
gcgacccttg gggggcctcc gggatttgct acctttttgg ctccctgctc gtcgaactgc   240
tcttctcacg ggctgtcgcc ttcaatctgg acgtgatggg tgccttgcgc aaggagggcg   300
agccaggcag cctcttcggc ttctctgtgg ccctgcaccg gcagttgcag ccccgacccc   360
agagctggct gctggtgggt gctccccagg ccctggctct tcctgggcag caggcgaatc   420
gcactggagg cctcttcgct tgcccgttga gcctggagga gactgactgc tacagagtgg   480
acatcgacca gggagctgat atgcaaaagg aaagcaagga gaaccagtgg ttgggagtca   540
gtgttcggag ccagggggcct ggggggcaaga ttgttacctg tgcacaccga tatgaggcaa   600
ggcagcgagt ggaccagatc ctggagacgc gggatatgat tggtcgctgc tttgtgctca   660
gccaggacct ggccatccgg gatgagttgg atggtgggga atggaagttc tgtgagggac   720
gcccccaagg ccatgaacaa tttgggttct gccagcaggg cacagctgcc gccttctccc   780
ctgatagcca ctacctcctc tttggggccc caggaaccta taattggaag gggttgcttt   840
ttgtgaccaa cattgatagc tcagaccccg accagctggt gtataaaact ttggaccctg   900
ctgaccggct cccaggacca gccggagact tggccctcaa tagctactta ggcttctcta   960
ttgactcggg gaaaggtctg gtgcgtgcag aagagctgag ctttgtggct ggagcccccc  1020
gcgccaacca caagggtgct gtggttatcc tgcgcaagga cagcgccagt cgcctggtgc  1080
ccgaggttat gctgtctggg gagcgcctga cctccggctt tggctactca ctggctgtgg  1140
ctgacctcaa cagtgatggc tggccagacc tgatagtggg tgcccctac  ttctttgagc  1200
gccaagaaga gctgggggggt gctgtgtatg tgtacttgaa ccaggggggt cactgggctg  1260
ggatctcccc tctccggctc tgcggctccc ctgactccat gttcgggatc agcctggctg  1320
tcctggggga cctcaaccaa gatgctcttt cagatattgc agtgggtgcc ccctttgatg  1380
gtgatgggaa agtcttcatc taccatggga gcagcctggg ggttgtcgcc aaaccttcac  1440
aggtgctgga gggcgaggct gtgggcatca agagcttcgg ctactccctg tcaggcagct  1500
tggatatgga tgggaaccaa taccctgacc tgctggtggg ctccctggct gacaccgcag  1560
tgctcttcag ggccagaccc atcctccatg tctcccatga ggtctctatt gctccacgaa  1620
gcatcgacct ggagcagccc aactgtgctg gcggccactc ggtctgtgtg gacctaaggg  1680
tctgtttcag ctacattgca gtccccagca gctatagccc tactgtggcc ctggactatg  1740
tgttagatgc ggacacagac cggaggctcc ggggccaggt tccccgtgtg acgttcctga  1800
gccgtaacct ggaagaaccc aagcaccagg cctcgggcac cgtgtggctg aagcaccagc  1860
atgaccgagt ctgtgagac gccatgttcc agctccagga aaatgtcaaa gacaagcttc  1920
gggccattgt agtgaccttg tcctacagtc tccagacccc tcggctccgg cgacaggctc  1980
ctggccaggg gctgcctcca gtggccccca tcctcaatgc ccaccagccc agcacccagc  2040
gggcagagat ccacttcctg aagcaaggct gtggtgaaga caagatctgc cagagcaatc  2100
```

```
tgcagctggt ccacgcccgc ttctgtaccc gggtcagcga cacggaattc caacctctgc   2160
ccatggatgt ggatggaaca cagccctgt tgcactgag tgggcagcca gtcattggcc     2220
tggagctgat ggtcaccaac ctgccatcgg acccagccca gccccaggct gatggggatg   2280
atgcccatga agcccagctc ctggtcatgc ttcctgactc actgcactac tcagggtcc    2340 gggccctgga ccctgcggag aagccactct gcctgtccaa tgagaatgcc tcccatgttg   2400
agtgtgagct ggggaacccc atgaagagag gtgcccaggt caccttctac ctcatcctta   2460
gcacctccgg gatcagcatt gagaccacgg aactggaggt agagctgctg ttggccacga   2520
tcagtgagca ggagctgcat ccagtctctg cacgagcccg tgtcttcatt gagctgccac   2580
tgtccattgc aggaatggcc attccccagc aactcttctt ctctggtgtg gtgaggggcg   2640
agagagccat gcagtctgag cgggatgtgg gcagcaaggt caagtatgag gtcacggttt   2700
ccaaccaagg ccagtcgctc agaaccctgg gctctgcctt cctcaacatc atgtggcctc   2760
atgagattgc caatgggaag tggttgctgt acccaatgca ggttgagctg gagggcgggc   2820 agggcctgg gcagaaaggg ctttgctctc ccaggcccaa catcctccac ctggatgtgg    2880
acagtaggga taggaggcgg cgggagctgg agccacctga gcagcaggag cctggtgagc   2940
ggcaggagcc cagcatgtcc tggtggccag tgtcctctgc tgagaagaag aaaaacatca   3000
ccctggactg cgcccggggc acggccaact gtgtggtgtt cagctgccca ctctacagct   3060
ttgaccgcgc ggctgtgctg catgtctggg gccgtctctg aacagcacc tttctggagg    3120 agtactcagc tgtgaagtcc ctggaagtga ttgtccgggc caacatcaca gtgaagtcct   3180
ccataaagaa cttgatgctc cgagatgcct ccacagtgat cccagtgatg gtatacttgg   3240
accccatggc tgtggtggca aaggagtgc cctggtgggt catcctcctg gctgtactgg    3300
ctgggctgct ggtgctagca ctgctggtgc tgctcctgtg aagatggga ttcttcaaac    3360 gggcgaagca ccccgaggcc accgtgcccc agtaccatgc ggtgaagatt cctcgggaag   3420
accgacagca gttcaaggag gagaagacgg gcaccatcct gaggaacaac tggggcagcc   3480
cccggcggga gggcccggat gcacacccca tcctggctgc tgacgggcat cccgagctgg   3540
gccccgatgg gcatccaggg ccaggcaccg cctaggttcc catgtcccag cctggcctgt   3600
ggctgccctc catcccttcc ccagagatgg ctccttggga tgaagagggt agagtgggct   3660
gctggtgtcg catcaagatt tggcaggatc ggcttcctca ggggcacaga cctctcccac   3720
ccacaagaac tcctcccacc caacttcccc ttagagtgct gtgagatgag agtgggtaaa   3780
tcagggacag ggccatgggg tagggtgaga agggcagggg tgtcctgatg caaaggtggg   3840
gagaagggat cctaatccct tcctctccca ttcaccctgt gtaacaggac cccaaggacc   3900
tgcctccccg gaagtgcctt aacctagagg gtcgggagg aggttgtgtc actgactcag    3960
gctgctcctt ctctagtttc ccctctcatc tgaccttagt ttgctgccat cagtctagtg   4020
gtttcgtggt ttcgtctatt tattaaaaaa tatttgagaa caaaaaaaaa aaaaaaaa     4079
```

<210> SEQ ID NO 334
<211> LENGTH: 3373
<212> TYPE: DNA
<213> ORGANISM: Homo sapiens

<400> SEQUENCE: 334

```
ggtggcaact tctcctcctg cggccgggag cggcctgcct gcctccctgc gcacccgcag    60
cctcccccgc tgcctcccta gggctcccct ccggccgcca gcgcccattt ttcattccct   120
```

-continued

```
agatagagat actttgcgcg cacacacata catacgcgcg caaaaaggaa aaaaaaaaaa        180
aaaagcccac cctccagcct cgctgcaaag agaaaaccgg agcagccgca gctcgcagct        240
cgcagctcgc agcccgcagc ccgcagagga cgcccagagc ggcgagcagg cgggcagacg        300
gaccgacgga ctcgcgccgc gtccacctgt cggccgggcc cagccgagcg cgcagcgggc        360
acgccgcgcg cgcggagcag ccgtgcccgc cgcccgggcc cgccgccagg gcgcacacgc        420
tcccgccccc ctacccggcc cgggcgggag tttgcacctc tccctgcccg ggtgctcgag        480
ctgccgttgc aaagccaact ttggaaaaag ttttttgggg gagacttggg ccttgaggtg        540
cccagctccg cgctttccga ttttgggggc ctttccagaa aatgttgcaa aaaagctaag        600
ccggcgggca gaggaaaacg cctgtagccg gcgagtgaag acgaaccatc gactgccgtg        660
ttccttttcc tcttggaggt tggagtcccc tgggcgcccc cacacggcta gacgcctcgg        720
ctggttcgcg acgcagcccc ccggccgtgg atgctgcact cgggctcggg atccgcccag        780
gtagccggcc tcggacccag gtcctgcgcc caggtcctcc cctgcccccc agcgacggag        840
ccggggccgg gggcggcggc gccggggggca tgcgggtgag ccgcggctgc agaggcctga        900
gcgcctgatc gccgcggacc tgagccgagc ccaccccccct ccccagcccc ccaccctggc        960 cgcggggggcg gcgcgctcga tctacgcgtc cggggccccg cggggccggg cccggagtcg        1020
gcatgaatcg ctgctgggcg ctcttcctgt ctctctgctg ctacctgcgt ctggtcagcg        1080
ccgaggggga ccccattccc gaggagcttt atgagatgct gagtgaccac tcgatccgct        1140
cctttgatga tctccaacgc ctgctgcacg gagaccccgg agaggaagat ggggccgagt        1200
tggacctgaa catgacccgc tcccactctg gaggcgagct ggagagcttg gctcgtggaa        1260
gaaggagcct gggttccctg accattgctg agccggccat gatcgccgag tgcaagacgc        1320
gcaccgaggt gttcgagatc tcccggcgcc tcatagaccg caccaacgcc aacttcctgg        1380
tgtggccgcc ctgtgtggag gtgcagcgct gctccggctg ctgcaacaac cgcaacgtgc        1440
agtgccgccc cacccaggtg cagctgcgac ctgtccaggt gagaaagatc gagattgtgc        1500
ggaagaagcc aatctttaag aaggccacgg tgacgctgga agaccacctg gcatgcaagt        1560
gtgagacagt ggcagctgca cggcctgtga cccgaagccc gggggttcc caggagcagc        1620 gagccaaaac gccccaaact cgggtgacca ttcggacggt gcgagtccgc cggcccccca        1680
agggcaagca ccggaaattc aagcacacgc atgacaagac ggcactgaag gagacccttg        1740
gagcctaggg gcatcggcag gagagtgtgt gggcagggtt atttaatatg gtatttgctg        1800
tattgccccc atgggtcct tggagtgata atattgtttc cctcgtccgt ctgtctcgat        1860
gcctgattcg gacggccaat ggtgcttccc ccaccccctcc acgtgtccgt ccacccttcc        1920
atcagcgggt ctcctcccag cggcctccgg tcttgcccag cagctcaaag aagaaaaaga        1980
aggactgaac tccatcgcca tcttcttccc ttaactccaa gaacttggga taagagtgtg        2040
agagagactg atgggtcgc tctttggggg aaacgggttc cttcccctgc acctggcctg        2100
ggccacacct gagcgctgtg gactgtcctg aggagccctg aggacctctc agcatagcct        2160
gcctgatccc tgaaccctg gccagctctg aggggaggca cctccaggca ggccaggctg        2220
cctcggactc catggctaag accacagacg ggcacacaga ctggagaaaa cccctcccac        2280
ggtgcccaaa caccagtcac ctcgtctccc tggtgcctct gtgcacagtg gcttcttttc        2340
gttttcgttt tgaagacgtg gactcctctt ggtgggtgtg gccagcacac caagtggctg        2400
ggtgccctct caggtgggtt agagatggag tttgctgttg aggtggtgta gatggtgacc        2460
tgggtatccc ctgcctcctg ccaccccttc ctccccatac tccactctga ttcacctctt        2520
```

| | |
|---|---|
| cctctggttc ctttcatctc tctacctcca ccctgcattt tcctcttgtc ctggcccttc | 2580 |
| agtctgctcc accaaggggc tcttgaaccc cttattaagg ccccagatga ccccagtcac | 2640 |
| tcctctctag ggcagaagac tagaggccag ggcagcaagg gacctgctca tcatattcca | 2700 |
| acccagccac gactgccatg taaggttgtg cagggtgtgt actgcacaag gacattgtat | 2760 |
| gcagggagca ctgttcacat catagataaa gctgatttgt atatttatta tgacaatttc | 2820 |
| tggcagatgt aggtaaagag gaaaaggatc cttttcctaa ttcacacaaa gactccttgt | 2880 |
| ggactggctg tgcccctgat gcagcctgtg gctggagtgg ccaaatagga gggagactgt | 2940 |
| ggtaggggca gggaggcaac actgctgtcc acatgacctc catttcccaa agtcctctgc | 3000 |
| tccagcaact gccttccag gtgggtgtgg gacacctggg agaaggtctc caagggaggg | 3060 |
| tgcagccctc ttgcccgcac ccctccctgc ttgcacactt ccccatcttt gatccttctg | 3120 |
| agctccacct ctggtggctc ctcctaggaa accagctcgt gggctgggaa tgggggagag | 3180 |
| aagggaaaag atccccaaga cccctgggg tgggatctga gctcccacct cccttcccac | 3240 |
| ctactgcact ttcccccttc ccgccttcca aaacctgctt ccttcagttt gtaaagtcgg | 3300 |
| tgattatatt tttgggggct ttcctttat tttttaaatg taaaatttat ttatattccg | 3360 |
| tatttaaagt tgt | 3373 |

<210> SEQ ID NO 335
<211> LENGTH: 2304
<212> TYPE: DNA
<213> ORGANISM: Homo sapiens

<400> SEQUENCE: 335

| | |
|---|---|
| gtccccgcag cgccgtcgcg ccctcctgcc gcaggccacc gaggccgccg ccgtctagcg | 60 |
| ccccgacctc gccaccatga gagccctgct ggcgcgcctg cttctctgcg tcctggtcgt | 120 |
| gagcgactcc aaaggcagca atgaacttca tcaagttcca tcgaactgtg actgtctaaa | 180 |
| tggaggaaca tgtgtgtcca acaagtactt ctccaacatt cactggtgca actgcccaaa | 240 |
| gaaattcgga gggcagcact gtgaaataga taagtcaaaa acctgctatg agggaatgg | 300 |
| tcacttttac cgaggaaagg ccagcactga caccatgggc cggccctgcc tgccctggaa | 360 |
| ctctgccact gtccttcagc aaacgtacca tgcccacaga tctgatgctc ttcagctggg | 420 |
| cctggggaaa cataattact gcaggaaccc agacaaccgg aggcgaccct ggtgctatgt | 480 |
| gcaggtgggc ctaaagccgc ttgtccaaga gtgcatggtg catgactgcg cagatggaaa | 540 |
| aaagccctcc tctcctccag aagaattaaa atttcagtgt ggccaaaaga ctctgaggcc | 600 |
| ccgctttaag attattgggg gagaattcac caccatcgag aaccagcccc tggtttgcgg | 660 |
| catctacagg aggcaccggg ggggctctgt cacctacgtg tgtggaggca gcctcatcag | 720 |
| cccttgctgg gtgatcagcg ccacacactg cttcattgat tacccaaaga aggaggacta | 780 |
| catcgtctac ctgggtcgct caaggcttaa ctccaacacg caaggggaga tgaagtttga | 840 |
| ggtgaaaaac ctcatcctac acaaggacta cagcgctgac acgcttgctc accacaacga | 900 |
| cattgccttg ctgaagatcc gttccaagga gggcaggtgt gcgcagccat cccggactat | 960 |
| acagaccatc tgcctgccct cgatgtataa cgatcccag tttggcacaa gctgtgagat | 1020 |
| cactggcttt ggaaaagaga attctaccga ctatctctat ccggagcagc tgaaaatgac | 1080 |
| tgttgtgaag ctgatttccc accgggagtg tcagcagccc cactactacg gctctgaagt | 1140 |
| caccaccaaa atgctatgtg ctgctgaccc ccaatggaaa acagattcct gccagggaga | 1200 |

```
ctcaggggga cccctcgtct gttccctcca aggccgcatg actttgactg gaattgtgag    1260
ctggggccgt ggatgtgccc tgaaggacaa gccaggcgtc tacacgagag tctcacactt    1320
cttaccctgg atccgcagtc acaccaagga agagaatggc ctggccctct gagggtcccc    1380
agggaggaaa cgggcaccac ccgctttctt gctggttgtc atttttgcag tagagtcatc    1440
tccatcagct gtaagaagag actgggaaga taggctctgc acagatggat ttgcctgtgg    1500
caccaccagg gtgaacgaca atagctttac cctcacggat aggcctgggt gctggctgcc    1560
cagaccctct ggccaggatg gagggtggt cctgactcaa catgttactg accagcaact    1620 tgtcttttc tggactgaag cctgcaggag ttaaaaaggg cagggcatct cctgtgcatg    1680
ggctcgaagg gagagccagc tcccccgacc ggtgggcatt tgtgaggccc atggttgaga    1740
aatgaataat ttcccaatta ggaagtgtaa gcagctgagg tctcttgagg gagcttagcc    1800
aatgtgggag cagcggtttg gggagcagag acactaacga cttcagggca gggctctgat    1860
attccatgaa tgtatcagga aatatatatg tgtgtgtatg tttgcacact tgttgtgtgg    1920
gctgtgagtg taagtgtgag taagagctgg tgtctgattg ttaagtctaa atatttcctt    1980
aaactgtgtg gactgtgatg ccacacagag tggtctttct ggagaggtta taggtcactc    2040
ctggggcctc ttgggtcccc cacgtgacag tgcctgggaa tgtacttatt ctgcagcatg    2100
acctgtgacc agcactgtct cagtttcact ttcacataga tgtccctttc ttggccagtt    2160
atcccttcct tttagcctag ttcatccaat cctcactggg tggggtgagg accactcctt    2220
acactgaata tttatatttc actattttta tttatatttt tgtaattttc aataaaagtg    2280
atcaataaaa tgtgattttt ctga                                          2304
```

<210> SEQ ID NO 336
<211> LENGTH: 1876
<212> TYPE: DNA
<213> ORGANISM: Homo sapiens

<400> SEQUENCE: 336

```
cgcggccgcg gttcgctgtg gcgggcgcct gggccgccgg ctgtttaact tcgcttccgc     60
tggcccatag tgatctttgc agtgacccag cagcatcact gtttcttggc gtgtgaagat    120
aacccaagga attgaggaag ttgctgagaa gagtgtgctg gagatgctct aggaaaaaat    180
tgaatagtga gacgagttcc agcgcaaggg tttctggttt gccaagaaga aagtgaacat    240
catggatcag aacaacagcc tgccaccttt acgctcaggg cttggcctcc ctcagggtgc    300
catgactccc ggaatcccta tctttagtcc aatgatgcct tatggcactg gactgacccc    360
acagcctatt cagaacacca atagtctgtc tattttggaa gagcaacaaa ggcagcagca    420
gcaacaacaa cagcagcagc agcagcagca gcagcagcaa cagcaacagc agcagcagca    480
gcagcagcag cagcagcagc agcagcagca gcagcagcag caacaggcag tggcagctgc    540
agccgttcag cagtcaacgt cccagcaggc aacacaggga acctcaggcc aggcaccaca    600
gctcttccac tcacagactc tcacaactgc acccttgccg ggcaccactc cactgtatcc    660
ctcccccatg actcccatga ccccatcac tcctgccacg ccagcttcgg agagttctgg    720
gattgtaccg cagctgcaaa atattgtatc cacagtgaat cttggttgta acttgacct    780 aaagaccatt gcacttcgtg cccgaaacgc gaatatataa cccaagcggt ttgctgcggt    840
aatcatgagg ataagagagc cacgaaccac ggcactgatt tcagttctg ggaaaatggt    900 gtgcacagga gccaagagtg aagaacagtc cagactggca gcaagaaaat atgctagagt    960
tgtacagaag ttgggtttc cagctaagtt cttggactc aagattcaga acatggtggg   1020
```

```
gagctgtgat gtgaagtttc ctataaggtt agaaggcctt gtgctcaccc accaacaatt    1080
tagtagttat gagccagagt tatttcctgg tttaatctac agaatgatca aacccagaat    1140
tgttctcctt atttttgttt ctggaaaagt tgtattaaca ggtgctaaag tcagagcaga    1200
aatttatgaa gcatttgaaa acatctaccc tattctaaag ggattcagga agacgacgta    1260
atggctctca tgtacccttg cctcccccac ccccttcttt ttttttttttt aaacaaatca    1320 gtttgttttg gtacctttaa atggtggtgt tgtgagaaga tggatgttga gttgcagggt    1380
gtggcaccag gtgatgccct tctgtaagtg cccaccgcgg gatgccggga aggggcatta    1440
tttgtgcact gagaacaccg cgcagcgtga ctgtgagttg ctcataccgt gctgctatct    1500
gggcagcgct gcccatttat ttatatgtag attttaaaca ctgctgttga caagttggtt    1560
tgagggagaa aactttaagt gttaaagcca cctctataat tgattggact tttaattttt    1620 aatgttttc cccatgaacc acagttttta tatttctacc agaaaagtaa aaatcttttt    1680
taaaagtgtt gttttctaa tttataactc ctaggggtta tttctgtgcc agacacattc    1740
cacctctcca gtattgcagg acggaatata tgtgttaatg aaaatgaatg gctgtacata    1800 ttttttttctt tcttcagagt actctgtaca ataaatgcag tttataaaag tgttaaaaaa    1860
aaaaaaaaaa aaaaa                                                     1876

<210> SEQ ID NO 337
<211> LENGTH: 6633
<212> TYPE: DNA
<213> ORGANISM: Homo sapiens

<400> SEQUENCE: 337
ttctccccgc cccccagttg ttgtcgaagt ctggggggttg ggactggacc ccctgattgc      60
gtaagagcaa aaagcgaagg cgcaatctgg acactgggag attcggagcg cagggagttt     120
gagagaaact tttattttga agagaccaag gttgagggggg ggcttatttc ctgacagcta     180
tttacttaga gcaaatgatt agttttagaa ggatggacta taacattgaa tcaattacaa     240
aacgcggttt tgagcccat tactgttgga gctacaggga gagaaacagg aggagactgc      300
aagagatcat ttgggaaggc cgtgggcacg ctctttactc catgtgtggg acattcattg     360
cggaataaca tcgaggagaa agtttcccag agctatgggg acttcccatc cggcgttcct     420
ggtcttaggc tgtcttctca cagggctgag cctaatcctc tgccagcttt cattacccttc    480 tatccttcca aatgaaaatg aaaaggttgt gcagctgaat tcatcctttt ctctgagatg     540
ctttggggag agtgaagtga gctggcagta ccccatgtct gaagaagaga gctccgatgt     600
ggaaatcaga aatgaagaaa acaacagcgg ccttttttgtg acggtcttgg aagtgagcag    660
tgcctcggcg gcccacacag ggttgtacac ttgctattac aaccacactc agacagaaga    720
gaatgagctt gaaggcaggc acatttacat ctatgtgcca gacccagatg tagcctttgt     780
acctctagga atgacggatt atttagtcat cgtggaggat gatgattctg ccattatacc     840
ttgtcgcaca actgatcccg agactcctgt aaccttacac aacagtgagg gggtggtacc     900
tgcctcctac gacagcagac agggcttttaa tgggaccttc actgtagggc cctatatctg     960
tgaggccacc gtcaaaggaa agaagttcca gaccatccca tttaatgttt atgctttaaa    1020
agcaacatca gagctggatc tagaaatgga agctcttaaa accgtgtata agtcagggga    1080
aacgattgtg gtcacctgtg ctgtttttta caatgaggtg gttgaccttc aatggactta    1140
ccctggagaa gtgaaaggca aaggcatcac aatgctggaa gaaatcaaag tcccatccat    1200
```

```
caaattggtg tacactttga cggtccccga ggccacggtg aaagacagtg gagattacga      1260
atgtgctgcc cgccaggcta ccagggaggt caaagaaatg aagaaagtca ctatttctgt      1320
ccatgagaaa ggtttcattg aaatcaaacc caccttcagc cagttggaag ctgtcaacct      1380
gcatgaagtc aaacattttg ttgtagaggt gcgggcctac ccacctccca ggatatcctg      1440
gctgaaaaac aatctgactc tgattgaaaa tctcactgag atcaccactg atgtggaaaa      1500
gattcaggaa ataaggtatc gaagcaaatt aaagctgatc cgtgctaagg aagaagacag      1560
tggccattat actattgtag ctcaaaatga agatgctgtg aagagctata cttttgaact      1620
gttaactcaa gttccttcat ccattctgga cttggtcgat gatcaccatg ctcaactggg      1680
gggacagacg gtgaggtgca cagctgaagg cacgccgctt cctgatattg agtggatgat      1740
atgcaaagat attaagaaat gtaataatga aacttcctgg actatttggg ccaacaatgt      1800
ctcaaacatc atcacggaga tccactcccg agacaggagt accgtggagg gccgtgtgac      1860
tttcgccaaa gtgaggagaa ccatcgccgt gcgatgcctg gctaagaatc tccttggagc      1920
tgagaaccga gagctgaagc tggtggctcc caccctgcgt tctgaactca cggtggctgc      1980
tgcagtcctg gtgctgttgg tgattgtgat catctcactt attgtcctgg ttgtcatttg      2040
gaaacagaaa ccgaggtatg aaattcgctg gagggtcatt gaatcaatca gcccggatgg      2100
acatgaatat atttatgtgg acccgatgca gctgccttat gactcaagat gggagttttc      2160
aagagatgga ctagtgcttg gtcgggtctt ggggtctgga gcgtttggga aggtggttga      2220
aggaacagcc tatggattaa gccggtccca acctgtcatg aaagttgcag tgaagatgct      2280
aaaacccacg gccagatcca gtgaaaaaca agctctcatg tctgaactga agataatgac      2340
tcacctgggg ccacatttga acattgtaaa cttgctggga gcctgcacca agtcaggccc      2400
catttacatc atcacagagt attgcttcta tggagatttg gtcaactatt tgcataagaa      2460
tagggatagc ttcctgagcc accccagag aagccaaag aaagagctgg atatctttgg      2520
attgaaccct gctgatgaaa gcacacggag ctatgttatt ttatcttttg aaaacaatgg      2580
tgactacatg gacatgaagc aggctgatac tacacagtat gtccccatgc tagaaaggaa      2640
agaggtttct aaatattccg acatccagag atcactctat gatcgtccag cctcatataa      2700
gaagaaatct atgttagact cagaagtcaa aaacctcctt tcagatgata actcagaagg      2760
ccttacttta ttggatttgt tgagcttcac ctatcaagtt gcccgaggaa tggagttttt      2820
ggcttcaaaa aattgtgtcc accgtgatct ggctgctcgc aacgtcctcc tggcacaagg      2880
aaaaattgtg aagatctgtg actttggcct ggccagagac atcatgcatg attcgaacta      2940
tgtgtcgaaa ggcagtacct ttctgcccgt gaagtggatg gctcctgaga gcatctttga      3000
caacctctac accacactga gtgatgtctg gtcttatggc attctgctct gggagatctt      3060
ttccctggt ggcacccctt accccggcat gatggtggat tctactttct acaataagat      3120
caagagtggg taccggatgg ccaagcctga ccacgctacc agtgaagtct acgagatcat      3180
ggtgaaatgc tggaacagtg agccggagaa gagaccctcc ttttaccacc tgagtgagat      3240
tgtgagaat ctgctgcctg acaatataaa aagagttat gaaaaattc acctggactt      3300
cctgaagagt gaccatcctg ctgtggcacg catgcgtgtg gactcagaca atgcatacat      3360
tggtgtcacc tacaaaaacg aggaagacaa gctgaaggac tggagggtg gtctggatga      3420
gcagagactg agcgctgaca gtggctacat cattcctctg cctgacattg accctgtccc      3480
tgaggaggag gacctgggca agaggaacag acacagctcg cagacctctg aagagagtgc      3540
cattgagacg ggttccagca gttccacctt catcaagaga gaggacgaga ccattgaaga      3600
```

-continued

```
catcgacatg atggacgaca tcggcataga ctcttcagac ctggtggaag acagcttcct    3660
gtaactggcg gattcgaggg gttccttcca cttctgggc cacctctgga tcccgttcag     3720
aaaaccactt tattgcaatg cggaggttga gaggaggact tggttgatgt ttaaagagaa    3780
gttcccagcc aagggcctcg gggagcgttc taaatatgaa tgaatgggat attttgaaat    3840
gaactttgtc agtgttgcct ctcgcaatgc ctcagtagca tctcagtggt gtgtgaagtt    3900
tggagataga tggataaggg aataataggc cacagaaggt gaactttgtg cttcaaggac    3960
attggtgaga gtccaacaga cacaatttat actgcgacag aacttcagca ttgtaattat    4020
gtaaataact ctaaccaagg ctgtgtttag attgtattaa ctatcttctt tggacttctg    4080
aagagaccac tcaatccatc catgtacttc cctcttgaaa cctgatgtca gctgctgttg    4140 aacttttaa agaagtgcat gaaaaaccat ttttgaacct taaaaggtac tggtactata     4200 gcatttgct atctttttta gtgttaagag ataaagaata ataattaacc aaccttgttt     4260
aatagatttg ggtcatttag aagcctgaca actcattttc atattgtaat ctatgtttat    4320
aatactacta ctgttatcag taatgctaaa tgtgtaataa tgtaacatga tttccctcca    4380
gagaaagcac aatttaaaac aatccttact aagtaggtga tgagtttgac agttttgac    4440 atttatatta ataacatgt ttctctataa agtatggtaa tagctttagt gaattaaatt     4500
tagttgagca tagagaacaa agtaaaagta gtgttgtcca ggaagtcaga atttttaact    4560
gtactgaata ggttccccaa tccatcgtat taaaaaacaa ttaactgccc tctgaaataa    4620
tgggattaga aacaaacaaa actcttaagt cctaaaagtt ctcaatgtag aggcataaac    4680
ctgtgctgaa cataacttct catgtatatt acccaatgga aaatataatg atcagcaaaa    4740
agactggatt tgcagaagtt tttttttttt ttcttcatgc ctgatgaaag ctttggcaac    4800
cccaatatat gtatttttttg aatctatgaa cctgaaaagg gtcagaagga tgcccagaca   4860
tcagcctcct tctttcaccc cttacccaa agagaaagag tttgaaactc gagaccataa     4920
agatattctt tagtggaggc tggatgtgca ttagcctgga tcctcagttc tcaaatgtgt    4980
gtggcagcca ggatgactag atcctgggtt tccatccttg agattctgaa gtatgaagtc    5040
tgagggaaac cagagtctgt atttttctaa actccctggc tgttctgatc ggccagtttt    5100
cggaaacact gacttaggtt tcaggaagtt gccatgggaa acaaataatt tgaactttgg    5160
aacagggttg gaattcaacc acgcaggaag cctactatt aaatccttgg cttcaggtta     5220
gtgacattta atgccatcta gctagcaatt gcgaccttaa tttaactttc cagtcttagc    5280
tgaggctgag aaagctaaag tttggttttg acaggttttc caaaagtaaa gatgctactt    5340
cccactgtat gggggagatt gaactttccc cgtctcccgt cttctgcctc ccactccata    5400
ccccgccaag gaaaggcatg tacaaaaatt atgcaattca gtgttccaag tctctgtgta    5460
accagctcag tgttttggtg gaaaaaacat tttaagtttt actgataatt tgaggttaga    5520
tgggaggatg aattgtcaca tctatccaca ctgtcaaaca ggttggtgtg ggttcattgg    5580
cattctttgc aatactgctt aattgctgat accatatgaa tgaaacatgg gctgtgatta    5640
ctgcaatcac tgtgctatcg gcagatgatg ctttggaaga tgcagaagca ataataaagt    5700
acttgactac ctactggtgt aatctcaatg caagccccaa ctttcttatc caactttttc    5760
atagtaagtg cgaagactga gccagattgg ccaattaaaa acgaaaacct gactaggttc    5820
tgtagagcca attagacttg aaatacgttt gtgtttctag aatcacagct caagcattct    5880
gtttatcgct cactctccct tgtacagcct tattttgttg gtgctttgca ttttgatatt    5940
```

```
gctgtgagcc ttgcatgaca tcatgaggcc ggatgaaact tctcagtcca gcagtttcca      6000
gtcctaacaa atgctcccac ctgaatttgt atatgactgc atttgtgggt gtgtgtgtgt      6060
tttcagcaaa ttccagattt gtttcctttt ggcctcctgc aaagtctcca gaagaaaatt      6120
tgccaatctt tcctactttc tattttatg atgacaatca aagccggcct gagaaacact        6180
atttgtgact ttttaaacga ttagtgatgt ccttaaaatg tggtctgcca atctgtacaa      6240
aatggtccta tttttgtgaa gagggacata agataaaatg atgttataca tcaatatgta      6300
tatatgtatt tctatataga cttggagaat actgccaaaa catttatgac aagctgtatc      6360
actgccttcg tttatatttt tttaactgtg ataatcccca caggcacatt aactgttgca      6420
cttttgaatg tccaaaattt atattttaga aataataaaa agaaagatac ttacatgttc      6480
ccaaaacaat ggtgtggtga atgtgtgaga aaaactaact tgataggatc taccaataca      6540
aaatgtatta cgaatgcccc tgttcatgtt tttgttttaa aacgtgtaaa tgaagatctt      6600
tatatttcaa taaatgatat ataatttaaa gtt                                    6633

<210> SEQ ID NO 338
<211> LENGTH: 994
<212> TYPE: DNA
<213> ORGANISM: Homo sapiens

<400> SEQUENCE: 338
tgctggccag cacctcgagg gaagatggcg gacgaggaga agctgccgcc cggctgggag        60
aagcgcatga gccgcagctc aggccgagtg tactacttca accacatcac taacgccagc      120
cagtgggagc ggcccagcgg caacagcagc agtggtggca aaaacgggca gggggagcct      180
gccagggtcc gctgctcgca cctgctggtg aagcacagcc agtcacgggcg gccctcgtcc      240 tggcggcagg agaagatcac ccggaccaag gaggaggccc tggagctgat caacggctac      300
atccagaaga tcaagtcggg agaggaggac tttgagtctc tggcctcaca gttcagcgac      360
tgcagctcag ccaaggccag gggagacctg gtgccttca gcagaggtca gatgcagaag       420
ccatttgaag acgcctcgtt tgcgctgcgg acggggaga tgagcgggcc cgtgttcacg       480
gattccggca tccacatcat cctccgcact gagtgagggt ggggagccca ggcctggcct      540
cggggcaggg cagggcggct aggccggcca gctcccccctt gcccgccagc cagtggccga    600
accccccact ccctgccacc gtcacacagt atttattgtt cccacaatgg ctgggagggg     660
gcccttccag attggggggcc ctgggtccc cactccctgt ccatcccag ttggggctgc      720 gaccgccaga ttctccctta aggaattgac ttcagcaggg gtgggaggct cccagaccca    780
gggcagtgtg gtgggagggg tgttccaaag agaaggcctg gtcagcagag ccgcccgtg    840 tccccccagg tgctggaggc agactcgagg gccgaattgt ttctagttag gccacgctcc     900
tctgttcagt cgcaaaggtg aacactcatg cggcagccat gggccctctg agcaactgtg    960
cagacccttt caccccaat taaacccaga acca                                  994

<210> SEQ ID NO 339
<211> LENGTH: 772
<212> TYPE: DNA
<213> ORGANISM: Homo sapiens

<400> SEQUENCE: 339
agctcgtgcc gaattcggca cgagccgggt cggagccatg gcggtggcaa attcaagtcc       60
tgttaacccc gtggtgttct ttgatgtcag tattggcggt caggaagttg gccgcatgaa    120
gatcgagctc tttgcagacg ttgtgcctaa gacggccgag aactttaggc agttctgcac    180
```

```
cggagaattc aggaaagatg gggttccaat aggatacaaa ggaagcacct tccacagggt     240
cataaaggat ttcatgattc agggtggaga ttttgttaat ggagatggta ctggagtcgc     300
cagtatttac cgggggccat ttgcagatga aaattttaaa cttagacact cagctccagg     360
cctgctttcc atggcgaaca gtggtccaag tacaaatggc tgtcagttct ttatcacctg     420
ctctaagtgc gattggctgg atgggaagca tgtggtgttt ggaaaaatca tcgatggact     480
tctagtgatg agaaagattg agaatgttcc cacaggcccc aacaataagc ccaagctacc     540
tgtggtgatc tcgcagtgtg gggagatgta gtccagacaa agactgaatc aggccttccc     600
ttcttcttgg tggtgttctt gagtaagata atctggactg ccccgtct ttgcttccct      660 gcctgctgct gccccatttg atcaagagac catggaagtg tcagagattc agaatccaag     720
attgtcttta agttttcaac tgtaaataaa gttttttgt atgcgtaaaa aa              772

<210> SEQ ID NO 340
<211> LENGTH: 919
<212> TYPE: DNA
<213> ORGANISM: Homo sapiens

<400> SEQUENCE: 340
cgctcgcctc cctcgctcca cgcgcgcccg gacgcggcgg ccaggcttgc gcgtggttcc      60
cctcccggtg ggcggattcc tgggcaagat gaagtgggtg tgggcgctct tgctgttggc     120
ggcgtgggca gcggccgagc gcgactgccg agtgagcagc ttccgagtca aggagaactt     180
cgacaaggct cgcttctctg ggacctggta cgccatggcc aagaaggacc ccgagggcct     240
cttcctgcag acaacatcg tcgcggagtt ctcggtggac gagaccggcc agatgagcgc      300
cacagccaag ggccgagtcc gtcttttgaa taactgggac gtgtgcgcag acatggtggg     360
caccttcaca gacaccgagg accctgccaa gttcaagatg aagtactggg gcgtagcctc     420
ctttctgcag aaaggaaatg atgaccactg gatcgtcgac acagactacg acacgtatgc     480
cgtacagtac tcctgccgcc tcctgaacct cgatggcacc tgtgctgaca gctactcctt     540
cgtgttttcc cgggacccca acggcctgcc cccagaagcg cagaagattg taaggcagcg     600
gcaggaggag ctgtgcctgg ccaggcagta caggctgatc gtccacaacg ttactgcga     660 tggcagatca gaaagaaacc ttttgtagca atatcaagaa tctagtttca tctgagaact     720
tctgattagc tctcagtctt cagctctatt tatcttagga gtttaatttg cccttctctc     780
cccatcttcc ctcagttccc ataaaacctt cattacacat aaagatacac gtggggtca      840 gtgaatctgc ttgcctttcc tgaaagtttc tggggcttaa gattccagac tctgattcat     900
taaactatag tcacccgtg                                                  919

<210> SEQ ID NO 341
<211> LENGTH: 7365
<212> TYPE: DNA
<213> ORGANISM: Homo sapiens

<400> SEQUENCE: 341
ggcagtttgt aggtcgcgag ggaagcgctg aggatcagga aggggcact gagtgtccgt       60 ggggggaatcc tcgtgatagg aactggaata tgccttgagg gggacactat gtctttaaaa    120
acgtcggctg gtcatgaggt caggagttcc agaccagcct gaccaacgtg gtgaaactcc     180
gtctctacta aaaatacaaa aattagccgg gcgtggtgcc gctccagcta ctcaggaggc     240
tgaggcagga gaatcgctag aacccgggag gcggaggttg cagtgagccg agatcgcgcc     300
```

-continued

```
attgcactcc agcctgggcg acagagcgag actgtctcaa aacaaaacaa aacaaaacaa      360
aacaaaaaac accggctgtt cattggaaca gaaagaaatg gatttatctg ctcttcgcgt      420
tgaagaagta caaaatgtca ttaatgctat gcagaaaatc ttagagtgtc ccatctgtct      480
ggagttgatc aaggaacctg tctccacaaa gtgtgaccac atattttgca aattttgcat      540
gctgaaactt ctcaaccaga gaaagggcc ttcacagtgt cctttatgta agaatgatat       600
aaccaaaagg agcctacaag aaagtacgag atttagtcaa cttgttgaag agctattgaa      660
aatcatttgt gcttttcagc ttgacacagg tttggagtat gcaaacagct ataattttgc      720
aaaaaaggaa ataactctc ctgaacatct aaaagatgaa gtttctatca tccaaagtat       780
gggctacaga aaccgtgcca aaagacttct acagagtgaa cccgaaaatc cttccttgca      840
ggaaaccagt ctcagtgtcc aactctctaa ccttggaact gtgagaactc tgaggacaaa      900
gcagcggata caacctcaaa agacgtctgt ctacattgaa ttgggatctg attcttctga      960
agataccgtt aataaggcaa cttattgcag tgtgggagat caagaattgt acaaatcac     1020 ccctcaagga accagggatg aaatcagttt ggattctgca aaaaaggctg cttgtgaatt     1080
ttctgagacg gatgtaacaa atactgaaca tcatcaaccc agtaataatg atttgaacac     1140
cactgagaag cgtgcagctg agaggcatcc agaaaagtat cagggtagtt ctgtttcaaa     1200
cttgcatgtg gagccatgtg gcacaaatac tcatgccagc tcattacagc atgagaacag     1260
cagtttatta ctcactaaag acagaatgaa tgtagaaaag gctgaattct gtaataaaag     1320
caaacagcct ggcttagcaa ggagccaaca taacagatgg gctggaagta aggaaacatg     1380
taatgatagg cggactccca gcacagaaaa aaaggtagat ctgaatgctg atccctgtg      1440 tgagagaaaa gaatggaata agcagaaact gccatgctca gagaatccta gagatactga     1500
agatgttcct tggataacac taaatagcag cattcagaaa gttaatgagt ggttttccag     1560
aagtgatgaa ctgttaggtt ctgatgactc acatgatggg gagtctgaat caaatgccaa     1620
agtagctgat gtattggacg ttctaaatga ggtagatgaa tattctggtt cttcagagaa     1680
aatagactta ctggccagtg atcctcatga ggctttaata tgtaaaagtg aaagagttca     1740
ctccaaatca gtagagagta atattgaaga caaaatattt gggaaaacct atcggaagaa     1800
ggcaagcctc cccaacttaa gccatgtaac tgaaaatcta attataggag catttgttac     1860
tgagccacag ataatacaag agcgtccct cacaaataaa ttaaagcgta aaaggagacc      1920
tacatcaggc cttcatcctg aggattttat caagaaagca gatttggcag ttcaaaagac     1980
tcctgaaatg ataaatcagg gaactaacca aacggagcag aatggtcaag tgatgaatat     2040
tactaatagt ggtcatgaga ataaaacaaa aggtgattct attcagaatg agaaaaatcc     2100
taacccaata gaatcactcg aaaaagaatc tgctttcaaa acgaaagctg aacctataag     2160
cagcagtata agcaatatgg aactcgaatt aaatatccac aattcaaaag cacctaaaaa     2220
gaataggctg aggaggaagt cttctaccag gcatattcat gcgcttgaac tagtagtcag     2280
tagaaatcta agcccaccta attgtactga attgcaaatt gatagttgtt ctagcagtga     2340
agagataaag aaaaaaaagt acaaccaaat gccagtcagg cacagcagaa acctacaact     2400
catggaaggt aaagaacctg caactggagc caagaagagt aacaagccaa atgaacagac     2460
aagtaaaaga catgacagcg atactttccc agagctgaag ttaacaaatg cacctggttc     2520
ttttactaag tgttcaaata ccagtgaact taaagaattt gtcaatccta gccttccaag     2580
agaagaaaaa gaagagaaac tagaaacagt taaagtgtct aataatgctg aagaccccaa     2640
agatctcatg ttaagtggag aaagggttt gcaaactgaa agatctgtag agagtagcag     2700
```

-continued

```
tatttcattg gtacctggta ctgattatgg cactcaggaa agtatctcgt tactggaagt    2760
tagcactcta gggaaggcaa aaacagaacc aaataaatgt gtgagtcagt gtgcagcatt    2820
tgaaaacccc aagggactaa ttcatggttg ttccaaagat aatagaaatg acacagaagg    2880
ctttaagtat ccattgggac atgaagttaa ccacagtcgg gaaacaagca tagaaatgga    2940
agaaagtgaa cttgatgctc agtatttgca gaatacattc aaggtttcaa agcgccagtc    3000
atttgctccg ttttcaaatc caggaaatgc agaagaggaa tgtgcaacat tctctgccca    3060
ctctgggtcc ttaaagaaac aaagtccaaa agtcactttt gaatgtgaac aaaaggaaga    3120
aaatcaagga aagaatgagt ctaatatcaa gcctgtacag acagttaata tcactgcagg    3180 cttttcctgtg gttggtcaga agataagcc agttgataat gccaaatgta gtatcaaagg    3240
aggctctagg ttttgtctat catctcagtt cagaggcaac gaaactggac tcattactcc    3300
aaataaacat ggacttttac aaacccata tcgtatacca ccacttttc ccatcaagtc    3360 atttgttaaa actaaatgta agaaaaatct gctagaggaa aactttgagg aacattcaat    3420
gtcacctgaa agagaaatgg gaatgagaaa cattccaagt acagtgagca caattagccg    3480
taataacatt agagaaaatg ttttttaaaga agccagctca agcaatatta atgaagtagg    3540
ttccagtact aatgaagtgg gctccagtat taatgaaata ggttccagtg atgaaaacat    3600
tcaagcagaa ctaggtagaa acagagggcc aaaattgaat gctatgctta gattaggggt    3660 tttgcaaccct gaggtctata acaaagtct cctggaagt aattgtaagc atcctgaaat    3720 aaaaagcaa gaatatgaag aagtagttca gactgttaat acagatttct ctccatatct    3780
gatttcagat aacttagaac agcctatggg aagtagtcat gcatctcagg tttgttctga    3840
gacacctgat gacctgttag atgatggtga ataaaggaa gatactagtt ttgctgaaaa    3900
tgacattaag gaaagttctg ctgtttttag caaaagcgtc cagaaaggag agcttagcag    3960
gagtcctagc cctttcaccc atacacattt ggctcaggt taccgaagag gggccaagaa    4020
attagagtcc tcagaagaga acttatctag tgaggatgaa gagcttccct gcttccaaca    4080 cttgttatttt ggtaaagtaa acaatatcc ttctcagtct actaggcata gcaccgttgc    4140
taccgagtgt ctgtctaaga acacagagga gaattatta tcattgaaga atagcttaaa    4200
tgactgcagt aaccaggtaa tattggcaaa ggcatctcag gaacatcacc ttagtgagga    4260
aacaaaatgt tctgctagct tgttttcttc acagtgcagt gaattggaag acttgactgc    4320
aaatacaaac acccaggatc ctttcttgat tggttcttcc aaacaaatga ggcatcagtc    4380
tgaaagccag ggagttggtc tgagtgacaa ggaattggtt tcagatgatg aagaaagagg    4440
aacgggcttg gaagaaaata atcaagaaga gcaaagcatg gattcaaact taggtgaagc    4500
agcatctggg tgtgagagtg aaacaagcgt ctctgaagac tgctcagggc tatcctctca    4560
gagtgacatt ttaaccactc agcagagga taccatgcaa cataacctga taaagctcca    4620
gcaggaaatg gctgaactag aagctgtgtt agaacagcat gggagccagc cttctaacag    4680
ctacccttcc atcataagtg actcttctgc ccttgaggac ctgcgaaatc cagaacaaag    4740
cacatcagaa aaagcagtat aacttcaca gaaaagtagt gaatacccta aagccagaa    4800 tccagaaggc ctttctgctg acaagtttga ggtgtctgca gatagttcta ccagtaaaaa    4860
taaagaacca ggagtggaaa ggtcatcccc ttctaaatgc ccatcattag atgataggtg    4920
gtacatgcac agttgctctg ggagtcttca gaatagaaac tacccatctc aagaggagct    4980
cattaaggtt gttgatgtgg aggagcaaca gctggaagag tctgggccac acgatttgac    5040
```

```
ggaaacatct tacttgccaa ggcaagatct agagggaacc ccttacctgg aatctggaat    5100
cagcctcttc tctgatgacc ctgaatctga tccttctgaa gacagagccc cagagtcagc    5160
tcgtgttggc aacataccat cttcaacctc tgcattgaaa gttccccaat tgaaagttgc    5220
agaatctgcc cagagtccag ctgctgctca tactactgat actgctgggt ataatgcaat    5280
ggaagaaagt gtgagcaggg agaagccaga attgacagct tcaacagaaa gggtcaacaa    5340
aagaatgtcc atggtggtgt ctggcctgac cccagaagaa tttatgctcg tgtacaagtt    5400
tgccagaaaa caccacatca ctttaactaa tctaattact gaagagacta ctcatgttgt    5460
tatgaaaaca gatgctgagt ttgtgtgtga acggacactg aaatattttc taggaattgc    5520
gggaggaaaa tgggtagtta gctatttctg ggtgacccag tctattaaag aaagaaaaat    5580
gctgaatgag catgattttg aagtcagagg agatgtggtc aatggaagaa accaccaagg    5640
tccaaagcga gcaagagaat cccaggacag aaagatcttc aggggctag aaatctgttg    5700
ctatgggccc ttcaccaaca tgcccacaga tcaactggaa tggatggtac agctgtgtgg    5760
tgcttctgtg gtgaaggagc tttcatcatt caccCttggc acaggtgtcc acccaattgt    5820
ggttgtgcag ccagatgcct ggacagagga caatggcttc catgcaattg gcagatgtg    5880
tgaggcacct gtggtgaccc gagagtgggt gttggacagt gtagcactct accagtgcca    5940
ggagctggac acctacctga taccccagat cccccacagc cactactgac tgcagccagc    6000
cacaggtaca gagccacagg accccaagaa tgagcttaca aagtggcctt tccaggccct    6060
gggagctcct ctcactcttc agtccttcta ctgtcctggc tactaaatat tttatgtaca    6120
tcagcctgaa aaggacttct ggctatgcaa gggtcccta aagattttct gcttgaagtc    6180
tcccttggaa atctgccatg agcacaaaat tatggtaatt tttcacctga aagatttta    6240
aaaccattta aacgccacca attgagcaag atgctgattc attatttatc agccctattc    6300
tttctattca ggctgttgtt ggcttagggc tggaagcaca gagtggcttg gcctcaagag    6360
aatagctggt ttccctaagt ttacttctct aaaaccctgt gttcacaaag cagagagtc    6420
agacccttca atggaaggag agtgcttggg atcgattatg tgacttaaag tcagaatagt    6480
ccttgggcag ttctcaaatg ttggagtgga acattgggga ggaaattctg aggcaggtat    6540
tagaaatgaa aaggaaactt gaaacctggg catggtggct cacgcctgta atcccagcac    6600
tttgggaggc caaggtgggc agatcactgg aggtcaggag ttcgaaacca gcctggccaa    6660
catggtgaaa ccccatctct actaaaaata cagaaattag ccggtcatgg tggtggacac    6720
ctgtaatccc agctactcag gtggctaagg caggagaatc acttcagccc gggaggtgga    6780
ggttgcagtg agccaagatc ataccacggc actccagcct gggtgacagt gagactgtgg    6840
ctcaaaaaa aaaaaaaa aggaaaatga actaggaaa ggtttcttaa agtctgagat    6900
atatttgcta gatttctaaa gaatgtgttc taaaacagca aagatttt aagaaccggt    6960
ttccaaagac agtcttctaa ttcctcatta gtaataagta aaatgtttat tgttgtagct    7020
ctggtatata atccattcct cttaaaatat aagacctctg gcatgaatat tcatatcta    7080
taaaatgaca gatcccacca ggaaggaagc tgttgctttc tttgaggtga ttttttttcct    7140
ttgctccctg ttgctgaaac catacagctt cataaataat tttgcttgct gaaggaagaa    7200
aaagtgtttt tcataaaccc attatccagg actgtttata gctgttggaa ggactaggtc    7260
ttccctagcc cccccagtgt gcaagggcag tgaagacttg attgtacaaa atacgttttg    7320
taaatgttgt gctgttaaca ctgcaaataa acttggtagc aaaca              7365
```

<210> SEQ ID NO 342
<211> LENGTH: 10386
<212> TYPE: DNA
<213> ORGANISM: Homo sapiens
<220> FEATURE:
<221> NAME/KEY: unsure
<222> LOCATION: (0)...(0)
<223> OTHER INFORMATION: n = a, t, c or g

<400> SEQUENCE: 342

| | | | | | |
|---|---|---|---|---|---|
| attgaggact | cggaaatgag | gtccaagggt | agccaaggat | ggctgcagct | tcatatgatc | 60 |
| agttgttaaa | gcaagttgag | gcactgaaga | tggagaactc | aaatcttcga | caagagctag | 120 |
| aagataattc | caatcatctt | acaaaactgg | aaactgaggc | atctaatatg | aaggaagtac | 180 |
| ttaaacaact | acaaggaagt | attgaagatg | aagctatggc | ttcttctgga | cagattgatt | 240 |
| tattagagcg | tcttaaagag | cttaacttag | atagcagtaa | tttccctgga | gtaaaactgc | 300 |
| ggtcaaaaat | gtccctccgt | tcttatggaa | gccgggaagg | atctgtatca | agccgttctg | 360 |
| gagagtgcag | tcctgttcct | atgggttcat | ttccaagaag | agggtttgta | aatggaagca | 420 |
| gagaaagtac | tggatattta | gaagaacttg | agaaagagag | gtcattgctt | cttgctgatc | 480 |
| ttgacaaaga | agaaaaggaa | aaagactggt | attacgctca | acttcagaat | ctcactaaaa | 540 |
| gaatagatag | tcttccttta | actgaaaatt | tttccttaca | aacagatatg | accagaaggc | 600 |
| aattggaata | tgaagcaagg | caaatcagag | ttgcgatgga | agaacaacta | ggtacctgcc | 660 |
| aggatatgga | aaaacgagca | cagcgaagaa | tagccagaat | tcagcaaatc | gaaaaggaca | 720 |
| tacttcgtat | acgacagctt | ttacagtccc | aagcaacaga | agcagagagg | tcatctcaga | 780 |
| acaagcatga | aaccggctca | catgatgctg | agcggcagaa | tgaaggtcaa | ggagtgggag | 840 |
| aaatcaacat | ggcaacttct | ggtaatggtc | agggttcaac | tacacgaatg | gaccatgaaa | 900 |
| cagccagtgt | tttgagttct | agtagcacac | actctgcacc | tcgaaggctg | acaagtcatc | 960 |
| tgggaaccaa | ggtggaaatg | gtgtattcat | tgttgtcaat | gcttggtact | catgataagg | 1020 |
| atgatatgtc | gcgaactttg | ctagctatgt | ctagctccca | agacagctgt | atatccatgc | 1080 |
| gacagtctgg | atgtcttcct | ctcctcatcc | agcttttaca | tggcaatgac | aaagactctg | 1140 |
| tattgttggg | aaattcccgg | ggcagtaaag | aggctcgggc | cagggccagt | gcagcactcc | 1200 |
| acaacatcat | tcactcacag | cctgatgaca | agagaggcag | gcgtgaaatc | cgagtccttc | 1260 |
| atcttttgga | acagatacgc | gcttactgtg | aaacctgttg | ggagtggcag | gaagctcatg | 1320 |
| aaccaggcat | ggaccaggac | aaaaatccaa | tgccagctcc | tgttgaacat | cagatctgtc | 1380 |
| ctgctgtgtg | tgttctaatg | aaactttcat | tgatgaaga | gcatagacat | gcaatgaatg | 1440 |
| aactaggggg | actacaggcc | attgcagaat | tattgcaagt | ggactgtgaa | atgtacgggc | 1500 |
| ttactaatga | ccactacagt | attacactaa | gacgatatgc | tggaatggct | ttgacaaact | 1560 |
| tgacttttgg | agatgtagcc | aacaaggcta | cgctatgctc | tatgaaaggc | tgcatgagag | 1620 |
| cacttgtggc | ccaactaaaa | tctgaaagtg | aagacttaca | gcaggttatt | gcaagtgttt | 1680 |
| tgaggaattt | gtcttggcga | gcagatgtaa | atagtaaaaa | gacgttgcga | gaagttggaa | 1740 |
| gtgtgaaagc | attgatggaa | tgtgctttag | aagttaaaaa | ggaatcaacc | ctcaaaagcg | 1800 |
| tattgagtgc | cttatggaat | ttgtcagcac | attgcactga | gaataagct | gatatatgtg | 1860 |
| ctgtagatgg | tgcacttgca | ttttggttg | gcactcttac | ttaccggagc | cagacaaaca | 1920 |
| ctttagccat | tattgaaagt | ggaggtggga | tattacggaa | tgtgtccagc | ttgatagcta | 1980 |
| caaatgagga | ccacaggcaa | atcctaagag | agaacaactg | tctacaaact | ttattacaac | 2040 |

```
acttaaaatc tcatagtttg acaatagtca gtaatgcatg tggaactttg tggaatctct    2100
cagcaagaaa tcctaaagac caggaagcat tatgggacat gggggcagtt agcatgctca    2160
agaacctcat tcattcaaag cacaaaatga ttgctatggg aagtgctgca gctttaagga    2220
atctcatggc aaataggcct gcgaagtaca aggatgccaa tattatgtct cctggctcaa    2280
gcttgccatc tcttcatgtt aggaaacaaa aagccctaga agcagaatta gatgctcagc    2340
acttatcaga aacttttgac aatatagaca atttaagtcc caaggcatct catcgtagta    2400
agcagagaca caagcaaagt ctctatggtg attatgtttt tgacaccaat cgacatgatg    2460
ataataggtc agacaatttt aatactggca acatgactgt cctttcacca tatttgaata    2520
ctacagtgtt acccagctcc tcttcatcaa gaggaagctt agatagttct cgttctgaaa    2580
aagatagaag tttggagaga gaacgcggaa ttggtctagg caactaccat ccagcaacag    2640
aaaatccagg aacttcttca aagcgaggtt tgcagatctc caccactgca gcccagattg    2700
ccaaagtcat ggaagaagtg tcagccattc atacctctca ggaagacaga agttctgggt    2760
ctaccactga attacattgt gtgacagatg agagaaatgc acttagaaga agctctgctg    2820
cccatacaca ttcaaacact tacaatttca ctaagtcgga aaattcaaat aggacatgtt    2880
ctatgcctta tgccaaatta gaatacaaga gatcttcaaa tgatagttta aatagtgtca    2940
gtagtagtga tggttatggt aaaagaggtc aaatgaaacc ctcgattgaa tcctattctg    3000
aagatgatga agtaagtttt tgcagttatg gtcaataccc agccgaccta gcccataaaa    3060
tacatagtgc aaatcatatg gatgataatg atggagaact agatacacca ataaattata    3120
gtcttaaata ttcagatgag cagttgaact ctggaaggca aagtccttca cagaatgaaa    3180
gatgggcaag acccaaacac ataatagaag atgaaataaa acaaagtgag caaagacaat    3240
caaggaatca aagtacaact tatcctgttt atactgagag cactgatgat aaacacctca    3300
agttccaacc acattttgga cagcaggaat gtgtttctcc atacaggtca cggggagcca    3360
atggttcaga aacaaatcga gtgggttcta atcatggaat taatcaaaat gtaagccagt    3420
ctttgtgtca agaagatgac tatgaagatg ataagcctac caattatagt gaacgttact    3480
ctgaagaaga acagcatgaa gaagaagaga gaccaacaaa ttatagcata aaatataatg    3540
aagagaaacg tcatgtggat cagcctattg attatagttt aaaatatgcc acagatattc    3600
cttcatcaca gaaacagtca tttttcattct caaagagttc atctggacaa agcagtaaaa    3660
ccgaacatat gtcttcaagc agtgagaata cgtccacacc ttcatctaat gccaagaggc    3720
agaatcagct ccatccaagt tctgcacaga gtagaagtgg tcagcctcaa aaggctgcca    3780
cttgcaaagt ttcttctatt aaccaagaaa caatacagac ttattgtgta aagatactc    3840 caatatgttt ttcaagatgt agttcattat catctttgtc atcagctgaa gatgaaatag    3900
gatgtaatca gacgacacag gaagcagatt ctgctaatac cctgcaaata gcagaaataa    3960
aagaaaagat tggaactagg tcagctgaag atcctgtgag cgaagttcca gcagtgtcac    4020
agcaccctag aaccaaatcc agcagactgc agggttctag tttatcttca gaatcagcca    4080
ggcacaaagc tgttgaattt tcttcaggag cgaaatctcc ctccaaaagt ggtgctcaga    4140
cacccaaaag tccacctgaa cactatgttc aggagacccc actcatgttt agcagatgta    4200
cttctgtcag ttcacttgat agttttgaga gtcgttcgat tgccagctcc gttcagagtg    4260
aaccatgcag tggaatggta agtggcatta taagccccag tgatcttcca gatagccctg    4320
gacaaaccat gccaccaagc agaagtaaaa cacctccacc acctcctcaa acagctcaaa    4380
ccaagcgaga agtacctaaa aataaagcac ctactgctga aaagagagag agtggaccta    4440
```

```
agcaagctgc agtaaatgct gcagttcaga gggtccaggt tcttccagat gctgatactt      4500
tattacattt tgccacggaa agtactccag atggattttc ttgttcatcc agcctgagtg      4560
ctctgagcct cgatgagcca tttatacaga aagatgtgga attaagaata atgcctccag      4620
ttcaggaaaa tgacaatggg aatgaaacag aatcagagca gcctaaagaa tcaaatgaaa      4680
accaagagaa agaggcagaa aaaactattg attctgaaaa ggacctatta gatgattcag      4740
atgatgatga tattgaaata ctagaagaat gtattatttc tgccatgcca acaaagtcat      4800
cacgtaaagc aaaaaagcca gcccagactg cttcaaaatt acctccacct gtggcaagga      4860
aaccaagtca gctgcctgtg tacaaacttc taccatcaca aaacaggttg caaccccaaa      4920
agcatgttag ttttacaccg ggggatgata tgccacgggt gtattgtgtt gaagggacac      4980
ctataaactt ttccacagct acatctctaa gtgatctaac aatcgaatcc cctccaaatg      5040
agttagctgc tggagaagga gttagaggag agcacagtc aggtgaattt gaaaaacgag        5100
ataccattcc tacagaaggc agaagtacag atgaggctca aggaggaaaa acctcatctg      5160
taaccatacc tgaattggat gacaataaag cagaggaagg tgatattctt gcagaatgca      5220
ttaattctgc tatgcccaaa gggaaaagtc acaagccttt ccgtgtgaaa aagataatgg      5280
accaggtcca gcaagcatct gcgtcgtctt ctgcacccaa caaaaatcag ttagatggta      5340
agaaaaagaa accaacttca ccagtaaaac ctataccaca aaatactgaa ataggacac       5400 gtgtaagaaa aaatgcagac tcaaaaaata atttaaatgc tgagagagtt ttctcagaca      5460
acaaagattc aaagaaacag aatttgaaaa ataattccaa ggacttcaat gataagctcc      5520
caaataatga agatagagtc agaggaagtt ttgcttttga ttcacctcat cattacacgc      5580
ctattgaagg aactccttac tgtttttcac gaaatgattc tttgagttct ctagattttg      5640
atgatgatga tgttgacctt tccagggaaa aggctgaatt aagaaaggca aagaaaata      5700 aggaatcaga ggctaaagtt accagccaca cagaactaac ctccaaccaa caatcagcta      5760
ataagacaca agctattgca aagcagccaa taaatcgagg tcagcctaaa cccatacttc      5820
agaaacaatc cacttttccc cagtcatcca agacatacc agacagaggg gcagcaactg       5880
atgaaaagtt acagaatttt gctattgaaa atactccagt ttgcttttct cataattcct      5940
ctctgagttc tctcagtgac attgaccaag aaaacaacaa taaagaaaat gaacctatca      6000
aagagactga gccccctgac tcacagggag aaccaagtaa acctcaagca tcaggctatg      6060
ctcctaaatc atttcatgtt gaagataccc cagtttgttt tcaagaaac agttctctca       6120 gttctcttag tattgactct gaagatgacc tgttgcagga atgtataagc tccgcaatgc      6180
caaaaaagaa aaagccttca agactcaagg gtgataatga aaacatagt cccagaaata       6240 tgggtggcat attaggtgaa gatctgacac ttgatttgaa agatatacag agaccagatt      6300
cagaacatgg tctatcccct gattcagaaa attttgattg gaaagctatt caggaaggtg      6360
caaattccat agtaagtagt ttacatcaag ctgctgctgc tgcatgttta tctagacaag      6420
cttcgtctga ttcagattcc atcctttccc tgaaatcagg aatctctctg ggatcaccat      6480
ttcatcttac acctgatcaa gaagaaaaac cctttacaag taataaaggc ccacgaattc      6540
taaaaccagg ggagaaaagt acattggaaa ctaaaaagat agaatctgaa agtaaaggaa      6600 tcaaggagg aaaaaaagtt tataaaagtt tgattactgg aaaagttcga tctaattcag       6660
aaatttcagg ccaaatgaaa cagccccttc aagcaaacat gccttcaatc tctcgaggca      6720
ggacaatgat tcatattcca ggagttcgaa atagctcctc aagtacaagt cctgtttcta      6780
```

```
aaaaaggccc acccctttaag actccagcct ccaaaagccc tagtgaaggt caaacagcca    6840
ccacttctcc tagaggagcc aagccatctg tgaaatcaga attaagccct gttgccaggc    6900
agacatccca aataggtggg tcaagtaaag caccttctag atcaggatct agagattcga    6960 cccccttcaag acctgcccag caaccattaa gtagacctat acagtctcct ggccgaaact   7020
caatttcccc tggtagaaat ggaataagtc ctcctaacaa attatctcaa cttccaagga    7080
catcatcccc tagtactgct tcaactaagt cctcaggttc tggaaaaatg tcatatacat    7140
ctccaggtag acagatgagc aacagaacc ttaccaaaca aacaggttta tccaagaatg     7200
ccagtagtat tccaagaagt gagtctgcct ccaaaggact aaatcagatg aataatggta    7260
atggagccaa taaaaaggta gaactttcta gaatgtcttc aactaaatca agtggaagtg    7320
aatctgatag atcagaaaga cctgtattag tacgccagtc aactttcatc aaagaagctc    7380
caagcccaac cttaagaaga aaattggagg aatctgcttc atttgaatct ctttctccat    7440
catctagacc agcttctccc actaggtccc aggcacaaac tccagttta agtccttccc     7500 ttcctgatat gtctctatcc acacattcgt ctgttcaggc tggtggatgg cgaaaactcc    7560
cacctaatct cagtcccact atagagtata atgatggaag accagcaaag cgccatgata    7620
ttgcacggtc tcattctgaa agtccttcta gacttccaat caataggtca ggaacctgga    7680
aacgtgagca cagcaaacat tcatcatccc ttcctcgagt aagcacttgg agaagaactg    7740
gaagttcatc ttcaattctt tctgcttcat cagaatccag tgaaaaagca aaaagtgagg    7800
atgaaaaaca tgtgaactct atttcaggaa ccaaacaaag taaagaaaac caagtatccg    7860
caaaaggaac atggagaaaa ataaaagaaa atgaattttc tcccacaaat agtacttctc    7920
agaccgtttc ctcaggtgct acaaatggtg ctgaatcaaa gactctaatt tatcaaatgg    7980
cacctgctgt ttctaaaaca gaggatgttt gggtgagaat tgaggactgt cccattaaca    8040
atcctagatc tggaagatct cccacaggta atactcccc ggtgattgac agtgtttcag      8100
aaaaggcaaa tccaaacatt aaagattcaa aagataatca ggcaaaacaa aatgtgggta    8160
atggcagtgt tccatgcgt accgtggggtt tggaaaatcg cctgaactcc tttattcagg     8220
tggatgcccc tgaccaaaaa ggaactgaga taaaaccagg acaaaataat cctgtccctg    8280
tatcagagac taatgaaagt tctatagtgg aacgtacccc attcagttct agcagctcaa    8340
gcaaacacag ttcacctagt gggactgttg ctgccagagt gactcctttt aattacaacc    8400
caagccctag gaaaagcagc gcagatagca cttcagctcg gccatctcag atcccaactc    8460
cagtgaataa caacacaaag aagcgagatt ccaaaactga cagcacagaa tccagtggaa    8520
cccaaagtcc taagcgccat tctgggtctt accttgtgac atctgtttaa agagaggaa     8580 gaatgaaact aagaaaattc tatgttaatt acaactgcta tatagacatt ttgtttcaaa    8640 tgaaactttta aaagactgaa aaattttgta aataggtttg attcttgtta gagggttttt   8700
gttctggaag ccatatttga tagtatactt tgtcttcact ggtcttattt tgggaggcac    8760
tcttgatggt taggaaaaaa atagtaaagc caagtatgtt tgtacagtat gttttacatg    8820
tatttaaagt agcatcccat cccaacttcc tttaattatt gcttgtctta aaataatgaa    8880
cactacagat agaaaatatg atatattgct gttatcaatc atttctagat tataaactga    8940
ctaaacttac atcagggaaa aattggtatt tatgcaaaaa aaatgtttt tgtccttgtg     9000 agtccatcta acatcataat taatcatgtg gctgtgaaat tcacagtaat atggttcccg    9060
atgaacaagc tttacccagc ctgtttgctt tactgcatga atgaaactga tggttcaatt    9120
tcagaagtaa tgattaacag ttatgtggtc acatgatgtg catagagata gctacagtgt    9180
```

-continued

```
aataatttac actattttgt gctccaaaca aaacaaaaat ctgtgtaact gtaaaacatt    9240
gaatgaaact attttacctg aactagattt tatctgaaag taggtagaat ttttgctatg    9300
ctgtaatttg ttgtatattc tggtatttga ggtgagatgg ctgctctttt attaatgaga    9360
catgaattgt gtctcaacag aaactaaatg aacatttcag aataaattat tgctgtatgt    9420
aaactgttac tgaaattggt atttgtttga agggtcttgt ttcacatttg tattaataat    9480
tgtttaaaat gcctctttta aaagcttata taaattttt ncttcagctt ctatgcatta     9540
agagtaaaat tcctcttact gtaataaaaa caattgaaga agactgttgc cacttaacca    9600
ttccatgcgt tggcacttat ctattcctga aattctttta tgtgattagc tcatcttgat    9660
ttttaacatt tttccactta aacttttttt tcttactcca ctggagctca gtaaaagtaa    9720
attcatgtaa tagcaatgca agcagcctag cacagactaa gcattgagca taataggccc    9780
acataatttc ctctttctta atattataga aattctgtac ttgaaattga ttcttagaca    9840
ttgcagtctc ttcgaggctt tacagtgtaa actgtcttgc cccttcatct tcttgttgca    9900
actgggtctg acatgaacac tttttatcac cctgtatgtt agggcaagat ctcagcagtg    9960
aagtataatc agcactttgc catgctcaga aaattcaaat cacatggaac tttagaggta    10020
gatttaatac gattaagata ttcagaagta tattttagaa tccctgcctg ttaaggaaac    10080
tttatttgtg gtaggtacag ttctggggta catgttaagt gtccccttat acagtggagg    10140
gaagtcttcc ttcctgaagg aaaataaact gacacttatt aactaagata atttacttaa    10200
tatatcttcc ctgatttgtt ttaaaagatc agagggtgac tgatgataca tgcatacata    10260
tttgttgaat aaatgaaaat ttattttag tgataagatt catacactct gtatttgggg     10320
agagaaaacc tttttaagca tggtggggca ctcagatagg agtgaataca cctacctggt    10380
ggtcat                                                                10386
```

```
<210> SEQ ID NO 343
<211> LENGTH: 2191
<212> TYPE: DNA
<213> ORGANISM: Homo sapiens

<400> SEQUENCE: 343
```

```
ggtggccgag cggggggaccg ggaagcatgg cccgggggtc ggcggttgcc tgggcggcgc    60
tcgggccgtt gttgtggggc tgcgcgctgg ggctgcaggg cgggatgctg tacccccagg    120
agagcccgtc gcgggagtgc aaggagctgg acggcctctg gagcttccgc gccgacttct    180
ctgacaaccg acgccggggc ttcgaggagc agtggtaccg gcggccgctg tgggagtcag    240
gccccaccgt ggacatgcca gttccctcca gcttcaatga catcagccag gactggcgtc    300
tgcggcattt tgtcggctgg gtgtggtacg aacgggaggt gatcctgccg gagcgatgga    360
cccaggacct gcgcacaaga gtggtgctga ggattggcag tgcccattcc tatgccatcg    420
tgtgggtgaa tgggtcgac acgctagagc atgagggggg ctacctcccc ttcgaggccg     480
acatcagcaa cctggtccag gtggggcccc tgccctcccg gctccgaatc actatcgcca    540
tcaacaacac actcaccccc accaccctgc caccagggac catccaatac ctgactgaca    600
cctccaagta tcccaagggt tactttgtcc agaacacata ttttgacttt ttcaactacg    660
ctggactgca gcggtctgta cttctgtaca cgacacccac cacctacatc gatgacatca    720
ccgtcaccac cagcgtggag caagacagtg ggctggtgaa ttaccagatc tctgtcaagg    780
gcagtaacct gttcaagttg gaagtgcgtc ttttggatgc agaaaacaaa gtcgtggcga    840
```

| | |
|---|---|
| atgggactgg gacccagggc caacttaagg tgccaggtgt cagcctctgg tggccgtacc | 900 |
| tgatgcacga acgccctgcc tatctgtatt cattggaggt gcagctgact gcacagacgt | 960 |
| cactggggcc tgtgtctgac ttctacacac tccctgtggg gatccgcact gtggctgtca | 1020 |
| ccaagagcca gttcctcatc aatgggaaac ctttctattt ccacggtgtc aacaagcatg | 1080 |
| aggatgcgga catccgaggg aagggcttcg actggccgct gctggtgaag gacttcaacc | 1140 |
| tgcttcgctg gcttggtgcc aacgcttttcc gtaccagcca ctaccccctat gcagaggaag | 1200 |
| tgatgcagat gtgtgaccgc tatgggattg tggtcatcga tgagtgtccc ggcgtgggcc | 1260 |
| tggcgctgcc gcagttcttc aacaacgttt ctctgcatca ccacatgcag gtgatgaag | 1320 |
| aagtggtgcg tagggacaag aaccacccccg cggtcgtgat gtggtctgtg ccaacgagc | 1380 |
| ctgcgtccca cctagaatct gctggctact acttgaagat ggtgatcgct cacaccaaat | 1440 |
| ccttggaccc ctcccggcct gtgacctttg tgagcaactc taactatgca gcagacaagg | 1500 |
| gggctccgta tgtggatgtg atctgtttga acagctacta ctcttggtat cacgactacg | 1560 |
| ggcacctgga gttgattcag ctgcagctgg ccacccagtt tgagaactgg tataagaagt | 1620 |
| atcagaagcc cattattcag agcgagtatg agcagaaaac gattgcaggg tttcaccagg | 1680 |
| atccacctct gatgttcact gaagagtacc agaaaagtct gctagagcag taccatctgg | 1740 |
| gtctggatca aaaacgcaga aaatatgtgg ttggagagct catttggaat tttgccgatt | 1800 |
| tcatgactga acagtcaccg acgagagtgc tggggaataa aaagggggatc ttcactcggc | 1860 |
| agagacaacc aaaaagtgca gcgttccttt tgcgagagag atactggaag attgccaatg | 1920 |
| aaaccaggta tccccactca gtagccaagt cacaatgttt ggaaaacagc ccgtttactt | 1980 |
| gagcaagact gataccacct gcgtgtccct tcctccccga gtcagggcga cttccacagc | 2040 |
| agcagaacaa gtgcctcctg gactgttcac ggcagaccag aacgtttctg gcctgggttt | 2100 |
| tgtggtcatc tattctagca gggaacacta aaggtggaaa taaagatttt tctattatgg | 2160 |
| aaataaagag ttggcatgaa agtcgctact g | 2191 |

<210> SEQ ID NO 344
<211> LENGTH: 2776
<212> TYPE: DNA
<213> ORGANISM: Homo sapiens

<400> SEQUENCE: 344

| | |
|---|---|
| cagggcagac tggtagcaaa gccccccacgc ccagccagga gcaccgccgc ggactccagc | 60 |
| acaccgaggg acatgctggg cctgcgcccc ccactgctcg ccctggtggg gctgctctcc | 120 |
| ctcgggtgcg tcctctctca ggagtgcacg aagttcaagg tcagcagctg ccggggaatgc | 180 |
| atcgagtcgg ggcccggctg cacctggtgc cagaagctga acttcacagg gccggggggat | 240 |
| cctgactcca ttcgctgcga cacccggcca cagctgctca tgagggggctg tgcggctgac | 300 |
| gacatcatgg accccacaag cctcgctgaa acccaggaag accacaatgg gggccagaag | 360 |
| cagctgtccc cacaaaaagt gacgctttac ctgcgaccag ccaggcagc agcgttcaac | 420 |
| gtgaccttcc ggcgggccaa gggctacccc atcgacctgt actatctgat ggacctctcc | 480 |
| tactccatgc ttgatgacct caggaatgtc aagaagctag gtggcgacct gctccgggcc | 540 |
| ctcaacgaga tcaccgagtc cggccgcatt ggcttcgggt ccttcgtgga caagaccgtg | 600 |
| ctgccgttcg tgaacacgca ccctgataag ctgcgaaacc catgccccaa caggagaaa | 660 |
| gagtgccagc cccgtttgc cttcaggcac gtgctgaagc tgaccaacaa ctccaaccag | 720 |
| tttcagaccg aggtcgggaa gcagctgatt tccggaaacc tggatgcacc cgagggtggg | 780 |

-continued

```
ctggacgcca tgatgcaggt cgccgcctgc ccggaggaaa tcggctggcg caacgtcacg      840
cggctgctgg tgtttgccac tgatgacggc ttccatttcg cgggcgacgg aaagctgggc      900
gccatcctga cccccaacga cggccgctgt cacctggagg acaacttgta caagaggagc      960
aacgaattcg actacccatc ggtgggccag ctggcgcaca agctggctga aaacaacatc     1020
cagcccatct tcgcggtgac cagtaggatg gtgaagacct acgagaaact caccgagatc     1080
atccccaagt cagccgtggg ggagctgtct gaggactcca gcaatgtggt ccatctcatt     1140
aagaatgctt acaataaact ctcctccagg gtcttcctgg atcacaacgc cctccccgac     1200
accctgaaag tcacctacga ctccttctgc agcaatggag tgacgcacag gaaccagccc     1260
agaggtgact gtgatggcgt gcagatcaat gtcccgatca ccttccaggt gaaggtcacg     1320
gccacagagt gcatccagga gcagtcgttt gtcatccggg cgctgggctt cacggacata     1380
gtgaccgtgc aggttcttcc ccagtgtgag tgccggtgcc gggaccagag cagagaccgc     1440
agcctctgcc atggcaaggg cttcttggag tgcggcatct gcaggtgtga cactggctac     1500
attgggaaaa actgtgagtg ccagacacag ggccggagca gccaggagct ggaaggaagc     1560
tgccggaagg acaacaactc catcatctgc tcagggctgg gggactgtgt ctgcgggcag     1620
tgcctgtgcc acaccagcga cgtccccggc aagctgatat acgggcagta ctgcgagtgt     1680
gacaccatca actgtgagcg ctacaacggc caggtctgcg gcggcccggg gagggggctc     1740
tgcttctgcg ggaagtgccg ctgccacccg ggctttgagg gctcagcgtg ccagtgcgag     1800
aggaccactg agggctgcct gaacccgcgg cgtgttgagt gtagtggtcg tggccggtgc     1860
cgctgcaacg tatgcgagtg ccattcaggc taccagctgc ctctgtgcca ggagtgcccc     1920
ggctgccccct cacccgtgg caagtacatc tcctgcgccg agtgcctgaa gttcgaaaag     1980
ggccccttgg ggaagaactg cagcgcggcg tgtccgggcc tgcagctgtc gaacaacccc     2040
gtgaagggca ggacctgcaa ggagagggac tcagagggct gctgggtggc ctacacgctg     2100
gagcagcagg acgggatgga ccgctacctc atctatgtgg atgagagccg agagtgtgtg     2160
gcaggcccca acatcgccgc catcgtcggg ggcaccgtgg caggcatcgt gctgatcggc     2220
attctcctgc tggtcatctg gaaggctctg atccacctga gcgacctccg ggagtacagg     2280
cgctttgaga aggagaagct caagtcccag tggaacaatg ataatcccct tttcaagagc     2340
gccaccacga cggtcatgaa ccccaagttt gctgagagtt aggagcactt ggtgaagaca     2400
aggccgtcag gacccaccat gtctgcccca tcacgcggcc gagacatggc ttggccacag     2460
ctcttgagga tgtcaccaat taaccagaaa tccagttatt ttccgccctc aaaatgacag     2520
ccatggccgg ccggtgcttc tgggggctcg tcgggggggac agctccactc tgactggcac     2580
agtctttgca tggagacttg aggagggctt gaggttggtg aggttaggtg cgtgtttcct     2640
gtgcaagtca ggcatcagt ctgattaaag gtggtgccaa tttatttaca tttaaacttg     2700
tcagggtata aaatgacatc ccattaatta tattgttaat caatcacgtg tatagaaaaa     2760
aaaataaaac ttcaat                                                    2776
```

<210> SEQ ID NO 345
<211> LENGTH: 3160
<212> TYPE: DNA
<213> ORGANISM: Homo sapiens

<400> SEQUENCE: 345

```
cctcccctcg cccggcgcgg tccgtccgc ctctcgctcg cctcccgcct ccccctcggtc      60
```

-continued

| | |
|---|---|
| ttccgaggcg cccgggctcc cggcgcggcg gcggaggggg cgggcaggcc ggcgggcggt | 120 |
| gatgtggcag gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gcccctctca gcgcctgtga gcagccgcgg gggcagcgcc ctcggggagc cggccggcct | 360 |
| gcggcggcgg cagcggcggc gtttctcgcc tcctcttcgt cttttctaac cgtgcagcct | 420 |
| cttcctcggc ttctcctgaa agggaaggtg gaagccgtgg gctcgggcgg gagccggctg | 480 |
| aggcgcggcg gcggcggcgg cggcacctcc cgctcctgga gcgggggga gaagcggcgg | 540 |
| cggcggcggc cgcggcggct gcagctccag ggaggggtc tgagtcgcct gtcaccattt | 600 |
| ccagggctgg gaacgccgga gagttggtct ctcccttct actgcctcca acacggcggc | 660 |
| ggcggcggcg gcacatccag ggacccgggc cggttttaaa cctcccgtcc gccgccgccg | 720 |
| cacccccgt ggcccgggct ccggaggccg ccggcggagg cagccgttcg gaggattatt | 780 |
| cgtcttctcc ccattccgct gccgccgctg ccaggcctct ggctgctgag gagaagcagg | 840 |
| cccagtcgct gcaaccatcc agcagccgcc gcagcagcca ttacccggct gcggtccaga | 900 |
| gccaagcggc ggcagagcga ggggcatcag ctaccgccaa gtccagagcc atttccatcc | 960 |
| tgcagaagaa gccccgccac cagcagcttc tgccatctct ctcctccttt tcttcagcc | 1020 |
| acaggctccc agacatgaca gccatcatca aagagatcgt tagcagaaac aaaaggagat | 1080 |
| atcaaggaga tggattcgac ttagacttga cctatattta tccaaacatt attgctatgg | 1140 |
| gatttcctgc agaaagactt gaaggcgtat acaggaacaa tattgatgat gtagtaaggt | 1200 |
| ttttggattc aaagcataaa aaccattaca agatatacaa tctttgtgct gaaagacatt | 1260 |
| atgacaccgc caaatttaat tgcagagttg cacaatatcc ttttgaagac cataacccac | 1320 |
| cacagctaga acttatcaaa ccctttgtg aagatcttga ccaatggcta agtgaagatg | 1380 |
| acaatcatgt tgcagcaatt cactgtaaag ctggaaaggg acgaactggt gtaatgatat | 1440 |
| gtgcatattt attacatcgg ggcaaatttt taaaggcaca agaggcccta gatttctatg | 1500 |
| gggaagtaag gaccagagac aaaaagggag taactattcc cagtcagagg cgctatgtgt | 1560 |
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |
| atacattctt cataccagga ccagaggaaa cctcagaaaa agtagaaaat ggaagtctat | 1920 |
| gtgatcaaga aatcgatagc atttgcagta tagagcgtgc agataatgac aaggaatatc | 1980 |
| tagtacttac tttaacaaaa aatgatcttg acaaagcaaa taaagacaaa gccaaccgat | 2040 |
| acttttctcc aaattttaag gtgaagctgt acttcacaaa aacagtagag gagccgtcaa | 2100 |
| atccagaggc tagcagttca acttctgtaa caccagatgt tagtgacaat gaacctgatc | 2160 |
| attatagata ttctgacacc actgactctg atccagagaa tgaacctttt gatgaagatc | 2220 |
| agcatacaca aattacaaaa gtctgaattt ttttttatca agaggataa acaccatga | 2280 |
| aaataaactt gaataaactg aaaatggacc tttttttttt taatggcaat aggacattgt | 2340 |
| gtcagattac cagttatagg aacaattctc ttttcctgac caatcttgtt ttaccctata | 2400 |
| catccacagg gttttgacac ttgttgtcca gttgaaaaaa ggttgtgtag ctgtgtcatg | 2460 |

-continued

```
tatatacctt tttgtgtcaa aggacattt  aaaattcaat taggattaat aaagatggca    2520
ctttcccgtt ttattccagt tttataaaaa gtggagacag actgatgtgt atacgtagga    2580 atttttcct  tttgtgttct gtcaccaact gaagtggcta aagagctttg tgatatactg    2640
gttcacatcc taccccttg  cacttgtggc aacagataag tttgcagttg gctaagagag    2700 gttccgaaa  ggttttgcta ccattctaat gcatgtattc gggttagggc aatggagggg    2760
aatgctcaga aggaaataa  ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                           3160

<210> SEQ ID NO 346
<211> LENGTH: 2629
<212> TYPE: DNA
<213> ORGANISM: Homo sapiens

<400> SEQUENCE: 346
acttgtcatg gcgactgtcc agctttgtgc caggagcctc gcaggggttg atgggattgg      60
ggttttcccc tcccatgtgc tcaagactgg cgctaaaagt tttgagcttc tcaaaagtct     120
agagccaccg tccagggagc aggtagctgc tgggctccgg ggacactttg cgttcgggct     180
gggagcgtgc tttccacgac ggtgacacgc ttccctggat tggcagccag actgccttcc     240
gggtcactgc catggaggag ccgcagtcag atcctagcgt cgagccccct ctgagtcagg     300
aaacattttc agacctatgg aaactacttc ctgaaaacaa cgttctgtcc cccttgccgt     360
cccaagcaat ggatgatttg atgctgtccc ggacgatat  tgaacaatgg ttcactgaag     420
acccaggtcc agatgaagct cccagaatgc cagaggctgc tccccgcgtg gcccctgcac     480
cagcagctcc tacaccggcg gcccctgcac cagcccccctc ctggcccctg tcatcttctg     540
tcccttccca gaaaacctac cagggcagct acgtttccg  tctgggcttc ttgcattctg     600
ggacagccaa gtctgtgact tgcacgtact cccctgccct caacaagatg ttttgccaac     660
tggccaagac ctgccctgtg cagctgtggg ttgattccac accccgccc  ggcacccgcg     720 tccgcgccat ggccatctac aagcagtcac agcacatgac ggaggttgtg aggcgctgcc     780
cccaccatga gcgctgctca gatagcgatg gtctggcccc tcctcagcat cttatccgag     840
tggaaggaaa tttgcgtgtg gagtatttgg atgacagaaa cacttttcga catagtgtgg     900
tggtgcccta tgagccgcct gaggttggct ctgactgtac caccatccac tacaactaca     960
tgtgtaacag ttcctgcatg ggcggcatga accggaggcc catcctcacc atcatcacac    1020
tggaagactc cagtggtaat ctactgggac ggaacagctt tgaggtgcgt gtttgtgcct    1080
gtcctgggag agaccggcgc acagaggaag agaatctccg caagaaaggg gagcctcacc    1140
acgagctgcc cccagggagc actaagcgag cactgcccaa caccaccagc tcctctcccc    1200
agccaaagaa gaaaccactg gatggagaat atttcaccct tcagatccgt gggcgtgagc    1260
gcttcgagat gttccgagag ctgaatgagg ccttggaact caaggatgcc caggctggga    1320
aggagccagg ggggagcagg gctcactcca gccacctgaa gtccaaaaag ggtcagtcta    1380
```

-continued

```
cctcccgcca taaaaaactc atgttcaaga cagaagggcc tgactcagac tgacattctc      1440
cacttcttgt tccccactga cagcctccca cccccatctc tccctcccct gccatttttgg     1500 gttttgggtc tttgaaccct tgcttgcaat aggtgtgcgt cagaagcacc caggacttcc     1560
atttgctttg tcccggggct ccactgaaca agttggcctg cactggtgtt ttgttgtggg     1620
gaggaggatg gggagtagga cataccagct tagattttaa ggttttttact gtgagggatg    1680 tttgggagat gtaagaaatg ttcttgcagt taagggttag tttacaatca gccacattct     1740
aggtaggtag gggcccactt caccgtacta accaggaaag ctgtccctca tgttgaattt     1800
tctctaactt caaggcccat atctgtgaaa tgctggcatt tgcacctacc tcacagagtg     1860
cattgtgagg gttaatgaaa taatgtacat ctggccttga aaccaccttt tattacatgg     1920
ggtctaaaac ttgacccccct tgagggtgcc tgttccctct ccctctccct gttggctggt    1980
gggttggtag tttctacagt tgggcagctg gttaggtaga gggagttgtc aagtcttgct     2040
ggcccagcca aaccctgtct gacaacctct tggtcgacct tagtacctaa aaggaaatct     2100
caccccatcc cacaccctgg aggatttcat ctcttgtata tgatgatctg gatccaccaa     2160 gacttgttt atgctcaggg tcaatttctt ttttctttttt tttttttttt tttctttttc     2220
tttgagactg ggtctcgctt tgttgcccag gctggagtgg agtggcgtga tcttggctta     2280
ctgcagcctt tgcctccccg gctcgagcag tcctgcctca gcctccggag tagctgggac     2340
cacaggttca tgccaccatg gccagccaac ttttgcatgt tttgtagaga tggggtctca     2400
cagtgttgcc caggctggtc tcaaactcct gggctcaggc gatccacctg tctcagcctc     2460
ccagagtgct gggattacaa ttgtgagcca ccacgtggag ctggaagggt caacatcttt     2520
tacattctgc aagcacatct gcattttcac cccaccccttc ccctccttct ccctttttat    2580
atcccatttt tatatcgatc tcttatttta caataaaact ttgctgcca                 2629
```

<210> SEQ ID NO 347
<211> LENGTH: 3442
<212> TYPE: DNA
<213> ORGANISM: Homo sapiens

<400> SEQUENCE: 347

```
agccggtgcg ccgcagacta gggcgcctcg ggccagggag cgcggaggag ccatggccac       60
cgctaacggg gccgtggaaa acgggcagcc ggacgggaag ccgccggccc tgccgcgccc      120
catccgcaac ctggaggtca agttcaccaa gatatttatc aacaatgaat ggcacgaatc      180
caagagtggg aaaaagtttg ctacatgtaa cccttcaact cgggagcaaa tatgtgaagt      240
ggaagaagga gataagcccg acgtggacaa ggctgtggag gctgcacagg ttgccttcca     300
gaggggctcg ccatggcgcc ggctggatgc cctgagtcgt gggcggctgc tgcaccagct     360
ggctgacctg gtggagaggg accgcgccac cttggccgcc ctggagacga tggatacagg     420
gaagccattt cttcatgctt ttttcatcga cctggaggggc tgtattagaa ccctcagata     480
ctttgcaggg tgggcagaca aaatccaggg caagaccatc cccacagatg acaacgtcgt     540
atgcttcacc aggcatgagc ccattggtgt ctgtggggcc atcactccat ggaacttccc     600
cctgctgatg ctggtgtgga agctggcacc cgccctctgc tgtgggaaca ccatggtcct     660
gaagcctgcg gagcagacac ctctcaccgc cctttatctc ggctctctga tcaaagaggc     720
cgggttccct ccaggagtgg tgaacattgt gccaggattc gggcccacag tgggagcagc     780
aatttcttct caccctcaga tcaacaagat cgccttcacc ggctcacaag aggttggaaa     840
actggttaaa gaagctgcgt cccggagcaa tctgaagcgg gtgacgctgg agctggggg    900
```

```
gaagaacccc tgcatcgtgt gtgcggacgc tgacttggac ttggcagtgg agtgtgccca      960
tcagggagtg ttcttcaacc aaggccagtg ttgcacggca gcctccaggg tgttcgtgga     1020
ggagcaggtc tactctgagt ttgtcaggcg gagcgtggag tatgccaaga acggcccgt     1080
gggagacccc ttcgatgtca aaacagaaca ggggcctcag attgatcaaa gcagttcga     1140
caaaatctta gagctgatcg agagtgggaa gaaggaaggg gccaagctgg aatgcggggg     1200
ctcagccatg aagacaaggg gctcttcat caaacccact gtcttctcag aagtcacaga     1260
caacatgcgg attgccaaag aggagatttt cgggccagtg caaccaatac tgaagttcaa     1320
aagtatcgaa gaagtgataa aaagagcgaa tagcaccgac tatggactca cagcagccgt     1380
gttcacaaaa aatctcgaca aagccctgaa gttggcttct gccttagagt ctggaacggt     1440
ctggatcaac tgctacaacg ccctctatgc acaggctcca tttggtggct ttaaaatgtc     1500
aggaaatggc agagaactag gtgaatacgc tttggccgaa tacacagaag tgaaaactgt     1560
caccatcaaa cttggcgaca agaaccctg aaggaaggc ggggctcctt cctcaaacat     1620
cggacggcgg aatgtggcag atgaaatgtg ctggaggaaa aaaatgacat ttctgacctt     1680
cccgggacac attcttctgg aggctttaca tctactggag ttgaatgatt gctgttttcc     1740
tctcactctc ctgtttattc accagactgg ggatgcctat aggttgtctg tgaaatcgca     1800
gtcctgcctg gggagggagc tgttggccat ttctgtgttt ccctttaaac cagatcctgg     1860
agacagtgag atactcaggg cgttgttaac agggagtggt atttgaagtg tccagcagtt     1920
gcttgaaatg ctttgccgaa tctgactcca gtaagaatgt gggaaaaccc cctgtgtgtt     1980
ctgcaagcag ggctcttgca ccagcggtct cctcagggtg gacctgctta cagagcaagc     2040
cacgcctctt tccgaggtga aggtgggacc attccttggg aaaggattca cagtaaggtt     2100
ttttggtttt tgttttttgt tttcttgttt ttaaaaaaag gatttcacag tgagaaagtt     2160
ttggttagtg cataccgtgg aagggcgcca gggtctttgt ggattgcatg ttgacattga     2220
ccgtgagatt cggcttcaaa ccaatactgc ctttggaata tgacagaatc aatagcccag     2280
agagcttagt caaagacgat atcacggtct accttaacca aggcactttc ttaagcagaa     2340
aatattgttg aggttacctt tgctgctaaa gatccaatct tctaacgcca caacagcata     2400
gcaaatccta ggataattca cctcctcatt tgacaaatca gagctgtaat tcactttaac     2460
aaattacgca tttctatcac gttcactaac agcttatgat aagtctgtgt agtcttcctt     2520
ttctccagtt ctgttaccca atttagatta gtaaagcgta cacaactgga aagactgctg     2580
taataacaca gccttgttat ttttaagtcc tattttgata ttaatttctg attagttagt     2640
aaataacacc tggattctat ggaggacctc ggtcttcatc caagtggcct gagtatttca     2700
ctggcaggtt gtgaattttt cttttcctct ttgggaatcc aaatgatgat gtgcaatttc     2760
atgttttaac ttgggaaact gaaagtgttc ccatatagct tcaaaaacaa aaacaaatgt     2820
gttatccgac ggatactttt atggttacta actagtactt tcctaattgg gaaagtagtg     2880
cttaagtttg caaattaagt tggggagggc aataataaaa tgagggcccg taacagaacc     2940
agtgtgtgta taacgaaaac catgtataaa atgggcctat cacccttgtc agagatataa     3000
attaccacat ttggcttccc ttcatcagct aacacttatc acttatacta ccataacttt     3060
gttaaatcag gatttggctt catacactga attttcagta ttttatctca gtagatata     3120
gacactaacc ttgatagtga tacgttagag ggttcctatt cttccattgt acgataatgt     3180
ctttaatatg aaatgctaca ttatttataa ttggtagagt tattgtatct ttttatagtt     3240
```

```
gtaagtacac agaggtggta tatttaaact tctgtaatat actgtattta gaaatggaaa    3300
tatatatagt gttaggtttc acttcttta aggtttaccc ctgtggtgtg gtttaaaaat    3360
ctataggcct gggaattccg atcctagctg cagatcgcat cccacaatgc gagaatgata    3420
aaataaaatt ggatatttga ga                                            3442

<210> SEQ ID NO 348
<211> LENGTH: 737
<212> TYPE: DNA
<213> ORGANISM: Homo sapiens

<400> SEQUENCE: 348
ggagtttcgc cgccgcagtc ttcgccacca tgccgcccta caccgtggtc tatttcccag      60
ttcgaggccg ctgcgcggcc ctgcgcatgc tgctggcaga tcagggccag agctggaagg     120
aggaggtggt gaccgtggag acgtggcagg agggctcact caaagcctcc tgcctatacg     180
ggcagctccc caagttccag gacggagacc tcaccctgta ccagtccaat accatcctgc     240
gtcacctggg ccgcacccct gggctctatg gaaggaccag caggaggca gccctggtgg     300 acatggtgaa tgacggcgtg gaggacctcc gctgcaaata catctccctc atctacacca     360
actatgaggc gggcaaggat gactatgtga aggcactgcc cgggcaactg aagccttttg     420
agaccctgct gtcccagaac cagggaggca agaccttcat tgtgggagac cagatctcct     480
tcgctgacta caacctgctg gacttgctgc tgatccatga ggtcctagcc cctggctgcc     540
tggatgcgtt ccccctgctc tcagcatatg tgggggcgcct cagcgcccgg cccaagctca     600
aggccttcct ggcctcccct gagtacgtga acctccccat caatggcaac gggaaacagt     660
gagggttggg gggactctga gcgggaggca gagtttgcct tccttctcc aggaccaata     720 aaatttctaa gagagct                                                   737

<210> SEQ ID NO 349
<211> LENGTH: 5189
<212> TYPE: DNA
<213> ORGANISM: Homo sapiens

<400> SEQUENCE: 349
atggccaagt cgggtggctg cggcgcggga gccggcgtgg gcggcggcaa cggggcactg      60
acctgggtga acaatgctgc aaaaaaagaa gagtcagaaa ctgccaacaa aaatgattct     120
tcaaagaagt tgtctgttga gagagtgtat cagaagaaga cacaacttga acacattctt     180
cttcgtcctg atacatatat tgggtcagtg gagccattga cgcagttcat gtgggtgtat     240
gatgaagatg taggaatgaa ttgcaggag gttacctttg tgccaggttt atacaagatc     300
tttgatgaaa ttttggttaa tgctgctgac aataaacaga gggataagaa catgacttgt     360
attaaagttt ctattgatcc tgaatctaac attataagca tttggaataa tgggaaaggc     420
attccagtag tagaacacaa ggtagagaaa gtttatgttc ctgctttaat ttttggacag     480
cttttaacat ccagtaacta tgatgatgat gagaaaaaag ttacaggtgg tcgtaatggt     540
tatggtgcaa actttgtaa tattttcagt acaaagttta cagtagaaac agcttgcaaa     600
gaatacaaac acagttttaa gcagacatgg atgaataata tgatgaagac ttctgaagcc     660
aaaattaaac attttgatgg tgaagattac acatgcataa cattccaacc agatctgtcc     720
aaatttaaga tggaaaaact tgacaaggat attgtggccc tcatgactag aagggcatat     780
gatttggctg gttcgtgtag aggggtcaag gtcatgtttta atggaaagaa attgcctgta     840
aatggatttc gcagttatgt agatctttat gtgaaagaca aattggatga aactgggggtg     900
```

| | |
|---|---|
| gccctgaaag ttattcatga gcttgcaaat gaaagatggg atgtttgtct cacattgagt | 960 |
| gaaaaaggat tccagcaaat cagctttgta aatagtattg caactacaaa aggtggacgg | 1020 |
| cacgtggatt atgtggtaga tcaagttgtt ggtaaactga ttgaagtagt taagaaaaag | 1080 |
| aacaaagctg gtgtatcagt gaaaccattt caagtaaaaa accatatatg gttttttatt | 1140 |
| aattgcctta ttgaaaatcc aacttttgat tctcagacta aggaaaacat gactctgcag | 1200 |
| cccaaaagtt ttgggtctaa atgccagctg tcagaaaaat ttttttaaagc agcctctaat | 1260 |
| tgtggcattg tagaaagtat cctgaactgg gtgaaattta aggctcagac tcagctgaat | 1320 |
| aagaagtgtt catcagtaaa atacagtaaa atcaaaggta ttcccaaact ggatgatgct | 1380 |
| aatgatgctg gtggtaaaca ttccctggag tgtacactga tattaacaga gggagactct | 1440 |
| gccaaatcac tggctgtgtc tggattaggt gtgattggac gagacagata cggagttttt | 1500 |
| ccactcaggg gcaaaattct taatgtacgg gaagcttctc ataaacagat catggaaaat | 1560 |
| gctgaaataa ataatattat taaaatagtt ggtctacaat ataagaaaag ttacgatgat | 1620 |
| gcagaatctc tgaaaacctt acgctatgga aagattatga ttatgaccga tcaggatcaa | 1680 |
| gatggttctc acataaaagg cctgcttatt aatttcatcc atcacaattg ccatcacttt | 1740 |
| ttgaagcatg gttttcttga agagttcatt actcctattg taaaggcaag caaaaataag | 1800 |
| caggaacttt ccttctacag tattcctgaa tttgacgaat ggaaaaaaca tatagaaaac | 1860 |
| cagaaagcct ggaaaataaa gtactataaa ggattgggta ctagtacagc taaagaagca | 1920 |
| aaggaatatt ttgctgatat ggaaaggcat cgcatcttgt ttagatatgc tggtcctgaa | 1980 |
| gatgatgctg ccattacctt ggcatttagt aagaagaaga ttgatgacag aaaagaatgg | 2040 |
| ttaacaaatt ttatggaaga ccggagacag cgtaggctac atggcttacc agagcaattt | 2100 |
| ttatatggta ctgcaacaaa gcatttgact tataatgatt tcatcaacaa ggaattgatt | 2160 |
| ctcttctcaa actcagacaa tgaaagatct ataccatctc ttgttgatgg ctttaaacct | 2220 |
| ggccagcgga agttttatt tacctgtttc aagaggaatg ataaacgtga agtaaaagtt | 2280 |
| gcccagttgg ctggctctgt tgctgagatg tcggcttatc atcatggaga acaagcattg | 2340 |
| atgatgacta ttgtgaattt ggctcagaac tttgtgggaa gtaacaacat taacttgctt | 2400 |
| cagcctattg gtcagtttgg aactcggctt catggtggca aagatgctgc aagccctcgt | 2460 |
| tatattttca caatgttaag cactttagca aggctacttt ttcctgctgt ggatgacaac | 2520 |
| ctccttaagt tcctttatga tgataatcaa cgtgtagagc ctgagtggta tattcctata | 2580 |
| attcccatgg ttttaataaa tggtgctgag ggcattggta ctggatgggc ttgtaaacta | 2640 |
| cccaactatg atgctaggga aattgtgaac aatgtcagac gaatgctaga tggcctggat | 2700 |
| cctcatccca tgcttccaaa ctacaaaaac tttaaaggca cgattcaaga acttggtcaa | 2760 |
| aaccagtatg cagtcagtgg tgaaatattt gtagtggaca gaaacacagt agaaattaca | 2820 |
| gagcttccag ttagaacttg gacacaggta tataagaac aggttttaga acctatgcta | 2880 |
| aatggaacag ataaaacacc agcattaatt tctgattata agaatatca tactgacaca | 2940 |
| actgtgaaat ttgtggtgaa aatgactgaa gagaaactag cacaagcaga agctgctgga | 3000 |
| ctgcataaag ttttttaaact tcaaactact cttacttgta attccatggt acttttttgat | 3060 |
| catatgggat gtctgaagaa atatgaaact gtgcaagaca ttctgaaaga attctttgat | 3120 |
| ttacgattaa gttattacgg tttacgtaag gagtggcttg tgggaatgtt gggagcagaa | 3180 |
| tctacaaagc ttaacaatca agcccgtttc attttagaga agatacaagg gaaaattact | 3240 |

```
atagagaata ggtcaaagaa agatttgatt caaatgttag tccagagagg ttatgaatct      3300
gacccagtga aagcctggaa agaagcacaa gaaaaggcag cagaagagga tgaaacacaa      3360
aaccagcatg atgatagttc ctccgattca ggaactcctt caggcccaga ttttaattat      3420
attttaaata tgtctctgtg gtctcttact aaagaaaaag ttgaagaact gattaaacag      3480
agagatgcaa aagggcgaga ggtcaatgat cttaaaagaa aatctccttc agatctttgg      3540
aaagaggatt tagcggcatt tgttgaagaa ctggataaag tggaatctca agaacgagaa      3600
gatgttctgg ctggaatgtc tggaaaagca attaaaggta agttggcaa acctaaggtg       3660 aagaaactcc agttggaaga gacaatgccc tcacctatg gcagaagaat aattcctgaa       3720
attacagcta tgaaggcaga tgccagcaaa aagttgctga agaagaagaa gggtgatctt      3780
gatactgcag cagtaaaagt ggaatttgat gaagaattca gtggagcacc agtagaaggt      3840
gcaggagaag aggcattgac tccatcagtt cctataaata aaggtcccaa acctaagagg      3900
gagaagaagg agcctggtac cagagtgaga aaaacaccta catcatctgg taaacctagt      3960
gcaaagaaag tgaagaaacg gaatccttgg tcagatgatg aatccaagtc agaaagtgat      4020
ttggaagaaa cagaacctgt ggttattcca agagattctt tgcttaggag agcagcagcc      4080
gaaagaccta atacacatt tgatttctca gaagaagagg atgatgatgc tgatgatgat       4140
gatgatgaca ataatgattt agaggaattg aaagttaaag catctcccat aacaaatgat      4200
ggggaagatg aatttgttcc ttcagatggg ttagataaag atgaatatac attttcacca      4260
ggcaaatcaa aagccactcc agaaaaatct ttgcatgaca aaaaagtca ggattttgga       4320 aatctcttct catttccttc atattctcag aagtcagaag atgattcagc taaatttgac      4380
agtaatgaag aagattctgc ttctgttttt tcaccatcat ttggtctgaa acagacagat      4440
aaagttccaa gtaaaacggt agctgctaaa aagggaaaac cgtcttcaga tacagtccct      4500
aagcccaaga gagcccccaaa acagaagaaa gtagtagagg ctgtaaactc tgactcggat     4560
tcagaatttg gcattccaaa gaagactaca acaccaaaag gtaaaggccg aggggcaaag      4620
aaaaggaaag catctggctc tgaaaatgaa ggcgattata accctggcag gaaaacatcc      4680
aaaacaacaa gcaagaaacc gaagaagaca tcttttgatc aggattcaga tgtggacatc      4740
ttcccctcag acttccctac tgagccacct tctctgccac gaaccggtcg ggctaggaaa      4800
gaagtaaaat attttgcaga gtctgatgaa gaagaagatg atgttgattt tgcaatgttt      4860
aattaagtgc ccaaagagca caaacatttt tcaacaaata tcttgtgttg tccttttgtc      4920
ttctctgtct cagacttttg tacatctggc ttattttaat gtgatgatgt aattgacggt      4980 ttttattat tgtggtaggc ctttaacat tttgttctta cacatacagt tttatgctct         5040
tttttactca ttgaaatgtc acgtactgtc tgattggctt gtagaattgt tatagactgc      5100
cgtgcattag cacagatttt aattgtcatg gttacaaact acagacctgc tttttgaaat      5160
gaaatttaaa cattaaaaat ggaactgtg                                        5189
```

<210> SEQ ID NO 350
<211> LENGTH: 1536
<212> TYPE: DNA
<213> ORGANISM: Homo sapiens

<400> SEQUENCE: 350

```
gggggggggg ggaccacttg gcctgcctcc gtcccgccgc gccacttggc ctgcctccgt        60
cccgccgcgc cacttcgcct gcctccgtcc ccgccccgcc gcgccatgcc tgtggccggc       120
tcggagctgc cgcgccggcc cttgcccccc gccgcacagg agcgggacgc cgagccgcgt       180
```

```
ccgccgcacg gggagctgca gtacctgggg cagatccaac acatcctccg ctgcggcgtc    240
aggaaggacg accgcacggg caccggcacc ctgtcggtat tcggcatgca ggcgcgctac    300
agcctgagag atgaattccc tctgctgaca accaaacgtg tgttctggaa gggtgttttg    360
gaggagttgc tgtggtttat caagggatcc acaaatgcta aagagctgtc ttccaaggga    420
gtgaaaatct gggatgccaa tggatcccga actttttgg acagcctggg attctccacc     480
agagaagaag gggacttggg cccagtttat ggcttccagt ggaggcattt tggggcagaa    540
tacagagata tggaatcaga ttattcagga caggagttg accaactgca aagagtgatt     600
gacaccatca aaaccaaccc tgacgacaga agaatcatca tgtgcgcttg gaatccaaga    660
gatcttcctc tgatggcgct gcctccatgc catgccctct gccagttcta tgtggtgaac    720
agtgagctgt cctgccagct gtaccagaga tcgggagaca tgggcctcgg tgtgcctttc    780
aacatcgcca gctacgccct gctcacgtac atgattgcgc acatcacggg cctgaagcca    840
ggtgacttta tacacacttt gggagatgca catatttacc tgaatcacat cgagccactg    900
aaaattcagc ttcagcgaga acccagacct ttcccaaagc tcaggattct tcgaaaagtt    960
gagaaaattg atgacttcaa agctgaagac tttcagattg aagggtacaa tccgcatcca   1020
actattaaaa tggaaatggc tgtttagggt gctttcaaag gagcttgaag gatattgtca   1080
gtctttaggg gttgggctgg atgccgaggt aaaagttctt tttgctctaa aagaaaaagg   1140
aactaggtca aaaatctgtc cgtgacctat cagttattaa ttttaagga tgttgccact    1200
ggcaaatgta actgtgccag ttctttccat aataaaaggc tttgagttaa ctcactgagg   1260
gtatctgaca atgctgaggt tatgaacaaa gtgaggagaa tgaaatgtat gtgctcttag   1320
caaaaacatg tatgtgcatt tcaatcccac gtacttataa agaaggttgg tgaatttcac   1380
aagctatttt tggaatattt ttagaatatt ttaagaattt cacaagctat tccctcaaat   1440
ctgagggagc tgagtaacac catcgatcat gatgtagagt gtggttatga actttatagt   1500
tgttttatat gttgctataa taaagaagtg ttctgc                             1536

<210> SEQ ID NO 351
<211> LENGTH: 2386
<212> TYPE: DNA
<213> ORGANISM: Homo sapiens

<400> SEQUENCE: 351
ggaggaggaa gcaagcgagg gggctggttc ctgagcttcg caattcctgt gtcgccttct     60
gggctcccag cctgccgggt cgcatgatcc ctccggccgg agctggtttt tttgccagcc    120
accgcgaggc cggctgagtt accggcatcc ccgcagccac ctcctctccc gacctgtgat    180
acaaaagatc ttccgggggc tgcacctgcc tgcctttgcc taaggcggat ttgaatctct    240
ttctctccct tcagaatctt atcttggctt tggatcttag aagagaatca ctaaccagag    300
acgagactca gtgagtgagc aggtgttttg gacaatggac tggttgagcc catccctatt    360
ataaaaatgt ctcagagcaa ccgggagctg gtggttgact ttctctccta caagcttttcc   420
cagaaaggat acagctggag tcagtttagt gatgtggaag agaacaggac tgaggcccca    480
gaagggactg aatcggagat ggagaccccc agtgccatca atggcaaccc atcctggcac    540
ctggcagaca gccccgcggt gaatggagcc actggccaca gcagcagttt ggatgcccgg    600
gaggtgatcc ccatgcagcc agtaaagcaa gcgctgaggg aggcaggcga cgagtttgaa    660
ctgcggtacc ggcgggcatt cagtgacctg acatcccagc tccacatcac cccagggaca    720
```

-continued

```
gcatatcaga gctttgaaca ggatactttt gtggaactct atgggaacaa tgcagcagcc      780
gagagccgaa agggccagga acgcttcaac cgctggttcc tgacgggcat gactgtggcc      840
ggcgtggttc tgctgggctc actcttcagt cggaaatgac cagacactga ccatccactc      900
taccctccca ccccttctc tgctccacca catcctccgt ccagccgcca ttgccaccag       960
gagaaccact acatgcagcc catgcccacc tgcccatcac agggttgggc ccagatctgg     1020
tcccttgcag ctagttttct agaatttatc acacttctgt gagaccccca cacctcagtt     1080
cccttggcct cagaattcac aaaatttcca caaaatctgt ccaaggagg ctggcaggta      1140
tggaagggtt tgtggctggg ggcaggaggg ccctacctga ttggtgcaac ccttacccct     1200
tagcctccct gaaaatgttt ttctgccagg gagcttgaaa gttttcagaa cctcttcccc     1260
agaaaggaga ctagattgcc tttgttttga tgtttgtggc ctcagaattg atcatttttcc    1320
ccccactctc cccacactaa cctgggttcc ctttccttcc atccctaccc cctaagagcc     1380
atttaggggc cacttttgac tagggattca ggctgcttgg gataaagatg caaggaccag     1440
gactccctcc tcacctctgg actggctaga gtcctcactc ccagtccaaa tgtcctccag     1500
aagcctctgg ctagaggcca gccccaccca ggagggaggg ggctatagct acaggaagca     1560
ccccatgcca aagctagggt ggcccttgca gttcagcacc accctagtcc cttcccctcc     1620
ctggctccca tgaccatact gagggaccaa ctgggcccaa cacagatgcc ccagagctgt     1680
ttatggcctc agctgcctca cttcctacaa gagcagcctg tggcatcttt gccttgggct     1740
gctcctcatg gtgggttcag gggactcagc cctgaggtga aagggagcta tcaggaacag     1800
ctatgggagc cccagggtct tccctacctc aggcaggaag ggcaggaagg agagcctgct     1860
gcatggggtg gggtagggct gactagaagg gccagtcctg cctggccagg cagatctgtg     1920
ccccatgcct gtccagcctg gcagccagg ctgccaaggc cagagtggcc tggccaggag      1980
ctcttcaggc ctccctctct cttctgctcc acccttggcc tgtctcatcc caggggtcc      2040
cagccacccc gggctctctg ctgtacatat ttgagactag ttttttattcc ttgtgaagat    2100
gatatactat ttttgttaag cgtgtctgta tttatgtgtg aggagctgct ggcttgcagt     2160
gcgcgtgcac gtggagagct ggtgcccgga gattggacgg cctgatgctc cctcccctgc     2220
cctggtccag ggaagctggc cgagggtcct ggctcctgag gggcatctgc ccctccccca     2280
acccccaccc cacacttgtt ccagctcttt gaaatagtct gtgtgaaggt gaaagtgcag     2340
ttcagtaata aactgtgttt actcagtgaa aaaaaaaaa aaaaaa                     2386
```

<210> SEQ ID NO 352
<211> LENGTH: 1270
<212> TYPE: DNA
<213> ORGANISM: Homo sapiens

<400> SEQUENCE: 352

```
agacgttcgc acacctgggt gccagcgccc cagaggtccc gggacagccc gaggcgccgc       60
gcccgccgcc ccgagctccc caagccttcg agagcggcgc acactcccgg tctccactcg      120
ctcttccaac acccgctcgt tttggcggca gctcgtgtcc cagagaccga gttgccccag      180
agaccgagac gccgccgctg cgaaggacca atgagagccc cgctgctacc gccggcgccg      240
gtggtgctgt cgctcttgat actcggctca ggccattatg ctgctggatt ggacctcaat      300
gacacctact ctgggaagcg tgaaccattt tctgggaccc acagtgctga tggatttgag      360
gttacctcaa gaagtgagat gtcttcaggg agtgagattt ccctgtgag tgaaatgcct       420
tctagtagtg aaccgtcctc gggagccgac tatgactact cagaagagta tgataacgaa      480
```

-continued

| | |
|---|---|
| ccacaaatac ctggctatat tgtcgatgat tcagtcagag ttgaacaggt agttaagccc | 540 |
| ccccaaaaca agacggaaag tgaaaatact tcagataaac ccaaaagaaa gaaaaaggga | 600 |
| ggcaaaaatg gaaaaaatag aagaaacaga aagaagaaaa atccatgtaa tgcagaattt | 660 |
| caaaatttct gcattcacgg agaatgcaaa tatatagagc acctggaagc agtaacatgc | 720 |
| aaatgtcagc aagaatattt cggtgaacgg tgtggggaaa agtccatgaa aactcacagc | 780 |
| atgattgaca gtagtttatc aaaaattgca ttagcagcca tagctgcctt tatgtctgct | 840 |
| gtgatcctca cagctgttgc tgttattaca gtccagctta aagacaata cgtcaggaaa | 900 |
| tatgaaggag aagctgagga acgaagaaa cttcgacaag agaatggaaa tgtacatgct | 960 |
| atagcataac tgaagataaa attacaggat atcacattgg agtcactgcc aagtcatagc | 1020 |
| cataaatgat gagtcggtcc tctttccagt ggatcataag acaatggacc ttttttgtta | 1080 |
| tgatggtttt aaactttcaa ttgtcacttt ttatgctatt tctgtatata aaggtgcacg | 1140 |
| aaggtaaaaa gtattttttc aagttgtaaa taatttattt aatatttaat ggaagtgtat | 1200 |
| ttattttaca gctcattaaa cttttttaac caaacagaaa aaaaaaaaaa aaaaaaaaa | 1260 |
| aaaaaaaaaa | 1270 |

<210> SEQ ID NO 353
<211> LENGTH: 1600
<212> TYPE: DNA
<213> ORGANISM: Homo sapiens

<400> SEQUENCE: 353

| | |
|---|---|
| gccccgccgc cggcagtgga ccgctgtgcg cgaaccctga accctacggt cccgacccgc | 60 |
| gggcgaggcc gggtacctgg gctgggatcc ggagcaagcg ggcagggca gcgccctaag | 120 |
| caggcccgga gcgatggcag ccttgatgac cccgggaacc ggggccccac ccgcgcctgg | 180 |
| tgacttctcc ggggaaggga gccagggact tcccgaccct tcgccagagc ccaagcagct | 240 |
| cccggagctg atccgcatga agcgagacgg aggccgcctg agcgaagcgg acatcagggg | 300 |
| cttcgtggcc gctgtggtga atgggagcgc gcagggcgca cagatcgggg ccatgctgat | 360 |
| ggccatccga cttcggggca tggatctgga ggagacctcg gtgctgaccc aggccctggc | 420 |
| tcagtcggga cagcagctgg agtggccaga ggcctggcgc cagcagcttg tggacaagca | 480 |
| ttccacaggg ggtgtgggtg acaaggtcag cctggtcctc gcacctgccc tggcggcatg | 540 |
| tggctgcaag gtgccaatga tcagcggacg tggtctgggg cacacaggag gcaccttgga | 600 |
| taagctggag tctattcctg gattcaatgt catccagagc ccagagcaga tgcaagtgct | 660 |
| gctggaccag gcgggctgct gtatcgtggg tcagagtgag cagctggttc ctgcggacgg | 720 |
| aatcctatat gcagccagag atgtgacagc caccgtggac agcctgccac tcatcacagc | 780 |
| ctccattctc agtaagaaac tcgtggaggg gctgtccgct ctggtggtgg acgttaagtt | 840 |
| cggagggggcc gccgtcttcc ccaaccagga gcaggcccgg gagctggcaa agacgctggt | 900 |
| tggcgtggga gccagcctag gcttcgggt cgcggcagcg ctgaccgcca tggacaagcc | 960 |
| cctgggtcgc tgcgtgggcc acgccctgga ggtggaggag gcgctgctct gcatggacgg | 1020 |
| cgcaggcccg ccagacttaa gggacctggt caccacgctc ggggcgcgcc tgctctggct | 1080 |
| cagcggacac gcggggactc aggctcaggg cgctgcccgg gtggccgcgg cgctggacga | 1140 |
| cggctcggcc cttggccgct tcgagcggat gctggcggcg cagggcgtgg atccggtct | 1200 |
| ggcccgagcc ctgtgctcgg gaagtccgc agaacgccgc cagctgctgc ctcgcgcccg | 1260 |

```
ggagcaggag gagctgctgg cgcccgcaga tggcaccgtg gagctggtcc gggcgctgcc      1320
gctggcgctg gtgctgcacg agctcggggc cgggcgcagc cgcgctgggg agccgctccg      1380
cctgggggtg ggcgcagagc tgctggtcga cgtgggtcag aggctgcgcc gtgggacccc      1440
ctggctccgc gtgcaccggg acggcccgc gctcagcggc ccgcagagcc gcgccctgca       1500
ggaggcgctc gtactctccg accgcgcgcc attcgccgcc ccctcgccct tcgcagagct      1560
cgttctgccg ccgcagcaat aaagctcctt tgccgcgaaa                           1600

<210> SEQ ID NO 354
<211> LENGTH: 1842
<212> TYPE: DNA
<213> ORGANISM: Homo sapiens

<400> SEQUENCE: 354
cgatcagatc gatctaagat ggcgactgtc gaaccggaaa ccaccccta tcctaatccc        60 ccgactacag aagaggagaa aacgaatct aatcaggagg ttgctaaccc agaacactat       120
attaaacatc ccctacagaa cagatgggca ctctggtttt ttaaaaatga taaaagcaaa      180
acttggcaag caaacctgcg gctgatctcc aagtttgata ctgttgaaga cttttgggct      240
ctgtacaacc atatccagtt gtctagtaat ttaatgcctg gctgtgacta ctcactttt       300 aaggatggta ttgagcctat gtgggaagat gagaaaaaca aacggggagg acgatggcta      360
attacattga acaaacagca gagacgaagt gacctcgatc gcttttggct agagacactt      420
ctgtgcctta ttggagaatc ttttgatgac tacagtgatg atgtatgtgg cgctgttgtt      480
aatgttagag ctaaaggtga taagatagca atatggacta ctgaatgtga aaacagagaa      540
gctgttacac atatagggag gtatacaag gaaaggttag acttcctcc aaagatagtg        600 attggttatc agtcccacgc agacacagct actaagagcg gctccaccac taaaaatagg      660
tttgttgttt aagaagacac cttctgagta ttctcatagg agactgcgtc aagcaatcga      720
gatttgggag ctgaaccaaa gcctcttcaa aaagcagagt ggactgcatt taaatttgat      780
ttccatctta atgttactca gatataagag aagtctcatt cgcctttgtc ttgtacttct      840
gtgttcattt tttttttttt ttttggcta gagtttccac tatcccaatc aaagaattac      900
agtacacatc cccagaatcc ataaatgtgt tcctggccca ctctgtaata gttcagtaga      960
attaccatta attacataca gatttacct atccacaata gtcagaaaac aacttggcat      1020
ttctatactt tacaggaaaa aaaattctgt tgttccattt tatgcagaag catattttgc      1080
tggtttgaaa gattatgatg catacagttt tctagcaatt ttctttgttt cttttttacag     1140 cattgtcttt gctgtactct tgctgatggc tgctagattt taatttatt gtttccctac      1200 ttgataatat tagtgattct gatttcagtt tttcatttgt tttgcttaaa tttttttttt      1260 tttttttcctc atgtaacatt ggtgaaggat ccaggaatat gacacaaagg tggaataaac      1320
attaattttg tgcattcttt ggtaatttt tttgtttttt gtaactacaa agctttgcta      1380
caaatttatg catttcattc aaatcagtga tctatgtttg tgtgatttcc taaacataat      1440
tgtggattat aaaaaatgta acatcataat tacattccta actagaatta gtatgtctgt      1500
ttttgtatct ttatgctgta ttttaacact tgtattact taggttattt tgctttggtt      1560
aaaaatggct caagtagaaa agcagtccca ttcatattaa gacagtgtac aaaactgtaa      1620
ataaaatgtg tacagtgaat tgtcttttag acaactagat ttgtcctttt atttctccat      1680
ctttatagaa ggaatttgta cttccttattg caggcaagtc tctatattat gtcctctttt      1740
gtggtgtctt ccatgtgaac agcataagtt tggagcacta gtttgattat tatgtttatt      1800
```

```
acaatttta ataaattgaa taggtagtat catatatatg ga            1842

<210> SEQ ID NO 355
<211> LENGTH: 4975
<212> TYPE: DNA
<213> ORGANISM: Homo sapiens

<400> SEQUENCE: 355
ctctcacaca cacacacccc tccctgcca tccctcccg gactccggct ccggctccga    60
ttgcaatttg caacctccgc tgccgtcgcc gcagcagcca ccaattcgcc agcggttcag   120
gtggctcttg cctcgatgtc ctagcctagg ggccccgggg ccggacttgg ctgggctccc   180
ttcaccctct gcggagtcat gagggcgaac gacgctctgc aggtgctggg cttgcttttc   240
agcctggccc ggggctccga ggtgggcaac tctcaggcag tgtgtcctgg gactctgaat   300
ggcctgagtg tgaccggcga tgctgagaac caataccaga cactgtacaa gctctacgag   360
aggtgtgagg tggtgatggg gaaccttgag attgtgctca cgggacacaa tgccgacctc   420
tccttcctgc agtggattcg agaagtgaca ggctatgtcc tcgtggccat gaatgaattc   480
tctactctac cattgcccaa cctccgcgtg gtgcgaggga cccaggtcta cgatgggaag   540
tttgccatct tcgtcatgtt gaactataac accaactcca gccacgctct gcgccagctc   600
cgcttgactc agctcaccga gattctgtca ggggtgtttt atattgagaa gaacgataag   660
ctttgtcaca tggacacaat tgactggagg gacatcgtga gggaccgaga tgctgagata   720
gtggtgaagg acaatggcag aagctgtccc ccctgtcatg aggtttgcaa ggggcgatgc   780
tgggggcctg gatcagaaga ctgccagaca ttgaccaaga ccatctgtgc tcctcagtgt   840
aatggtcact gctttgggcc caaccccaac cagtgctgcc atgatgagtg tgccgggggc   900
tgctcaggcc ctcaggacac agactgcttt gcctgccggc acttcaatga cagtggagcc   960
tgtgtacctc gctgtccaca gcctcttgtc tacaacaagc taactttcca gctgaaccc   1020
aatccccaca ccaagtatca gtatggagga gtttgtgtag ccagctgtcc cataactttt  1080
gtggtggatc aaacatcctg tgtcagggcc tgtcctcctg acaagatgga agtagataaa  1140
aatgggctca agatgtgtga gccttgtggg ggactatgtc ccaaagcctg tgagggaaca  1200
ggctctggga gccgcttcca gactgtgac tcgagcaaca ttgatggatt tgtgaactgc  1260
accaagatcc tgggcaacct ggactttctg atcaccggcc tcaatggaga ccctggcac   1320
aagatccctg ccctggaccc agagaagctc aatgtcttcc ggacagtacg ggagatcaca  1380
ggttacctga acatccagtc ctggccgccc cacatgcaca acttcagtgt tttttccaat  1440
ttgacaacca ttggaggcag aagcctctac aaccgggct tctcattgtt gatcatgaag  1500
aacttgaatg tcacatctct gggcttccga tccctgaagg aaattagtgc tgggcgtatc  1560
tatataagtg ccaataggca gctctgctac caccactctt tgaactggac caaggtgctt  1620
cgggggccta cggaagagcg actagacatc aagcataatc ggccgcgcag agactgcgtg  1680
gcagagggca aagtgtgtga cccactgtgc tcctctgggg gatgctgggg cccaggccct  1740
ggtcagtgct tgtcctgtcg aaattatagc cgaggaggtg tctgtgtgac ccactgcaac  1800
tttctgaatg gggagcctcg agaatttgcc catgaggccg aatgcttctc ctgccacccg  1860
gaatgccaac ccatgggggg cactgccaca tgcaatggct cgggctctga tacttgtgct  1920
caatgtgccc attttcgaga tgggccccac tgtgtgagca gctgccccca tggagtccta  1980
ggtgccaagg gcccaatcta caagtaccca gatgttcaga atgaatgtcg gccctgccat  2040
```

```
gagaactgca cccaggggtg taaaggacca gagcttcaag actgtttagg acaaacactg    2100
gtgctgatcg gcaaaaccca tctgacaatg gctttgacag tgatagcagg attggtagtg    2160
attttcatga tgctgggcgg cacttttctc tactggcgtg ggcgccggat tcagaataaa    2220
agggctatga ggcgatactt ggaacggggt gagagcatag agcctctgga ccccagtgag    2280
aaggctaaca aagtcttggc cagaatcttc aaagagacag agctaaggaa gcttaaagtg    2340
cttggctcgg gtgtctttgg aactgtgcac aaaggagtgt ggatccctga gggtgaatca    2400
atcaagattc cagtctgcat taaagtcatt gaggacaaga gtggacggca gagttttcaa    2460
gctgtgacag atcatatgct ggccattggc agcctggacc atgcccacat tgtaaggctg    2520
ctgggactat gcccagggtc atctctgcag cttgtcactc aatatttgcc tctgggttct    2580
ctgctggatc atgtgagaca acaccggggg gcactgggc cacagctgct gctcaactgg    2640
ggagtacaaa ttgccaaggg aatgtactac cttgaggaac atggtatggt gcatagaaac    2700
ctggctgccc gaaacgtgct actcaagtca cccagtcagg ttcaggtggc agattttggt    2760
gtggctgacc tgctgcctcc tgatgataag cagctgctat acagtgaggc caagactcca    2820
attaagtgga tggcccttga gagtataccac tttgggaaat acacacacca gagtgatgtc    2880
tggagctatg gtgtgacagt ttgggagttg atgaccttcg gggcagagcc ctatgcaggg    2940
ctacgattgg ctgaagtacc agacctgcta gagaagggg agcggttggc acagccccag    3000
atctgcacaa ttgatgtcta catggtgatg gtcaagtgtt ggatgattga tgagaacatt    3060
cgcccaacct ttaaagaact agccaatgag ttcaccagga tggcccgaga cccaccacgg    3120
tatctggtca taaagagaga gagtgggcct ggaatagccc ctgggccaga gccccatggt    3180
ctgacaaaca agaagctaga ggaagtagag ctggagccag aactagacct agacctagac    3240
ttggaagcag aggaggacaa cctggcaacc accacactgg gctccgccct cagcctacca    3300
gttgaaacac ttaatcggcc acgtgggagc cagagccttt taagtccatc atctggatac    3360
atgcccatga accagggtaa tcttgggggg tcttgccagg agtctgcagt ttctgggagc    3420
agtgaacggt gcccccgtcc agtctctcta cacccaatgc cacggggatg cctggcatca    3480
gagtcatcag agggggcatgt aacaggctct gaggctgagc tccaggagaa agtgtcaatg    3540
tgtagaagcc ggagcaggag ccggagccca cggccacgcg gagatagcgc ctaccattcc    3600
cagcgccaca gtctgctgac tcctgttacc ccactctccc cacccgggtt agaggaagag    3660
gatgtcaacg gttatgtcat gccagataca cacctcaaag gtactccctc ctcccgggaa    3720
ggcacccttt cttcagtggg tctcagttct gtcctgggta ctgaagaaga agatgaagat    3780
gaggagtatg aatacatgaa ccggaggaga aggcacagtc cacctcatcc ccctaggcca    3840
agttcccttg aggagctggg ttatgagtac atggatgtgg ggtcagacct cagtgcctct    3900
ctgggcagca cacagagttg cccactccac cctgtaccca tcatgcccac tgcaggcaca    3960
actccagatg aagactatga atatatgaat cggcaacgat atgaggtgg tcctgggggt    4020
gattatgcag ccatggggc ctgcccagca tctgagcaag ggtatgaaga gatgagagct    4080
tttcagggggc ctggacatca ggccccccat gtccattatg cccgcctaaa aactctacgt    4140
agcttagagg ctacagactc tgcctttgat aaccctgatt actggcatag caggcttttc    4200
cccaaggcta atgcccagag aacgtaactc ctgctccctg tggcactcag ggagcattta    4260
atggcagcta gtgcctttag agggtaccgt cttctcccta ttccctctct ctcccaggtc    4320
ccagccccctt ttccccagtc ccagacaatt ccattcaatc tttggaggct tttaaacatt    4380
ttgacacaaa attcttatgg tatgtagcca gctgtgcact ttcttctctt tcccaacccc    4440
```

```
aggaaaggtt ttccttattt tgtgtgcttt cccagtccca ttcctcagct tcttcacagg      4500
cactcctgga gatatgaagg attactctcc atatcccttc ctctcaggct cttgactact      4560
tggaactagg ctcttatgtg tgcctttgtt tcccatcaga ctgtcaagaa gaggaaaggg      4620
aggaaaccta gcagaggaaa gtgtaatttt ggtttatgac tcttaacccc ctagaaagac      4680
agaagcttaa aatctgtgaa gaaagaggtt aggagtagat attgattact atcataattc      4740
agcacttaac tatgagccag gcatcatact aaacttcacc tacattatct cacttagtcc      4800
tttatcatcc ttaaaacaat tctgtgacat acatattatc tcattttaca caaagggaag      4860
tcgggcatgg tggctcatgc ctgtaatctc agcactttgg gaggctgagg cagaaggatt      4920
acctgaggca aggagtttga gaccagctta gccaacatag taagacccccc atctc          4975
```

<210> SEQ ID NO 356
<211> LENGTH: 4627
<212> TYPE: DNA
<213> ORGANISM: Homo sapiens

<400> SEQUENCE: 356

```
tcacttgcct gatatttcca gtgtcagagg gacacagcca acgtggggtc ccttctaggc       60
tgacagccgc tctccagcca ctgccgcgag cccgtctgct cccgccctgc ccgtgcactc      120
tccgcagccg ccctccgcca agcccagcg cccgctccca tcgccgatga ccgcggggag      180
gaggatggag atgctctgtg ccggcagggt ccctgcgctg ctgctctgcc tgggtttcca      240
tcttctacag gcagtcctca gtacaactgt gattccatca tgtatcccag gagagtccag      300
tgataactgc acagctttag ttcagacaga agacaatcca cgtgtggctc aagtgtcaat      360
aacaaagtgt agctctgaca tgaatggcta ttgtttgcat ggacagtgca tctatctggt      420
ggacatgagt caaaactact gcaggtgtga agtgggttat actggtgtcc gatgtgaaca      480
cttcttttta accgtccacc aacctttaag caaagagtat gtggctttga ccgtgattct      540
tattattttg tttcttatca cagtcgtcgg ttccacatat tatttctgca gatggtacag      600
aaatcgaaaa agtaaagaac caaagaagga atatgagaga gttacctcag ggatccaga       660 gttgccgcaa gtctgaatgg cgccatcaaa cttatgggca gggataacag tgtgcctggt      720
taatattaat attccatttt attaataata tttatgttgg gtcaagtgtt aggtcaataa      780
cactgtattt taatgtactt gaaaaatgtt tttatttttg ttttattttt gacagactat      840
ttgctaatgt ataatgtgca gaaaatattt aatatcaaaa gaaaattgat atttttatac      900
aagtaatttc ctgagctaaa tgcttcattg aaagcttcaa agtttatatg cctggtgcac      960
agtgcttaga agtaagcaat tcccaggtca tagctcaaga attgttagca aatgacagat     1020
ttctgtaagc ctatatatat agtcaaatcg atttagtaag tatgtttttt atgttcctca     1080
aatcagtgat aattggtttg actgtaccat ggtttgatat gtagttggca ccatggtatc     1140
atatattaaa acaataatgc aattagaatt tgggagaagc aaatataggt cctgtgttaa     1200
acactacaca tttgaaacaa gctaaccctg gggagtctat ggtctcttca ctcaggtctc     1260
agctataatt ctgttatatg aggggcagtg gacagttccc tatgccaact cacgactcct     1320
acaggtacta gtcactcatc taccagattc tgcctatgta aaatgaattg aaaaacaatt     1380
ttctgtaatc ttttattaa gtagtgggca tttcatagct tcacaatgtt cctttttgt      1440 atattacaac atttatgtga ggtaattatt gctcaacaga caattagaaa aaagtccaca     1500
cttgaagcct aaatttgtgc tttttaagaa tatttttaga ctatttcttt ttatagggggc    1560
```

-continued

```
tttgctgaat tctaacatta aatcacagcc caaaatttga tggactaatt attattttaa      1620
aatatatgaa gacaataatt ctacatgttg tcttaagatg gaaatacagt tatttcatct      1680
tttattcaag gaagttttaa ctttaataca gctcagtaaa tggcttcttc tagaatgtaa      1740
agttatgtat ttaaagttgt atcttgacac aggaaatggg aaaaaactta aaaattaata      1800
tggtgtattt ttccaaatga aaaatctcaa ttgaaagctt ttaaaatgta gaacttaaaa      1860
cacaccttcc tgtggaggct gagatgaaaa ctagggctca ttttcctgac atttgtttat      1920
tttttggaag agacaaagat ttcttctgca ctctgagccc ataggtctca gagagttaat      1980
aggagtattt ttgggctatt gcataaggag ccactgctgc caccactttt ggattttatg      2040
ggaggctcct tcatcgaatg ctaaacctt gagtagagtc tccctggatc acataccagg       2100
tcagggagga tctgttcttc ctctacgttt atcctggcat gtgctagggt aaacgaaggc      2160
ataataagcc atggctgacc tctggagcac caggtgccag gacttgtctc catgtgtatc      2220
catgcattat atacctggt gcaatcacac gactgtcatc taaagtcctg gccctggccc       2280
ttactattag gaaaataaac agacaaaaac aagtaaatat atatggtcct atacatattg      2340
tatatatatt catatacaaa catgtatgta tacatgacct taatggatca tagaattgca      2400
gtcatttggt gctctgctaa ccatttatat aaaacttaaa aacaagagaa agaaaaatc       2460 aattagatct aaacagttat ttctgtttcc tatttaatat agctgaagtc aaaatatgta      2520
agaacacatt ttaaatactc tacttacagt tggccctctg tggttagttc cacatctgtg      2580
gattcaacca accaaggacg gaaaatgctt aaaaaataat acaacaacaa caaaaaatac      2640
attataacaa ctatttactt ttttttttt cttttgaga tggagtctcg ctctgttgcc        2700
caggttggag tgcagtggca cgatctcggc tcactgcaac ctcacctccc gggttcaaga     2760
gatcctcctg cctcagcctc ctgagcagct gggactacag gcgcatgcca ccatgcccag     2820 ctaattttg tattttagt agaggcgggg tttcaccatg ttggccagga tggtctcaat       2880
ctcctaacct tgagatccac cctccacagc ctcccaaact gctgggatta caggcgtgag     2940
ccaccgcacg tagcatttac attaggtatt acaagtaatg taaagatgat ttaagtatac     3000
aggaggatgt gaataggtta tatgcaagca ctatgccctt ttatataagt gacttgaaca     3060
tctgtgcccg attttagtat gtgcaggggg gcgatctggg aatcagtccc ctgtggatac     3120
caaggtacaa ctgtatttat taacgcttac tagatgtgag gagagtctga atattttcag    3180
tgatcttggc tgtttcaaaa aaatctattg acttttcaat aaatcagctg caatccattt     3240
atttcattta caaagatttt attgtaagcc tctcaatctt ggttttttcag ttgatcttaa    3300 gcatgtcaat tcataaaaac aagtcatttt tgtattttc atctttaaga atgcttaaaa     3360
aagctaatcc ctaaaatagt tagatctttg taaatgcata ttaaataata aagtatgacc    3420
cacattactt tttatgggtg aaaataagac aaaaataata gttttagtga ggatggtgct    3480
gagtaaacat aaaaactgat ttgctctcag ctgatgtgtc ctgtacacag tgggaagatt    3540
ttagttcaca cttagtctaa ctcccccatt ttacagattt ctcactatat atatttctag    3600
aaggggctat gcatattcaa tgtattgaga accaaagcaa ccacaaatgc ataaatgcat    3660
aatttatggt cttcaaccaa ggccacataa taccccagtt aacttactct ttaaccagga    3720
atattaagtt ctataactag tactcaaggt ttaaccttaa aattaagatt tccttaacct   3780
taaccttaaa attgatatta tattaaacat acataataca atgtaactcc actgttctcc    3840
tgaatatttt ttgctctaat ctctctgccg aaagtcaaag tgatgggaga attggtatac    3900
tggtatgact acgtcttaag tcagattttt atttatgagt ctttgagact aaattcaatc    3960
```

| | |
|---|---|
| accaccaggt atcaaatcaa cttttatgca gcaaatatat gattctagtg tctgactttt | 4020 |
| gttaaattca gtaatgcagt ttttaaaaac ctgtatctga cccactttgt aattttgct | 4080 |
| ccaatatcca ttctgtagac ttttgaaaaa aaagtttta atttgatgcc caatatattc | 4140 |
| tgaccgttaa aaaattcttg ttcatatggg agaaggggga gtaatgactt gtacaaacag | 4200 |
| tatttctggt gtatatttta atgttttaa aaagagtaat ttcatttaaa tatctgttat | 4260 |
| tcaaatttga tgatgttaaa tgtaatataa tgtattttct ttttattttg cactctgtaa | 4320 |
| ttgcactttt taagtttgaa gagccatttt ggtaaacggt ttttattaaa gatgctatgg | 4380 |
| aacataaagt tgtattgcat gcaatttaaa gtaacttatt tgactatgaa tattatcgga | 4440 |
| ttactgaatt gtatcaattt gtttgtgttc aatatcagct ttgataattg tgtaccttaa | 4500 |
| gatattgaag gagaaaatag ataatttaca agatattatt aattttttatt tattttctt | 4560 |
| gggaattgaa aaaattgaa ataaataaaa atgcattgaa catcttgcat tcaaaatctt | 4620 |
| cactgac | 4627 |

<210> SEQ ID NO 357
<211> LENGTH: 2634
<212> TYPE: DNA
<213> ORGANISM: Homo sapiens

<400> SEQUENCE: 357

| | |
|---|---|
| ggcacgaggc tgagtgtccg tctcgcgccc ggaagcgggc gaccgccgtc agcccggagg | 60 |
| aggaggagga ggaggaggag gaggggcgg ccatggggct gctgtcccag ggctcgccgc | 120 |
| tgagctggga ggaaaccaag cgccatgccc accacgtgcg gcggcacggg atcctccagt | 180 |
| tcctgcacat ctaccacgcc gtcaaggacc ggcacaagga cgttctcaag tggggcgatg | 240 |
| aggtggaata catgttggta tcttttgatc atgaaaataa aaaagtccgg ttggtcctgt | 300 |
| ctggggagaa agttcttgaa actctgcaag agaaggggga aaggacaaac ccaaaccatc | 360 |
| ctaccctttg gagaccagag tatgggagtt acatgattga agggacacca ggacagccct | 420 |
| acggaggaac aatgtccgag ttcaatacag ttgaggccaa catgcgaaaa cgccggaagg | 480 |
| aggctacttc tatattagaa gaaaatcagg ctctttgcac aataacttca tttcccagat | 540 |
| taggctgtcc tgggttcaca ctgcccgagg tcaaacccaa cccagtggaa ggaggagctt | 600 |
| ccaagtccct cttctttcca gatgaagcaa taaacaagca ccctcgcttc agtaccttaa | 660 |
| caagaaatat ccgacatagg agaggagaaa aggttgtcat caatgtacca atatttaagg | 720 |
| acaagaatac accatctcca tttatagaaa catttactga ggatgatgaa gcttcaaggg | 780 |
| cttctaagcc ggatcatatt tacatggatg ccatgggatt tggaatgggc aattgctgtc | 840 |
| tccaggtgac attccaagcc tgcagtatat ctgaggccag ataccttat gatcagttgg | 900 |
| ctactatctg tccaattgtt atggctttga gtgctgcatc tccctttac cgaggctatg | 960 |
| tgtcagacat tgattgtcgc tggggagtga tttctgcatc tgtagatgat agaactcggg | 1020 |
| aggagcgagg actggagcca ttgaagaaca taactatag gatcagtaaa tcccgatatg | 1080 |
| actcaataga cagctatta tctaagtgtg gtgagaaata taatgacatc gacttgacga | 1140 |
| tagataaaga gatctacgaa cagctgttgc aggaaggcat tgatcatctc ctggcccagc | 1200 |
| atgttgctca tctctttatt agagacccac tgacactgtt tgaagagaaa atacacctgg | 1260 |
| atgatgctaa tgagtctgac catttttgaga atattcagtc cacaaattgg cagacaatga | 1320 |
| gatttaagcc ccctcctcca aactcagaca ttggatggag agtagaattt cgacccatgg | 1380 |

```
aggtgcaatt aacagacttt gagaactctg cctatgtggt gtttgtggta ctgctcacca    1440
gagtgatcct ttcctacaaa ttggattttc tcattccact gtcaaaggtt gatgagaaca    1500
tgaaggtagc acagaaaaga gatgctgtct gcagggaat gttttatttc aggaaagata     1560
tttgcaaagg tggcaatgca gtggtggatg gttgtggcaa ggcccagaac agcacggagc    1620
tcgctgcaga ggagtacacc ctcatgagca tagacaccat catcaatggg aaggaaggtg    1680
tgtttcctgg actgatccca attctgaact cttaccttga aaacatggaa gtggatgtgg    1740
acaccagatg tagtattctg aactacctaa agctaattaa gaagagagca tctggagaac    1800
taatgacagt tgccagatgg atgagggagt ttatcgcaaa ccatcctgac tacaagcaag    1860
acagtgtcat aactgatgaa atgaattata gccttatttt gaagtgtaac caaattgcaa    1920
atgaattatg tgaatgccca gagttacttg gatcagcatt taggaaagta aaatatagtg    1980
gaagtaaaac tgactcatcc aactagacat tctacagaaa gaaaaatgca ttattgacga    2040
actggctaca gtaccatgcc tctcagcccg tgtgtataat atgaagacca aatgatagaa    2100
ctgtactgtt ttctgggcca gtgagccaga aattgattaa ggctttcttt ggtaggtaaa    2160
tctagagttt atacagtgta catgtacata gtaaagtatt tttgattaac aatgtatttt    2220
aataacatat ctaaagtcat catgaactgg cttgtacatt tttaaattct tactctggag    2280
caacctactg tctaagcagt tttgtaaatg tactggtaat tgtacaatac ttgcattcca    2340
gagttaaaat gtttactgta aattttgtt cttttaaga ctacctggga cctgatttat      2400
tgaaattttt ctctttaaaa acattttctc tcgttaattt tcctttgtca tttcctttgt    2460
tgtctacatt aaatcacttg aatccattga aagtgcttca agggtaatct tgggtttcta    2520
gcaccttatc tatgatgttt cttttgcaat tggaataatc acttggtcac cttgccccaa    2580
gctttcccct ctgaataaat acccattgaa ctctgaaaaa aaaaaaaaaa aaaa          2634

<210> SEQ ID NO 358
<211> LENGTH: 1246
<212> TYPE: DNA
<213> ORGANISM: Homo sapiens

<400> SEQUENCE: 358
gaccagccta cagccgcctg catctgtatc cagcgccagg tcccgccagt cccagctgcg    60 cgcgccccc agtcccgcac ccgttcggcc caggctaagt tagccctcac catgccggtc     120
aaaggaggca ccaagtgcat caaataccctg ctgttcggat ttaacttcat cttctggctt    180
gccgggattg ctgtccttgc cattggacta tggctccgat tcgactctca gaccaagagc    240
atcttcgagc aagaaactaa taataataat tccagcttct acacaggagt ctatattctg    300
atcggagccg gcgccctcat gatgctggtg ggcttcctgg gctgctgcgg ggctgtgcag    360
gagtcccagt gcatgctggg actgttcttc ggcttcctct tggtgatatt cgccattgaa    420
atagctgcgg ccatctgggg atattcccac aaggatgagg tgattaagga agtccaggag    480
ttttacaagg acacctacaa caagctgaaa accaaggatg agcccagcg ggaaacgctg    540 aaagccatcc actatgcgtt gaactgctgt ggtttggctg ggggcgtgga acagtttatc    600
tcagacatct gccccaagaa ggacgtactc gaaaccttca ccgtgaagtc ctgtcctgat    660
gccatcaaag aggtcttcga caataaattc cacatcatcg cgcagtgggg catcggcatt    720
gccgtggtca tgatatttgg catgatcttc agtatgatct tgtgctgtgc tatccgcagg    780
aaccgcgaga tggtctagag tcagcttaca tccctgagca ggaaagttta cccatgaaga    840
ttggtgggat ttttgtttg tttgttttgt tttgtttgtt gtttgttgtt tgttttttg     900
```

-continued

| | |
|---|---|
| ccactaattt tagtattcat tctgcattgc tagataaaag ctgaagttac tttatgtttg | 960 |
| tcttttaatg cttcattcaa tattgacatt tgtagttgag cgggggtttt ggtttgcttt | 1020 |
| ggtttatatt ttttcagttg tttgtttttg cttgttatat taagcagaaa tcctgcaatg | 1080 |
| aaaggtacta tatttgctag actctagaca agatattgta cataaaagaa ttttttttgtc | 1140 |
| tttaaataga tacaaatgtc tatcaactt aatcaagttg taacttatat tgaagacaat | 1200 |
| ttgatacata ataaaaaatt atgacaatgt caaaaaaaaa aaaaaa | 1246 |

<210> SEQ ID NO 359
<211> LENGTH: 2360
<212> TYPE: DNA
<213> ORGANISM: Homo sapiens

<400> SEQUENCE: 359

| | |
|---|---|
| gctacgcggg ccacgctgct ggctggcctg acctaggcgc gcgggtcgg gcggccgcgc | 60 |
| gggcgggctg agtgagcaag acaagacact caagaagagc gagctgcgcc tgggtcccgg | 120 |
| ccaggcttgc acgcagaggc gggcggcaga cggtgcccgg cggaatctcc tgagctccgc | 180 |
| cgcccagctc tggtgccagc gcccagtggc cgccgcttcg aaagtgactg gtgcctcgcc | 240 |
| gcctcctctc ggtgcgggac catgaagctg ctgccgtcgg tggtgctgaa gctcttcctg | 300 |
| gctgcagttc tctcggcact ggtgactggc gagagcctgg agcggcttcg gagagggcta | 360 |
| gctgctggaa ccagcaaccc ggaccctccc actgtatcca cggaccagct gctacccccta | 420 |
| ggaggcggcc gggaccggaa agtccgtgac ttgcaagagg cagatctgga ccttttgaga | 480 |
| gtcactttat cctccaagcc acaagcactg ccacaccaa acaaggagga gcacgggaaa | 540 |
| agaaagaaga aaggcaaggg gctagggaag aagagggacc catgtcttcg gaaatacaag | 600 |
| gacttctgca tccatggaga atgcaaatat gtgaaggagc tccgggctcc ctcctgcatc | 660 |
| tgccaccccgg gttaccatgg agagaggtgt catgggctga gcctcccagt ggaaaatcgc | 720 |
| ttatatacct atgaccacac aaccatcctg gccgtggtgg ctgtggtgct gtcatctgtc | 780 |
| tgtctgctgg tcatcgtggg gcttctcatg tttaggtacc ataggagagg aggttatgat | 840 |
| gtggaaaatg aagagaaagt gaagttgggc atgactaatt cccactgaga gagacttgtg | 900 |
| ctcaaggaat cggctgggga ctgctaccctc tgagaagaca aaggtgatt tcagactgca | 960 |
| gaggggaaag acttccatct agtcacaaag actccttcgt ccccagttgc cgtctaggat | 1020 |
| tgggcctccc ataattgctt tgccaaaata ccagagcctt caagtgccaa acagagtatg | 1080 |
| tccgatggta tctgggtaag aagaaagcaa aagcaaggga ccttcatgcc cttctgattc | 1140 |
| ccctccacca aacccacttt ccctcataaa gtttgtttaa acacttatct tctggattag | 1200 |
| aatgccggtt aaattccata tgctccagga tctttgactg aaaaaaaaaa agaagaagaa | 1260 |
| gaaggagagc aagaaggaaa gatttgtgaa ctggaagaaa gcaacaaaga ttgagaagcc | 1320 |
| atgtactcaa gtaccaccaa gggatctgcc attgggaccc tccagtgctg gatttgatga | 1380 |
| gttaactgtg aaataccaca agcctgagaa ctgaattttg ggacttctac ccagatggaa | 1440 |
| aaataacaac tattttttgtt gttgttgttt gtaaatgcct cttaaattat atatttattt | 1500 |
| tattctatgt atgttaattt atttagtttt taacaatcta acaataatat ttcaagtgcc | 1560 |
| tagactgtta ctttggcaat ttcctggccc tccactcctc atccccacaa tctggcttag | 1620 |
| tgccacccac ctttgccaca aagctaggat ggttctgtga cccatctgta gtaatttatt | 1680 |
| gtctgtctac atttctgcag atcttccgtg gtcagagtgc cactgcggga gctctgtatg | 1740 |

| | |
|---|---:|
| gtcaggatgt aggggttaac ttggtcagag ccactctatg agttggactt cagtcttgcc | 1800 |
| taggcgattt tgtctaccat ttgtgttttg aaagcccaag tgctgatgt caaagtgtaa | 1860 |
| cagatatcag tgtctccccg tgtcctctcc ctgccaagtc tcagaagagg ttgggcttcc | 1920 |
| atgcctgtag ctttcctggt ccctcacccc catggcccca ggccacagcg tgggaactca | 1980 |
| ctttcccttg tgtcaagaca tttctctaac tcctgccatt cttctggtgc tactccatgc | 2040 |
| aggggtcagt gcagcagagg acagtctgga gaaggtatta gcaaagcaaa aggctgagaa | 2100 |
| ggaacaggga acattggagc tgactgttct tggtaactga ttacctgcca attgctaccg | 2160 |
| agaaggttgg aggtggggaa ggctttgtat aatcccaccc acctcaccaa aacgatgaag | 2220 |
| gtatgctgtc atggtccttt ctggaagttt ctggtgccat ttctgaactg ttacaacttg | 2280 |
| tatttccaaa cctggttcat atttatactt tgcaatccaa ataaagataa cccttattcc | 2340 |
| ataaaaaaaa aaaaaaaaaa | 2360 |

<210> SEQ ID NO 360
<211> LENGTH: 1433
<212> TYPE: DNA
<213> ORGANISM: Homo sapiens

<400> SEQUENCE: 360

| | |
|---|---:|
| attcggggcg agggaggagg aagaagcgga ggaggcggct cccgctcgca gggccgtgca | 60 |
| cctgcccgcc cgcccgctcg ctcgctcgcc cgccgcgccg cgctgccgac cgccagcatg | 120 |
| ctgccgagag tgggctgccc cgcgctgccg ctgccgccgc cgccgctgct gccgctgctg | 180 |
| ccgctgctgc tgctgctact gggcgcgagt ggcggcggcg gcggggcgcg cgcggaggtg | 240 |
| ctgttccgct gccgccctg cacacccgag cgcctggccg cctgcgggcc ccgccggtt | 300 |
| gcgccgcccg ccgcggtggc cgcagtggcc ggaggcgccc gcatgccatg cgcggagctc | 360 |
| gtccgggagc cgggctgcgg ctgctgctcg tgtgcgccc ggctggaggg cgaggcgtgc | 420 |
| ggcgtctaca ccccgcgctg cggccagggg ctgcgctgct atccccaccc gggctccgag | 480 |
| ctgcccctgc aggcgctggt catgggcgag ggcacttgtg agaagcgccg ggacgccgag | 540 |
| tatgcgcca gcccggagca ggttgcagac aatggcgatg accactcaga aggaggcctg | 600 |
| gtggagaacc acgtggacag caccatgaac atgttgggcg ggggaggcag tgctggccgg | 660 |
| aagcccctca gtcgggtat gaaggagctg gccgtgttcc gggagaaggt cactgagcag | 720 |
| caccggcaga tgggcaaggg tgcaagcat caccttggcc tggaggagcc caagaagctg | 780 |
| cgaccacccc ctgccaggac tccctgccaa caggaactgg accaggtcct ggagcggatc | 840 |
| tccaccatgc gccttccgga tgagcggggc cctctggagc acctctactc cctgcacatc | 900 |
| cccaactgtg acaagcatgg cctgtacaac ctcaaacagt gcaagatgtc tctgaacggg | 960 |
| cagcgtgggg agtgctggtg tgtgaacccc acaccgggga agctgatcca gggagccccc | 1020 |
| accatccggg gggaccccga gtgtcatctc ttctacaatg agcagcagga ggcttgcggg | 1080 |
| gtgcacaccc agcggatgca gtagaccgca gccagccggt gcctggcgcc cctgccccc | 1140 |
| gcccctctcc aaacaccggc agaaaacgga gagtgcttgg gtggtgggtg ctggaggatt | 1200 |
| ttccagttct gacacacgta tttatatttg gaaagagacc agcaccgagc tcggcacctc | 1260 |
| cccggcctct ctcttcccag ctgcagatgc cacacctgct ccttcttgct ttccccgggg | 1320 |
| gaggaagggg gttgtggtcg gggagctggg gtacaggttt ggggaggggg aagagaaatt | 1380 |
| tttattttg aaccctgtg tcccttttgc ataagattaa aggaaggaaa agt | 1433 |

<210> SEQ ID NO 361
<211> LENGTH: 1632
<212> TYPE: DNA
<213> ORGANISM: Homo sapiens

<400> SEQUENCE: 361

| | |
|---|---|
| gccggccgaa cccagacccg aggttttaga agcagagtca ggcgaagctg ggccagaacc | 60 |
| gcgacctccg caaccttgag cggcatccgt ggagtgcgcc tgcgcagcta cgaccgcagc | 120 |
| aggaaagcgc cgccggccag gcccagctgt ggccggacag ggactggaag agaggacgcg | 180 |
| gtcgagtagg tgtgcaccag ccctggcaac gagagcgtct accccgaact ctgctggcct | 240 |
| tgaggtgggg aagccgggga gggcagttga ggaccccgcg gaggcgcgtg actggttgag | 300 |
| cgggcaggcc agcctccgag ccgggtggac acaggtttta aaacatgaat cctacactca | 360 |
| tccttgctgc cttttgcctg ggaattgcct cagctactct aacatttgat cacagtttag | 420 |
| aggcacagtg gaccaagtgg aaggcgatgc acaacagatt atacggcatg aatgaagaag | 480 |
| gatggaggag agcagtgtgg gagaagaaca tgaagatgat tgaactgcac aatcaggaat | 540 |
| acagggaagg gaaacacagc ttcacaatgg ccatgaacgc ctttggagac atgaccagtg | 600 |
| aagaattcag gcaggtgatg aatggctttc aaaaccgtaa gcccaggaag gggaaagtgt | 660 |
| tccaggaacc tctgttttat gaggccccca gatctgtgga ttggagagag aaaggctacg | 720 |
| tgactcctgt gaagaatcag ggtcagtgtg gttcttgttg ggcttttagt gctactggtg | 780 |
| ctcttgaagg acagatgttc cggaaaactg ggaggcttat ctcactgagt gagcagaatc | 840 |
| tggtagactg ctctgggcct caaggcaatg aaggctgcaa tggtggccta atggattatg | 900 |
| ctttccagta tgttcaggat aatggaggcc tggactctga ggaatcctat ccatatgagg | 960 |
| caacagaaga atcctgtaag tacaatccca agtattctgt tgctaatgac accggctttg | 1020 |
| tggacatccc taagcaggag aaggccctga tgaaggcagt tgcaactgtg gggcccattt | 1080 |
| ctgttgctat tgatgcaggt catgagtcct tcctgttcta taaagaaggc atttatttg | 1140 |
| agccagactg tagcagtgaa gacatggatc atggtgtgct ggtggttggc tacggatttg | 1200 |
| aaagcacaga atcagataac aataaatatt ggctggtgaa gaacagctgg ggtgaagaat | 1260 |
| ggggcatggg tggctacgta aagatggcca agaccggag aaaccattgt ggaattgcct | 1320 |
| cagcagccag ctaccccact gtgtgagctg gtggacggtg atgaggaagg acttgactgg | 1380 |
| ggatggcgca tgcatgggag gaattcatct tcagtctacc agcccccgct gtgtcggata | 1440 |
| cacactcgaa tcattgaaga tccgagtgtg atttgaattc tgtgatattt tcacactggt | 1500 |
| aaatgttacc tctatttaa ttactgctat aaataggttt atattattga ttcacttact | 1560 |
| gactttgcat tttcgttttt aaaaggatgt ataaattttt acctgtttaa ataaaattta | 1620 |
| atttcaaatg ta | 1632 |

<210> SEQ ID NO 362
<211> LENGTH: 2756
<212> TYPE: DNA
<213> ORGANISM: Homo sapiens

<400> SEQUENCE: 362

| | |
|---|---|
| atgctgtcct tccagtaccc cgacgtgtac cgcgacgaga ccgccgtaca ggattatcat | 60 |
| ggtcataaaa tttgtgaccc ttacgcctgg cttgaagacc ccgacagtga acagactaag | 120 |
| gcctttgtgg aggcccagaa taagattact gtgccatttc ttgagcagtg tcccatcaga | 180 |
| ggtttataca aagagagaat gactgaacta tatgattatc ccaagtatag ttgccacttc | 240 |

-continued

| | |
|---|---|
| aagaaaggaa aacggtattt ttattttac aatacaggtt tgcagaacca gcgagtatta | 300 |
| tatgtacagg attccttaga gggtgaggcc agagtgttcc tggaccccaa catactgtct | 360 |
| gacgatggca cagtggcact ccgaggttat gcgttcagcg aagatggtga atattttgcc | 420 |
| tatggtctga gtgccagtgg ctcagactgg gtgacaatca agttcatgaa agttgatggt | 480 |
| gccaaagagc ttccagatgt gcttgaaaga gtcaagttca gctgtatggc ctggacccat | 540 |
| gatgggaagg gaatgttcta caactcatac cctcaacagg atggaaaaag tgatggcaca | 600 |
| gagacatcta ccaatctcca ccaaaagctc tactaccatg tcttgggaac cgatcagtca | 660 |
| gaagatattt tgtgtgctga gtttcctgat gaacctaaat ggatgggtgg agctgagtta | 720 |
| tctgatgatg ccgctatgt cttgttatca ataagggaag gatgtgatcc agtaaaccga | 780 |
| ctctggtact gtgacctaca gcaggaatcc agtggcatcg cgggaatcct gaagtgggta | 840 |
| aaactgattg acaactttga agggaatat gactacgtga ccaatgaggg ggcggtgttc | 900 |
| acattcaaga cgaatcgcca gtctcccaac tatcgcgtga tcaacattga cttcagggat | 960 |
| cctgaagagt ctaagtggaa agtacttgtt cctgagcatg agaaagatgt cttagaatgg | 1020 |
| atagcttgtg tcaggtccaa cttccttggtc ttatgctacc tccatgacgt caagaacatt | 1080 |
| ctgcagctcc atgacctgac tactggtgct ctccttaaga ccttcccgct cgatgtcggc | 1140 |
| agcattgtag ggtacagcgg tcagaagaag gacactgaaa tcttctatca gtttacttcc | 1200 |
| tttttatctc caggtatcat ttatcactgt gatcttacca agaggagct ggagccaaga | 1260 |
| gttttccgag aggtgaccgt aaaggaatt gatgcttctg attaccagac agtccagatt | 1320 |
| ttctacccta gcaaggatgg tacgaagatt ccaatgttca ttgtgcataa aaaaagcata | 1380 |
| aaattggatg gctctcatcc agcttttctta tatggctatg gcggcttcaa catatccatc | 1440 |
| acacccaact acagtgtttc caggcttatt tttgtgagac acatgggtgg tatcctggca | 1500 |
| gtggccaaca tcagaggagg tggcgaatat ggagagacgt ggcataaagg tggtatcttg | 1560 |
| gccaacaaac aaaactgctt tgatgacttt cagtgtgctg ctgagtatct gatcaaggaa | 1620 |
| ggttacacat ctcccaagag gctgactatt aatggaggtt caatggagg cctcttagtg | 1680 |
| gctgcttgtg caaatcagag acctgacctc tttggttgtg ttattgccca agttggagta | 1740 |
| atggacatgc tgaagtttca taaatatacc atcggccatg cttggaccac tgattatggg | 1800 |
| tgctcggaca gcaaacaaca ctttgaatgg cttgtcaaat actctccatt gcataatgtg | 1860 |
| aagttaccag aagcagatga catccagtac ccgtccatgc tgctcctcac tgctgaccat | 1920 |
| gatgaccgcg tggtcccgct tcactccctg aagttcattg ccaccttca gtacatcgtg | 1980 |
| ggccgcagca ggaagcaaag caaccccctg cttatccacg tggacaccaa ggcgggccac | 2040 |
| ggggcgggga agcccacagc caaagtgata gaggaagtct cagacatgtt tgcgttcatc | 2100 |
| gcgcggtgcc tgaacgtcga ctggattcca taaacagttt tcgtgcttcc tcctgacagc | 2160 |
| gacagaaaac ctcaagggct ttcccacgtt gacaccaaga aaccactggg cataatgctt | 2220 |
| ccccacggga acattattcc tggactgaca ggctacagtt gaacagaact gccgtgggaa | 2280 |
| ttttatcttt tttaggcttc tccttttag caaggcttg gtgtttcttt ttccaccctg | 2340 |
| tctaggcaca tgtggttttt tggtgttttt tttaagggca tgttgggata aatagctaaa | 2400 |
| tgcaacaaa cacattgtga atattagatt gctgaattaa ggatcatagt cgggcatact | 2460 |
| tatctatatc cataacctct atatctttaa ataaatgtga gaactgttct catggagaag | 2520 |
| acttcttttgc aacaataata aatgttattt aagaatgaca gggatttact tccggtttct | 2580 |
| tcatattgag gggcaactcc agaagtggag ttttctgtga gaataaagca tttcaccttt | 2640 |

-continued

| | |
|---|---|
| ctgcaacaag ttagttttca agcagttaag tcatagaatg tttgttagct gtgaaaataa | 2700 |
| gttgttcatc caaaaaaaaa aaaaaaaaaa aaaaaaaaaa aaaaaaaaag gaattc | 2756 |

<210> SEQ ID NO 363
<211> LENGTH: 2768
<212> TYPE: DNA
<213> ORGANISM: Homo sapiens

<400> SEQUENCE: 363

| | |
|---|---|
| cactgctgtg cagggcagga aagctccatg cacatagccc agcaaagagc aacacagagc | 60 |
| tgaaaggaag actcagagga gagagataag taaggaaagt agtgatggct ctcatcccag | 120 |
| acttggccat ggaaacctgg cttctcctgg ctgtcagcct ggtgctcctc tatctatatg | 180 |
| gaacccattc acatggactt tttaagaagc ttggaattcc agggcccaca cctctgcctt | 240 |
| tttttgggaaa tattttgtcc taccataagg gcttttgtat gtttgacatg gaatgtcata | 300 |
| aaaagtatgg aaaagtgtgg ggcttttatg atggtcaaca gcctgtgctg gctatcacag | 360 |
| atcctgacat gatcaaaaca gtgctagtga agaatgttta ttctgtcttc acaaaccgga | 420 |
| ggccttttgg tccagtggga tttatgaaaa gtgccatctc tatagctgag gatgaagaat | 480 |
| ggaagagatt acgatcattg ctgtctccaa ccttcaccag tggaaaactc aaggagatgg | 540 |
| tccctatcat tgcccagtat ggagatgtgt tggtgagaaa tctgaggcgg aagcagaga | 600 |
| caggcaagcc tgtcaccttg aaagacgtct ttggggccta cagcatggat gtgatcacta | 660 |
| gcacatcatt tggagtgaac atcgactctc tcaacaatcc acaagacccc tttgtggaaa | 720 |
| acaccaagaa gcttttaaga tttgattttt tggatccatt cttttctctca ataacagtct | 780 |
| ttccattcct catcccaatt cttgaagtat taaatatctg tgtgttttcca agagaagtta | 840 |
| caaatttttt aagaaaatct gtaaaaagga tgaaagaaag tcgcctcgaa gatacacaaa | 900 |
| agcaccgagt ggatttcctt cagctgatga ttgactctca gaattcaaaa gaaactgagt | 960 |
| cccacaaagc tctgtccgat ctggagctcg tgcccaatc aattatcttt attttttgctg | 1020 |
| gctatgaaac cacgagcagt gttctctcct tcattatgta tgaactggcc actcaccctg | 1080 |
| atgtccagca gaaactgcag gaggaaattg atgcagtttt acccaataag gcaccaccca | 1140 |
| cctatgatac tgtgctacag atggagtatc ttgacatggt ggtgaatgaa acgctcagat | 1200 |
| tattcccaat tgctatgaga cttgagaggg tctgcaaaaa agatgttgag atcaatggga | 1260 |
| tgttcattcc caaaggggtg gtggtgatga ttccaagcta tgctcttcac cgtgacccaa | 1320 |
| agtactggac agagcctgag aagttcctcc ctgaaagatt cagcaagaag aacaaggaca | 1380 |
| acatagatcc ttacatatac acacccttttg gaagtggacc cagaaactgc attggcatga | 1440 |
| ggtttgctct catgaacatg aaacttgctc taatcagagt ccttcagaac ttctccttca | 1500 |
| aaccttgtaa agaaacacag atccccctga aattaagctt aggaggactt cttcaaccag | 1560 |
| aaaaacccgt tgttctaaag gttgagtcaa gggatggcac cgtaagtgga gcctgaattt | 1620 |
| tcctaaggac ttctgctttg ctcttcaaga aatctgtgcc tgagaacacc agagacctca | 1680 |
| aattactttg tgaatagaac tctgaaatga agatgggctt catccaatgg actgcataaa | 1740 |
| taaccgggga ttctgtacat gcattgagct ctctcattgt ctgtgtagag tgttatactt | 1800 |
| gggaatataa aggaggtgac caaatcagtg tgaggaggta gatttggctc ctctgcttct | 1860 |
| cacgggacta tttccaccac ccccagttag caccattaac tcctcctgag ctctgataag | 1920 |
| agaatcaaca tttctcaata atttcctcca caaattatta atgaaaataa gaattatttt | 1980 |

| | |
|---|---|
| gatggctcta acaatgacat ttatatcaca tgttttctct ggagtattct ataagtttta | 2040 |
| tgttaaatca ataaagacca ctttacaaaa gtattatcag atgctttcct gcacattaag | 2100 |
| gagaaatcta tagaactgaa tgagaaccaa caagtaaata tttttggtca ttgtaatcac | 2160 |
| tgttggcgtg gggcctttgt cagaactaga atttgattat taacataggt gaaagttaat | 2220 |
| ccactgtgac tttgcccatt gtttagaaag aatattcata gtttaattat gccttttttg | 2280 |
| atcaggcaca gtggctcacg cctgtaatcc tagcagtttg ggaggctgag ccgggtggat | 2340 |
| cgcctgaggt caggagttca agacaagcct ggcctacatg gttgaaaccc catctctact | 2400 |
| aaaaatacac aaattagcta ggcatggtgg actcgcctgt aatctcacta cacaggaggc | 2460 |
| tgaggcagga gaatcacttg aacctgggag gcggatgttg aagtgagctg agattgcacc | 2520 |
| actgcactcc agtctgggtg agagtgagac tcagtcttaa aaaaatatgc cttttgaag | 2580 |
| cacgtacatt ttgtaacaaa gaactgaagc tcttattata ttattagttt tgatttaatg | 2640 |
| ttttcagccc atctcctttc atatttctgg gagacagaaa acatgtttcc ctacacctct | 2700 |
| tgcattccat cctcaacacc caactgtctc gatgcaatga acacttaata aaaaacagtc | 2760 |
| gattggtc | 2768 |

<210> SEQ ID NO 364
<211> LENGTH: 2984
<212> TYPE: DNA
<213> ORGANISM: Homo sapiens
<400> SEQUENCE: 364

| | |
|---|---|
| gaggaggaac agaaaagaaa agaaaagaaa aagtgggaaa caaataatct aagaatgagg | 60 |
| agaaagcaag aagagtgacc cccttgtggg cactccattg gttttatggc gcctctactt | 120 |
| tctggagttt gtgtaaaaca aaatattat ggtctttgtg cacatttaca tcaagctcag | 180 |
| cctgggcggc acagccagat gcgagatgcg tctctgctga tctgagtctg cctgcagcat | 240 |
| ggacctgggt cttccctgaa gcatctccag ggctggaggg acgactgcca tgcaccgagg | 300 |
| gctcatccat ccacagagca gggcagtggg aggagacgcc atgaccccca tcctcacggt | 360 |
| cctgatctgt ctcgggctga gtctgggccc ccggacccac gtgcaggcag gcacctccc | 420 |
| caagcccacc ctctgggctg aaccaggctc tgtgatcacc caggggagtc ctgtgaccct | 480 |
| caggtgtcag gggggccagg agacccagga gtaccgtcta tatagagaaa agaaaacagc | 540 |
| accctggatt acacggatcc cacaggagct tgtgaagaag gccagttccc catcccatc | 600 |
| catcacctgg gaacatgcag gcggtatcg ctgttactat ggtagcgaca ctgcaggccg | 660 |
| ctcagagagc agtgaccccc tggagctggt ggtgacagga gcctacatca aacccaccct | 720 |
| ctcagcccag cccagcccg tggtgaactc aggagggaat gtaaccctcc agtgtgactc | 780 |
| acaggtggca tttgatggct tcattctgtg taaggaagga gaagatgaac acccacaatg | 840 |
| cctgaactcc cagcccatg cccgtgggtc gtcccgcgcc atcttctccg tgggccccgt | 900 |
| gagcccgagt cgcaggtggt ggtacaggtg ctatgcttat gactcgaact ctccctatga | 960 |
| gtggtctcta cccagtgatc tcctggagct cctggtccta ggtgtttcta agaagccatc | 1020 |
| actctcagtg cagccaggtc ctatcgtggc ccctgaggag accctgactc tgcagtgtgg | 1080 |
| ctctgatgct ggctacaaca gatttgttct gtataaggac ggggaacgtg acttccttca | 1140 |
| gctcgctggc gcacagcccc aggctgggct ctcccaggcc aacttcaccc tgggccctgt | 1200 |
| gagccgctcc tacggggggcc agtacagatg ctacggtgca cacaacctct cctccgagtg | 1260 |
| gtcggccccc agcgaccccc tggacatcct gatcgcagga cagttctatg acagagtctc | 1320 |

-continued

```
cctctcggtg cagccgggcc ccacggtggc ctcaggagag aacgtgaccc tgctgtgtca   1380
gtcacaggga tggatgcaaa cttttccttct gaccaaggag ggggcagctg atgacccatg   1440
gcgtctaaga tcaacgtacc aatctcaaaa ataccaggct gaattcccca tgggtcctgt   1500
gacctcagcc catgcgggga cctacaggtg ctacggctca cagagctcca aaccctacct   1560
gctgactcac cccagtgacc ccctggagct cgtggtctca ggaccgtctg ggggccccag   1620
ctccccgaca acaggcccca cctccacatc tggccctgag accagcccc tcaccccac    1680 cgggtcggat cccagagtg gtctgggaag gcacctgggg gttgtgatcg gcatcttggt    1740
ggccgtcatc ctactgctcc tcctcctcct cctcctcttc ctcatcctcc gacatcgacg    1800
tcagggcaaa cactggacat cgacccgag aaaggctgat ttccaacatc ctgcaggggc    1860
tgtggggcca gagcccacag acagaggcct gcagtggagg tccagcccag ctgccgatgc    1920
ccaggaagaa aacctctatg ctgccgtgaa gcacacacag cctgaggatg gggtggagat    1980
ggacactcgg agcccacacg atgaagaccc ccaggcagtg acgtatgccg aggtgaaaca    2040
ctccagacct aggagagaaa tggcctctcc tccttcccca ctgtctgggg aattcctgga    2100
cacaaaggac agacaggcgg aagaggacag gcagatggac actgaggctg ctgcatctga    2160 agcccccag gatgtgacct acgcccagct gcacagcttg acccttagac ggaaggcaac    2220
tgagcctcct ccatcccagg aagggccctc tccagctgtg cccagcatct acgccactct    2280
ggccatccac tagcccaggg ggggacgcag accccacact ccatggagtc tggaatgcat    2340
gggagctgcc ccccagtgg acaccattgg accccaccca gcctggatct accccaggag    2400
actctgggaa cttttagggg tcactcaatt ctgcagtata ataactaat gtctctacaa    2460 ttttgaaata aagcaacaga cttctcaata atcaatgaag tagctgagaa aactaagtca    2520
gaaagtgcat taaactgaat cacaatgtaa atattacaca tcaagcgatg aaactggaaa    2580
actacaagcc acgaatgaat gaattaggaa agaaaaaaag taggaaatga atgatcttgg    2640
cttccctata agaaatttag ggcagggcac ggtggctcac gcctgtaatt ccagcacttt    2700
gggaggccga ggcgggcaga tcacgagttc aggagatcga gaccatcttg gccaacatgg    2760
tgaaaccctg tctctcctaa aaatacaaaa attagctgga tgtggtggca gtgcctgtaa    2820
tcccagctat tgggaggct gaggcaggag aatcgcttga accagggagt cagaggtttc    2880
agtgagccaa gatcgcacca ctgctctcca gcctggcgac agagggagac tccatctcaa    2940
attaaaaaaa aaaaaaaaa agaaagaaaa aaaaaaaaa aaaa                       2984
```

<210> SEQ ID NO 365
<211> LENGTH: 3061
<212> TYPE: DNA
<213> ORGANISM: Homo sapiens

<400> SEQUENCE: 365

```
cggcacgagg cgactttggt ggaggtagtt ctttggcagc gggcatggcg ggtaccgtgg      60
tgctggacga tgtggagctg cgggaggctc agagagatta cctggacttc ctggacgacg    120
aggaagacca gggaatttat cagagcaaag ttcgggagct gatcagtgac aaccaatacc    180
ggctgattgt caatgtgaat gacctgcgca ggaaaaacga aagagggct aaccggcttc    240 tgaacaatgc ctttgaggag ctggttgcct tccagcgggc cttaaaggat tttgtggcct    300
ccattgatgc tacctatgcc aagcagtatg aggagttcta cgtaggactg gaaggcagct    360
ttggctccaa gcacgtctcc ccgcggactc ttacctcctg cttcctcagc tgtgtggtct    420
```

-continued

| | |
|---|---|
| gtgtggaggg cattgtcact aaatgttctc tagttcgtcc caaagtcgtc cgcagtgtcc | 480 |
| actactgtcc tgctactaag aagaccatag agcgacgtta ttctgatctc accaccctgg | 540 |
| tggcctttcc ctccagctct gtctatccta ccaaggatga ggagaacaat ccccttgaga | 600 |
| cagaatatgg cctttctgtc tacaaggatc accagaccat caccatccag gagatgccgg | 660 |
| agaaggcccc agccggccag ctcccccgct ctgtggacgt cattctggat gatgacttgg | 720 |
| tggataaagc gaagcctggt gaccgggttc aggtggtggg aacctaccgt tgccttcctg | 780 |
| gaaagaaggg aggctacacc tctgggacct tcaggactgt cctgattgcc tgtaatgtta | 840 |
| agcagatgag caaggatgct cagccctctt tctctgctga ggatatagcc aagatcaaga | 900 |
| agttcagtaa aacccgatcc aaggatatct tgaccagct ggccaagtca ttggccccaa | 960 |
| gtatccatgg gcatgactat gtcaagaaag caatcctctg cttgctcttg ggaggggtgg | 1020 |
| aacgagacct agaaaatggc agccacatcc gtggggacat caatattctt ctaataggag | 1080 |
| acccatccgt tgccaagtct cagcttctgc ggtatgtgct ttgcactgca ccccgagcta | 1140 |
| tccccaccac tggccggggc tcctctggag tgggtctgac ggctgctgtc accacagacc | 1200 |
| aggaaacagg agagcgccgt ctggaagcag gggccatggt cctggctgac cgaggcgtgg | 1260 |
| tttgcattga tgaatttgac aaaatgtctg acatggatcg cacagccatc catgaagtga | 1320 |
| tggagcaggt tcgagtgacc attgccaagg ctggcatcca tgctcggctg aatgcccgct | 1380 |
| gcagtgtttt ggcagctgcc aaccctgtct acggcaggta tgaccagtat aagactccaa | 1440 |
| tggagaacat tgggctacag gactcactgc tgtcacgatt tgacttgctc ttcatcatgc | 1500 |
| tggatcagat ggatcctgag caggatcggg agatctcaga ccatgtcctt cggatgcacc | 1560 |
| gttacagagc acctggggag caggatgcg atgctatgcc cttgggtagt gctgtggata | 1620 |
| tcctggccac agatgatccc aactttagcc aggaagatca gcaggacacc cagatttatg | 1680 |
| agaagcatga caaccttcta catgggacca agaagaaaaa ggagaagatg gtgagtgcag | 1740 |
| cattcatgaa gaagtacatc catgtggcca aaatcatcaa gcctgtcctg acacaggagt | 1800 |
| cggccaccta cattgcagaa gagtattcac gcctgcgcag ccaggatagc atgagctcag | 1860 |
| acaccgccag gacatctcca gttacagccc gaacactgga aactctgatt cgactggcca | 1920 |
| cagcccatgc gaaggcccgc atgagcaaga ctgtggacct gcaggatgca gaggaagctg | 1980 |
| tggagttggt ccagtatgct tactttaaga aggttctgga gaaggagaag aaacgtaaga | 2040 |
| agcgaagtga ggatgaatca gagacagaag atgaagagga gaaaagccaa gaggaccagg | 2100 |
| agcagaagag gaagagaagg aagactcgcc agccagatgc caaagatggg gattcatacg | 2160 |
| accccctatga cttcagtgac acagaggagg aaatgcctca agtacacact ccaaagacgg | 2220 |
| cagactcaca ggagaccaag gaatcccaga agtggagtt gagtgaatcc aggttgaagg | 2280 |
| cattcaaggt ggccctcttg gatgtgttcc gggaagctca tgcgcagtca atcggcatga | 2340 |
| atcgcctcac agaatccatc aaccgggaca gcgaagagcc cttctcttca gttgagatcc | 2400 |
| aggctgctct gagcaagatg caggatgaca atcaggtcat ggtgtctgag gcatcatct | 2460 |
| tcctcatctg aggaggcctc gtctctgaac ttgggttgtg ccgagagagt ttgttctgtg | 2520 |
| tttcccaccc tctccctgac ccaagtcttt gcctctactc ccttaacagt gttgaattca | 2580 |
| actgaaggcg aggaatgttg gtgatgaagc tgagttcagg actcggtgga ccctttggga | 2640 |
| atgggtcatg aaagctgcca tggggtgagg aaagaggaga cagtgggaga ggacaatgac | 2700 |
| tattgcatct tcattgcaaa agcactggct catccgccct acttcccatc ccacacaaac | 2760 |
| ccaattgtaa ataacatatg acttctgagt acttttgggg gcacaactgt tttctgtttg | 2820 |

```
ctgttttttt gttttgtttt ttttctccag agcactttgg tctagactag gctttgggtg      2880
gttccaattg gtggagagaa gctctgaggc acgtcatgca ggtcaagaaa gctttctttg      2940
cagtagcacc agttaaggtg aatatgtatt gtatcacaaa acaaacccaa tatccagatg      3000
aatatccgag atgttgaata aacttagcca tttcgtacaa aaaaggggg gcccggtaaa      3060 c                                                                     3061
```

<210> SEQ ID NO 366
<211> LENGTH: 1360
<212> TYPE: DNA
<213> ORGANISM: Homo sapiens

<400> SEQUENCE: 366

```
cgggggttgc tccgtccgtg ctccgcctcg ccatgacttc ctacagctat cgccagtcgt        60
cggccacgtc gtccttcgga ggcctgggcg cgggctccgt gcgttttggg ccggggggtcg      120 cttttcgcgc gcccagcatt cacgggggct ccggcggccg cggcgtatcc gtgtcctccg       180
cccgctttgt gtcctcgtcc tcctcggggg gctacggcgg cggctacggc ggcgtcctga      240
ccgcgtccga cgggctgctg gcgggcaacg agaagctaac catgcagaac ctcaacgacc      300
gcctggcctc ctacctggac aaggtgcgcg ccctggaggc ggccaacggc gagctagagg      360
tgaagatccg cgactggtac cagaagcagg ggcctgggcc ctcccgcgac tacagccact      420
actacacgac catccaggac ctgcgggaca agattcttgg tgccaccatt gagaactcca      480
ggattgtcct gcagatcgac aacgcccgtc tggctgcaga tgacttccga accaagtttg      540
agacggaaca ggctctgcgc atgagcgtgg aggccgacat caacggcctg cgcagggtgc      600
tggatgagct gaccctggcc aggaccgacc tggagatgca gatcgaaggc ctgaaggaag      660
agctggccta cctgaagaag aaccatgagg aggaaatcag tacgctgagg ggccaagtgg      720
gaggccaggt cagtgtggag gtggattccg ctccgggcac cgatctcgcc aagatcctga      780
gtgacatgcg aagccaatat gaggtcatgg ccgagcagaa ccggaaggat gctgaagcct      840
ggttcaccag ccgggactgaa gaattgaacc gggaggtcgc tggccacacg gagcagctcc      900
agatgagcag gtccgaggtt actgacctgc ggcgcaccct tcagggtctt gagattgagc      960
tgcagtcaca gctgagcatg aaagctgcct tggaagacac actggcagaa acggaggcgc     1020
gctttggagc ccagctggcg catatccagg cgctgatcag cggtattgaa gcccagctgg     1080
cggatgtgcg agctgatagt gagcggcaga atcaggagta ccagcggctc atggacatca     1140
agtcgcggct ggagcaggag attgccacct accgcagcct gctcgaggga caggaagatc     1200
actacaacaa tttgtctgcc tccaaggtcc tctgaggcag caggctctgg ggcttctgct     1260
gtcctttgga gggtgtcttc tgggtagagg gatgggaagg aagggaccct tacccccggc     1320
tcttctcctg acctgccaat aaaaatttat ggtccaaggg                           1360
```

<210> SEQ ID NO 367
<211> LENGTH: 1412
<212> TYPE: DNA
<213> ORGANISM: Homo sapiens

<400> SEQUENCE: 367

```
cggggtcgtc cgcaaagcct gagtcctgtc ctttctctct ccccggacag catgagcttc        60
accactcgct ccaccttctc caccaactac cggtccctgg gctctgtcca ggcgcccagc       120
tacggcgccc ggccggtcag cagcgcggcc agcgtctatg caggcgctgg gggctctggt       180
```

-continued

```
tcccggatct ccgtgtcccg ctccaccagc ttcaggggcg gcatgggtc cggggcctg        240 gccaccggga tagccggggg tctggcagga atgggaggca tccagaacga gaaggagacc      300
atgcaaagcc tgaacgaccg cctggcctct tacctggaca gagtgaggag cctggagacc      360
gagaaccgga ggctggagag caaaatccgg gagcacttgg agaagaaggg accccaggtc      420
agagactgga gccattactt caagatcatc gaggacctga gggctcagat cttcgcaaat      480
actgtggaca atgcccgcat cgttctgcag attgacaatg cccgtcttgc tgctgatgac      540
tttagagtca agtatgagac agagctggcc atgcgccagt ctgtggagaa cgacatccat      600
gggctccgca aggtcattga tgacaccaat atcacacgac tgcagctgga gacagagatc      660
gaggctctca aggaggagct gctcttcatg aagaagaacc acgaagagga agtaaaaggc      720
ctacaagccc agattgccag ctctgggttg accgtgaggg tagatgcccc caaatctcag      780
gacctcgcca agatcatggc agacatccgg gcccaatatg acgagctggc tcggaagaac      840
cgagaggagc tagacaagta ctggtctcag cagattgagg agagcaccac agtggtcacc      900
acacagtctg ctgaggttgg agctgctgag acgacgctca cagagctgag acgtacagtc      960
cagtccttgg agatcgacct ggactccatg agaaatctga aggccagctt ggagaacagc      1020
ctgagggagg tggaggcccg ctacgcccta cagatggagc agctcaacgg gatcctgctg      1080
caccttgagt cagagctggc acagacccgg gcagagggac agcgccaggc ccaggagtat      1140
gaggccctgc tgaacatcaa ggtcaagctg gaggctgaga tcgccaccta ccgccgcctg      1200
ctggaagatg gcgaggactt taatcttggt gatgccttgg acagcagcaa ctccatgcaa      1260
accatccaaa agaccaccac ccgccggata gtggatggca agtggtgtc tgagaccaat      1320 gacaccaaag ttctgaggca ttaagccagc agaagcaggg taccctttgg ggagcaggag      1380
gccaataaaa agttcagagt tcattggatg tc                                    1412
```

<210> SEQ ID NO 368
<211> LENGTH: 1075
<212> TYPE: DNA
<213> ORGANISM: Homo sapiens

<400> SEQUENCE: 368

```
cgcagcaaac acatccgtag aaggcagcgc ggccgccgag agccgcagcg ccgctcgccc       60 gccgccccccc accccgccgc cccgcccggc gaattgcgcc ccgcgcccct ccctcgcgc      120 ccccgagaca aagaggagag aaagtttgcg cggccgagcg gggcaggtga ggagggtgag      180
ccgcgcggga gggcccgcc tcggccccgg ctcagccccc gccgcgcccc cagcccgcc       240 gccgcgagca gcgcccggac cccccagcgg cggcccccgc ccgccagcc cccggcccg       300 ccatgggcgc gcgcggcccgc accctgcggc tggcgctcgg cctcctgctg ctggcgacgc     360
tgcttcgccc ggccgacgcc tgcagctgct cccccggtgca cccgcaacag gcgttttgca    420
atgcagatgt agtgatcagg gccaaagcgg tcagtgagaa ggaagtggac tctggaaacg     480
acatttatgg caaccctatc aagaggatcc agtatgagat caagcagata aagatgttca     540
aagggcctga gaaggatata gagtttatct acacggcccc ctcctcggca gtgtgtgggg     600
tctcgctgga cgttggagga aagaaggaat atctcattgc aggaaaggcc gaggggacg      660 gcaagatgca catcaccctc tgtgacttca tcgtgccctg ggcacccctg agcaccaccc     720
agaagaagag cctgaaccac aggtaccaga tgggctgcga gtgcaagatc acgcgctgcc     780
ccatgatccc cgtgctacat tcctccccgg acgagtgcct ctggatggac tgggtcacag     840
agaagaacat caacgggcac caggccaagt tcttcgcctg catcaagaga agtgacggct     900
```

| | |
|---|---|
| cctgtgcgtg gtaccgcggc gcggcgcccc ccaagcagga gtttctcgac atcgaggacc | 960 |
| cataagcagg cctccaacgc ccctgtggcc aactgcaaaa aaagcctcca aggGTttcga | 1020 |
| ctggtccagc tctgacatcc cttcctggaa acagcatgaa taaaacactc atccc | 1075 |

<210> SEQ ID NO 369
<211> LENGTH: 1127
<212> TYPE: DNA
<213> ORGANISM: Homo sapiens

<400> SEQUENCE: 369

| | |
|---|---|
| cacgggcggg gcggggcctg ggtccaccgg ggttctgagg ggagactgag gtcctgagcc | 60 |
| gacagcctca gctccctgcc aggccagacc cggcagacag atgagggccc aggaggcctg | 120 |
| gcgggcctgg gggcgctacg gtgggagagg aagccagggg tacctgcctc tgccttccag | 180 |
| ggccaccgtt ggccccagct gtgccttgac tacgtaacat cttgtcctca cagcccagag | 240 |
| catgttccag atcccagagt ttgagccgag tgagcaggaa gactccagct ctgcagagag | 300 |
| gggcctgggc cccagcccg caggggacgg gccctcaggc tccggcaagc atcatcgcca | 360 |
| ggccccaggc ctcctgtggg acgccagtca ccagcaggag cagccaacca gcagcagcca | 420 |
| tcatggaggc gctggggctg tggagatccg gagtcgccac agctcctacc ccgcggggac | 480 |
| ggaggacgac gaagggatgg gggaggagcc cagccccttt cggggccgct cgcgctcggc | 540 |
| gccccccaac ctctgggcag cacagcgcta tggccgcgag ctccggagga tgagtgacga | 600 |
| gtttgtggac tcctttaaga agggacttcc tcgcccgaag agcgcgggca cagcaacgca | 660 |
| gatgcggcaa agctccagct ggacgcgagt cttccagtcc tggtgggatc ggaacttggg | 720 |
| caggggaagc tccgccccct cccagtgacc ttcgctccac atcccgaaac tccacccgtt | 780 |
| cccactgccc tgggcagcca tcttgaatat gggcggaagt acttccctca ggcctatgca | 840 |
| aaaagaggat ccgtgctgtc tcctttggag ggagggctga cccagattcc cttccggtgc | 900 |
| gtgtgaagcc acggaaggct tggtcccatc ggaagttttg ggttttccgc ccacagccgc | 960 |
| cggaagtggc tccgtggccc cgccctcagg ctccgggctt tcccccaggc gcctgcgcta | 1020 |
| agtcgcgagc caggtttaac cgttgcgtca ccgggacccg agccccgcg atgccctggg | 1080 |
| ggccgtgctc actaccaaat gttaataaag cccgcgtctg tgccgcc | 1127 |

<210> SEQ ID NO 370
<211> LENGTH: 1890
<212> TYPE: DNA
<213> ORGANISM: Homo sapiens

<400> SEQUENCE: 370

| | |
|---|---|
| cttaataaga agagaaggct tcaatggaac cttttgtggt cctggtgctg tgtctctctt | 60 |
| ttatgcttct cttttcactc tggagacaga gctgtaggag aaggaagctc cctcctggcc | 120 |
| ccactcctct tcctattatt ggaaatatgc tacagataga tgttaaggac atctgcaaat | 180 |
| ctttcaccaa tttctcaaaa gtctatggtc ctgtgttcac cgtgtatttt ggcatgaatc | 240 |
| ccatagtggt gtttcatgga tatgaggcag tgaaggaagc cctgattgat aatggagagg | 300 |
| agttttctgg aagaggcaat tccccaatat ctcaaagaat tactaaagga cttgaatca | 360 |
| tttccagcaa tggaaagaga tggaaggaga tccggcgttt ctccctcaca aacttgcgga | 420 |
| attttgggat gggaagagg agcattgagg accgtgttca agaggaagct cactgccttg | 480 |
| tggaggagtt gagaaaaacc aaggcttcac cctgtgatcc cacttcatc ctgggctgtg | 540 |

-continued

```
ctccctgcaa tgtgatctgc tccgttgttt tccagaaacg atttgattat aaagatcaga      600
attttctcac cctgatgaaa agattcaatg aaaacttcag gattctgaac tccccatgga      660
tccaggtctg caataatttc cctctactca ttgattgttt cccaggaact cacaacaaag      720
tgcttaaaaa tgttgctctt acacgaagtt acattaggga gaaagtaaaa gaacaccaag      780
catcactgga tgttaacaat cctcgggact ttatggattg cttcctgatc aaaatggagc      840
aggaaaagga caaccaaaag tcagaattca atattgaaaa cttggttggc actgtagctg      900
atctatttgt tgctggaaca gagacaacaa gcaccactct gagatatgga ctcctgctcc      960
tgctgaagca cccagaggtc acagctaaag tccaggaaga gattgatcat gtaattggca     1020
gacacaggag cccctgcatg caggatagga gccacatgcc ttacactgat gctgtagtgc     1080
acgagatcca gagatacagt gaccttgtcc ccaccggtgt gccccatgca gtgaccactg     1140
atactaagtt cagaaactac ctcatcccca gagctttga taacaagata atgctggctg     1200
cataaaacta gggcacaacc ataatggcat tactgacttc cgtgctacat gatgacaaag     1260
aatttcctaa tccaaatatc tttgaccctg ccactttct agataagaat ggcaacttta     1320
agaaaagtga ctacttcatg cctttctcag caggaaaacg aatttgtgca ggagaaggac     1380
ttgcccgcat ggagctattt ttatttctaa ccacaatttt acagaacttt aacctgaaat     1440
ctgttgatga tttaaagaac ctcaatacta ctgcagttac caaagggatt gtttctctgc     1500
caccctcata ccagatctgc ttcatccctg tctgaagaat gctagcccat ctggctgctg     1560
atctgctatc acctgcaact ctttttttat caaggacatt cccactatta tgtcttctct     1620
gacctctcat caaatcttcc cattcactca atatcccata agcatccaaa ctccattaag     1680
gagagttgtt caggtcactg cacaaatata tctgcaatta ttcatactct gtaacacttg     1740
tattaattgc tgcatatgct aatacttttc taatgctgac ttttttaatat gttatcactg     1800
taaaacacag aaaagtgatt aatgaatgat aattagtcc atttcttttg tgaatgtgct     1860
aaataaaaag tgttattaat tgctggttca                                        1890
```

<210> SEQ ID NO 371
<211> LENGTH: 4946
<212> TYPE: DNA
<213> ORGANISM: Homo sapiens

<400> SEQUENCE: 371

```
agtcagccct gctgccagcc agtgccgggt gctggggact cagggaggcc cgccgggacc       60
actgcgggac agtgagccga gcagaagctg gaacgcagga gaggaaggag aggggcggt      120
cagggctctc aggagccggg tcctgggcaa ggcgcagccg ttttcaaatt ttcaggaaag      180
cggtcggctc acactcgagc agtaaaaaga tgcctctggg gaggaggccc gtgcagctct      240
ccgggcaatg gtggtggctc ggcctagaga ggcggtagtg gaacgcagac cctggtgggg      300
gaatgacatc aagggaggag acgggcggga ccccagattt ctgcctgtgg gcgatggaag      360
tgaggttcac tggccagcgg agccggacac agaacgcgca aaacgccgtg taggcctgga      420
ggagccgaag agcaggcgga cccctccgc ggggaacag tttccgccgg agcacaaag       480
caacggaccg gaagtggggg gcggaagtgc agtgggctca gcgccgactg cgcgcctctg      540
cccgcgaaaa ctctgagctg gctgacagct ggggacgggt ggcggccctc gactggagtc      600
ggttgagttc ctgagggacc ccggttctgg aaggttcgcc gcggagacaa gtgagcagtc      660
tgtgccatag ggattctcga agagaacagc gttgtgtccc agtgcacatg ctcgcatcgc      720
ttaccaggag tgcccgagac cctaagatgt tcggagtggt ttttttcgcac agacccgaat      780
```

```
agcctgcccc tcagccacgc tctgtgccct tctgagaaca ggctgatatg cccaagatag    840
tcctgaatgg tgtgaccgta gacttccctt ccagccccta caaatgccaa caggagtaca    900
tgaccaaggt cctggaatgt ctgcagcaga aggtgaatgg catcctggag agccctacgg    960
gtacagggaa gacgctgtgc ctgctgtgca ccacgctggc ctggcgagaa cacctccgag   1020
acggcatctc tgcccgcaag attgccgaga gggcgcaagg agagcttttc ccggatcggg   1080
ccttgtcatc ctggggcaac gctgctgctg ctgctggaga ccccatagct tgctacacgg   1140
acatcccaaa gattatttac gcctccagga cccactcgca actcacacag gtcatcaacg   1200
agcttcggaa cacctcctac cggcctaagg tgtgtgtgct gggctcccgg gagcagctgt   1260
gcatccatcc tgaggtgaag aaacaagaga gtaaccatct acagatccac ttgtgccgta   1320
agaaggtggc aagtcgctcc tgtcatttct acaacaacgt agaagaaaaa agcctggagc   1380
aggagctggc cagccccatc ctggacattg aggacttggt caagagcgga agcaagcaca   1440
gggtgtgccc ttactacctg tcccggaacc tgaagcagca agccgacatc atattcatgc   1500
cgtacaatta cttgttggat gccaagagcg cagagcaca caacattgac ctgaagggga   1560
cagtcgtgat ctttgacgaa gctcacaacg tggagaagat gtgtgaagaa tcggcatcct   1620
ttgacctgac tccccatgac ctggcttcag gactggacgt catagaccag gtgctggagg   1680
agcagaccaa ggcagcgcag cagggtgagc cccacccgga gttcagcgcg gactcccca    1740
gcccagggct gaacatggag ctggaagaca ttgcaaagct gaagatgatc ctgctgcgcc   1800
tggagggggc catcgatgct gttgagctgc tggagacga cagcggtgtc accaagccag   1860
ggagctacat ctttgagctg tttgctgaag cccagatcac gtttcagacc aagggctgca   1920
tcctggactc gctggaccag atcatccagc acctggcagg acgtgctgga gtgttcacca   1980
acacggccgg actgcagaag ctggcggaca ttatccagat tgtgttcagt gtggacccct   2040
ccgagggcag ccctggttcc ccagcagggc tggggccctt acagtcctat aaggtgcaca   2100
tccatcctga tgctggtcac cggaggacgg ctcagcggtc tgatgcctgg agcaccactg   2160
cagccagaaa gcgagggaag gtgctgagct actggtgctt cagtcccggc cacagcatgc   2220
acgagctggt ccgccagggc gtccgctccc tcatccttac cagcggcacg ctggccccgg   2280
tgtcctcctt tgctctggag atgcagatcc ctttcccagt ctgcctggag aacccacaca   2340
tcatcgacaa gcaccagatc tgggtggggg tcgtccccag aggccccgat ggagcccagt   2400
tgagctccgc gtttgacaga cggttttccg aggagtgctt atcctccctg ggaaggctc    2460
tgggcaacat cgcccgcgtg gtgccctatg ggctcctgat cttcttccct tcctatcctg   2520
tcatggagaa gagcctggag ttctggcggg cccgcgactt ggccaggaag atggaggcgc   2580
tgaagccgct gtttgtggag cccaggagca aaggcagctt ctccgagacc atcagtgctt   2640
actatgcaag ggttgccgcc cctgggtcca ccggcgccac cttcctggcg gtctgccggg   2700
gcaaggccag cgagggctg gacttctcag acacgaatgg ccgtggtgtg attgtcacgg    2760
gcctcccgta cccccacgc atggaccccc gggttgtcct caagatgcag ttcctggatg   2820
agatgaaggg ccagggtggg gctgggggcc agttcctctc tgggcaggag tggtaccggc   2880
agcaggcgtc cagggctgtg aaccaggcca tcgggcgagt gatccggcac cgccaggact   2940
acggagctgt cttcctctgt gaccacaggt tcgcctttgc cgacgcaaga gcccaactgc   3000
cctcctgggt gcgtccccac gtcagggtgt atgacaactt ggccatgtc atccgagacg    3060
tggcccagtt cttccgtgtt gccgagcgaa ctatgccagc gccggccccc cgggctacag   3120
```

```
cacccagtgt gcgtggagaa gatgctgtca gcgaggccaa gtcgcctggc cccttcttct   3180
ccaccaggaa agctaagagt ctggacctgc atgtccccag cctgaagcag aggtcctcag   3240
ggtcaccagc tgccgggac cccgagagta gcctgtgtgt ggagtatgag caggagccag    3300
ttcctgcccg gcagaggccc aggggctgc tggccgccct ggagcacagc gaacagcggg    3360
cggggagccc tggcgaggag caggcccaca gctgctccac cctgtccctc ctgtctgaga   3420
agaggccggc agaagaaccg cgaggaggga ggaagaagat ccggctggtc agccaccgg    3480 aggagcccgt ggctggtgca cagacggaca gggccaagct cttcatggtg gccgtgaagc   3540
aggagttgag ccaagccaac tttgccacct tcacccaggc cctgcaggac tacaagggtt   3600
ccgatgactt cgccgccctg gccgcctgtc tcggcccct ctttgctgag acccccaaga    3660
agcacaacct gctccaaggc ttctaccagt ttgtgcggcc ccaccataag cagcagtttg   3720
aggaggtctg tatccagctg acaggacgag gctgtggcta tcggcctgag cacagcattc   3780
cccgaaggca gcgggcacag ccggtcctgg accccactgg aagaacggcg ccggatccca   3840
agctgaccgt gtccacggct gcagcccagc agctggaccc caagagcac ctgaaccagg    3900 gcaggccccca cctgtcgccc aggccacccc caacaggaga ccctggcagc caaccacagt   3960
gggggtctgg agtgcccaga gcagggaagc agggccagca cgccgtgagc gcctacctgg   4020
ctgatgcccg cagggccctg ggtccgcgg gctgtagcca actcttggca gcgctgacag    4080
cctataagca agacgacgac ctcgacaagg tgctggctgt gttggccgcc ctgaccactg   4140
caaagccaga ggacttcccc ctgctgcaca ggttcagcat gtttgtgcgt ccacaccaca   4200
agcagcgctt ctcacagacg tgcacagacc tgaccggccg gccctacccg gcatggagc    4260 caccgggacc ccaggaggag aggcttgccg tgcctcctgt gcttacccac agggctcccc   4320
aaccaggccc ctcacggtcc gagaagaccg ggaagaccca gagcaagatc tcgtccttcc   4380
ttagacagag gccagcaggg actgtggggg cgggcggtga ggatgcaggt cccagccagt   4440
cctcaggacc tccccacggg cctgcagcat ctgagtgggg cctctaggat gtgcccagcc   4500
tgccacaccg cctccaggaa gcagagcgtc atgcaggtct tctggccaga gccccagtga   4560
gtgcccacgg aggcccccag cacacccaac gtggcttgat cacctgcctg tccagctctg   4620
gtgggccaag aacccacccca acagaatagg ccagcccatg ccagccggct ggcccgctg   4680 caggcctcag gcaggcgggg cccatggttg gtccctgcgg tgggaccgga tctgggcctg   4740
cctctgagaa gccctgagct accttggggt ctggggtggg tttctgggaa agtgcttccc   4800
cagaacttcc ctggctcctg gcctgtgagt ggtgccacag gggcacccca gctgagcccc   4860
tcaccgggaa ggaggagacc cccgtgggca cgtgtccact tttaatcagg ggacagggct   4920
ctctaataaa gctgctggca gtgccc                                       4946

<210> SEQ ID NO 372
<211> LENGTH: 1743
<212> TYPE: DNA
<213> ORGANISM: Homo sapiens

<400> SEQUENCE: 372
cagtatccct cctgacaaaa ctaacaaaaa tcctgttagc caaataatca gccacattca     60
tatttaccgt caaagttttt atcctcattt tacagcagtg gagagcgatt gccccgggtc    120
ccacgttagg aagagagaga actgggattt gcacccaggc aatctgggga cagagctgtg    180
atcacaactc catgagtcag ggccgagcca gccccttcac caccagccgg ccgcgccccg    240
ggaaggaagt ttgtggcgga ggaggttcgt acgggaggag ggggaggcgc ccacgcatct    300
```

```
ggggctgact cgctctttcg caaaacgtct gggaggagtc cctggggcca caaaactgcc    360
tccttcctga ggccagaagg agagaagacg tgcagggacc ccgcgcacag gagctgccct    420
cgcgacatgg gtcacccgcc gctgctgccg ctgctgctgc tgctccacac ctgcgtccca    480
gcctcttggg gcctgcggtg catgcagtgt aagaccaacg gggattgccg tgtggaagag    540
tgcgccctgg gacaggacct ctgcaggacc acgatcgtgc gcttgtggga agaaggagaa    600
gagctggagc tggtggagaa aagctgtacc cactcagaga agaccaacag gaccctgagc    660
tatcggactg gcttgaagat caccagcctt accgaggttg tgtgtgggtt agacttgtgc    720
aaccagggca actctggccg ggctgtcacc tattcccgaa gccgttacct cgaatgcatt    780
tcctgtggct catcagacat gagctgtgag aggggccggc accagagcct gcagtgccgc    840
agccctgaag aacagtgcct ggatgtggtg acccactgga tccaggaagg tgaagaaggg    900
cgtccaaagg atgaccgcca cctccgtggc tgtggctacc ttcccggctg cccgggctcc    960
aatggtttcc acaacaacga caccttccac ttcctgaaat gctgcaacac caccaaatgc   1020
aacgagggcc caatcctgga gcttgaaaat ctgccgcaga atggccgcca gtgttacagc   1080
tgcaagggga acagcaccca tggatgctcc tctgaagaga ctttcctcat tgactgccga   1140
ggccccatga atcaatgtct ggtagccacc ggcactcacg aaccgaaaaa ccaaagctat   1200
atggtaagag gctgtgcaac cgcctcaatg tgccaacatg cccacctggg tgacgccttc   1260
agcatgaacc acattgatgt ctcctgctgt actaaaagtg gctgtaacca cccagacctg   1320
gatgtccagt accgcagtgg ggctgctcct cagcctggcc ctgcccatct cagcctcacc   1380
atcaccctgc taatgactgc cagactgtgg ggaggcactc tcctctggac ctaaacctga   1440
aatcccctc tctgccctgg ctggatccgg gggacccctt tgcccttccc tcggctccca   1500
gccctacaga cttgctgtgt gacctcaggc cagtgtgccg acctctctgg gcctcagttt   1560
tcccagctat gaaaacagct atctcacaaa gttgtgtgaa gcagaagaga aaagctggag   1620
gaaggccgtg ggcaatggga gagctcttgt tattattaat attgttgccg ctgttgtgtt   1680
gttgttatta attaatattc atattattta ttttatactt acataaagat tttgtaccag   1740
tgg                                                                 1743

<210> SEQ ID NO 373
<211> LENGTH: 5061
<212> TYPE: DNA
<213> ORGANISM: Homo sapiens

<400> SEQUENCE: 373
atggctcaga tatttagcaa cagcggattt aaagaatgtc catttcaca tccggaacca     60
acaagagcaa agatgtggga caaagaagaa gcattacaga tggaagcaga ggctttagca    120
aaactgcaaa aggatagaca agtgactgac aatcagagag gctttgagtt gtcaagcagc    180
accagaaaaa agcacaggt ttataacaag caggattatg atctcatggt gtttcctgaa    240
tcagattccc aaaaagagc attagatatt gatgtagaaa agctcaccca agctgaactt    300
gagaaactat tgctggatga cagtttcgag actaaaaaaa cacctgtatt accagttact    360
cctattctga gccttccctt ttcagcacag ctctatttta gacctactat tcagagagga    420
cagtggccac ctggattacc tgggccttcc acttatgctt taccttctat ttatccttct    480
acttacagta acaggctgc attccaaaat ggcttcaatc caagaatgcc cactttccca    540
tctacagaac ctatatattt aagtcttccg ggacaatctc catatttctc atatccttg     600
```

```
acacctgcca cacccttttca tccacaagga agcttaccta tctatcgtcc agtagtcagt    660
actgacatgg caaaactatt tgacaaaata gctagtacat cagaatttt aaaaaatggg      720 aaagcaagga ctgatttgga gataacagat tcaaaagtca gcaatctaca ggtatctcca    780
aagtctgagg atatcagtaa atttgactgg ttagacttgg atcctctaag taagcctaag    840
gtggataatg tggaggtatt agaccatgag gaagagaaaa atgtttcaag tttgctagca    900
aaggatcctt gggatgctgt tcttcttgaa gagagatcga cagcaaattg tcatcttgaa    960
agaaaggtga atggaaaatc cctttctgtg gcaactgtta caagaagcca gtctttaaat   1020
attcgaacaa ctcagcttgc aaaagcccag ggccatatat ctcagaaaga cccaaatggg   1080
accagtagtt tgccaactgg aagttctctt cttcaagaag ttgaagtaca gaatgaggag   1140
atggcagctt tttgtcgatc cattacaaaa ttgaagacca aatttccata taccaatcac   1200
cgcacaaacc caggctattt gttaagtcca gtcacagcgc aaagaaacat gcggagaa     1260 aatgctagtg tgaaggtctc cattgacatt gaaggatttc agctaccagt tactttacg    1320 tgtgatgtga gttctactgt agaaatcatt ataatgcaag ccctttgctg gtacatgat   1380 gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta aacaaacacc tgtatcaaat agaaaaacct   1620
tgcaaagaag ccatgacgag acaccctgtt gaagaactct tagattctta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca agagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
cctggaacag ttaccaaaaa aggatatgtc atgaaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
aaagactcat cacttggact ttctaaagaa gataaagctt ttttatggga gaaacgttat   2700
tattgcttca acacccaaa ttgtcttcct aaaatattag caagcgcccc aaactggaaa   2760
tggggtaatc ttgccaaaac ttactcattg cttcaccagt ggcctgcatt gtacccacta   2820
attgcattgg aacttcttga ttcaaaattt gctgatcagg aagtaagatc cctagctgtg   2880
acctggattg aggccattag tgatgatgag ctaacagatc ttcttccaca gtttgtacaa   2940
gctttgaaat atgaaattta cttgaatagt tcattagtgc aattccttt gtccagggca    3000
```

-continued

```
ttgggaaata tccagatagc acacaattta tattggcttc tcaaagatgc cctgcatgat    3060
gtacagttta gtacccgata cgaacatgtt ttgggtgctc tcctgtcagt aggaggaaaa    3120
cgacttagag aagaacttct aaaacagacg aaacttgtac agcttttagg aggagtagca    3180
gaaaaagtaa ggcaggctag tggatcagcc agacaggttg ttctccaaag aagtatggaa    3240
cgagtacagt cctttttca gaaaaataaa tgccgtctcc ctctcaagcc aagtctagtg     3300
gcaaaagaat taaatattaa gtcgtgttcc ttcttcagtt ctaatgctgt cccctaaaa     3360
gtcacaatgg tgaatgctga ccctctggga aagaaaatta atgtcatgtt taaggttggt    3420
gaagatcttc ggcaagatat gttagcttta cagatgataa agattatgga taagatctgg    3480
cttaaagaag gactagatct gaggatggta attttcaaat gtctctcaac tggcagagat    3540
cgaggcatgg tggagctggt tcctgcttcc gatacctca ggaaaatcca agtggaatat     3600
ggtgtgacag gatcctttaa agataaacca cttgcagagt ggctaaggaa atacaatccc    3660
tctgaagaag aatatgaaaa ggcttcagag aactttatct attcctgtgc tggatgctgt    3720
gtagccacct atgttttagg catctgtgat cgacacaatg acaatataat gcttcgaagc    3780
acgggacaca tgtttcacat tgactttgga aagttttgg gacatgcaca gatgtttggc     3840
agcttcaaaa gggatcgggc tccttttgtg ctgacctctg atatggcata tgtcattaat    3900
gggggtgaaa agcccaccat tcgttttcag ttgtttgtgg acctctgctg tcaggcctac    3960
aacttgataa gaaagcagac aaacctttt cttaacctcc tttcactgat gattccttca     4020
gggttaccag aacttacaag tattcaagat ttgaaatacg ttagagatgc acttcaaccc    4080
caaactacag acgcagaagc tacaattttc tttactaggc ttattgaatc aagtttggga    4140
agcattgcca caagtttaa cttcttcatt cacaaccttg ctcagcttcg ttttctggt      4200
cttccttcta atgatgagcc catccttca ttttcaccta aaacatactc ctttagacaa     4260
gatggtcgaa tcaaggaagt ctctgttttt acatatcata agaaatacaa cccagataaa    4320
cattatattt atgtagtccg aattttgtgg gaaggacaga ttgaaccatc atttgtcttc    4380
cgaacatttg tcgaatttca ggaacttcac aataagctca gtattatttt tccactttgg    4440
aagttaccag gctttcctaa taggatggtt ctaggaagaa cacacataaa agatgtagca    4500
gccaaaagga aaattgagtt aaacagttac ttacagagtt tgatgaatgc ttcaacggat    4560
gtagcagagt gtgatcttgt ttgtactttc ttccacccttt tacttcgtga tgagaaagct    4620
gaagggatag ctaggtctgc agatgcaggt tccttcagtc ctactccagg ccaaatagga    4680
ggagctgtga aattatccat ctcttaccga aatggtactc ttttcatcat ggtgatgcat    4740
atcaaagatc ttgttactga agatggagct gacccaaatc catatgtcaa acatacccta    4800
cttccagata accacaaaac atccaaacgt aaaaccaaaa tttcacgaaa aacgaggaat    4860
ccgacattca atgaaatgct tgtatacagt ggatatagca agaaaccct aagacagcga     4920
gaacttcaac taagtgtact cagtgcagaa tctctgcggg agaattttttt cttgggtgga   4980
gtaaccctgc ctttgaaaga tttcaacttg agcaaagaga cggttaaatg gtatcagctg    5040
actgcggcaa catacttgta a                                              5061
```

<210> SEQ ID NO 374
<211> LENGTH: 6802
<212> TYPE: DNA
<213> ORGANISM: Homo sapiens

<400> SEQUENCE: 374

-continued

| | | | | | |
|---|---|---|---|---|---|
| cggccccaga | aaacccgagc | gagtaggggg | cggcgcgcag | gagggaggag | aactgggggc | 60 |
| gcgggaggct | ggtgggtgtc | gggggtggag | atgtagaaga | tgtgacgccg | cggcccggcg | 120 |
| ggtgccagat | tagcggacgg | ctgcccgcgg | ttgcaacggg | atcccgggcg | ctgcagcttg | 180 |
| ggaggcggct | ctccccaggc | ggcgtccgcg | gagacaccca | tccgtgaacc | ccaggtcccg | 240 |
| ggccgccggc | tcgccgcgca | ccaggggccg | gcggacagaa | gagcggccga | gcggctcgag | 300 |
| gctgggggac | cgcgggcgcg | gccgcgcgct | gccgggcggg | aggctggggg | gccggggccg | 360 |
| gggccgtgcc | ccggagcggg | tcggaggccg | gggccggggc | cggggacgg | cggctccccg | 420 |
| cgcggctcca | gcggctcggg | gatcccggcc | gggccccgca | gggaccatgg | cagccgggag | 480 |
| catcaccacg | ctgcccgcct | tgcccgagga | tggcggcagc | ggcgccttcc | cgccggcca | 540 |
| cttcaaggac | cccaagcggc | tgtactgcaa | aaacgggggc | ttcttcctgc | gcatccaccc | 600 |
| cgacggccga | gttgacgggg | tccgggagaa | gagcgaccct | cacatcaagc | tacaacttca | 660 |
| agcagaagag | agaggagttg | tgtctatcaa | aggagtgtgt | gctaaccgtt | acctggctat | 720 |
| gaaggaagat | ggaagattac | tggcttctaa | atgtgttacg | gatgagtgtt | tcttttttga | 780 |
| acgattggaa | tctaataact | acaatactta | ccggtcaagg | aaatacacca | gttggtatgt | 840 |
| ggcactgaaa | cgaactgggc | agtataaact | tggatccaaa | acaggacctg | ggcagaaagc | 900 |
| tatactttt | cttccaatgt | ctgctaagag | ctgattttaa | tggccacatc | taatctcatt | 960 |
| tcacatgaaa | gaagaagtat | attttagaaa | tttgttaatg | agagtaaaag | aaaataaatg | 1020 |
| tgtatagctc | agtttggata | attggtcaaa | caatttttta | tccagtagta | aaatatgtaa | 1080 |
| ccattgtccc | agtaaagaaa | aataacaaaa | gttgtaaaat | gtatattctc | cctttatat | 1140 |
| tgcatctgct | gttacccagt | gaagcttacc | tagagcaatg | atcttttca | cgcatttgct | 1200 |
| ttattcgaaa | agaggctttt | aaaatgtgca | tgtttagaaa | caaaatttct | tcatggaaat | 1260 |
| catatacatt | agaaaatcac | agtcagatgt | ttaatcaatc | caaaatgtcc | actatttctt | 1320 |
| atgtcattcg | ttagtctaca | tgtttctaaa | catataaatg | tgaatttaat | caattccttt | 1380 |
| catagtttta | taattctctg | gcagttcctt | atgatagagt | ttataaaaca | gtcctgtgta | 1440 |
| aactgctgga | agttcttcca | cagtcaggtc | aattttgtca | aacccttctc | tgtacccata | 1500 |
| cagcagcagc | ctagcaactc | tgctggtgat | gggagttgta | ttttcagtct | tcgccaggtc | 1560 |
| attgagatcc | atccactcac | atcttaagca | ttcttcctgg | caaaaattta | tggtgaatga | 1620 |
| atatggcttt | aggcggcaga | tgatatacat | atctgacttc | ccaaaagctc | caggatttgt | 1680 |
| gtgctgttgc | cgaatactca | ggacggacct | gaattctgat | tttataccag | tctcttcaaa | 1740 |
| aacttctcga | accgctgtgt | ctcctacgta | aaaaaagaga | tgtacaaatc | aataataatt | 1800 |
| acactttag | aaactgtatc | atcaaagatt | ttcagttaaa | gtagcattat | gtaaaggctc | 1860 |
| aaaacattac | cctaacaaag | taaagttttc | aatacaaatt | ctttgccttg | tggatatcaa | 1920 |
| gaaatcccaa | aatattttct | taccactgta | aattcaagaa | gcttttgaaa | tgctgaatat | 1980 |
| ttctttggct | gctacttgga | ggcttatcta | cctgtacatt | tttggggtca | gctcttttta | 2040 |
| acttcttgct | gctcttttc | ccaaaaggta | aaaatataga | ttgaaaagtt | aaaacatttt | 2100 |
| gcatggctgc | agttcctttg | tttcttgaga | taagattcca | agaacttag | attcatttct | 2160 |
| tcaacaccga | aatgctggag | gtgtttgatc | agttttcaag | aaacttggaa | tataaataat | 2220 |
| tttataattc | aacaaggtt | ttcacatttt | ataaggttga | ttttcaatt | aaatgcaaat | 2280 |
| ttgtgtggca | ggattttat | tgccattaac | atatttttgt | ggctgctttt | tctacacatc | 2340 |
| cagatggtcc | ctctaactgg | gctttctcta | attttgtgat | gttctgtcat | tgtctcccaa | 2400 |

```
agtatttagg agaagccctt taaaaagctg ccttcctcta ccactttgct ggaaagcttc    2460
acaattgtca cagacaaaga tttttgttcc aatactcgtt ttgcctctat ttttcttgtt    2520
tgtcaaatag taaatgatat ttgcccttgc agtaattcta ctggtgaaaa acatgcaaag    2580
aagaggaagt cacagaaaca tgtctcaatt cccatgtgct gtgactgtag actgtcttac    2640
catagactgt cttacccatc ccctggatat gctcttgttt tttccctcta atagctatgg    2700
aaagatgcat agaaagagta taatgtttta aaacataagg cattcatctg ccattttca    2760 attacatgct gacttccctt acaattgaga tttgcccata ggttaaacat ggttagaaac    2820
aactgaaagc ataaagaaa atctaggcc gggtgcagtg gctcatgcct atattccctg    2880
cactttggga ggccaaagca ggaggatcgc ttgagcccag gagttcaaga ccaacctggt    2940 gaaacccgt ctctacaaaa aaacacaaaa aatagccagg catggtggcg tgtacatgtg    3000
gtctcagata cttgggaggc tgaggtggga gggttgatca cttgaggctg agaggtcaag    3060
gttgcagtga gccataatcg tgccactgca gtccagccta ggcaacagag tgagactttg    3120
tctcaaaaaa agagaaattt tccttaataa gaaaagtaat ttttactctg atgtgcaata    3180
catttgttat taaatttatt atttaagatg gtagcactag tcttaaattg tataaaatat    3240
cccctaacat gtttaaatgt ccattttat tcattatgct ttgaaaaata attatgggga    3300
aatacatgtt tgttattaaa tttattatta agatagtag cactagtctt aaatttgata    3360
taacatctcc taacttgttt aaatgtccat ttttattctt tatgcttgaa aataaattat    3420
ggggatccta tttagctctt agtaccacta atcaaaagtt cggcatgtag ctcatgatct    3480
atgctgtttc tatgtcgtgg aagcaccgga tggggtagt gagcaaatct gccctgctca    3540
gcagtcacca tagcagctga ctgaaaatca gcactgcctg agtagttttg atcagtttaa    3600
cttgaatcac taactgactg aaaattgaat gggcaaataa gtgcttttgt ctccagagta    3660
tgcgggagac ccttccacct caagatggat atttcttccc caaggatttc aagatgaatt    3720
gaaattttta atcaagatag tgtgctttat tctgttgtat ttttattat tttaatatac    3780 tgtaagccaa actgaaataa catttgctgt tttataggtt tgaagaacat aggaaaaact    3840
aagaggtttt gttttatttt ttgctgatga agagatatgt ttaaatatgt tgtattgttt    3900
tgtttagtta caggacaata atgaaatgga gtttatattt gttatttcta ttttgttata    3960
tttaataata gaattagatt gaaataaaat ataatgggaa ataatctgca gaatgtgggt    4020
ttcctggtgt ttcctctgac tctagtgcac tgatgatctc tgataaggct cagctgcttt    4080
atagttctct ggctaatgca gcagatactc ttcctgccag tggtaatacg atttttttaag    4140 aaggcagttt gtcaattta atcttgtgga tacctttata ctcttagggt attattttat    4200
acaaaagcct tgaggattgc attctatttt ctatatgacc ctcttgatat ttaaaaaaca    4260
ctatggataa caattcttca tttacctagt attatgaaag aatgaaggag ttcaaacaaa    4320
tgtgtttccc agttaactag ggtttactgt ttgagccaat ataaatgttt aactgtttgt    4380
gatggcagta ttcctaaagt acattgcatg ttttcctaaa tacagagttt aaataatttc    4440
agtaattctt agatgattca gcttcatcat taagaatatc ttttgtttta tgttgagtta    4500
gaaatgccct catatagaca tagtctttca gacctctact gtcagttttc atttctagct    4560
gctttcaggg ttttatgaat tttcaggcaa agctttaatt tatactaagc ttaggaagta    4620
tggctaatgc caacggcagt ttttttcttc ttaattccac atgactgagg catatatgat    4680
ctctgggtag gtgagttgtt gtgacaacca caagcacttt tttttttttt aaagaaaaaa    4740
```

```
aggtagtgaa ttttaatca tctggacttt aagaaggatt ctggagtata cttaggcctg    4800
aaattatata tatttggctt ggaaatgtgt ttttcttcaa ttacatctac aagtaagtac    4860
agctgaaatt cagaggaccc ataagagttc acatgaaaaa atcaattca tttgaaaagg    4920 caagatgcag gagagaggaa gccttgcaaa cctgcagact gcttttttgcc caatatagat    4980 tgggtaaggc tgcaaaacat aagcttaatt agctcacatg ctctgctctc acgtggcacc    5040
agtggatagt gtgagagaat taggctgtag aacaaatggc cttctcttttc agcattcaca    5100 ccactacaaa atcatctttt atatcaacag aagaataagc ataaactaag caaaaggtca    5160
ataagtacct gaaaccaaga ttggctagag atatatctta atgcaatcca tttttctgatg    5220 gattgttacg agttggctat ataatgtatg tatggtattt tgatttgtgt aaaagttta     5280 aaaatcaagc tttaagtaca tggacatttt taaataaaat atttaaagac aatttagaaa    5340
attgccttaa tatcattgtt ggctaaatag aatagggac atgcatatta aggaaaaggt    5400
catggagaaa taatattggt atcaaacaaa tacattgatt tgtcatgata cacattgaat    5460
ttgatccaat agtttaagga ataggtagga aaatttggtt tctatttttc gatttcctgt    5520
aaatcagtga cataaataat tcttagctta ttttatattt ccttgtctta aatactgagc    5580
tcagtaagtt gtgttagggg attatttctc agttgagact ttcttatatg acattttact    5640
atgttttgac ttcctgacta ttaaaaataa atagtagaaa caattttcat aaagtgaaga    5700
attatataat cactgcttta taactgactt tattatattt atttcaaagt tcatttaaag    5760
gctactattc atcctctgtg atggaatggt caggaatttg ttttctcata gtttaattcc    5820
aacaacaata ttagtcgtat ccaaaataac ctttaatgct aaactttact gatgtatatc    5880
caaagcttct ccttttcaga cagattaatc cagaagcagt cataaacaga agaataggtg    5940
gtatgttcct aatgatatta tttctactaa tggaataaac tgtaatatta gaaattatgc    6000
tgctaattat atcagctctg aggtaatttc tgaaatgttc agactcagtc ggaacaaatt    6060
ggaaaattta aatttttatt cttagctata aagcaagaaa gtaaacacat taatttcctc    6120 aacatttta agccaattaa aaatataaaa gatacacacc aatatcttct tcaggctctg    6180
acaggcctcc tggaaacttc cacatatttt tcaactgcag tataaagtca gaaaataaag    6240
ttaacataac tttcactaac acacacatat gtagatttca caaatccac ctataattgg    6300 tcaaagtggt tgagaatata ttttttagta attgcatgca aaatttttct agcttccatc    6360
cttctcccct cgtttcttct ttttttgggg gagctggtaa ctgatgaaat cttttcccac    6420
cttttctctt caggaaatat aagtggtttt gtttggttaa cgtgatacat tctgtatgaa    6480
tgaaacattg gagggaaaca tctactgaat ttctgtaatt taaaatattt tgctgctagt    6540
taactatgaa cagatagaag aatcttacag atgctgctat aaataagtag aaaatataaa    6600
tttcatcact aaaatatgct atttttaaaat ctatttccta tattgtattt ctaatcagat    6660
gtattactct tattatttct attgtatgtg ttaatgattt tatgtaaaaa tgtaattgct    6720
tttcatgagt agtatgaata aaattgatta gtttgtgttt tcttgtctcc cgaaaaaaaa    6780
aaaaaaaaaa aaaaaaaaaa aa                                             6802
```

<210> SEQ ID NO 375
<211> LENGTH: 1840
<212> TYPE: DNA
<213> ORGANISM: Homo sapiens

<400> SEQUENCE: 375

```
cccattaggt gacaggtttt tagagaagcc aatcacgtcg ccgcggtcct ggttctaaag     60
```

| | |
|---|---|
| tcctcgctca cccacccgga ctcattctcc ccagacgcca aggatggtgg tcatggcgcc | 120 |
| ccgaaccctc ttcctgctgc tctcgggggc cctgaccctg accgagacct gggcgggctc | 180 |
| ccactccatg aggtatttca cgccgccgt gtcccggccc ggccgcgggg agccccgctt | 240 |
| catcgccatg ggctacgtgg acgacacgca gttcgtgcgg ttcgacagcg actcggcgtg | 300 |
| tccgaggatg gagccgcggg cgccgtgggt ggagcaggag gggccggagt attgggaaga | 360 |
| ggagacacgg aacaccaagg cccacgcaca gactgacaga atgaacctgc agaccctgcg | 420 |
| cggctactac aaccagagcg aggccagttc tcacaccctc cagtggatga ttggctgcga | 480 |
| cctggggtcc gacggacgcc tcctccgcgg gtatgaacag tatgcctacg atggcaagga | 540 |
| ttacctcgcc ctgaacgagg acctgcgctc tggaccgca gcggacactg cggctcagat | 600 |
| ctccaagcgc aagtgtgagg cggccaatgt ggctgaacaa ggagagcct acctggaggg | 660 |
| cacgtgcgtg gagtggctcc acagatacct ggagaacggg aaggagatgc tgcagcgcgc | 720 |
| ggaccccccc aagacacacg tgacccacca ccctgtcttt gactatgagg ccaccctgag | 780 |
| gtgctgggcc ctgggcttct accctgcgga gatcatactg acctggcagc gggatgggga | 840 |
| ggaccagacc caggacgtgg agctcgtgga gaccaggcct gcagggatg gaaccttcca | 900 |
| gaagtgggca gctgtggtgg tgccttctgg agaggagcag agatacacgt gccatgtgca | 960 |
| gcatgagggg ctgccggagc ccctcatgct gagatggaag cagtcttccc tgcccaccat | 1020 |
| ccccatcatg ggtatcgttg ctggcctggt tgtccttgca gctgtagtca ctggagctgc | 1080 |
| ggtcgctgct gtgctgtgga gaaagaagag ctcagattga aaaggaggga gctactctca | 1140 |
| ggctgcaagt aagtatgaag gaggctgatc cctgagatcc ttgggatctt gtgtttggga | 1200 |
| gccatggggg agctcaccca ccccacaatt cctcctctgg ccacatctcc tgtggtctct | 1260 |
| gaccaggtgc tgttttgtt ctactctagg cagtgacagt gcccagggct ctaatgtgtc | 1320 |
| tctcacggct tgtaaatgtg acaccccggg gggcctgatg tgtgtgggtt gttgagggga | 1380 |
| acagggacca tagctgtgct atgaggtttc tttgacttca atgtattgag catgtgatgg | 1440 |
| gctgtttaaa gtgtcacccc tcactgtgac tgatatgaat ttgttcatga atattttct | 1500 |
| gtagtgtgaa acagctgccc tgtgtgggac tgagtggcaa gtcccttgt gacttcaaga | 1560 |
| accctgactt ctctttgtgc agagaccagc ccacccctgt gcccaccatg accctcttcc | 1620 |
| tcatgctgaa ctgcattcct tccccaatca cctttcctgt tccagaaaag gggctgggat | 1680 |
| gtctccgtct ctgtctcaaa tttgtggtcc actgagctat aacttacttc tgtattaaaa | 1740 |
| ttagaatctg agtgtaaatt tactttttca aattatttcc aagagagatt gatgggttaa | 1800 |
| ttaaaggaga agattcctga aatttgagag acaaaataaa | 1840 |

<210> SEQ ID NO 376
<211> LENGTH: 6754
<212> TYPE: DNA
<213> ORGANISM: Homo sapiens

<400> SEQUENCE: 376

| | |
|---|---|
| gtcgacgtgg cggccggcgg cggctgcggg ctgagcggcg agtttccgat ttaaagctga | 60 |
| gctgcgagga aaatggcggc gggaggatca aaatacttgc tggatggtgg actcagagac | 120 |
| caataaaaat aaaactgctt gaacatcctt gactggttag ccagttgctg atgtatattc | 180 |
| aagatgagtg gattaggaga aaacttggat ccactggcca gtgattcacg aaaacgcaaa | 240 |
| ttgccatgtg atactccagg acaaggtctt acctgcagtg gtgaaaaacg gagacgggag | 300 |

```
caggaaagta aatatattga agaattggct gagctgatat ctgccaatct tagtgatatt    360
gacaatttca atgtcaaacc agataaatgt gcgattttaa aggaaacagt aagacagata    420
cgtcaaataa aagagcaagg aaaaactatt tccaatgatg atgatgttca aaaagccgat    480
gtatcttcta caggcaggg agttattgat aaagactcct taggaccgct tttacttcag     540
gcattggatg gtttcctatt tgtggtgaat cgagacggaa acattgtatt tgtatcagaa    600
aatgtcacac aatacctgca atataagcaa gaggacctgg ttaacacaag tgtttacaat    660
atcttacatg aagaagacag aaaggatttt cttaagaatt taccaaaatc tacagttaat    720
ggagtttcct ggacaaatga gacccaaaga caaaaaagcc atacatttaa ttgccgtatg    780
ttgatgaaaa caccacatga tattctggaa gacataaacg ccagtcctga aatgcgccag    840
agatatgaaa caatgcagtg cttttgccctg tctcagccac gagctatgat ggaggaaggg    900
gaagatttgc aatcttgtat gatctgtgtg gcacgccgca ttactacagg agaaagaaca    960
tttccatcaa accctgagag ctttattacc agacatgatc tttcaggaaa ggttgtcaat    1020
atagatacaa attcactgag atcctccatg aggcctggct ttgaagatat aatccgaagg    1080
tgtattcaga gattttttag tctaaatgat gggcagtcat ggtcccagaa acgtcactat    1140
caagaagtta ccagtgatgg gatattttcc ccaacagctt atcttaatgg ccatgcagaa    1200
accccagtat atcgattctc gttggctgat ggaactatag tgactgcaca gacaaaaagc    1260
aaactcttcc gaaatcctgt aacaaatgat cgacatggct ttgtctcaac ccacttcctt    1320
cagagagaac agaatggata tagaccaaac ccaaatcctg ttggacaagg gattagacca    1380
cctatggctg gatgcaacag ttcggtaggc ggcatgagta tgtcgccaaa ccaaggctta    1440
cagatgccga gcagcagggc ctatggcttg gcagaccta gcaccacagg gcagatgagt    1500
ggagctaggt atgggggttc cagtaacata gcttcattga cccctgggcc aggcatgcaa    1560
tcaccatctt cctaccagaa caacaactat aggctcaaca tgagtagccc cccacatggg    1620
agtcctggtc ttgccccaaa ccagcagaat atcatgattt ctcctcgtaa tcgtgggagt    1680
ccaaagatag cctcacatca gttttctcct gttgcaggtg tgcactctcc catggcatct    1740
tctggcaata ctgggaacca cagctttttcc agcagctctc tcagtgccct gcaagccatc    1800
agtgaaggtg tggggacttc ccttttatct actctgtcat caccaggccc caaattggat    1860
aactctccca atatgaatat tacccaacca gtaaagtaa gcaatcagga ttccaagagt    1920
cctctgggct tttattgcga ccaaaatcca gtggagagtt caatgtgtca gtcaaatagc    1980
agagatcacc tcagtgacaa agaaagtaag gagagcagtg ttgaggggc agagaatcaa    2040 aggggtccctt tggaaagcaa aggtcataaa aaattactgc agttactac ctgttcttct    2100 gatgaccggg gtcattcctc cttgaccaac tcccccctag attcaagttg taagaatct     2160 tctgttagtg tcaccagccc ctctggagtc tcctcctcta catctggagg agtatcctct    2220
acatccaata tgcatgggtc actgttacaa gagaagcacc ggattttgca caagttgctg    2280
cagaatggga attcaccagc tgaggtagcc aagattactg cagaagccac tgggaaagac    2340
accagcagta taacttcttg tggggacgga atgttgtca agcaggagca gctaagtcct    2400
aagaagaagg agaataatgc acttcttaga tacctgctgg acaggatga tcctagtgat    2460 gcactctcta aagaactaca gccccaagtg aaggagtgg ataataaaat gagtcagtgc    2520
accagctcca ccattcctag ctcaagtcaa gagaaagacc ctaaaattaa gacagagaca    2580
agtgaagagg gatctggaga cttggataat ctagatgcta ttcttggtga tctgactagt    2640
tctgactttt acaataattc catatcctca aatggtagtc atctgggac taagcaacag    2700
```

```
gtgtttcaag gaactaattc tctgggtttg aaaagttcac agtctgtgca gtctattcgt   2760
cctccatata accgagcagt gtctctggat agccctgttt ctgttggctc aagtcctcca   2820
gtaaaaaata tcagtgcttt ccccatgtta ccaaagcaac ccatgttggg tgggaatcca   2880
agaatgatgg atagtcagga aaattatggc tcaagtatgg gagactgggg cttaccaaac   2940
tcaaaggccg gcagaatgga acctatgaat tcaaactcca tgggaagacc aggaggagat   3000
tataatactt ctttacccag acctgcactg ggtggctcta ttcccacatt gcctcttcgg   3060
tctaatagca taccaggtgc gagaccagta ttgcaacagc agcagcagat gcttcaaatg   3120
aggcctggtg aaatccccat gggaatgggg gctaatccct atggccaagc agcagcatct   3180
aaccaactgg gttcctggcc cgatggcatg ttgtccatgg aacaagtttc tcatggcact   3240
caaaataggc ctcttcttag gaattccctg gatgatcttg ttgggccacc ttccaacctg   3300
gaaggccaga gtgacgaaag agcattattg gaccagctgc acactcttct cagcaacaca   3360
gatgccacag gcctggaaga aattgacaga gctttgggca ttcctgaact tgtcaatcag   3420
ggacaggcat tagagcccaa acaggatgct ttccaaggcc aagaagcagc agtaatgatg   3480
gatcagaagg caggattata tggacagaca tacccagcac aggggcctcc aatgcaagga   3540
ggctttcatc ttcagggaca atcaccatct tttaactcta tgatgaatca gatgaaccag   3600
caaggcaatt ttcctctcca aggaatgcac ccacgagcca acatcatgag accccggaca   3660
aacacccccca gcaacttag aatgcagctt cagcagaggc tgcagggcca gcagttttg    3720
aatcagagcc gacaggcact tgaattgaaa atggaaaacc ctactgctgg tggtgctgcg   3780
gtgatgaggc ctatgatgca gccccagcag ggttttctta atgctcaaat ggtcgcccaa   3840
cgcagcagag agctgctaag tcatcacttc gacaacagaa gggtggctat gatgatgcag   3900
cagcagcaac agcagcagca gcagcagcag cagcagcaac agcaacagca acagcaacag   3960
cagcaacagc agcaaaccca ggccttcagc ccacctccta atgtgactgc ttcccccagc   4020
atggatgggc ttttggcagg acccacaatg ccacaagctc ctccgcaaca gtttccatat   4080
caaccaaatt atggaatggg acaacaacca gatccagcct ttggtcgagt gtctagtcct   4140
cccaatgcaa tgatgtcgtc aagaatgggt ccctcccaga atcccatgat gcaacacccg   4200
caggctgcat ccatctatca gtcctcagaa atgaagggct ggccatcagg aaatttggcc   4260
aggaacagct ccttttccca gcagcagttt gcccaccagg ggaatcctgc agtgtatagt   4320
atggtgcaca tgaatggcag cagtggtcac atgggacaga tgaacatgaa ccccatgccc   4380
atgtctggca tgcctatggg tcctgatcag aaatactgct gacatctctg caccaggacc   4440
tcttaaggaa accactgtac aaatgacact gcactaggat tattgggaag gaatcattgt   4500
tccaggcatc catcttggaa gaaaggacca gctttgagct ccatcaaggg tattttaagt   4560
gatgtcattt gagcaggact ggattttaag ccgaagggca atatctacgt gtttttcccc   4620
cctccttctg ctgtgtatca tggtgttcaa aacagaaatg tttttggca ttccacctcc    4680
tagggatata attctggaga catggagtgt tactgatcat aaaacttttg tgtcactttt   4740
ttctgccttg ctagccaaaa tctcttaaat acacgtaggt gggccagaga acattggaag   4800
aatcaagaga gattagaata tctggttttct ctagttgcag tattggacaa agagcatagt   4860
cccagccttc aggtgtagta gttctgtgtt gacccttgt ccagtggaat tggtgattct     4920
gaattgtcct ttactaatgg tgttgagttg ctctgtccct attatttgcc ctaggctttc   4980
tcctaatgaa ggttttcatt tgccattcat gtcctgtaat acttcacctc caggaactgt   5040
```

| | |
|---|---|
| catggatgtc caaatggctt tgcagaaagg aaatgagatg acagtattta atcgcagcag | 5100 |
| tagcaaactt ttcacatgct aatgtgcagc tgagtgcact ttatttaaaa agaatggata | 5160 |
| aatgcaatat tcttgaggtc ttgagggaat agtgaaacac attcctggtt tttgcctaca | 5220 |
| cttacgtgtt agacaagaac tatgattttt tttttttaaag tactggtgtc acccttgcc | 5280 |
| tatatggtag agcaataatg cttttaaaa ataaacttct gaaaacccaa ggccaggtac | 5340 |
| tgcattctga atcagaatct cgcagtgttt ctgtgaatag attttttgt aaatatgacc | 5400 |
| tttaagatat tgtattatgt aaaatatgta tatacctttt tttgtaggtc acaacaactc | 5460 |
| attttacag agtttgtgaa gctaaatatt taacattgtt gatttcagta agctgtgtgg | 5520 |
| tgaggctacc agtggaagag acatcccttg acttttgtgg cctgggggag gggtagtgca | 5580 |
| ccacagcttt tccttcccca cccccagcc ttagatgcct cgctcttttc aatctcttaa | 5640 |
| tctaaatgct ttttaaagag attatttgtt tagatgtagg catttttaatt ttttaaaaat | 5700 |
| tcctctacca gaactaagca ctttgttaat ttgggggggaa agaatagata tgggaaata | 5760 |
| aacttaaaaa aaaatcagga atttaaaaaa aacgagcaat ttgaagagaa tcttttggat | 5820 |
| tttaagcagt ccgaaataat agcaattcat gggctgtgtg tgtgtgtgta tgtgtgtgtg | 5880 |
| tgtgtgtgta tgtttaatta tgttacccttt tcatccccctt taggagcgtt ttcagattt | 5940 |
| ggttcgtaag acctgaatcc catattgaga tctcgagtag aatccttggt gtggtttctg | 6000 |
| gtgtctgctc agctgtcccc tcattctact aatgtgatgc tttcattatg tccctgtgga | 6060 |
| ttagaatagt gtcagttatt tcttaagtaa ctcagtaccc agaacagcca gttttactgt | 6120 |
| gattcagagc cacagtctaa ctgagcacct tttaaacccc tccctcttct gccccctacc | 6180 |
| acttttctgc tgttgcctct ctttgacacc tgttttagtc agttgggagg aagggaaaaa | 6240 |
| tcaagtttaa ttcccttat ctgggttaat tcattttggtt caaatagttg acggaattgg | 6300 |
| gtttctgaat gtctgtgaat ttcagaggtc tctgctagcc ttggtatcat tttctagcaa | 6360 |
| taactgagag ccagttaatt ttaagaattt cacacattta gccaatctttt ctagatgtct | 6420 |
| ctgaaggtaa gatcatttaa tatctttgat atgcttacga gtaagtgaat cctgattatt | 6480 |
| tccagaccca ccaccagagt ggatcttatt ttcaaagcag tatagacaat tatgagtttg | 6540 |
| ccctctttcc cctaccaagt tcaaaatata tctaagaaag attgtaaatc cgaaaacttc | 6600 |
| cattgtagtg gcctgtgctt ttcagatagt atactctcct gtttggagac agaggaagaa | 6660 |
| ccaggtcagt ctgtctcttt ttcagctcaa ttgtatctga cccttcttta agttatgtgt | 6720 |
| gtggggagaa atagaatggt gctcttatgt cgac | 6754 |

<210> SEQ ID NO 377
<211> LENGTH: 757
<212> TYPE: DNA
<213> ORGANISM: Homo sapiens

<400> SEQUENCE: 377

| | |
|---|---|
| ggaaccgaga ggctgagact aacccagaaa catccaattc tcaaactgaa gctcgcactc | 60 |
| tcgcctccag catgaaagtc tctgccgccc ttctgtgcct gctgctcata gcagccacct | 120 |
| tcattcccca agggctcgct cagccagatg caatcaatgc cccagtcacc tgctgttata | 180 |
| acttcaccaa taggaagatc tcagtgcaga ggctcgcgag ctatagaaga atcaccagca | 240 |
| gcaagtgtcc caaagaagct gtgatcttca agaccattgt ggccaaggag atctgtgctg | 300 |
| accccaagca gaagtgggtt caggattcca tggaccacct ggacaagcaa acccaaactc | 360 |
| cgaagacttg aacactcact ccacaaccca agaatctgca gctaacttat tttcccctag | 420 |

| | |
|---|---:|
| ctttccccag acaccctgtt ttattttatt ataatgaatt ttgtttgttg atgtgaaaca | 480 |
| ttatgcctta agtaatgtta attcttattt aagttattga tgttttaagt ttatctttca | 540 |
| tggtactagt gttttttaga tacagagact tggggaaatt gcttttcctc ttgaaccaca | 600 |
| gttctacccc tgggatgttt tgagggtctt tgcaagaatc attaatacaa agaattttt | 660 |
| ttaacattcc aatgcattgc taaaatatta ttgtggaaat gaatattttg taactattac | 720 |
| accaaataaa tatattttg tacaaaaaaa aaaaaaa | 757 |

<210> SEQ ID NO 378
<211> LENGTH: 476
<212> TYPE: DNA
<213> ORGANISM: Homo sapiens

<400> SEQUENCE: 378

| | |
|---|---:|
| taaaggcaaa gaaggttttt atttaagtga caacatttga gagctaaaaa ccagctcaca | 60 |
| tcaaaatcaa gacccagttg taaaaatctt ttaactccat aatgctgttt ttgtcttgtt | 120 |
| agaaatctga tatcttacat tagcgtttct aacggatttt gtacaaggca gccataagga | 180 |
| atataataaa cctttttcac cacagaacca tctgtcacag ataatactga aagttacaca | 240 |
| cttaggaaca gtcagaccac agacaaggtc agactggctg ccaccaccaa gtaaacaact | 300 |
| agaaaaggac agcggggtcc aagggtgggg gtccctgtgc acgagtcgcc ctcctctggc | 360 |
| ctgccccccc tcgggtcacc tgtttctcct ttgccccaaa gagggtggag tcaaatgcag | 420 |
| attttcctcc caactgcctg ttagtgtctc aacaaggaga gcagagccca ggtcag | 476 |

<210> SEQ ID NO 379
<211> LENGTH: 2518
<212> TYPE: DNA
<213> ORGANISM: Homo sapiens

<400> SEQUENCE: 379

| | |
|---|---:|
| gggtgcgctc ggccgtggcg cacctggtga gctccggggg cgctccgcct ccgcgcccca | 60 |
| aatccccgga cctgcccaac gccgcctcgg cgccgcccgc cgccgctcca gaagcgccca | 120 |
| ggagccctcc cgcgaaggct gggagcggga gcgcgacgcc cgcgaaggct gttgaggctc | 180 |
| gagcgagctt ctccagaccg accttttctgc agctgagccc cgggggggctg cgacgcgccg | 240 |
| atgaccacgc gggccgggct gtgcaaagcc ccccggacac gggccgccgc ctgccctgga | 300 |
| gcacaggcta cgccgagtga cgccccctg gggcacccaa accaggatgg ggctcccacc | 360 |
| cctctcccca gctccgcatc cccggcgcta ggacgcgttc cccacgccgc gtccgggcca | 420 |
| ggagctccct tttccgtgga cctttgctat cctctggtct tcgggccgca ccccctccca | 480 |
| acccattttc cagtgggggg cagcctgtgt caccttcttc acgtccttcc cgctcattga | 540 |
| ctgccctcgc ccacgccgcc tcaggaccct gttctgcccc agagcccgga gggcggagag | 600 |
| cccggcgaag gatgagttgg ccagttcccc gtcgcggccc ggcagcttaa aggctaaggg | 660 |
| aaaaggggtt tcacgaagga gcggggttct ttttaatagg ggacatagcg gttgggaaga | 720 |
| ctcgctcacc cgcttcccgg ctccagcgcc ccagttccct gtccctctta ccgtagttcc | 780 |
| cctcccccctc cacacccaga aatagcccgc gacaccagga ggccgccagc ttccccagga | 840 |
| gcggggaggg ggacgcccgg ggtagaggag ggtcccattt agatgcccctt cagcctgcca | 900 |
| actcgtgctg gcctgcaaa gaagcggacc cctgcccgg agcggccggc tggccccgg | 960 |
| gctgtgtgta tttaaatgc atctgccggg aacgcagagc accgagggag atgggggcgc | 1020 |

-continued

```
tcagttcgct gaggaaggtg gctggtggcc catggaccca ccaccacctc ccttagcctc   1080
ctgtgtggga ggagtttatg ggtatgtggc tcctgcccag tccaggtggg cttttcacttc  1140 tactctattt cagttcctct ttcccgatct gggctggaga gcttcctcat tgttaaggca   1200
gcagaaactt tcgctggatg gttttaggat aaggggtcat caatgctggc aagagtcggc   1260
acaatgagga ccaggcttgc tgtgaagtgg tgtatgtgga aggtcggagg agtgttacag   1320
gagtacctag ggagcctagc cgaggccagg gactctgctt ctactactgg ggcctatttg   1380
atgggcatgc aggggcggga gctgctgaaa tggcctcacg gctcctgcat cgccatatcc   1440
gagagcagct aaaggacctg aaggaagtga gccacgagag cctggtagtg ggggccattg   1500
agaatgcctt ccagctcatg gatgagcaga tggcccggga gcggcgtggc caccaagtgg   1560 agggggggctg ctgtgcactg gttgtgatct acctgctagg caaggtgtac gtggccaatg   1620
caggcgatag cagggccatc attgtccgga atggtgaaat cattccaatg tcccgggagt   1680 ttacccccgga gactgagcgc cagcgtcttc agctgcttgg cttcctgaaa ccagagctgc   1740
taggcagtga attcacccac cttgagttcc cccgcagagt tctgcccaag gagctggggc   1800
agaggatgtt gtaccgggac cagaacatga ccggctgggc ctacaaaaag atcgagctgg   1860
aggatctcag gtttcctctg gtctgtgggg agggcaaaaa ggctcgggtg atggccacca   1920
ttggggtgac ccgaggcttg ggagaccaca gccttaaggt ctgcagttcc accctgccca   1980
tcaagccctt tctctcctgc ttccctgagg tacgagtgta tgacctgaca caatatgagc   2040
actgcccaga tgatgtgcta gtcctgggaa cagatggcct gtgggatgtc actactgact   2100
gtgaggtagc tgccactgtg gacagggtgc tgtcggccta tgagcctaat gaccacagca   2160
ggtatacagc tctggcccaa gctctggtcc tgggggcccg gggtaccccc cgagaccgtg   2220
gctggcgtct ccccaacaac aagctgggtt ccggggatga catctctgtc ttcgtcatcc   2280
ccctgggagg gccaggcagt tactcctgag gggctgaaca ccatccctcc cactagcctc   2340
tccatactta ctcctctcac agcccaaatt ctgaagttgt ctccctgacc cttctttagt   2400
ggcaacttaa ctgaagaagg gatgtccgct atatccaaaa ttacagctat tggcaaataa   2460
acgagatgga taaaaaaaaa aaaaaaaaaa aaaaaaaaaa aaaaaaaaaa aaaaaaa      2518
```

<210> SEQ ID NO 380
<211> LENGTH: 4160
<212> TYPE: DNA
<213> ORGANISM: Homo sapiens

<400> SEQUENCE: 380

```
gcgcttgcgg aggattgcgt tgacgagact cttatttatt gtcaccaacc tgtggtggaa    60
tttgcagttg cacattggat ctgattcgcc ccgccccgaa tgacgcctgc ccggaggcag   120
tgaaagtaca gccgcgccgc cccaagtcag cctggacaca taaatcagca cgcggccgga   180
gaaccccgca atctctgcgc ccacaaaata caccgacgat gcccgatcta ctttaagggc   240
tgaaacccac gggcctgaga gactataaga gcgttcccta ccgccatgga acaacgggga   300
cagaacgccc cggccgcttc ggggggcccgg aaaaggcacg gccaggacc cagggaggcg   360 cggggagcca ggcctgggct ccgggtcccc aagacccttg tgctcgttgt cgccgcggtc   420
ctgctgttgg tctcagctga gtctgctctg atcacccaac aagacctagc tccccagcag   480
agagcggccc cacaacaaaa gaggtccagc ccctcagagg gattgtgtcc acctggacac   540
catatctcag aagacggtag agattgcatc tcctgcaaat atggacagga ctatagcact   600
cactggaatg acctcctttt ctgcttgcgc tgcaccaggt gtgattcagg tgaagtggag   660
```

-continued

| | |
|---|---|
| ctaagtccct gcaccacgac cagaaacaca gtgtgtcagt gcgaagaagg caccttccgg | 720 |
| gaagaagatt ctcctgagat gtgccggaag tgccgcacag ggtgtcccag agggatggtc | 780 |
| aaggtcggtg attgtacacc ctggagtgac atcgaatgtg tccacaaaga atcaggtaca | 840 |
| aagcacagtg gggaagcccc agctgtggag gagacggtga cctccagccc agggactcct | 900 |
| gcctctccct gttctctctc aggcatcatc ataggagtca cagttgcagc cgtagtcttg | 960 |
| attgtggctg tgtttgtttg caagtctttta ctgtggaaga aagtccttcc ttacctgaaa | 1020 |
| ggcatctgct caggtggtgg tggggaccct gagcgtgtgg acagaagctc acaacgacct | 1080 |
| ggggctgagg acaatgtcct caatgagatc gtgagtatct gcagcccac ccaggtccct | 1140 |
| gagcaggaaa tggaagtcca ggagccagca gagccaacag tgtcaacat gttgtccccc | 1200 |
| ggggagtcag agcatctgct ggaaccggca gaagctgaaa ggtctcagag gaggaggctg | 1260 |
| ctggttccag caaatgaagg tgatcccact gagactctga acagtgctt cgatgacttt | 1320 |
| gcagacttgg tgcctttga ctcctgggag ccgctcatga ggaagttggg cctcatggac | 1380 |
| aatgagataa aggtggctaa agctgaggca gcgggccaca gggacacctt gtacacgatg | 1440 |
| ctgataaagt gggtcaacaa aaccgggcga gatgcctctg tccacaccct gctggatgcc | 1500 |
| ttggagacgc tgggagagag acttgccaag cagaagattg aggaccactt gttgagctct | 1560 |
| ggaaagttca tgtatctaga aggtaatgca gactctgcca tgtcctaagt gtgattctct | 1620 |
| tcaggaagtc agaccttccc tggtttacct tttttctgga aaaagcccaa ctggactcca | 1680 |
| gtcagtagga aagtgccaca attgtcacat gaccggtact ggaagaaact ctcccatcca | 1740 |
| acatcaccca gtggatggaa catcctgtaa cttttcactg cacttggcat tattttata | 1800 |
| agctgaatgt gataataagg acactatgga aatgtctgga tcattccgtt tgtgcgtact | 1860 |
| ttgagatttg gtttgggatg tcattgtttt cacagcactt ttttatccta atgtaaatgc | 1920 |
| tttatttatt tatttgggct acattgtaag atccatctac acagtcgttg tccgacttca | 1980 |
| cttgatacta tatgatatga acctttttg ggtgggggt gcgggcagt tcactctgtc | 2040 |
| tcccaggctg gagtgcaatg gtgcaatctt ggctcactat agccttgacc tctcaggctc | 2100 |
| aagcgattct cccacctcag ccatccaaat agctgggacc acaggtgtgc accaccacgc | 2160 |
| ccggctaatt ttttgtattt tgtctagata tagggctct ctatgttgct cagggtggtc | 2220 |
| tcgaattcct ggactcaagc agtctgccca cctcagactc ccaaagcggt ggaattagag | 2280 |
| gcgtgagccc ccatgcttgg ccttaccttt ctactttat aattctgtat gttattattt | 2340 |
| tatgaacatg aagaaacttt agtaaatgta cttgtttaca tagttatgtg aatagattag | 2400 |
| ataaacataa aaggaggaga catacaatgg gggaagaaga agaagtcccc tgtaagatgt | 2460 |
| cactgtctgg gttccagccc tccctcagat gtactttggc ttcaatgatt ggcaacttct | 2520 |
| acaggggcca gtcttttgaa ctggacaacc ttacaagtat atgagtatta tttataggta | 2580 |
| gttgtttaca tatgagtcgg gaccaaagag aactggatcc acgtgaagtc ctgtgtgtgg | 2640 |
| ctggtcccta cctgggcagt ctcatttgca cccatagccc ccatctatgg acaggctggg | 2700 |
| acagaggcag atgggttaga tcacacataa caataggtc tatgtcatat cccaagtgaa | 2760 |
| cttgagccct gtttgggctc aggagataga agacaaaatc tgtctcccac gtctgccatg | 2820 |
| gcatcaaggg ggaagagtag atggtgcttg agaatggtgt gaaatggttg ccatctcagg | 2880 |
| agtagatggc ccggctcact tctggttatc tgtcaccctg agcccatgag ctgccttta | 2940 |
| gggtacagat tgcctacttg aggaccttgg ccgctctgta agcatctgac tcatctcaga | 3000 |

-continued

```
aatgtcaatt cttaaacact gtggcaacag gacctagaat ggctgacgca ttaaggtttt      3060
cttcttgtgt cctgttctat tattgtttta agacctcagt aaccatttca gcctctttcc      3120
agcaaaccct tctccatagt atttcagtca tggaaggatc atttatgcag gtagtcattc      3180
caggagtttt tggtctttc tgtctcaagg cattgtgtgt tttgttccgg gactggtttg       3240
ggtgggacaa agttagaatt gcctgaagat cacacattca gactgttgtg tctgtggagt      3300
tttaggagtg gggggtgacc tttctggtct ttgcacttcc atcctctccc acttccatct      3360
ggcatcccac gcgttgtccc ctgcacttct ggaaggcaca gggtgctgct gcctcctggt      3420 cttttgccttt gctgggcctt ctgtgcagga cgctcagcct cagggctcag aaggtgccag     3480
tccggtccca ggtcccttgt cccttccaca gaggccttcc tagaagatgc atctagagtg     3540
tcagccttat cagtgtttaa gatttgtctt ttatttttaa ttttttttgag acagaatctc    3600 actctctcgc ccaggctgga gtgcaacggt acgatcttgg ctcagtgcaa cctccgcctc     3660
ctgggttcaa gcgattctcg tgcctcagcc tccggagtag ctgggattgc aggcacccgc    3720
caccacgcct ggctaatttt tgtatttta gtagagacgg gtttcacca tgttggtcag       3780 gctggtctcg aactcctgac ctcaggtgat ccaccttggc ctcgaaagt gctgggatta       3840 caggcgtgag ccaccagcca ggccaagcta ttcttttaaa gtaagcttcc tgacgacatg    3900
aaataattgg gggttttgtt gtttagttac attaggcttt gctatatccc caggccaaat    3960
agcatgtgac acaggacagc catagtatag tgtgtcactc gtggttggtg tcctttcatg     4020
cttctgccct gtcaaaggtc cctatttgaa atgtgttata atacaaacaa ggaagcacat    4080
tgtgtacaaa atacttatgt atttatgaat ccatgaccaa attaaatatg aaaccttata    4140
taaaaaaaaa aaaaaaaaaa                                                 4160
```

<210> SEQ ID NO 381
<211> LENGTH: 1295
<212> TYPE: DNA
<213> ORGANISM: Homo sapiens

<400> SEQUENCE: 381

```
gtgcggagtt tggctgctcc ggggttagca ggtgagcctg cgatgcgcgg aagacgttc        60 cgctttgaaa tgcagcggga tttggtgagt ttcccgctgt ctccagcggt gcgggtgaag      120
ctggtgtctg cggggttcca gactgctgag gaactcctag aggtgaaacc ctccgagctt     180
agcaaagaag ttgggatatc taaagcagaa gccttagaaa ctctgcaaat tatcagaaga     240
gaatgtctca caaataaacc aagatatgct ggtacatctg agtcacacaa gaagtgtaca     300
gcactggaac ttcttgagca ggagcatacc cagggcttca taatcacctt ctgttcagca    360
ctagatgata ttcttggggg tggagtgccc ttaatgaaaa caacagaaat tgtggtgca     420 ccaggtgttg gaaaacaca attatgtatg cagttggcag tagatgtgca gataccagaa    480
tgttttggag gagtggcagg tgaagcagtt tttattgata cagagggaag ttttatggtt    540
gatagagtgg tagaccttgc tactgcctgc attcagcacc ttcagcttat agcagaaaaa    600
cacaagggag aggaacaccg aaaagctttg gaggatttca ctcttgataa tattctttct    660
catatttatt atttttcgctg tcgtgactac acagagttac tggcacaagt ttatcttctt    720
ccagatttcc tttcagaaca ctcaaaggtt cgactagtga tagtggatgg tattgctttt    780
ccatttcgtc atgacctaga tgacctgtct cttcgtactc ggttattaaa tggcctagcc     840
cagcaaatga tcagccttgc aaataatcac agattagctg taattttaac caatcagatg    900
acaacaaaga ttgatagaaa tcaggccttg cttgttcctg cattagggga aagttgggga    960
```

-continued

| | |
|---|---|
| catgctgcta caatacggct aatctttcat tgggaccgaa agcaaaggtt ggcaacattg | 1020 |
| tacaagtcac ccagccagaa ggaatgcaca gtactgtttc aaatcaaacc tcagggattt | 1080 |
| agagatactg ttgttacttc tgcatgttca ttgcaaacag aaggttcctt gagcacccgg | 1140 |
| aaacggtcac gagacccaga ggaagaatta taccagaaaa caaatctca aagtgtacaa | 1200 |
| atttattgat gttgtgaaat caatgtgtac aagtggactt gttaccttaa agtataaata | 1260 |
| aacacactat ggcatgaatg aaaaaaaaaa aaaaa | 1295 |

<210> SEQ ID NO 382
<211> LENGTH: 2210
<212> TYPE: DNA
<213> ORGANISM: Homo sapiens

<400> SEQUENCE: 382

| | |
|---|---|
| cgcgcccctc cctcctcgcg gacctggcgg tgccggcgcc cggagtggcc ctttaaaagg | 60 |
| cagcttattg tccggagggg gcgggcgggg ggcgccgacc gcggcctgag gcccggcccc | 120 |
| tccctctcc ctccctctgt ccccgcgtcg ctcgctggct agctcgctgg ctcgctcgcc | 180 |
| cgtccggcgc acgctccgcc tccgtcagtt ggctccgctg tcgggtgcgc ggcgtggagc | 240 |
| ggcagccggt ctggacgcgc ggccggggct ggggctggg agcgcggcgc gcaagatctc | 300 |
| cccgcgcgag agcggcccct gccaccgggc gaggcctgcg ccgcgatggc agagatgggc | 360 |
| agtaaagggg tgacggcggg aaagatcgcc agcaacgtgc agaagaagct cacccgcgcg | 420 |
| caggagaagg ttctccagaa gctggggaag gcagatgaga ccaaggatga gcagtttgag | 480 |
| cagtgcgtcc agaatttcaa caagcagctg acggagggca cccggctgca gaaggatctc | 540 |
| cggacctacc tggcctccgt caaagccatg cacgaggctt ccaagaagct gaatgagtgt | 600 |
| ctgcaggagg tgtatgagcc cgattggccc ggcagggatg aggcaaacaa gatcgcagag | 660 |
| aacaacgacc tgctgtggat ggattaccac cagaagctgg tggaccaggc gctgctgacc | 720 |
| atggacacgt acctgggcca gttccccgac atcaagtcac gcattgccaa gcgggggcgc | 780 |
| aagctggtgg actacgacag tgcccggcac cactacgagt cccttcaaac tgccaaaaag | 840 |
| aaggatgaag ccaaaattgc caaggccgag gaggagctca tcaaagccca gaaggtgttt | 900 |
| gaggagatga atgtggatct gcaggaggag ctgccgtccc tgtggaacag ccgcgtaggt | 960 |
| ttctacgtca acacgttcca gagcatcgcg ggcctggagg aaaacttcca aggagatg | 1020 |
| agcaagctca accagaacct caatgatgtg ctggtcggcc tggagaagca cacgggagc | 1080 |
| aacaccttca cggtcaaggc ccagcccaga agaaaagta aactgttttc gcggctgcgc | 1140 |
| agaaagaaga acagtgacaa cgcgcctgca aagggaaca agagcccttc gcctccagat | 1200 |
| ggctcccctg ccgccacccc cgagatcaga gtcaaccacg agccagagcc ggccggcggg | 1260 |
| gccacgcccg gggccaccct ccccaagtcc ccatctcagc cagcagaggc ctcgaggtg | 1320 |
| gcgggtggga cccaacctgc ggctggagcc caggagccag gggagacggc ggcaagtgaa | 1380 |
| gcagcctcca gctctcttcc tgctgtcgtg gtggagacct cccagcaac tgtgaatggc | 1440 |
| accgtggagg gcggcagtgg ggccgggcgc ttggacctgc cccaggtttt catgttcaag | 1500 |
| gtacaggccc agcacgacta cacggccact gacacagacg agctgcagct caaggctggt | 1560 |
| gatgtggtgc tggtgatccc cttccagaac cctgaagagc aggatgaagg ctggctcatg | 1620 |
| ggcgtgaagg agagcgactg gaaccagcac aaggagctgg agaagtgccg tgcgtcttc | 1680 |
| cccgagaact tcactgagag ggtcccatga cggcggggcc caggcagcct ccgggcgtgt | 1740 |

```
gaagaacacc tcctcccgaa aaatgtgtgg ttcttttttt tgttttgttt tcgtttttca    1800
tcttttgaag agcaaaggga aatcaagagg agaccccag gcagagggc gttctcccaa     1860 agattaggtc gttttccaaa gagccgcgtc ccggcaagtc cggcggaatt caccagtgtt    1920
cctgaagctg ctgtgtcctc tagttgagtt tctggcgccc ctgcctgtgc ccgcatgtgt   1980
gcctggccgc agggcgggc tgggggctgc cgagccacca tgcttgcctg aagcttcggc    2040
cgcgccaccc gggcaagggt cctcttttcc tggcagctgc tgtgggtggg gcccagacac   2100
cagcctagcc tggctctgcc ccgcagacgg tctgtgtgct gtttgaaaat aaatcttagt   2160
gttcaaaaca aaatgaaaca aaaaaaaaat gataaaaact ctcaaaaaaa              2210

<210> SEQ ID NO 383
<211> LENGTH: 4604
<212> TYPE: DNA
<213> ORGANISM: Homo sapiens

<400> SEQUENCE: 383
ggaacagctt gtccacccgc cggccggacc agaagccttt gggtctgaag tgtctgtgag     60
acctcacaga agagcacccc tgggctccac ttacctgccc cctgctcctt cagggatgga    120
ggcaatggcg gccagcactt ccctgcctga ccctggagac tttgaccgga acgtgccccg    180
gatctgtggg gtgtgtggag accgagccac tggctttcac ttcaatgcta tgacctgtga    240
aggctgcaaa ggcttcttca gcgaagcat gaagcggaag gcactattca cctgccccctt   300 caacggggac tgccgcatca ccaaggacaa ccgacgccac tgccaggcct gccggctcaa    360
acgctgtgtg gacatcggca tgatgaagga gttcattctg acagatgagg aagtgcagag    420
gaagcgggag atgatcctga gcggaagga ggaggaggcc ttgaaggaca gtctgcggcc    480
caagctgtct gaggagcagc agcgcatcat tgccatactg ctggacgccc accataagac    540
ctacgacccc acctactccg acttctgcca gttccggcct ccagttcgtg tgaatgatgg    600
tggagggagc catccttcca ggcccaactc cagacacact cccagcttct ctggggactc    660
ctcctcctcc tgctcagatc actgtatcac ctcttcagac atgatggact cgtccagctt    720
ctccaatctg gatctgagtg aagaagattc agatgaccct tctgtgaccc tagagctgtc    780
ccagctctcc atgctgcccc acctggctga cctggtcagt tacagcatcc aaaaggtcat    840
tggctttgct aagatgatac caggattcag agacctcacc tctgaggacc agatcgtact    900
gctgaagtca gtgccattg aggtcatcat gttgcgctcc aatgagtcct tcaccatgga    960
cgacatgtcc tggacctgtg gcaaccaaga ctacaagtac cgcgtcagtg acgtgaccaa   1020
agccggacac agcctggagc tgattgagcc cctcatcaag ttccaggtgg gactgaagaa    1080
gctgaacttg catgaggagg agcatgtcct gctcatggcc atctgcatcg tctccccaga   1140
tcgtcctggg gtgcaggacg ccgcgctgat tgaggccatc caggaccgcc tgtccaacac   1200
actgcagacg tacatccgct gccgccaccc gccccgggc agccacctgc tctatgccaa    1260
gatgatccag aagctagccg acctgcgcag cctcaatgag gagcactcca agcagtaccg    1320
ctgcctctcc ttccagcctg agtgcagcat gaagctaacg cccctgtgc tcgaagtgtt    1380 tggcaatgag atctcctgac taggacagcc tgtgcggtgc tgggtgggg ctgctcctcc    1440 agggccacgt gccaggcccg gggctggcgg ctactcagca gccctcctca cccgtctggg    1500
gttcagcccc tcctctgcca cctccctat ccacccagcc cattctctct cctgtccaac    1560 ctaaccccctt tcctgcgggc ttttcccgg tcccttgaga cctcagccat gaggagttgc   1620
tgtttgtttg acaaagaaac ccaagtgggg gcagagggca gaggctggag gcaggccttg   1680
```

```
cccagagatg cctccaccgc tgcctaagtg gctgctgact gatgttgagg gaacagacag      1740
gagaaatgca tccattcctc agggacagag acacctgcac ctcccccccac tgcaggcccc     1800 gcttgtccag cgcctagtgg ggtctccctc tcctgcctta ctcacgataa ataatcggcc      1860
cacagctccc accccacccc cttcagtgcc caccaacatc ccattgccct ggttatattc      1920
tcacgggcag tagctgtggt gaggtgggtt ttcttcccat cactggagca ccaggcacga      1980
acccacctgc tgagagaccc aaggaggaaa acagacaaa aacagcctca cagaagaata       2040
tgacagctgt ccctgtcacc aagctcacag ttcctcgccc tgggtctaag gggttggttg      2100
aggtggaagc cctccttcca cggatccatg tagcaggact gaattgtccc cagtttgcag      2160
aaaagcacct gccgacctcg tcctcccccct gccagtgcct tacctcctgc ccaggagagc     2220
cagccctccc tgtcctcctc ggatcaccga gagtagccga gagcctgctc ccccacccc       2280 tccccagggg agagggtctg gagaagcagt gagccgcatc ttctccatct ggcagggtgg      2340
gatggaggag aagaatttc agaccccagc ggctgagtca tgatctccct gccgcctcaa       2400
tgtggttgca aggccgctgt tcaccacagg gctaagagct aggctgccgc accccagagt      2460
gtgggaaggg agagcggggc agtctcgggt ggctagtcag agagagtgtt tgggggttcc     2520
gtgatgtagg gtaaggtgcc ttcttattct cactccacca cccaaaagtc aaaaggtgcc     2580
tgtgaggcag gggcggagtg atacaacttc aagtgcatgc tctctgcagg tcgagcccag    2640
cccagctggt gggaagcgtc tgtccgttta ctccaaggtg ggtctttgtg agagtgagct     2700
gtaggtgtgc gggaccggta cagaaaggcg ttcttcgagg tggatcacag aggcttcttc     2760
agatcaatgc ttgagtttgg aatcggccgc attccctgag tcaccaggaa tgttaaagtc     2820
agtgggaacg tgactgcccc aactcctgga agctgtgtcc ttgcacctgc atccgtagtt     2880
ccctgaaaac ccagagagga atcagacttc acactgcaag agccttggtg tccacctggc    2940
cccatgtctc tcagaattct tcaggtggaa aaacatctga agccacgtt ccttactgca     3000 gaatagcata tatatcgctt aatcttaaat ttattagata tgagttgttt tcagactcag   3060
actccatttg tattatagtc taatatacag ggtagcaggt accactgatt tggagatatt    3120
tatgggggga gaacttacat tgtgaaactt ctgtacatta attattattg ctgttgttat    3180
tttacaaggg tctagggaga gaccttgtt tgattttagc tgcagaactg tattggtcca    3240
gcttgctctt cagtgggaga aaaacacttg taagttgcta aacgagtcaa tcccctcatt    3300
caggaaaact gacagaggag ggcgtgactc acccaagcca tatataacta gctagaagtg   3360
ggccaggaca ggccgggcgc ggtggctcac gcctgtaatc ccagcagttt gggaggtcga    3420
ggtaggtgga tcacctgagg tcgggagttc gagaccaacc tgaccaacat ggagaaaccc   3480
tgtctctatt aaaaatacaa aaaaaaaaa aaaaaaaat agccgggcat ggtggcgcaa     3540
gcctgtaatc ccagctactc aggaggctga ggcagaagaa ttgaacccag gaggtggagg   3600
ttgcagtgag ctgagatcgt gccgttactc tccaacctgg acaacaagag cgaaactccg   3660
tcttagaagt ggaccaggac aggaccagat tttggagtca tggtccggtg tccttttcac   3720
tacaccatgt ttgagctcag acccccactc tcattcccca ggtggctgac ccagtccctg   3780
ggggaagccc tggatttcag aaagagccaa gtctggatct gggacccttt ccttccttcc    3840
ctggcttgta actccaccaa gcccatcaga aggaaggga aggagactca cctctgcctc    3900
aatgtgaatc agaccctacc ccaccacgat gtgccctggc tgctgggctc tccacctcag   3960
gccttggata atgctgttgc ctcatctata acatgcattt gtctttgtaa tgtcaccacc    4020
```

-continued

```
ttcccagctc tccctctggc cctgcttctt cggggaactc ctgaaatatc agttactcag    4080
ccctgggccc caccacctag gccactcctc caaaggaagt ctaggagctg ggaggaaaag    4140
aaaagagggg aaaatgagtt tttatggggc tgaacgggga gaaaaggtca tcatcgattc    4200
tactttagaa tgagagtgtg aaatagacat ttgtaaatgt aaaacttta aggtatatca     4260 ttataactga aggagaaggt gccccaaaat gcaagatttt ccacaagatt cccagagaca    4320
ggaaaatcct ctggctggct aactggaagc atgtaggaga atccaagcga ggtcaacaga    4380
gaaggcagga atgtgtggca gatttagtga aagctagaga tatggcagcg aaaggatgta    4440
aacagtgcct gctgaatgat ttccaaagag aaaaaaagtt tgccagaagt ttgtcaagtc    4500
aaccaatgta gaaagctttg cttatggtaa taaaaatggc tcatacttat atagcactta    4560
ctttgtttgc aagtactgct gtaaataaat gctttatgca aacc                    4604

<210> SEQ ID NO 384
<211> LENGTH: 545
<212> TYPE: DNA
<213> ORGANISM: Homo sapiens

<400> SEQUENCE: 384
gagtgactct cacgagagcc gcgagagtca gcttggccaa tccgtgcggt cggcggccgc      60 tcccttata agccgactcg cccggcagcg caccgggttg cggagggtgg gcctgggagg     120
ggtggtggcc attttttgtc taaccctaac tgagaagggc gtaggcgccg tgcttttgct    180
ccccgcgcgc tgtttttctc gctgactttc agcgggcgga aaagcctcgg cctgccgcct    240
tccaccgttc attctagagc aaacaaaaaa tgtcagctgc tggcccgttc gccctcccg     300 gggacctgcg gcgggtcgcc tgcccagccc ccgaacccg cctggaggcc gcggtcggcc     360
cggggcttct ccggaggcac ccactgccac cgcgaagagt tgggctctgt cagccgcggg    420
tctctcgggg gcgagggcga ggttcaggcc tttcaggccg caggaagagg aacggagcga    480
gtccccgcgc gcggcgcgat tccctgagct gtgggacgtg cacccaggac tcggctcaca    540
catgc                                                                545
```